(12) United States Patent
Liu et al.

(10) Patent No.: US 9,573,954 B2
(45) Date of Patent: Feb. 21, 2017

(54) PYRAZOLOPYRIMIDINE COMPOUNDS

(71) Applicant: University Health Network, Toronto (CA)

(72) Inventors: Yong Liu, Oakville (CA); Heinz W. Pauls, Oakville (CA); Radoslaw Laufer, Oakville (CA); Sze-Wan Li, Toronto (CA); Peter Brent Sampson, Oakville (CA); Miklos Feher, New York, NY (US); Grace Ng, Markham (CA); Narendra Kumar B. Patel, Brampton (CA); Yunhui Lang, Markham (CA)

(73) Assignee: University Health Network, Toronto (CA)

( * ) Notice: Subject to any disclaimer, the term of this patent is extended or adjusted under 35 U.S.C. 154(b) by 0 days.

(21) Appl. No.: 14/443,072

(22) PCT Filed: Nov. 15, 2013

(86) PCT No.: PCT/CA2013/000957
§ 371 (c)(1),
(2) Date: May 15, 2015

(87) PCT Pub. No.: WO2014/075168
PCT Pub. Date: May 22, 2014

(65) Prior Publication Data
US 2015/0299203 A1 Oct. 22, 2015

Related U.S. Application Data

(60) Provisional application No. 61/727,581, filed on Nov. 16, 2012, provisional application No. 61/808,152, filed on Apr. 3, 2013.

(51) Int. Cl.
C07D 487/04 (2006.01)
C07D 519/00 (2006.01)

(52) U.S. Cl.
CPC .......... C07D 487/04 (2013.01); C07D 519/00 (2013.01)

(58) Field of Classification Search
CPC .......................... C07D 487/04; C07D 519/00
See application file for complete search history.

(56) References Cited

U.S. PATENT DOCUMENTS

| | | | |
|---|---|---|---|
| 4,021,556 A * | 5/1977 | Springer | A61K 31/505 514/259.3 |
| 6,060,478 A | 5/2000 | Gilligan et al. | |
| 6,124,289 A | 9/2000 | He et al. | |
| 6,191,131 B1 | 2/2001 | He et al. | |
| 6,313,124 B1 | 11/2001 | He et al. | |
| 6,372,743 B1 | 4/2002 | Darrow et al. | |
| 6,476,038 B1 | 11/2002 | Darrow et al. | |
| 7,723,336 B2 | 5/2010 | Vaccaro et al. | |
| 2002/0147338 A1 | 10/2002 | Gilligan et al. | |
| 2004/0043998 A1 | 3/2004 | Kato et al. | |
| 2004/0254220 A1 | 12/2004 | Bressi et al. | |
| 2005/0187219 A1 | 8/2005 | Guzi et al. | |
| 2005/0229333 A1 | 10/2005 | Glenn et al. | |
| 2006/0025426 A1 | 2/2006 | Fraley | |
| 2006/0079536 A1 | 4/2006 | Yasuma et al. | |
| 2006/0089362 A1 | 4/2006 | Seno et al. | |
| 2006/0106019 A1 | 5/2006 | Bernard | |
| 2006/0276475 A1 | 12/2006 | Vu et al. | |
| 2007/0078136 A1 | 4/2007 | Vaccaro et al. | |
| 2007/0082900 A1 | 4/2007 | Guzi et al. | |
| 2007/0173505 A1 | 7/2007 | Peng et al. | |
| 2007/0232623 A1 | 10/2007 | Gudmundsson et al. | |
| 2010/0029657 A1 | 2/2010 | Levin et al. | |
| 2010/0216798 A1 | 8/2010 | Nakai et al. | |
| 2011/0190319 A1 | 8/2011 | Combs et al. | |
| 2011/0281866 A1 | 11/2011 | Ren et al. | |
| 2012/0003215 A1 | 1/2012 | Babaoglu et al. | |
| 2012/0059162 A1 | 3/2012 | Kusakabe et al. | |
| 2012/0077814 A1 | 3/2012 | Wang et al. | |
| 2012/0083498 A1 | 4/2012 | Kashanchi | |
| 2012/0095005 A1 | 4/2012 | Allen et al. | |
| 2012/0149708 A1 | 6/2012 | Kashanchi | |
| 2012/0322791 A1 | 12/2012 | Siddiqui et al. | |
| 2014/0038953 A1 | 2/2014 | Yu et al. | |
| 2014/0249147 A1 | 9/2014 | Blum et al. | |
| 2014/0329807 A1 | 11/2014 | Xu et al. | |
| 2016/0137651 A1 | 5/2016 | Laufer et al. | |

FOREIGN PATENT DOCUMENTS

| | | | |
|---|---|---|---|
| CA | 2656419 A1 | 12/2007 | |
| CA | 2693915 A1 | 1/2009 | |

(Continued)

OTHER PUBLICATIONS

Nie Z. et al., "Structure-based design, synthesis, and study of pyrazolo[1,5-a][1,3,5]triazine derivatives as potent inhibitors of protein kinase CK2," Bioorganic and Medicinal Chemistry Letters, vol. 17, pp. 4191-4195, 2007.

*Primary Examiner* — Alexander R Pagano
*Assistant Examiner* — Ebenezer O Sackey
(74) *Attorney, Agent, or Firm* — McCarter & English, LLP; Steven G. Davis; Wei Song

(57) ABSTRACT

The present teachings provide a compound represented by structural formula (1-0), or a pharmaceutically acceptable salt thereof. Also described are pharmaceutical compositions and methods of use thereof.

(I)

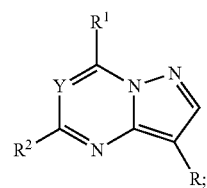

(I-0)

22 Claims, No Drawings

FOREIGN PATENT DOCUMENTS

| | | |
|---|---|---|
| EP | 2402337 A1 | 1/2012 |
| JP | H04156452 A | 5/1992 |
| JP | H04156453 A | 5/1992 |
| WO | 0123387 A2 | 4/2001 |
| WO | 2004022559 A1 | 3/2004 |
| WO | 2004/052315 A2 | 6/2004 |
| WO | 2004/087707 A1 | 10/2004 |
| WO | 2005063766 A2 | 7/2005 |
| WO | 2007044441 A2 | 4/2007 |
| WO | 2007147647 A1 | 12/2007 |
| WO | 2008025822 A1 | 3/2008 |
| WO | 2008045267 A2 | 4/2008 |
| WO | 2008056176 A1 | 5/2008 |
| WO | 2010086040 A1 | 8/2010 |
| WO | 2011013729 A1 | 2/2011 |
| WO | 2011151259 A1 | 12/2011 |
| WO | 2012032031 A1 | 3/2012 |
| WO | 2012080229 A1 | 6/2012 |
| WO | 2012080236 A1 | 6/2012 |
| WO | 2012136531 A1 | 10/2012 |
| WO | 2015070349 A1 | 5/2015 |

* cited by examiner

PYRAZOLOPYRIMIDINE COMPOUNDS

RELATED APPLICATIONS

This application is a National Stage Application of International Application No. PCT/CA2013/000957, filed Nov. 15, 2013, which claims the benefit of U.S. Provisional Application No. 61/727,581, filed Nov. 16, 2012, and U.S. Provisional Application No. 61/808,152, filed Apr. 3, 2013. The entire teachings of each of the aforementioned applications are incorporated herein by reference.

BACKGROUND OF THE INVENTION

Protein kinases have been the subject of extensive study in the search for new therapeutic agents in various diseases, for example, cancer. Protein kinases are known to mediate intracellular signal transduction by effecting a phosphoryl transfer from a nucleoside triphosphate to a protein acceptor that is involved in a signaling pathway. There are a number of kinases and pathways through which extracellular and other stimuli cause a variety of cellular responses to occur inside the cell.

Human TTK protein kinase (TTK), also known as tyrosine threonine kinase, dual specificity protein kinase TTK, Monopolar Spindle 1 (Mps1) and Phosphotyrosine-Picked Threonine Kinase (PYT), is a conserved multispecific kinase that is capable of phosphorylating serine, threonine and tyrosine residues when expressed in *E. coli* (Mills et al., *J. Biol. Chem.* 22(5): 16000-16006 (1992)). TTK mRNA is not expressed in the majority of physiologically normal tissues in human (Id). TTK mRNA is expressed in some rapidly proliferating tissues, such as testis and thymus, as well as in some tumors (for example, TTK mRNA was not expressed in renal cell carcinoma, was expressed in 50% of breast cancer samples, was expressed in testicular tumors and ovarian cancer samples) (Id). TTK is expressed in some cancer cell lines and tumors relative to normal counterparts (Id.; see also WO 02/068444 A1).

Therefore, agents which inhibit a protein kinase, in particular TTK, have the potential to treat cancer. There is a need for additional agents which can act as protein kinase inhibitors, in particular TTK inhibitors.

In addition, cancer recurrence, drug resistance or metastasis is one of the major challenges in cancer therapies. Cancer patients who responded favorably to the initial anti-cancer therapy often develop drug resistance and secondary tumors that lead to the relapse of the disease. Recent research evidences suggest that the capability of a tumor to grow and propagate is dependent on a small subset of cells within the tumor. These cells are termed tumor-initiating cells (TICs) or cancer stem cells. It is thought that the TICs are responsible for drug resistance, cancer relapse and metastasis. Compounds that can inhibit the growth and survival of these tumor-initiating cells can be used to treat cancer, metastasis or prevent recurrence of cancer. Therefore, a need exists for new compounds that can inhibit the growth and survival of tumor-imitating cells.

SUMMARY OF THE INVENTION

Applicants have now discovered that certain pyrazolotriazine and pyrazolopyrimidine compounds are potent kinase inhibitors, such as TTK protein kinase (see Example B). Applicants have also discovered that these compounds have potent anticancer activity against pancreatic cancer, prostate cancer, lung cancer, melanoma, breast cancer, colon cancer, and ovarian cancer cells in cell culture study (see Examples C-D). Based on these discoveries, pyrazolotriazine and pyrazolopyrimidine compounds, pharmaceutical compositions thereof, and methods of treating cancer with the pyrazolotriazine and pyrazolopyrimidine compounds are disclosed herein.

The present teachings are directed, at least in part, to a compound represented by the following structural formula:

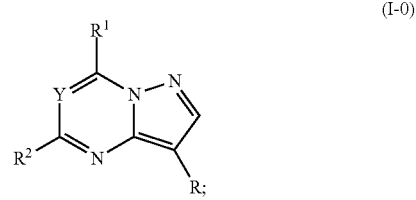

(I-0)

or a pharmaceutically acceptable salt thereof, wherein:

Y is N or CH;

R is phenyl or monocyclic 5-6 membered heteroaryl, both of which are substituted with —C(=O)NR$^d$R$^e$ or —NHC(=O)R$^5$, —C(=S)NR$^d$R$^e$, or —NHC(=S)R$^5$ and optionally substituted with one or more groups selected from one or more groups selected from halogen, hydroxy, (C$_1$-C$_3$) alkyl, (C$_1$-C$_3$)haloalkyl, (C$_1$-C$_3$)alkoxy, and (C$_1$-C$_3$)haloalkoxy;

R$^1$ is —NR$^{a1}$R$^{b1}$, —OR$^{c1}$, —SR$^{c1}$, —SOR$^{c1}$, or —SO$_2$R$^{c1}$;

R$^2$ is —NR$^{a2}$R$^{b2}$, —OR$^{c2}$, —SR$^{c2}$, optionally substituted phenyl or optionally substituted 5-10 membered heteroaryl;

R$^5$ is optionally substituted (C$_1$-C$_3$)alkyl, optionally substituted (C$_3$-C$_7$)cycloalkyl, optionally substituted 3-7 membered monocyclic heterocycloalkyl, optionally substituted phenyl, or optionally substituted 5-6 membered monocyclic heteroaryl;

R$^{a1}$ and R$^{b1}$ are each independently selected from —H, optionally substituted (C$_1$-C$_6$)alkyl, optionally substituted (C$_3$-C$_7$)cycloalkyl, optionally substituted 3-7 membered monocyclic heterocycloalkyl, optionally substituted phenyl, and optionally substituted 5-6 membered monocyclic heteroaryl; or R$^{a1}$ and R$^{b1}$, together with the nitrogen to which they are attached, form an optionally substituted 3-7 membered ring;

R$^{a2}$ and R$^{b2}$ are each independently selected from —H, optionally substituted (C$_1$-C$_6$)alkyl, optionally substituted (C$_3$-C$_7$)cycloalkyl, optionally substituted 3-7 membered monocyclic heterocycloalkyl, optionally substituted phenyl, and optionally substituted 5-6 membered monocyclic heteroaryl; or R$^{a2}$ and R$^{b2}$, together with the nitrogen to which they are attached, form an optionally substituted 3-8 membered ring (e.g., a bridged bicyclic ring);

R$^{c1}$ is optionally substituted (C$_1$-C$_6$)alkyl, optionally substituted (C$_3$-C$_7$)cycloalkyl, optionally substituted 3-7 membered monocyclic heterocycloalkyl, optionally substituted phenyl, or optionally substituted 5-6 membered monocyclic heteroaryl;

R$^{c2}$ is optionally substituted (C$_1$-C$_6$)alkyl, optionally substituted (C$_3$-C$_7$)cycloalkyl, optionally substituted 3-7 membered monocyclic heterocycloalkyl, optionally substituted phenyl, or optionally substituted 5-6 membered monocyclic heteroaryl;

R$^d$ and R$^e$ are each independently selected from —H, optionally substituted (C$_1$-C$_7$)alkyl, optionally substituted ($C_3$-$C_7$)cycloalkyl, optionally substituted 3-7 membered monocyclic heterocycloalkyl, optionally substituted phenyl, and optionally substituted 5-6 membered monocyclic heteroaryl; or $R^d$ and $R^e$, together with the nitrogen to which they are attached, form an optionally substituted 3-7 membered ring.

In one embodiment, the present teachings include a pharmaceutical composition comprising a pharmaceutically acceptable carrier or diluent and a compound represented by structural formula (I-0) described above or a pharmaceutically acceptable salt thereof.

In another embodiment, the present teachings provide a method of treating a subject having cancer comprising administering to the subject an effective amount of a compound of structural formula (I-0) or a pharmaceutically acceptable salt thereof.

Another embodiment of the present teachings provides a method of inhibiting TTK activity in a subject in need of inhibition of TTK activity, comprising administering to the subject an effective amount of a compound represented by Structural Formula (I-0) or a pharmaceutically acceptable salt thereof.

Another embodiment of the present teachings includes the use of a compound represented by Structural Formula (I-0) or a pharmaceutically acceptable salt thereof in therapy. In some embodiments, the therapy is for treating a subject with cancer. Alternatively, the therapy is for inhibiting TTK activity in a subject in need of inhibition of TTK activity.

Another embodiment of the present teachings includes the use of a compound represented by Structural Formula (I-0) or a pharmaceutically acceptable salt thereof for the manufacture of a medicament for treating a subject with cancer.

Another embodiment of the present teachings includes the use of a compound represented by Structural Formulas (I-0) or a pharmaceutically acceptable salt thereof for the manufacture of a medicament for inhibiting TTK activity in a subject in need of inhibition of TTK activity.

DETAILED DESCRIPTION OF THE INVENTION

In one embodiment, the present teachings are directed to a compound represented by Structural Formula (I-0) or a pharmaceutically acceptable salt thereof; and values and alternative values for the variables in Structural Formula (I-0) are provided in the following paragraphs:

In a first embodiment, the compound is represented by the following structural formula:

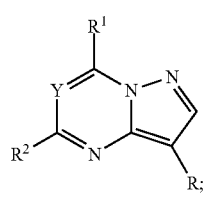

(I)' or a pharmaceutically acceptable salt thereof, wherein:
Y is N or CH;
R is phenyl or monocyclic 5-6 membered heteroaryl, both of which are substituted with —C(=O)NR$^d$R$^e$ or —NHC(=O)R$^5$, and optionally substituted with one or more groups selected from halogen, hydroxy, ($C_1$-$C_3$)alkyl, ($C_1$-$C_3$)haloalkyl, ($C_1$-$C_3$)alkoxy, and ($C_1$-$C_3$)haloalkoxy;

$R^1$ is —NR$^{a1}$R$^{b1}$ or —OR$^{c1}$;
$R^2$ is —NR$^{a2}$R$^{b2}$, —OR$^{c2}$, —SR$^{c2}$, optionally substituted phenyl or optionally substituted 5-6 membered monocyclic heteroaryl;
$R^5$ is optionally substituted ($C_1$-$C_3$)alkyl, optionally substituted ($C_3$-$C_7$)cycloalkyl, optionally substituted 3-7 membered monocyclic heterocycloalkyl, optionally substituted phenyl, or optionally substituted 5-6 membered monocyclic heteroaryl;
$R^{a1}$ and $R^{b1}$ are each independently selected from —H, optionally substituted ($C_1$-$C_6$)alkyl, optionally substituted ($C_3$-$C_7$)cycloalkyl, optionally substituted 3-7 membered monocyclic heterocycloalkyl, optionally substituted phenyl, and optionally substituted 5-6 membered monocyclic heteroaryl;
$R^{a2}$ and $R^{b2}$ are each independently selected from —H, optionally substituted ($C_1$-$C_6$)alkyl, optionally substituted ($C_3$-$C_7$)cycloalkyl, optionally substituted 3-7 membered monocyclic heterocycloalkyl, optionally substituted phenyl, and optionally substituted 5-6 membered monocyclic heteroaryl; or
$R^{a2}$ and $R^{b2}$, together with the nitrogen to which they are attached, form an optionally substituted 3-7 membered ring;
$R^{c1}$ is optionally substituted ($C_1$-$C_6$)alkyl, optionally substituted ($C_3$-$C_7$)cycloalkyl, optionally substituted 3-7 membered monocyclic heterocycloalkyl, optionally substituted phenyl, or optionally substituted 5-6 membered monocyclic heteroaryl;
$R^{c2}$ is optionally substituted ($C_1$-$C_6$)alkyl, optionally substituted ($C_3$-$C_7$)cycloalkyl, optionally substituted 3-7 membered monocyclic heterocycloalkyl, optionally substituted phenyl, or optionally substituted 5-6 membered monocyclic heteroaryl; and
$R^d$ and $R^e$ are each independently selected from —H, optionally substituted ($C_1$-$C_7$)alkyl, optionally substituted ($C_3$-$C_7$)cycloalkyl, optionally substituted 3-7 membered monocyclic heterocycloalkyl, optionally substituted phenyl, and optionally substituted 5-6 membered monocyclic heteroaryl; or
$R^d$ and $R^e$, together with the nitrogen to which they are attached, form an optionally substituted 3-7 membered ring.

In a second embodiment, the compound is represented by the following structural formula:

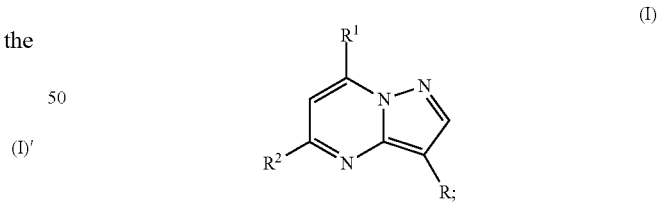

(I)

or a pharmaceutically acceptable salt thereof, wherein:
R is phenyl or monocyclic 5-6 membered heteroaryl, both of which are substituted with —C(=O)NR$^d$R$^e$, —NHC(=O)R$^5$, —C(=S)NR$^d$R$^e$, or —NHC(=S)R$^5$ and optionally substituted with one or more groups selected from halogen, hydroxy, ($C_1$-$C_3$)alkyl, ($C_1$-$C_3$)haloalkyl, ($C_1$-$C_3$)alkoxy, and ($C_1$-$C_3$)haloalkoxy;
$R^1$ is —NR$^{a1}$R$^{b1}$, —OR$^{c1}$, —SR$^{c1}$, —SOR$^{c1}$, or —SO$_2$R$^{c1}$;
$R^2$ is —NR$^{a2}$R$^{b2}$, —OR$^{c2}$, —SR$^{c2}$, optionally substituted phenyl or optionally substituted 5-6 membered monocyclic heteroaryl;

$R^5$ is optionally substituted $(C_1-C_3)$alkyl, optionally substituted $(C_3-C_7)$cycloalkyl, optionally substituted 3-7 membered monocyclic heterocycloalkyl, optionally substituted phenyl, or optionally substituted 5-6 membered monocyclic heteroaryl;

$R^{a1}$ and $R^{b1}$ are each independently selected from —H, optionally substituted $(C_1-C_6)$alkyl, optionally substituted $(C_3-C_7)$cycloalkyl, optionally substituted 3-7 membered monocyclic heterocycloalkyl, optionally substituted phenyl, and optionally substituted 5-6 membered monocyclic heteroaryl;

$R^{a2}$ and $R^{b2}$ are each independently selected from —H, optionally substituted $(C_1-C_6)$alkyl, optionally substituted $(C_3-C_7)$cycloalkyl, optionally substituted 3-7 membered monocyclic heterocycloalkyl, optionally substituted phenyl, and optionally substituted 5-6 membered monocyclic heteroaryl; or $R^{a2}$ and $R^{b2}$, together with the nitrogen to which they are attached, form an optionally substituted 3-7 membered ring;

$R^{c1}$ is optionally substituted $(C_1-C_6)$alkyl, optionally substituted $(C_3-C_7)$cycloalkyl, optionally substituted 3-7 membered monocyclic heterocycloalkyl, optionally substituted phenyl, or optionally substituted 5-6 membered monocyclic heteroaryl;

$R^{c2}$ is optionally substituted $(C_1-C_6)$alkyl, optionally substituted $(C_3-C_7)$cycloalkyl, optionally substituted 3-7 membered monocyclic heterocycloalkyl, optionally substituted phenyl, or optionally substituted 5-6 membered monocyclic heteroaryl; and $R^d$ and $R^e$ are each independently selected from —H, optionally substituted $(C_1-C_7)$alkyl, optionally substituted $(C_3-C_7)$cycloalkyl, optionally substituted 3-7 membered monocyclic heterocycloalkyl, optionally substituted phenyl, and optionally substituted 5-6 membered monocyclic heteroaryl; or $R^d$ and $R^e$, together with the nitrogen to which they are attached, form an optionally substituted 3-7 membered ring.

In a third embodiment, the compound is represented by structural formula:

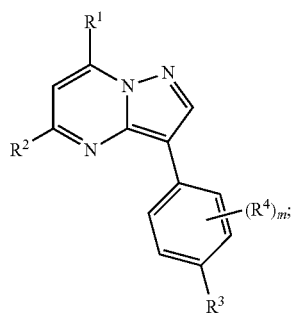

(I-A)

or a pharmaceutically acceptable salt thereof, wherein $R^3$ is —C(=O)NR$^d$R$^e$ or NHC(=O)R$^5$; each $R^4$ is independently selected from hydrogen, halogen, hydroxy, $(C_1-C_3)$alkyl, $(C_1-C_3)$haloalkyl, and $(C_1-C_3)$alkoxy; and m is 1, 2, or 3; and values for the remainder of the variables are as described for Structural Formula (I) or in the second embodiment.

In a fourth embodiment, the compound is represented by the following structural formula:

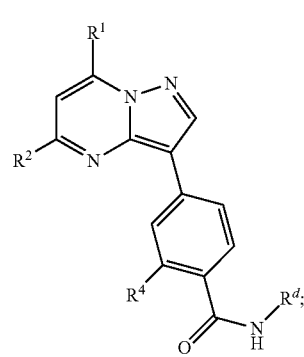

(II-A0)

or a pharmaceutically acceptable salt thereof; and values for the remainder of the variables are as described for Structural Formula (I-0), (I), or (I)', or in the first, second, or third embodiment.

In a fifth embodiment, the compound is represented by the following structural formula:

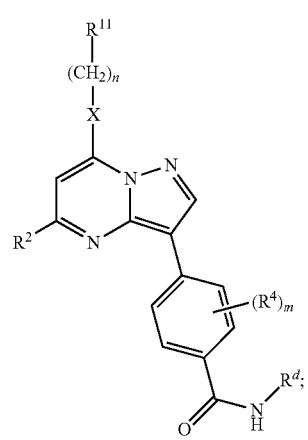

(II-A1)

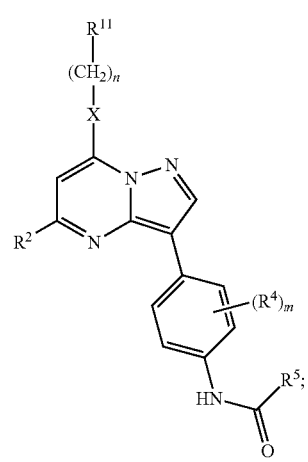

(II-A2)

or a pharmaceutically acceptable salt thereof, wherein X is NH or O; $R^5$ is selected from $(C_1-C_3)$alkyl and $(C_3-C_7)$cycloalkyl, each of which is optionally substituted with one or more groups selected from halogen, hydroxy, $(C_1-C_3)$ alkyl, (C₁-C₃)haloalkyl, and (C₁-C₃)alkoxy; $R^{11}$ is (C₁-C₃) alkyl, (C₃-C₇)cycloalkyl, 3-7 membered monocyclic heterocycloalkyl, phenyl, or 5-6 membered monocyclic heteroaryl, each of which is optionally substituted with one or more groups selected from halogen, hydroxy, CN, amino, (C₁-C₃) alkyl, (C₁-C₃)haloalkyl, (C₁-C₃)alkoxy, —C(=O)NH₂, —C(=O)NH(C₁-C₃)alkyl, —C(=O)N((C₁-C₃)alkyl)₂, and —SO₂(C₁-C₃)alkyl; $R^d$ is independently selected from —H, (C₁-C₃)alkyl, (C₃-C₇)cycloalkyl, 4-5 membered heterocycloalkyl wherein each of the (C₁-C₃)alkyl, (C₃-C₇)cycloalkyl, and 4-5 membered heterocycloalkyl is optionally substituted with one or more groups selected from halogen, hydroxy, (C₁-C₃)alkyl, (C₁-C₃)haloalkyl, and (C₁-C₃) alkoxy; n is 0, 1, 2, or 3; and values and alternative values for the remainder of the variables are as described for Structural Formula (I) or in the second or third embodiment.

In a sixth embodiment, the compound is represented by the following structural formula:

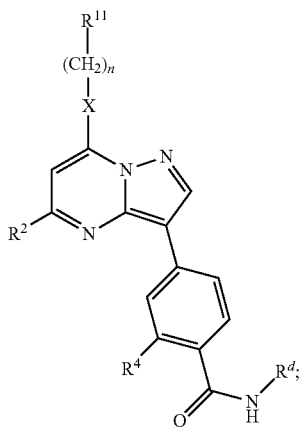

(II-B1)

or a pharmaceutically acceptable salt thereof; and values and alternative values for the remainder of the variables are as described for Structural Formula (I) or in the second, third, or fifth embodiment.

In a seventh embodiment, the compound is represented by the following structural formula:

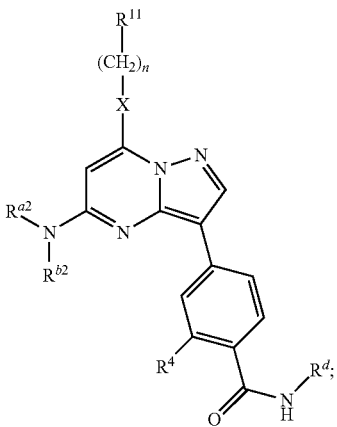

(II-C1)

or a pharmaceutically acceptable salt thereof; and values and alternative values for the remainder of the variables are as described for Structural Formula (I), or in the second, third, or fifth embodiment.

In an eighth embodiment, for compounds represented by any one of structural formulae (I), (I-A), (II-A1), (II-B1), (II-C1), or (II-A2), $R^{b2}$ is —H or CH₃; and values and alternative values for the remainder of the variables are as described for Structural Formula (I), or in the second, third, or fifth embodiment.

In a ninth embodiment, for compounds represented by any one of structural formulae (I), (I-A), (II-A1), (II-B1), (II-C1), or (II-A2), $R^{a2}$ is (C₁-C₆)alkyl, (C₃-C₇)cycloalkyl, 3-7 membered monocyclic heterocycloalkyl, phenyl, and 5-6 membered monocyclic heteroaryl (preferably, 3-7 membered monocyclic heterocycloalkyl, phenyl, and 5-6 membered monocyclic heteroaryl); wherein each of which is optionally substituted with one or more groups selected from halogen, hydroxy, CN, (C₁-C₃)alkyl, (C₁-C₃)haloalkyl, (C₁-C₃)alkoxy, (C₁-C₃)hydroxyalkyl, 3-7 membered monocyclic heterocycloalkyl; and values and alternative values for the remainder of the variables are as described for Structural Formula (I), or in the second, third, fifth, or eighth embodiment.

In a tenth embodiment, for compounds represented by any one of structural formulae (I), (I-A), (II-A1), (II-B1), (II-C1), or (II-A2), $R^{a2}$ is methyl, ethyl, propyl, isopropyl, butyl, isobutyl, tert-butyl, pentyl, cyclopropyl, cyclobutyl, cyclopentyl, cyclohexyl, oxetanyl, tetrahydro-2H-pyranyl, tetrahydrofuranyl, piperidinyl, pyridyl, or phenyl (preferably, methyl, propyl, butyl, pentyl, cyclopentyl, cyclohexyl, oxetanyl, tetrahydro-2H-pyranyl, tetrahydrofuranyl; more preferably, oxetanyl, tetrahydro-2H-pyranyl, tetrahydrofuranyl, piperidinyl, pyridyl, or phenyl), wherein each of the methyl, ethyl, propyl, isopropyl, isobutyl, tert-butyl, cyclopropyl, cyclobutyl, cyclopentyl, cyclohexyl, oxetanyl, tetrahydro-2H-pyranyl, tetrahydrofuranyl, piperidinyl, pyridyl, and phenyl (preferably, methyl, propyl, butyl, pentyl, cyclopentyl, cyclohexyl, oxetanyl, tetrahydro-2H-pyranyl, tetrahydrofuranyl; more preferably, oxetanyl, tetrahydro-2H-pyranyl, tetrahydrofuranyl, piperidinyl, pyridyl, or phenyl) is optionally substituted with one or more groups selected from halogen, hydroxy, CN, (C₁-C₃)alkyl, (C₁-C₃)haloalkyl, (C₁-C₃)alkoxy, and oxetanyl; and values and alternative values for the remainder of the variables are as described for Structural Formula (I), or in the second, third, fifth, eighth or ninth embodiment.

In an eleventh embodiment, for compounds represented by any one of structural formulae (I), (I-A), (II-A1), (II-B1), (II-C1), or (II-A2), $R^{a2}$ and $R^{b2}$, together with the nitrogen to which they are attached, form a 3-7 membered monocyclic heterocycloalkyl, optionally substituted with one or more groups selected from halogen, CN, hydroxy, (C₁-C₃) alkyl, (C₁-C₃)haloalkyl, (C₁-C₃)hydroxylalkyl, (C₁-C₃) alkoxy, —C(=O)H, —C(=O)(C₃-C₇)cycloalkyl, —C(=O)(C₁-C₃)alkyl, and 3-7 membered monocyclic heterocycloalkyl; and values and alternative values for the remainder of the variables are as described for Structural Formula (I), or in the second, third, or fifth embodiment.

Alternatively, $R^{a2}$ and $R^{b2}$, together with the nitrogen to which they are attached, form piperidinyl, morpholinyl, or piperazinyl (preferably, morpholinyl), wherein each substitutable carbon atom in the piperidinyl, morpholinyl, or piperazinyl (preferably, morpholinyl) is optionally substituted with halogen, hydroxy, (C₁-C₃)alkyl, (C₁-C₃)haloalkyl, (C₁-C₃)hydroxylalkyl or (C₁-C₃)alkoxy; and each substitutable nitrogen atom in the piperazinyl is optionally substituted with (C₁-C₃)alkyl, (C₁-C₃)haloalkyl, (C₁-C₃) hydroxylalkyl, (C₃-C₅)cycloalkyl, —C(=O)(C₃-C₅)cycloalkyl, —C(=O)(C₁-C₃)alkyl, oxetanyl, or —C(=O)H.

In a twelfth embodiment, the compound is represented by the following structural formula:

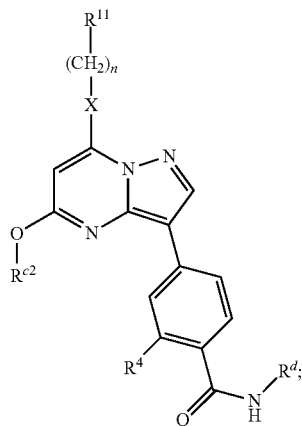

(II-D1)

or a pharmaceutically acceptable salt thereof; and values and alternative values for the remainder of the variables are as described for Structural Formula (I), or in the second, third, fifth, or sixth embodiment.

In a thirteen embodiment, for compounds represented by any one of structural formulae (I), (I-A), (II-A1), (II-B1), (II-D1), or (II-A2), $R^{c2}$ is $(C_1-C_6)$alkyl, $(C_3-C_7)$cycloalkyl, 3-7 membered monocyclic heterocycloalkyl, phenyl, or 5-6 membered monocyclic heteroaryl (preferably, 3-7 membered monocyclic heterocycloalkyl, phenyl, or 5-6 membered monocyclic heteroaryl), each of which is optionally substituted with one or more groups selected from halogen, hydroxy, $(C_1-C_3)$alkyl, $(C_1-C_3)$haloalkyl, $(C_1-C_3)$hydroxylalkyl, $(C_1-C_3)$alkoxy, —C(=O)$(C_1-C_3)$alkyl, —C(=O)$(C_3-C_7)$cycloalkyl, —C(=O)H, and 3-7 membered monocyclic heterocycloalkyl; and values and alternative values for the remainder of the variables are as described for Structural Formula (I), or in the second, third, or fifth embodiment.

In a fourteenth embodiment, for compounds represented by any one of structural formulae (I), (I-A), (II-A1), (II-B1), (II-D1), or (II-A2), $R^{c2}$ is cyclobutyl, cyclopentyl, cyclohexyl, tetrahydro-2H-pyranyl, phenyl, pyridyl, oxetanyl, tetrahydrofuranyl, pyrrolidinyl, piperidinyl, or azetidinyl (preferably, cyclopentyl, cyclohexyl, oxetanyl, tetrahydrofuranyl, tetrahydro-2H-pyranyl, phenyl, pyridyl, azetidinyl, pyrrolidinyl, piperidinyl; more preferably, tetrahydro-2H-pyranyl, phenyl, pyridyl, oxetanyl, tetrahydrofuranyl, pyrrolidinyl, piperidinyl, or azetidinyl;), wherein each substitutable carbon atom in the cyclobutyl, cyclopentyl, cyclohexyl, tetrahydro-2H-pyranyl, phenyl, pyridyl, oxetanyl, tetrahydrofuranyl, pyrrolidinyl, piperidinyl and azetidinyl (preferably, cyclopentyl, cyclohexyl, oxetanyl, tetrahydrofuranyl, tetrahydro-2H-pyranyl, phenyl, pyridyl, azetidinyl, pyrrolidinyl, and piperidinyl; more preferably, tetrahydro-2H-pyranyl, phenyl, pyridyl, oxetanyl, tetrahydrofuranyl, pyrrolidinyl, piperidinyl, and azetidinyl;) is optionally substituted with one or more groups selected from halogen, $(C_1-C_3)$alkyl, $(C_1-C_3)$haloalkyl, $(C_1-C_3)$hydroxylalkyl, $(C_1-C_3)$alkoxy, oxetanyl; and each substitutable nitrogen atom in the azetidinyl, pyrrolidinyl, or piperidinyl, is optionally substituted with $(C_1-C_3)$alkyl, $(C_3-C_5)$heterocycloalkyl, $(C_1-C_3)$hydroxylalkyl, —C(=O)$(C_1-C_3)$alkyl, —C(=O)$(C_3-C_5)$cycloalkyl, or —C(=O)H; and values and alternative values for the remainder of the variables are as described for Structural Formula (I), or in the second, third, fifth, or thirteenth embodiment.

In a fifteenth embodiment, for compounds represented by any one of structural formulae (I-A), (II-A1), (II-B1), (II-C1), (II-D1), or (II-A2), $R^4$ is selected from hydrogen, halogen, and $(C_1-C_3)$alkyl (preferably, $R^4$ is chlorine or methyl; and is ortho to —C(=O)$NR^dR^e$); and values and alternative values for the remainder of the variables are as described for Structural Formula (I), or in the third, fifth, sixth, seventh, eighth, ninth, tenth, eleventh, twelfth, thirteenth, or fourteenth embodiment.

In a sixteenth embodiment, for compounds represented by any one of structural formulae (I), (I-A), (II-A1), (II-B1), (II-C1), (II-D1), or (II-A2), $R^d$ is $(C_2-C_7)$alkyl or $(C_3-C_7)$cycloalkyl (preferably, $R^d$ is cyclopropyl), wherein both of which are optionally substituted with one or more groups selected from halogen, hydroxy, $(C_1-C_3)$alkyl, $(C_1-C_3)$haloalkyl, and $(C_1-C_3)$alkoxy; and values and alternative values for the remainder of the variables are as described for Structural Formula (I), or in the third, fifth, sixth, seventh, eighth, ninth, tenth, eleventh, twelfth, thirteenth, fourteenth, or fifteenth embodiment.

In a seventeenth embodiment, for compounds represented by any one of structural formulae (II-A1), (II-B1), (II-C1), (II-D1), or (II-A2), $R^{11}$ is $(C_1-C_6)$alkoxy, ethyl, propyl, isopropyl, isobutyl, tert-butyl, cyclopropyl, cyclobutyl, cyclopentyl, cyclohexyl, morpholinyl, tetrahydro-2H-pyranyl, piperidinyl, piperazinyl, pyridinyl, imidazolyl, or oxetanyl (preferably, methoxy, ethyl, isopropyl, cyclohexyl, morpholinyl, tetrahydro-2H-pyranyl, pyridinyl, or oxetanyl), wherein each substitutable carbon atom in the ethyl, propyl, isopropyl, isobutyl, tert-butyl, cyclopropyl, cycylobutyl, cyclopentyl, cyclohexyl, morpholinyl, tetrahydro-2H-pyranyl, piperidinyl, piperazinyl, pyridinyl, imidazolyl, and oxetanyl (preferably, methoxy, ethyl, isopropyl, cyclohexyl, morpholinyl, tetrahydro-2H-pyranyl, pyridinyl, or oxetanyl) is optionally substituted with halogen, hydroxy, $(C_1-C_3)$alkyl, $(C_1-C_3)$haloalkyl, or $(C_1-C_3)$alkoxy; and each substitutable nitrogen atom in the piperazinyl is optionally substituted with $(C_1-C_3)$alkyl, $(C_1-C_3)$haloalkyl, $(C_1-C_3)$hydroxylalkyl, oxetanyl, tetrahydro-2H-pyranyl, —C(=O)$(C_3-C_5)$cycloalkyl, —C(=O)$(C_1-C_3)$alkyl, or —C(=O)H; and values and alternative values for the remainder of the variables are as described for Structural Formula (I), or in the fifth, sixth, seventh, eighth, ninth, tenth, eleventh, twelfth, thirteenth, fourteenth, fifteenth, or sixteenth embodiment.

In a eighteenth embodiment, for compounds represented by any one of structural formulae (I-0), (I), (I)', (I-A), or (II-A0), $R^1$ is —$NHR^{b1}$, $R^{b1}$ is $(C_1-C_4)$alkyl optionally substituted with one or more groups selected from hydroxy, $(C_1-C_3)$alkoxy, hydroxy$(C_1-C_3)$alkyl, —$SO_2(C_1-C_3)$alkyl, $(C_3-C_7)$cycloalkyl, or 3-7 membered heterocycloalkyl containing one ring heteroatom, the heteroatom being oxygen, wherein the $(C_3-C_7)$cycloalkyl or the 3-7 membered heterocycloalkyl substituent is optionally substituted with halogen, hydroxyl, or $(C_1-C_3)$alkyl; alternatively, $R^{b1}$ is $(C_1-C_4)$alkyl optionally substituted with one or more groups selected from hydroxy, $(C_1-C_3)$alkoxy, hydroxymethyl, —$SO_2(C_1-C_3)$alkyl, cyclopropyl, cyclobutyl, cyclohexyl, oxetanyl, tetrahydrofuranyl, tetrahydropyranyl, wherein the cyclobutyl, cyclohexyl, oxetanyl, tetrahydrofuranyl, or tetrahydropyranyl substituent is optionally substituted with 1-2 groups selected from hydroxy or $(C_1-C_3)$alkyl; and values and alternative values for the remainder of the variables are as described for Structural Formula (I-0), (I), or (I)', or in the first, second, third, or fourth embodiment.

Preferably in the eighteenth embodiment, $R^1$ is represented by the one of the following structural formulae:

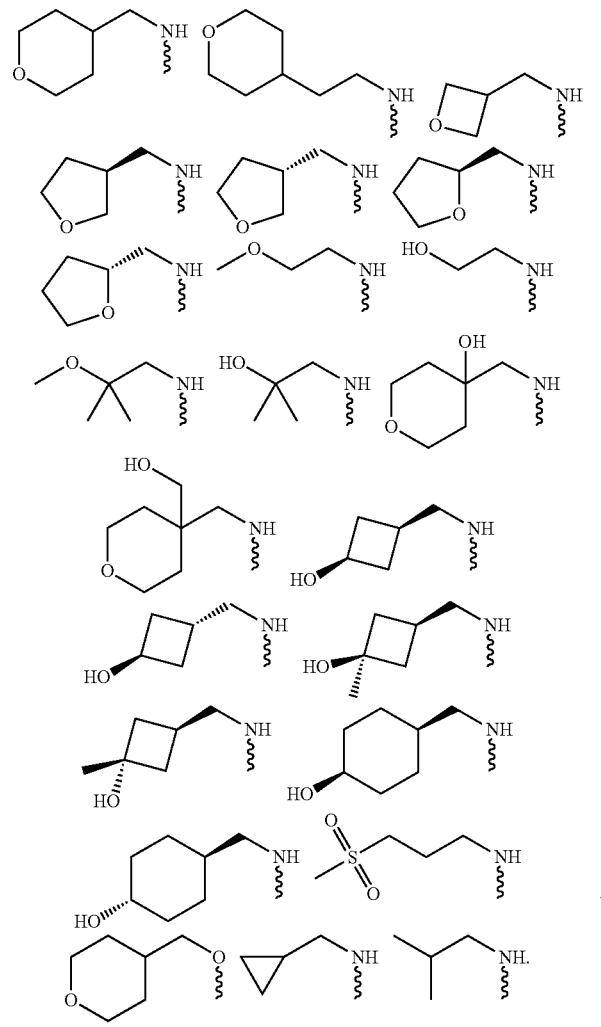

In a nineteenth embodiment, for compounds represented by any one of structural formulae (I-0), (I), (I)', (I-A), or (II-A0), $R^1$ is —NHR$^{b1}$, R$^{b1}$ is (C$_1$-C$_4$)alkyl optionally substituted with one or more groups selected from i) 4-6 membered heterocycloalkyl substituted with —N(R$^{a1}$)$_2$, wherein the heterocycloalkyl contains one ring heteroatom which is oxygen; ii) —N(R$^{a1}$)$_2$; iii) 4-6 membered heterocycloalkyl containing one ring heteroatom which is nitrogen; or iv) 5-6 membered nitrogen-containing heteroaryl; wherein R$^{a1}$ is H or (C$_1$-C$_3$)alkyl; and the 4-6 membered heterocycloalkyl or 5-6 membered nitrogen-containing heteroaryl substituent is optionally substituted with one or more groups selected from (C$_1$-C$_3$)alkyl, hydroxy, halogen, —NH$_2$, —NH(C$_1$-C$_3$)alkyl, —N((C$_1$-C$_3$)alkyl)$_2$; alternatively, R$^{b1}$ is (C$_1$-C$_4$)alkyl optionally substituted with one or more groups selected from tetrahydropyranyl substituted with —N(R$^{a1}$)$_2$; —N(R$^{a1}$)$_2$; morpholinyl; piperazinyl; piperidinyl; pyridinyl; and imidazolyl; wherein the morpholinyl, piperazinyl, piperidinyl, pyridinyl, or imidazolyl substituent is optionally substituted with 1-2 groups selected from (C$_1$-C$_3$)alkyl, halo, or hydroxyl; and values and alternative values for the remainder of the variables are as described for Structural Formula (I-0), (I), or (I)', or in the first, second, third, or fourth embodiment.

Preferably in the nineteenth embodiment, $R^1$ is represented by the one of the following structural formulae:

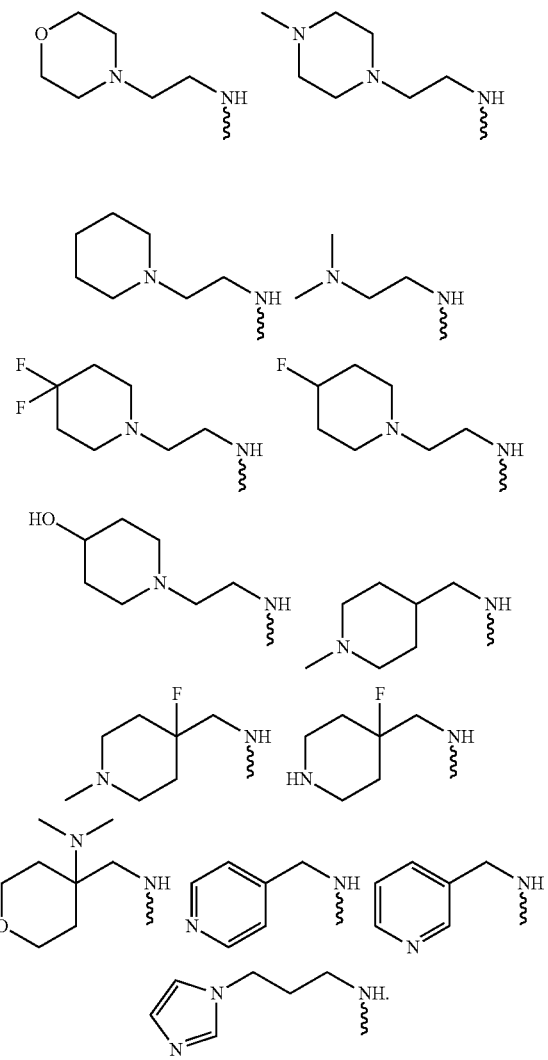

In a twentieth embodiment, for compounds represented by any one of structural formulae (I-0), (I), (I)', (I-A), (II-A0), (II-A1), (II-A2), or (II-B1), $R^2$ is $R^2$ or —OR$^{c2}$, and R$^{c2}$ is (C$_3$-C$_7$)cycloalkyl; 4-7 membered heterocycloalkyl containing one ring heteroatom which is oxygen; phenyl; or 5-6 membered nitrogen-containing heteroaryl; each of which is optionally substituted with halogen, hydroxy, (C$_1$-C$_3$)alkyl, (C$_1$-C$_3$)alkoxy, or —SO$_2$(C$_1$-C$_3$)alkyl; alternatively, R$^{c2}$ is cyclobutyl, cyclopentyl, cyclohexanyl, oxetanyl, tetrahydrofuranyl, tetrahydropyranyl, phenyl, pyrazolyl, or pyridyl-N-oxide, each of which is optionally substituted with one or more groups selected from halogen, hydroxy, (C$_1$-C$_3$)alkyl, (C$_1$-C$_3$)alkoxy, —SO$_2$(C$_1$-C$_3$)alkyl; and values and alternative values for the remainder of the variables are as described for Structural Formula (I-0), (I), or (I)', or in the first, second, third, fourth, eighteenth, or nineteenth embodiment.

Preferably in the twentieth embodiment, $R^2$ is represented by the one of the following structural formulae:

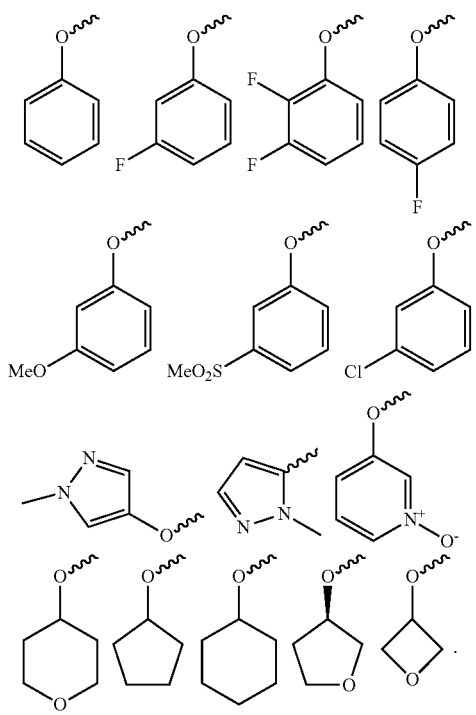

In a twenty first embodiment, for compounds represented by any one of structural formulae (I-0), (I), (I)', (I-A), (II-A0), (II-A1), (II-A2), or (II-B1), $R^2$ is 4-10 membered heterocycloalkyl containing one ring heteroatom which is nitrogen optionally substituted with hydroxy, hydroxy($C_1$-$C_3$)alkyl, —C(=O)($C_1$-$C_3$)alkyl, or ($C_3$-$C_7$)cycloalkyl;

5-10 membered nitrogen-containing heteroaryl;

$OR^{c2}$, wherein $R^{c2}$ is phenyl optionally substituted with halogen, ($C_1$-$C_3$)alkyl, —N($R^{a1}$)$_2$ or 4-6 membered heterocycloalkyl containing one ring heteroatom which is nitrogen; pyridinyl optionally substituted with halogen or ($C_1$-$C_3$)alkyl; piperidinyl optionally substituted with 4-6 membered heterocycloalkyl containing one ring heteroatom which is oxygen, or ($C_1$-$C_3$)alkoxy; pyrrolidinyl optionally substituted with 4-6 membered heterocycloalkyl containing one ring heteroatom which is oxygen or ($C_1$-$C_3$)alkoxy; or azetidinyl optionally substituted with 4-6 membered heterocycloalkyl containing one ring heteroatom which is oxygen or ($C_1$-$C_3$)alkoxy; wherein $R^{a1}$ is H or ($C_1$-$C_3$)alkyl, or $NHR^{b2}$ or $N(($C_1$-$C_3$)alkyl)$R^{b2}$ wherein $R^{b2}$ is ($C_1$-$C_4$)alkyl, ($C_3$-$C_7$)cycloalkyl, 3-7 membered heterocycloalkyl containing one ring heteroatom which is oxygen, phenyl, or 5-6 membered nitrogen-containing heteroaryl;

wherein the ($C_1$-$C_4$)alkyl represented by $R^{b2}$ is optionally substituted with one or more groups selected from hydroxy, —C(=O)NH$_2$, ($C_1$-$C_4$)alkyl, hydroxy($C_1$-$C_3$)alkyl, ($C_3$-$C_7$)cycloalkyl, 3-7 membered heterocycloalkyl containing one ring heteroatom which is oxygen, and wherein the ($C_3$-$C_7$)cycloalkyl, 3-7 membered heterocycloalkyl, phenyl, and 5-6 membered nitrogen-containing heteroaryl substituents in the group represented by $R^{b2}$ are optionally substituted with hydroxy, halogen, ($C_1$-$C_3$)alkyl, ($C_1$-$C_3$)alkoxy, hydroxy($C_1$-$C_3$)alkyl.

Alternatively in the twenty first embodiment, $R^2$ is
azetidinyl optionally substituted with hydroxyl, hydroxymethyl, ($C_3$-$C_6$)cycloalkyl, or —C(=O)($C_1$-$C_3$)alkyl; pyrrolidinyl optionally substituted with hydroxyl, hydroxymethyl, ($C_3$-$C_6$)cycloalkyl, or —C(=O)($C_1$-$C_3$)alkyl; piperidinyl optionally substituted with hydroxyl, hydroxymethyl, ($C_3$-$C_6$)cycloalkyl, or —C(=O)($C_1$-$C_3$)alkyl; piperazinyl optionally substituted with hydroxyl, hydroxymethyl, ($C_3$-$C_6$)cycloalkyl, or —C(=O)($C_1$-$C_3$)alkyl; morpholinyl optionally substituted with hydroxyl, hydroxymethyl, ($C_3$-$C_6$)cycloalkyl, or —C(=O)($C_1$-$C_3$)alkyl;

pyridinyl, quinolinyl, $OR^{c2}$, wherein $R^{c2}$ is phenyl optionally substituted with —N($R^{a1}$)$_2$ or with 4-6 membered heterocycloalkyl with one ring heteroatom which is nitrogen; pyridinyl optionally substituted with halogen; piperidinyl optionally substituted with oxetanyl; or pyrrolidinyl optionally substituted with oxetanyl; wherein $R^{a1}$ is H or ($C_1$-$C_3$)alkyl;

—NH-cyclopentyl, —N—(($C_1$-$C_3$)alkyl)-cyclopentyl or $NHR^{b2}$, wherein $R^{b2}$ is phenyl or pyridinyl, each of which is optionally substituted with halo or ($C_1$-$C_3$)alkyl;

cyclopropyl optionally substituted with hydroxyl, hydroxymethyl, or oxetanyl; cyclobutyl optionally substituted with hydroxyl, hydroxymethyl, or oxetanyl; cyclopentyl optionally substituted with hydroxyl, hydroxymethyl, or oxetanyl; cyclohexanyl optionally substituted with hydroxyl, hydroxymethyl, or oxetanyl;

tetrahydropyranyl optionally substituted with hydroxyl or hydroxymethyl, tetrahydrofuranyl optionally substituted with hydroxyl or ($C_1$-$C_3$)alkoxy; oxetanyl; or ($C_1$-$C_4$)alkyl, wherein the ($C_1$-$C_4$)alkyl is optionally substituted with one or more groups selected from hydroxy, —C(=O)NH$_2$, ($C_1$-$C_4$)alkoxy, hydroxy($C_1$-$C_3$)alkyl, ($C_3$-$C_6$)cycloalkyl, 3-6 membered heterocycloalkyl containing one ring heteroatom which is oxygen; and values and alternative values for the remainder of the variables are as described for Structural Formula (I-0), (I), or (I)', or in the first, second, third, fourth, eighteenth, or nineteenth embodiment.

Preferably in the twenty first embodiment, $R^2$ is represented by the one of the following structural formulae:

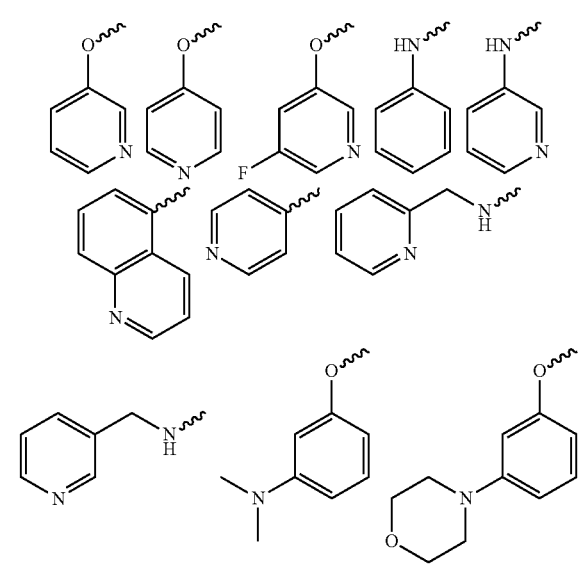

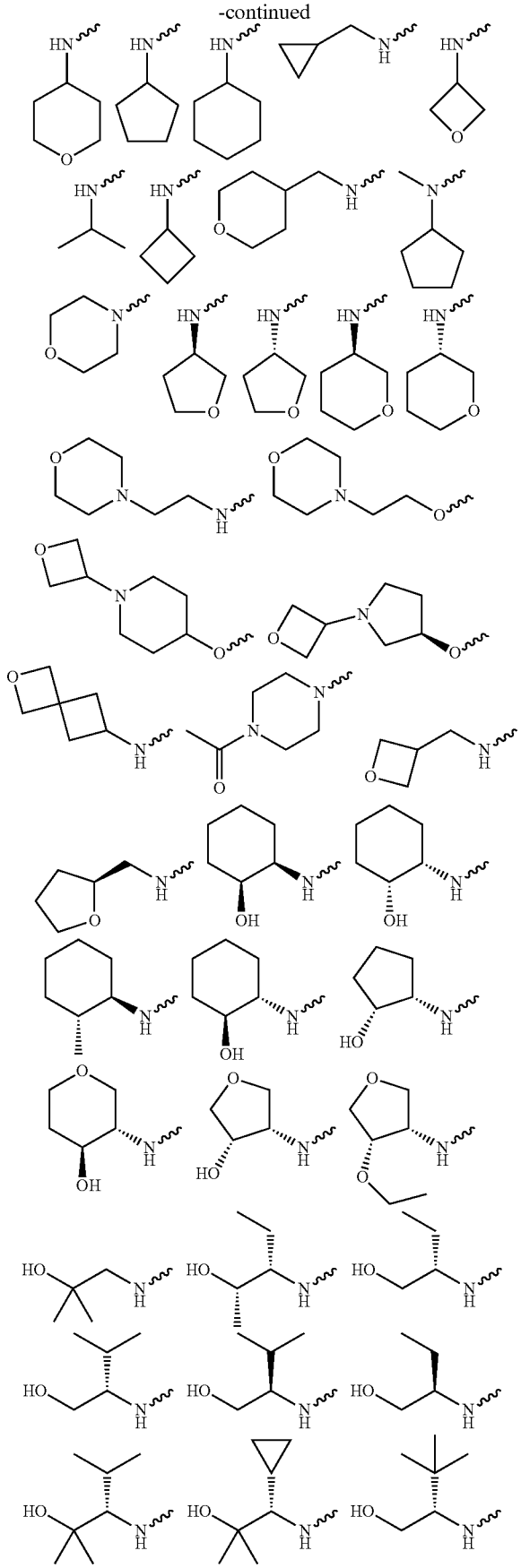
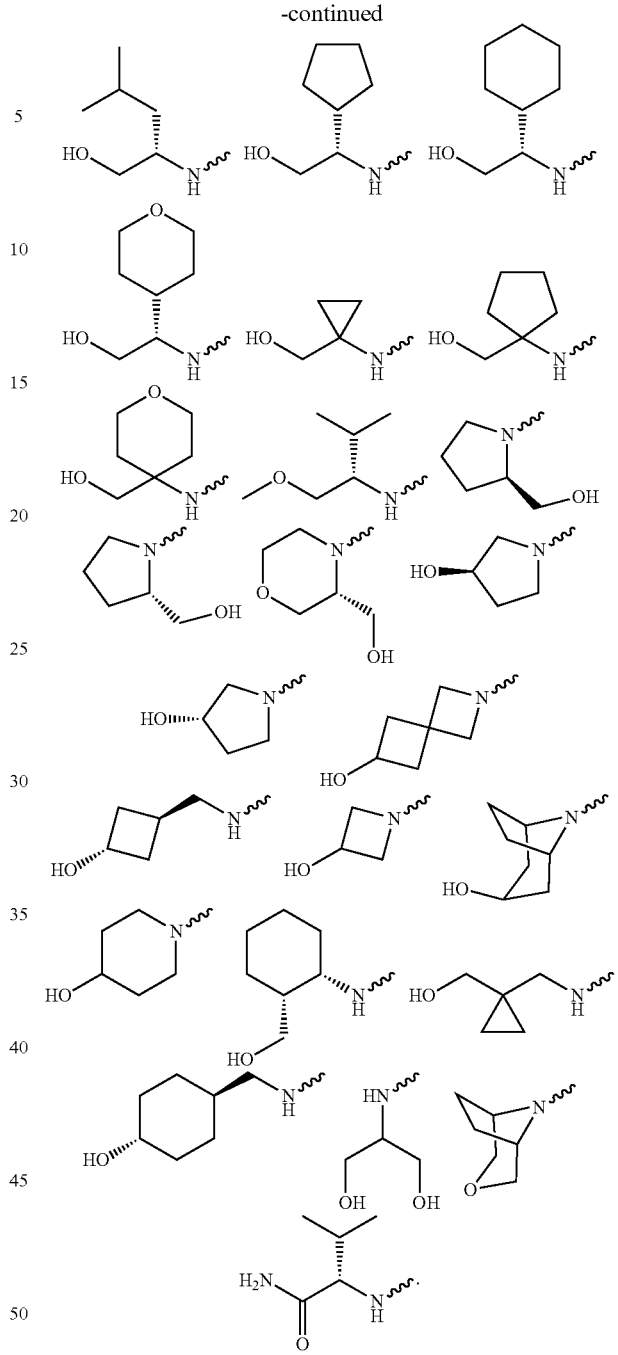

In a twenty second embodiment, for compounds represented by structural formula (I-0) or (II-A0), $R^2$ is R is —NH—$(CH_2)_x$—Cy, wherein x is 1 or 2, and Cy is morpholinyl or piperidinyl optionally substituted with $(C_1$-$C_3)$ alkyl or F; and $R^2$ is —O-phenyl optionally substituted with one or two F. Alternatively, $R^1$ is —NH—$(CH_2)_x$—Cy, wherein x is 1 or 2, and Cy is —N-morpholinyl, -piperidyl N-substituted with $(C_1$-$C_3)$alkyl or —N-piperidyl optionally substituted with fluorine; and $R^2$ is —O-phenyl optionally substituted with one or two F. Alternatively, $R^1$ is —NH—$CH_2$—Cy, wherein Cy is $C_3$-$C_4$ cycloalkyl optionally substituted with one or two groups selected from alkyl and hydroxyl; or 4-6 membered heterocycloalkyl containing one ring heteroatom atom which is oxygen; and $R^2$ is —O- pyridinyl; —NH—(C$_2$-C$_6$)hydroxyalkyl optionally substituted with cyclopropyl or isopropyl; or —NH—(C$_3$-C$_6$)cycloalkyl optionally substituted with hydroxyl or (C$_1$-C$_2$) hydroxylalkyl. Values and alternative values for the remainder of the variables are as described for Structural Formula (I-0).

Alternatively for the 22$^{nd}$ embodiment, the following compounds or pharmaceutically acceptable salts thereof are excluded:

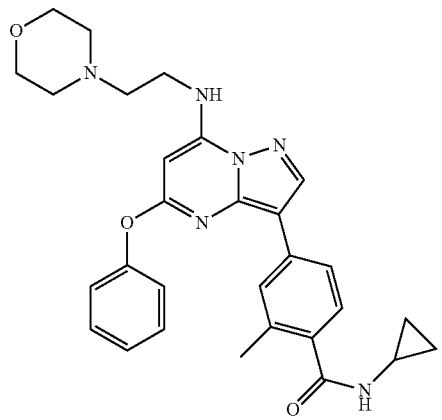

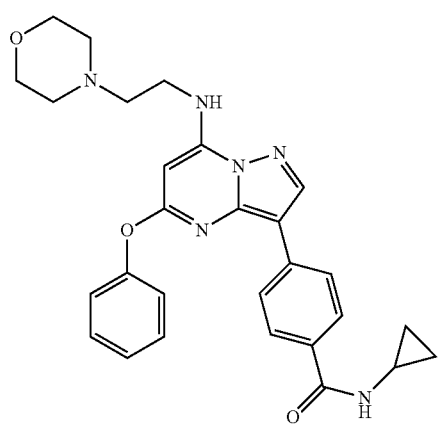

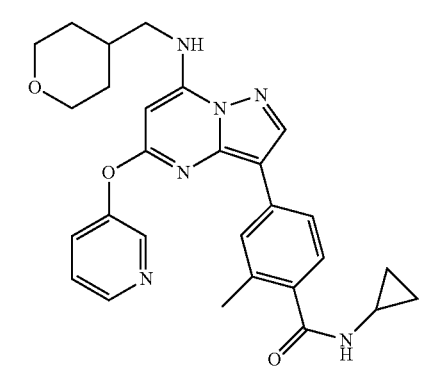

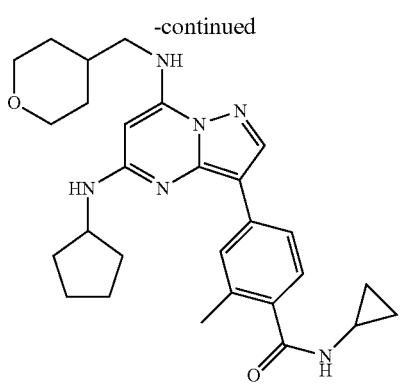

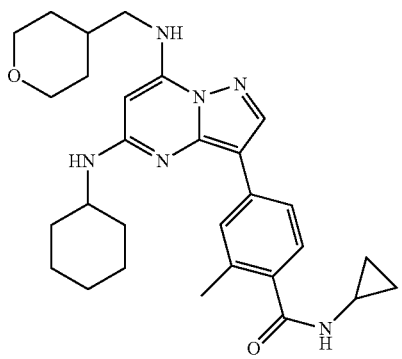

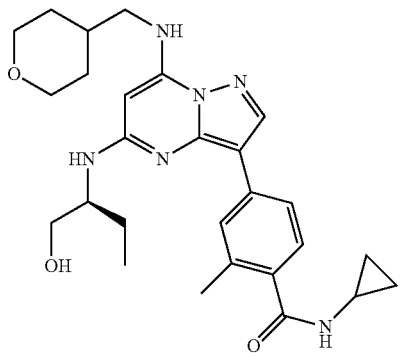

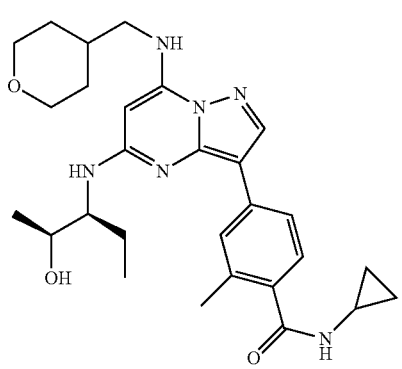

-continued

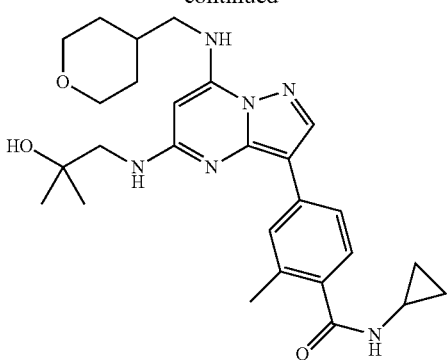

In a twenty third embodiment, the compound is represented by the following structural formula:

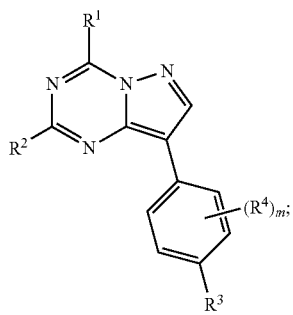
(I-A)' or a pharmaceutically acceptable salt thereof, wherein $R^3$ is —C(=O)$NR^dR^e$ or —NHC(=O)$R^5$; each $R^4$ is independently selected from halogen, hydroxy, $(C_1-C_3)$alkyl, $(C_1-C_3)$haloalkyl, and $(C_1-C_3)$alkoxy; and m is 0, 1, 2, or 3; and values and alternative values for the remainder of the variables are as described for Structural Formula (I)'.

In a twenty fourth embodiment, the compound is represented by the following structural formula:

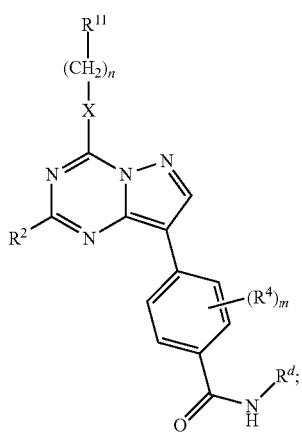
(II-A1)'

-continued

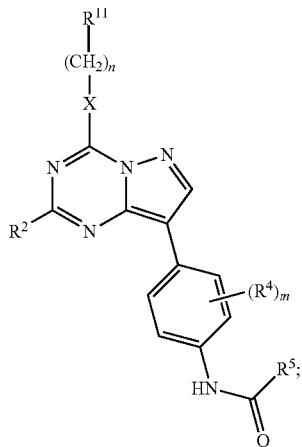
(II-A2)' or a pharmaceutically acceptable salt thereof, wherein:
X is NH or O;
$R^5$ is selected from $(C_1-C_3)$alkyl and $(C_3-C_7)$cycloalkyl, each of which is optionally substituted with one or more groups selected from halogen, hydroxy, $(C_1-C_3)$alkyl, $(C_1-C_3)$haloalkyl, and $(C_1-C_3)$alkoxy;
$R^{11}$ is $(C_1-C_3)$alkyl, $(C_3-C_7)$cycloalkyl, 3-7 membered monocyclic heterocycloalkyl, phenyl, or 5-6 membered monocyclic heteroaryl, each of which is optionally substituted with one or more groups selected from halogen, hydroxy, CN, amino, $(C_1-C_3)$alkyl, $(C_1-C_3)$haloalkyl, $(C_1-C_3)$alkoxy, —C(=O)$NH_2$, and —$SO_2CH_3$;
$R^d$ and $R^e$ are each independently selected from —H, $(C_1-C_7)$alkyl, $(C_3-C_7)$cycloalkyl, wherein each of the $(C_1-C_3)$alkyl and $(C_3-C_7)$cycloalkyl is optionally substituted with one or more groups selected from halogen, hydroxy, $(C_1-C_3)$alkyl, $(C_1-C_3)$haloalkyl, and $(C_1-C_3)$alkoxy; and
n is 0, 1, 2, or 3;
and values and alternative values for the remainder of the variables are as described for Structural Formula (I)' or in the twenty third embodiment.

In a twenty fifth embodiment, the compound is represented by the following structural formula:

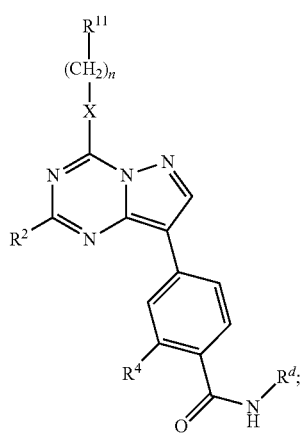
(II-B1)' or a pharmaceutically acceptable salt thereof; and values and alternative values for the remainder a of the variables are as described for Structural Formula (I)' or in the twenty third or twenty fourth embodiment.

In a twenty sixth embodiment, the compound is represented by the following structural formula:

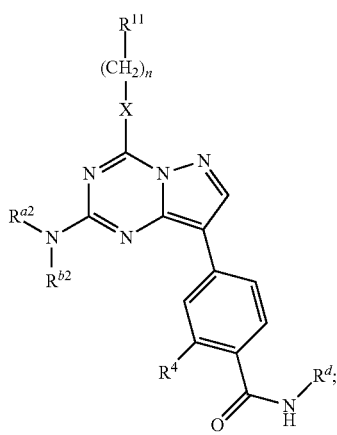

(II-C1)' or a pharmaceutically acceptable salt thereof; and values and alternative values for the remainder of the variables are as described for Structural Formula (I)' or in the first, twenty third, twenty fourth, or twenty fifth embodiment.

In a twenty seventh embodiment, for compounds represented by any one of structural formulae (I)', (I-A)', (II-A1)', (II-B1)', (II-C1)', or (II-A2)', $R^{b2}$ is —H or $CH_3$; and values and alternative values for the remainder of the variables are as described for Structural Formula (I)', or in the first, twenty third, twenty fourth, twenty fifth, or twenty sixth embodiment.

In a twenty eighth embodiment, for compounds represented by any one of structural formulae (I)', (I-A)', (II-A1)', (II-B1)', (II-C1)', or (II-A2)', $R^{a2}$ is $(C_1-C_6)$alkyl, $(C_3-C_7)$ cycloalkyl, 3-7 membered monocyclic heterocycloalkyl, phenyl, and 5-6 membered monocyclic heteroaryl; wherein each of which is optionally substituted with one or more groups selected from halogen, hydroxy, CN, $(C_1-C_3)$alkyl, $(C_1-C_3)$haloalkyl, and $(C_1-C_3)$alkoxy; alternatively, $R^{a2}$ is methyl, ethyl, t-butyl, cyclopentyl, cyclohexyl, tetrahydro-2H-pyranyl, pyridyl, or phenyl, wherein each of the cyclopentyl, cyclohexyl, tetrahydro-2H-pyranyl, pyridyl, and phenyl is optionally substituted with one or more groups selected from halogen, hydroxy, CN, $(C_1-C_3)$alkyl, $(C_1-C_3)$ haloalkyl, and $(C_1-C_3)$alkoxy; and values and alternative values for the remainder of the variables are as described for Structural Formula (I)', or in the first, twenty third, twenty fourth, twenty fifth, twenty sixth, or twenty seventh embodiment.

In a twenty ninth embodiment, for compounds represented by any one of structural formulae (I)', (I-A)', (II-A1)', (II-B)', (II-C1)', or (II-A2)', $R^{a2}$ and $R^{b2}$, together with the nitrogen to which they are attached, form a 3-7 membered monocyclic heterocycloalkyl, optionally substituted with one or more groups selected from halogen, CN, hydroxy, $(C_1-C_3)$alkyl, $(C_1-C_3)$haloalkyl, $(C_1-C_3)$hydroxylalkyl, $(C_1-C_3)$alkoxy, —C(=O)H, —C(=O)$(C_3-C_7)$cycloalkyl, —C(=O)$(C_1-C_3)$alkyl, and 3-7 membered monocyclic heterocycloalkyl; alternatively, $R^{a2}$ and $R^{b2}$, together with the nitrogen to which they are attached, form piperidinyl, morpholinyl, or piperazinyl, wherein each substitutable carbon atom in the piperidinyl, morpholinyl, or piperazinyl is optionally substituted with halogen, hydroxy, $(C_1-C_3)$alkyl, $(C_1-C_3)$haloalkyl, or $(C_1-C_3)$alkoxy; and each substitutable nitrogen atom in the piperazinyl is optionally substituted $(C_1-C_3)$alkyl, $(C_1-C_3)$haloalkyl, $(C_1-C_3)$hydroxylalkyl, —C(=O)$(C_3-C_5)$cycloalkyl, —C(=O)$(C_1-C_3)$alkyl, oxetanyl, or —C(=O)H; and values and alternative values for the remainder of the variables are as described for Structural Formula (I)', or in the first, twenty third, twenty fourth, twenty fifth, twenty sixth, or twenty seventh embodiment.

In a thirtieth embodiment, the compound is represented by the following structural formula:

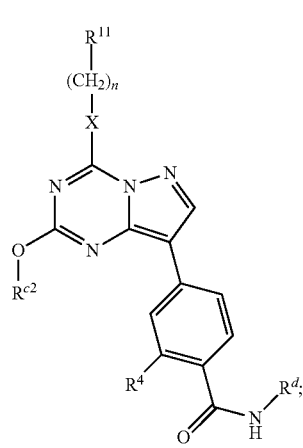

(II-D1)' or a pharmaceutically acceptable salt thereof; and values and alternative values for the remainder of the variables are as described for Structural Formula (I)', or in the first, twenty third, twenty fourth, or twenty fifth embodiment.

In a thirty first embodiment, for compounds represented by any one of structural formulae (I)', (I-A)', (II-A1)', (II-B1)', (II-D1)', or (II-A2)', $R^{c2}$ is $(C_3-C_7)$cycloalkyl, 3-7 membered monocyclic heterocycloalkyl, phenyl, or 5-6 membered monocyclic heteroaryl, each of which is optionally substituted with one or more groups selected from halogen, hydroxy, $(C_1-C_3)$alkyl, $(C_1-C_3)$haloalkyl, $(C_1-C_3)$ hydroxylalkyl, $(C_1-C_3)$alkoxy, —C(=O)$(C_1-C_3)$alkyl, —C(=O)$(C_3-C_7)$cycloalkyl, and —C(=O)H; alternatively, $R^{c2}$ is cyclopentyl, cyclohexyl, tetrahydro-2H-pyranyl, phenyl, pyridyl, or azetidinyl, wherein each of the cyclopentyl, cyclohexyl, tetrahydro-2H-pyranyl, phenyl, and pyridyl is optionally substituted with one or more groups selected from halogen, $(C_1-C_3)$alkyl, $(C_1-C_3)$haloalkyl, $(C_1-C_3)$hydroxylalkyl, and $(C_1-C_3)$alkoxy; and the nitrogen in the azetidinyl is optionally substituted with $(C_1-C_3)$alkyl, $(C_1-C_3)$hydroxylalkyl, —C(=O)$(C_1-C_3)$alkyl, —C(=O)$(C_3-C_5)$cycloalkyl, or —C(=O)H; and values and alternative values for the remainder of the variables are as described for Structural Formula (I)', or in the first, twenty third, twenty fourth, or twenty fifth embodiment.

In a thirty second embodiment, for compounds represented by any one of structural formulae (II-A1)-(II-D1), (II-A1)'-(II-D1)', (II-A2), or (II-A2)', X is NH; and values and alternative values for the remainder of the variables are as described for Structural Formula (I) or (I)', or in the fifth, sixth, seventh, eighth, ninth, tenth, eleventh, twelfth, thirteenth, fourteenth, twenty fourth, twenty fifth, twenty sixth, twenty seventh, twenty eighth, twenty ninth, thirtieth, or thirty first embodiment. Alternatively, X is O.

In a thirty third embodiment, for compounds represented by any one of structural formulae (I-A)', (II-A1)', (II-B1)', (II-C1)', (II-D1)', or (II-A2)', $R^4$ is selected from hydrogen, halogen, and (C$_1$-C$_3$)alkyl (preferably, R$^4$ is chlorine or methyl; and is ortho to —C(═O)NR$^d$R$^e$); and values and alternative values for the remainder of the variables are as described for Structural Formula (I)', or in the twenty third, twenty fourth, twenty fifth, twenty sixth, twenty seventh, twenty eighth, twenty ninth, thirtieth, thirty first, thirty second embodiment.

In a thirty fourth embodiment, for compounds represented by any one of structural formulae (II-A1)', (II-B1)', or (II-A2)', R$^{11}$—(CH$_2$)$_n$—X— is represented by the one of the following structural formulae:

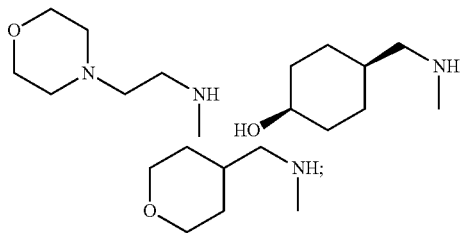

and values and alternative values for the remainder of the variables are as described for Structural Formula (I)', or in the first, twenty third, twenty fourth, or twenty fifth embodiment.

In a thirty fifth embodiment, for compounds represented by any one of structural formulae (I)', (I-A)', (II-A1)', (II-B1)', or (II-A2)', R$^2$ is represented by the one of the following structural formulae:

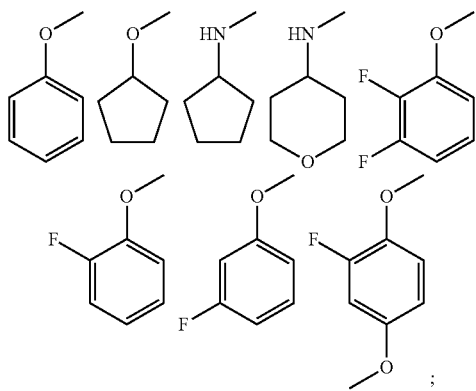

and values and alternative values for the remainder of the variables are as described for Structural Formula (I)', or in the first, twenty third, twenty fourth, or twenty fifth embodiment.

In a thirty sixth embodiment, for compounds represented by any one of structural formulae (I-0), (I), (I)', (I-A), (I-A)', (II-A0), (II-A1)', (II-B1)', or (II-A2)', R$^4$ is selected from hydrogen, halogen, and (C$_1$-C$_3$)alkyl (preferably, R$^4$ is chlorine or methyl; and is ortho to —C(═O)NR$^d$R$^e$); and values and alternative values for the remainder of the variables are as described for Structural Formula (I-0), (I), (I)', (I-A), (II-A0), or in the eighteenth, nineteenth, twentieth, twenty first, twenty second, twenty third, twenty fourth, twenty fifth, thirty fourth, or thirty fifth embodiment.

In a thirty seventh embodiment, for compounds represented by any one of structural formulae (II-A1)', (II-B1)', (II-C1)', (II-D1)', or (II-A2)', R$^{11}$ is ethyl, isopropyl, cyclohexyl, morpholinyl, tetrahydro-2H-pyranyl, piperidinyl, piperazinyl, pyridinyl, imidazolyl, or oxetanyl, wherein each substitutable carbon in the morpholinyl, tetrahydro-2H-pyranyl, piperidinyl, piperazinyl, pyridinyl, imidazolyl, or oxetanyl is optionally substituted with —OH, halogen, (C$_1$-C$_3$)alkyl, (C$_1$-C$_3$)haloalkyl, or (C$_1$-C$_3$)alkoxy; and each substitutable nitrogen in the piperazinyl is optionally substituted with (C$_1$-C$_3$)alkyl, (C$_1$-C$_3$)haloalkyl, (C$_1$-C$_3$)hydroxylalkyl, —C(═O)(C$_3$-C$_5$)cycloalkyl, —C(═O)(C$_1$-C$_3$)alkyl, or —C(═O)H; alternatively, R$^{11}$ is isopropyl, morpholinyl, tetrahydro-2H-pyranyl, piperidinyl, piperazinyl, pyridinyl, imidazolyl, or oxetanyl, wherein each substitutable carbon in the morpholinyl, tetrahydro-2H-pyranyl, piperidinyl, piperazinyl, pyridinyl, imidazolyl, or oxetanyl is optionally substituted with halogen, (C$_1$-C$_3$)alkyl, (C$_1$-C$_3$)haloalkyl, or (C$_1$-C$_3$)alkoxy; and each substitutable nitrogen in the piperazinyl is optionally substituted with (C$_1$-C$_3$)alkyl, (C$_1$-C$_3$)haloalkyl, (C$_1$-C$_3$)hydroxylalkyl, —C(═O)(C$_3$-C$_5$)cycloalkyl, —C(═O)(C$_1$-C$_3$)alkyl, or —C(═O)H; and values and alternative values for the remainder of the variables are as described for Structural Formula (I)', (I-A)', (II-A0), or in the twenty fourth, twenty fifth, twenty sixth, twenty seventh, twenty eighth, twenty ninth, thirtieth, thirty first, or thirty second embodiment.

In a thirty eighth embodiment, for compounds represented by any one of structural formulae (I)', (I), (I-A), (I-A)', (II-A1)-(II-D1), (II-A1)'-(II-D1)', (II-A2) or (II-A2)', R$^d$ is (C$_2$-C$_7$)alkyl or (C$_3$-C$_7$) cycloalkyl, wherein both of which are optionally substituted with one or more groups selected from halogen, hydroxy, (C$_1$-C$_3$)alkyl, (C$_1$-C$_3$)haloalkyl, and (C$_1$-C$_3$)alkoxy (preferably, R$^d$ is cyclopropyl); and values and alternative values for the remainder of the variables are as described for Structural Formula (I), (I)', or in the third, fifth, sixth, seventh, eighth, ninth, tenth, eleventh, twelfth, thirteenth, fourteenth, fifteenth, sixteenth, twenty third, twenty fourth, twenty fifth, twenty sixth, twenty seventh, twenty eighth, twenty ninth, thirtieth, thirty first, thirty second, thirty third, or thirty seventh embodiment.

In a thirty ninth embodiment, for compounds represented by structural formula (II-A0), R$^d$ is (C$_2$-C$_7$)alkyl or (C$_3$-C$_7$) cycloalkyl, wherein both of which are optionally substituted with one or more groups selected from halogen, hydroxy, (C$_1$-C$_3$)alkyl, (C$_1$-C$_3$)haloalkyl, and (C$_1$-C$_3$)alkoxy (preferably, R$^d$ is cyclopropyl); and values and alternative values for the remainder of the variables are as described for Structural Formula (I-0), (I), (I)', (I-A), or in the seventeenth, eighteenth, nineteenth, twentieth, twenty first, thirty fourth, or thirty fifth embodiment.

The invention also includes the compounds depicted by structure and/or described by name in the Exemplification, and includes both the neutral forms and as well as pharmaceutically acceptable salts thereof. Treatments with and/or uses of these compounds (including neutral forms and pharmaceutically acceptable salts thereof) as described herein are also included in the invention.

The term "alkyl" used alone or as part of a larger moiety, such as "alkoxy", "haloalkyl", "cycloalkyl", "heterocycloalkyl", "aralkyl", "heteroaralkyl" and the like, means saturated aliphatic straight-chain or branched monovalent hydrocarbon radical. Unless otherwise specified, an alkyl group typically has 1-6 carbon atoms, i.e., (C$_1$-C$_6$)alkyl. As used herein, a "(C$_1$-C$_6$)alkyl" group is means a radical having from 1 to 6 carbon atoms in a linear or branched arrangement.

"Alkoxy" means an alkyl radical attached through an oxygen linking atom, represented by —O-alkyl. For example, "($C_1$-$C_3$)alkoxy" includes methoxy, ethoxy, and propoxy.

The terms "haloalkyl" and "haloalkoxy" means alkyl or alkoxy, as the case may be, substituted with one or more halogen atoms. The term "halogen" means F, Cl, Br or I. Preferably the halogen in a haloalkyl or haloalkoxy is F or Cl.

The term "ring" used herein means a cyclic group, which includes cycloalkyl, heterocycloaklyl, aryl, and heteroaryl. It can be monocyclic, bicyclic (e.g., a bridged bicyclic ring), polycyclic (e.g., tricyclic), or fused.

The term "aryl group" used alone or as part of a larger moiety as in "aralkyl", "aralkoxy", or "aryloxyalkyl", means an aromatic hydrocarbon ring system having six to fourteen carbon ring atoms. The term "aryl" may be used interchangeably with the terms "aryl ring" "aromatic ring", "aryl group" and "aromatic group". An aryl group typically has six to fourteen ring atoms. Examples includes phenyl, naphthyl, anthracenyl, 1,2-dihydronaphthyl, 1,2,3,4-tetrahydronaphthyl, fluorenyl, indanyl, indenyl and the like. A "substituted aryl group" is substituted at any one or more substitutable ring atom, which is a ring carbon atom bonded to a hydrogen.

"Cycloalkyl" means a saturated aliphatic cyclic hydrocarbon radical optionally containing one or more double bonds. It can be monocyclic, bicyclic (e.g., a bridged bicyclic ring), polycyclic (e.g., tricyclic), or fused. For example, monocyclic ($C_3$-$C_7$)cycloalkyl means a radical having from 3-7 carbon atoms arranged in a monocyclic ring. A ($C_3$-$C_7$) cycloalkyl includes, but is not limited to, cyclopropyl, cyclobutyl, cyclopentyl, cyclohexyl, and cycloheptyl.

"Heterocycloalkyl" means a saturated or unsaturated non-aromatic 3-12 membered ring radical optionally containing one or more double bonds. It can be monocyclic, bicyclic (e.g., a bridged bicyclic ring), tricyclic, or fused. The heterocycloalkyl contains 1 to 4 heteroatoms, which may be the same or different, selected from N, O or S. The heterocycloalkyl ring optionally contains one or more double bonds and/or is optionally fused with one or more aromatic rings (e.g., phenyl ring). "3-7 membered monocyclic heterocycloalkyl" means a radical having from 3-7 atoms (including 1-3 heteroatoms) arranged in a monocyclic ring. The term "heterocycloalkyl" is intended to include all the possible isomeric forms. Examples of heterocycloalkyl include, but are not limited to, azetidinyl, morpholinyl, thiomorpholinyl, pyrrolidinonyl, pyrrolidinyl, piperidinyl, piperazinyl, hydantoinyl, valerolactamyl, oxiranyl, oxetanyl, dihydroimidazole, dihydrofuranyl, dihydropyranyl, dihydropyridinyl, dihydropyrimidinyl, dihydrothienyl, dihydrothiophenyl, dihydrothiopyranyl, tetrahydroimidazole, tetrahydrofuranyl, tetrahydropyranyl, tetrahydrothienyl, tetrahydropyridinyl, tetrahydropyrimidinyl, tetrahydrothiophenyl, and tetrahydrothiopyranyl.

The term "heteroaryl", "heteroaromatic", "heteroaryl ring", "heteroaryl group", "heteroaromatic ring", and "heteroaromatic group", are used interchangeably herein. "Heteroaryl" when used alone or as part of a larger moiety as in "heteroaralkyl" or "heteroarylalkoxy", refers to aromatic ring groups having five to fourteen ring atoms selected from carbon and at least one (typically 1 to 4, more typically 1 or 2) heteroatoms (e.g., oxygen, nitrogen or sulfur). "Heteroaryl" includes monocyclic rings and polycyclic rings in which a monocyclic heteroaromatic ring is fused to one or more other aromatic or heteroaromatic rings. As such, "5-14 membered heteroaryl" includes monocyclic, bicyclic or tricyclic ring systems.

"Monocyclic 5-6 membered heteroaryl" means a monocyclic aromatic ring system having five or six ring atoms selected from carbon and at least one (typically 1 to 3, more typically 1 or 2) heteroatoms (e.g., oxygen, nitrogen or sulfur). Examples of monocyclic 5-6 membered heteroaryl groups include furanyl (e.g., 2-furanyl, 3-furanyl), imidazolyl (e.g., N-imidazolyl, 2-imidazolyl, 4-imidazolyl, 5-imidazolyl), isoxazolyl (e.g., 3-isoxazolyl, 4-isoxazolyl, 5-isoxazolyl), oxadiazolyl (e.g., 2-oxadiazolyl, 5-oxadiazolyl), oxazolyl (e.g., 2-oxazolyl, 4-oxazolyl, 5-oxazolyl), pyrazolyl (e.g., 3-pyrazolyl, 4-pyrazolyl), pyrrolyl (e.g., 1-pyrrolyl, 2-pyrrolyl, 3-pyrrolyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl), thiazolyl (e.g., 2-thiazolyl, 4-thiazolyl, 5-thiazolyl), isothiazolyl, triazolyl (e.g., 2-triazolyl, 5-triazolyl), tetrazolyl (e.g., tetrazolyl), and thienyl (e.g., 2-thienyl, 3-thienyl). Examples of polycyclic aromatic heteroaryl groups include carbazolyl, benzimidazolyl, benzothienyl, benzofuranyl, isobenzofuranyl, indolyl, benzotriazolyl, benzothiazolyl, benzoxazolyl, quinolinyl, isoquinolinyl, indazolyl, isoindolyl, acridinyl, or benzisoxazolyl. A "substituted heteroaryl group" is substituted at any one or more substitutable ring atom, which is a ring carbon or ring nitrogen atom bonded to a hydrogen.

Unless otherwise indicated, suitable substituents for a substituted alkyl, cycloalkyl, heterocycloalkyl, aryl group (e.g., phenyl) and heteroaryl group include the groups represented by halogen, —$OR^c$, —$NR^aR^b$, —$S(O)_iR^c$, —$NR^{d1}S(O)_iR^e$, —$S(O)_iNR^{e1}R^f$, —$C(=O)OR^c$, —$OC(=O)OR^c$, —$C(=S)OR^c$, —$O(C=S)R^c$, —$C(=O)NR^{e1}R^f$, —$NR^{d1}C(=O)R^c$, —$C(=S)NR^{e1}R^f$, —$NR^{d1}C(=S)R^c$, —$NR^{d1}(C=)OR^c$, —$O(C=O)NR^{e1}R^f$, —$NR^{d1}(C=S)OR^c$, —$O(C=S)NR^{e1}R^f$, —$NR^{d1}(C=O)NR^{e1}R^f$, —$NR^{d1}(C=S)NR^{e1}R^f$, —$C(=S)R^c$, —$C(=O)R^c$, ($C_1$-$C_6$) alkyl, cycloalkyl, cycloalkyl($C_1$-$C_3$)alkyl, heterocycloalkyl, heterocycloalkyl($C_1$-$C_3$)alkyl, aryl, aryl($C_1$-$C_3$)alkyl, heteroaryl and heteroaryl($C_1$-$C_3$)alkyl, wherein:

"cycloalkyl" and "heterocylalkyl" include spiro and as well as cycloalkyl and heterocycloalkyl connected by a single bond to the core of the molecule.

The term "spiro" refers to a cycloalkyl or heterocycloalkyl that shares one ring carbon atom with another cycloalkyl or heterocycloalkyl group in the molecule $R^a$ and $R^b$ are each independently selected from —H and ($C_1$-$C_6$)alkyl, optionally substituted with 1 to 3 substituents independently selected from halogen, hydroxy, —$NR^gR^h$ and ($C_1$-$C_3$)alkoxy;

$R^c$ is —H or ($C_1$-$C_6$)alkyl, optionally substituted with 1 to 3 substituents independently selected from halogen, —$NR^gR^h$, hydroxy and ($C_1$-$C_3$)alkoxy;

$R^{d1}$ is —H or ($C_1$-$C_6$)alkyl, optionally substituted with 1 to 3 substituents independently selected from halogen, —$NR^gR^h$, hydroxy and ($C_1$-$C_3$)alkoxy;

$R^{e1}$ and $R^f$ are each independently selected from —H and ($C_1$-$C_6$)alkyl optionally substituted with 1 to 3 substituents independently selected from halogen, —$NR^gR^h$, hydroxy and ($C_1$-$C_3$)alkoxy;

or $R^{e1}$ and $R^f$, together with the nitrogen to which they are attached, form a 3-8 membered ring optionally substituted with 1 to 3 substituents independently selected from halogen, —$NR^gR^h$, CN, ($C_1$-$C_6$)alkyl, halo($C_1$-$C_6$)alkyl, ($C_1$-$C_3$) alkoxy, halo($C_1$-$C_3$)alkoxy, and ($C_1$-$C_3$)alkoxy($C_1$-$C_6$)alkyl;

$R^g$ and $R^h$ are each independently selected from —H, $(C_1$-$C_6)$alkyl, halo$(C_1$-$C_6)$alkyl, hydroxy$(C_1$-$C_6)$alkyl and $(C_1$-$C_3)$alkoxy$(C_1$-$C_6)$alkyl; and i is 0, 1 or 2;

Unless otherwise indicated, in a preferred embodiment, suitable substituents for a substituted alkyl, cycloalkyl, heterocycloalkyl, aryl group (e.g., phenyl) and heteroaryl group include the groups represented by halogen, hydroxy, CN, amino, $(C_1$-$C_3)$alkyl, $(C_1$-$C_3)$haloalkyl, $(C_1$-$C_3)$hydroxylalkyl, $(C_1$-$C_3)$alkoxy, $(C_1$-$C_3)$haloalkoxy, —C(=O)NH$_2$, —SO$_2$CH$_3$, —C(=O)H, —C(=O)(C$_3$-C$_7$)cycloalkyl (e.g., —C(=O)(C$_3$-C$_5$)cycloalkyl), —C(=O)(C$_1$-C$_3$)alkyl, 3-7 membered monocyclic heterocycloalkyl (e.g., oxetanyl).

Unless otherwise indicated, in a preferred embodiment, when phenyl or monocyclic 5-6 membered heteroaryl is optionally substituted, suitable substituents are selected from halogen, hydroxy, CN, amino, $(C_1$-$C_3)$alkyl, $(C_1$-$C_3)$haloalkyl, $(C_1$-$C_3)$alkoxy, $(C_1$-$C_3)$haloalkoxy, —C(=O)NH$_2$, and —SO$_2$CH$_3$.

Unless otherwise indicated, in a preferred embodiment, suitable substituents for a substituted alkyl, cycloalkyl, heterocycloalkyl include halogen, hydroxy, CN, $(C_1$-$C_3)$alkyl, $(C_1$-$C_3)$haloalkyl, $(C_1$-$C_3)$alkoxy and 3-7 membered monocyclic heterocycloalkyl (e.g., oxetanyl).

Regarding connectivity, an "arylalkyl" moiety, for example, refers to an alkyl group substituted with an aryl group (e.g., phenylmethyl (i.e., benzyl)). Similarly, a "heteroarylalkyl" moiety refers to an alkyl group substituted with a heteroaryl group.

Certain of the compounds described herein may exist in various stereoisomeric or tautomeric forms. Stereoisomers are compounds which differ only in their spatial arrangement. The present teachings encompass all such forms, including compounds in the form of essentially pure enantiomers, racemic mixtures and tautomers, which includes forms not depicted structurally. When a disclosed compound is named or depicted by structure without indicating stereochemistry, it is understood that the name or structure encompasses all possible stereoisomers, tautomers, geometric isomers or a combination thereof.

When a geometric isomer is depicted by name or structure, it is to be understood that the geometric isomeric purity of the named or depicted geometric isomer is at least 60%, 70%, 80%, 90%, 99% or 99.9% pure by weight. Geometric isomeric purity is determined by dividing the weight of the named or depicted geometric isomer in the mixture by the total weight of all of the geomeric isomers in the mixture.

Racemic mixture means 50% of one enantiomer and 50% of is corresponding enantiomer. The present teachings encompass all enantiomerically-pure, enantiomerically-enriched, diastereomerically pure, diastereomerically enriched, and racemic mixtures, and diastereomeric mixtures of the compounds described herein.

Enantiomeric and diastereomeric mixtures can be resolved into their component enantiomers or stereoisomers by well known methods, such as chiral-phase gas chromatography, chiral-phase high performance liquid chromatography, crystallizing the compound as a chiral salt complex, or crystallizing the compound in a chiral solvent. Enantiomers and diastereomers can also be obtained from diastereomerically- or enantiomerically-pure intermediates, reagents, and catalysts by well known asymmetric synthetic methods.

When a compound is designated by a name or structure that indicates a single enantiomer, unless indicated otherwise, the compound is at least 60%, 70%, 80%, 90%, 99% or 99.9% optically pure (also referred to as "enantiomerically pure"). Optical purity is the weight in the mixture of the named or depicted enantiomer divided by the total weight in the mixture of both enantiomers.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers are included. It is to be further understood that the stereoisomeric purity of the named or depicted stereoisomers at least 60%, 70%, 80%, 90%, 99% or 99.9% by weight. The stereoisomeric purity in this case is determined by dividing the total weight in the mixture of the stereoisomers encompassed by the name or structure by the total weight in the mixture of all of the stereoisomers.

Included in the present teachings are pharmaceutically acceptable salts of the compounds disclosed herein. The disclosed compounds have basic amine groups and therefore can form pharmaceutically acceptable salts with pharmaceutically acceptable acid(s). Suitable pharmaceutically acceptable acid addition salts of the compounds described herein include salts of inorganic acids (such as hydrochloric acid, hydrobromic, phosphoric, nitric, and sulfuric acids) and of organic acids (such as, acetic acid, benzenesulfonic, benzoic, methanesulfonic, and p-toluenesulfonic acids). Compounds of the present teachings with acidic groups such as carboxylic acids can form pharmaceutically acceptable salts with pharmaceutically acceptable base(s). Suitable pharmaceutically acceptable basic salts include ammonium salts, alkali metal salts (such as sodium and potassium salts) and alkaline earth metal salts (such as magnesium and calcium salts). Compounds with a quaternary ammonium group also contain a counteranion such as chloride, bromide, iodide, acetate, perchlorate and the like. Other examples of such salts include hydrochlorides, hydrobromides, sulfates, methanesulfonates, nitrates, benzoates and salts with amino acids such as glutamic acid.

Compounds described herein can inhibit various kinases, including the TTK. Thus, generally, compounds described herein are useful in the treatment of diseases or conditions associated with such kinases. In some embodiments, compounds described herein can inhibit TTK.

In one embodiment, the compounds described herein are TTK inhibitors, and are useful for treating diseases, such as cancer, associated with such kinase(s).

Another aspect of the present teachings relates to a method of treating a subject with cancer comprising administering to the subject an effective amount of a compound described herein. In one embodiment, the compounds described herein inhibit the growth of a tumor. For example, the compounds described herein inhibit the growth of a tumor that overexpresses TTK.

Cancers that can be treated (including reduction in the likelihood of recurrence) by the methods of the present teachings include lung cancer, breast cancer, colon cancer, brain cancer, neuroblastoma, prostate cancer, melanoma, glioblastoma multiform, ovarian cancer, lymphoma, leukemia, melanoma, sarcoma, paraneoplasia, osteosarcoma, germinoma, glioma and mesothelioma. In one embodiment, the cancer is selected from leukemia, acute myeloid leukemia, chronic myelogenous leukemia, breast cancer, brain cancer, colon cancer, colorectal cancer, head and neck cancer, hepatocellular carcinoma, lung adenocarcinoma, metastatic melanoma, pancreatic cancer, prostate cancer, ovarian cancer and renal cancer. In one embodiment, the cancer is lung cancer, colon cancer, brain cancer, neuroblastoma, prostate cancer, melanoma, glioblastoma mutiform or ovarian cancer. In another embodiment, the cancer is pancreatic cancer, prostate cancer, lung cancer, melanoma, breast cancer, colon cancer, or ovarian cancer. In yet another embodiment, the cancer is breast cancer, colon cancer and ovarian cancer. In yet another embodiment, the cancer is a breast cancer. In yet another embodiment, the cancer is a basal sub-type breast cancer or a luminal B sub-type breast cancer. In yet another embodiment, the cancer is a basal sub-type breast cancer that overexpresses TTK. In yet another embodiment, the basal sub-type breast cancer is ER (estrogen receptor), HER2 and PR (progesterone receptor) negative breast cancer. In yet another embodiment, the cancer is a soft tissue cancer. A "soft tissue cancer" is an art-recognized term that encompasses tumors derived from any soft tissue of the body. Such soft tissue connects, supports, or surrounds various structures and organs of the body, including, but not limited to, smooth muscle, skeletal muscle, tendons, fibrous tissues, fatty tissue, blood and lymph vessels, perivascular tissue, nerves, mesenchymal cells and synovial tissues. Thus, soft tissue cancers can be of fat tissue, muscle tissue, nerve tissue, joint tissue, blood vessels, lymph vessels, and fibrous tissues. Soft tissue cancers can be benign or malignant. Generally, malignant soft tissue cancers are referred to as sarcomas, or soft tissue sarcomas. There are many types of soft tissue tumors, including lipoma, lipoblastoma, hibernoma, liposarcoma, leiomyoma, leiomyosarcoma, rhabdomyoma, rhabdomyosarcoma, neurofibroma, schwannoma (neurilemoma), neuroma, malignant schwannoma, neurofibrosarcoma, neurogenic sarcoma, nodular tenosynovitis, synovial sarcoma, hemangioma, glomus tumor, hemangiopericytoma, hemangioendothelioma, angiosarcoma, Kaposi sarcoma, lymphangioma, fibroma, elastofibroma, superficial fibromatosis, fibrous histiocytoma, fibrosarcoma, fibromatosis, dermatofibrosarcoma protuberans (DFSP), malignant fibrous histiocytoma (MFH), myxoma, granular cell tumor, malignant mesenchymomas, alveolar soft-part sarcoma, epithelioid sarcoma, clear cell sarcoma, and desmoplastic small cell tumor. In a particular embodiment, the soft tissue cancer is a sarcoma selected from the group consisting of a fibrosarcoma, a gastrointestinal sarcoma, a leiomyosarcoma, a dedifferentiated liposarcoma, a pleomorphic liposarcoma, a malignant fibrous histiocytoma, a round cell sarcoma, and a synovial sarcoma.

In some embodiments, the present teachings provide methods of inhibiting the growth of tumor-initiating cells or reducing the likelihood of recurrence of a cancer in a subject who is undergoing an anti-cancer therapy. The method comprises the steps of:

a) assessing the subject to determine whether the cancer is in remission; and b) if the cancer is in remission; then administering to the subject an effective amount of a TTK inhibitor (e.g., a compound represented by Structural Formula (I-0), (I) or (I)'). If the cancer is not in remission, the method optionally further comprises the step of continuing the anti-cancer therapy until the cancer goes into remission and then the step b) of administering an effective amount of a TTK inhibitor (e.g., a compound represented by Structural Formula (I-0), (I) or (I)').

As used herein, the term "tumor-initiating cells" or "TICs" refer to cells present within some tumors that possess the ability to self-renew and proliferate. These cells are sometimes called cancer stem cells (CSCs) and may be observed to share certain characteristics with normal stem cells, including a stem cell-like phenotype and function. In some embodiments, TICs are characterized by their ability to form tumors after xenotransplantation in immunodeficient mice.

In some embodiments, the present teachings provide methods of inhibiting the growth of tumor-initiating cells or reducing the likelihood of recurrence of a cancer in a subject whose cancer is in remission comprising administering to the subject an effective amount of a TTK inhibitor (e.g., a compound represented by Structural Formula (I-0), (I) or (I)').

In some embodiments, e.g., where the subject is being treated to reduce the likelihood of recurrence of a cancer, the subject has already been treated with an anti-cancer therapy. Alternatively, the subject has already been treated with an anti-cancer therapy and the subject is in remission.

In some embodiments, the present teachings provide methods of treating a subject with a cancer comprising administering to the subject an effective amount of a compound represented by Structural Formula (I-0), (I) or (I)' in combination with an effective anti-cancer therapy. In one embodiment, the cancer is a metastatic cancer. A "metastatic cancer" is a cancer that has spread from its primary site to other parts of the body.

In another embodiment, the present teachings are directed to a method of treating a subject with a drug-resistant cancer. A "drug-resistant cancer" is a cancer that is not responsive to one, two, three, four, five or more drugs that are typically used for the treatment of the cancer. In one embodiment, the drug-resistant cancer is mediated by the growth of tumor-initiating cells.

Suitable methods known in the art can be used for assessing a subject to determine whether the cancer is in remission. For example, the size of the tumor and/or tumor markers, usually proteins associated with tumors, can be monitored to determine the state of the cancer. Size of the tumor can be monitored with imaging devices, such as X-ray, MRI, CAT scans, ultrasound, mammography, PET and the like or via biopsy.

For methods described herein, e.g., coadministration methods, the anti-cancer therapy are selected from the group consisting of surgery, radiation therapy, immunotherapy, endocrine therapy, gene therapy and administration of an anti-cancer agent. Alternatively, the anti-cancer therapy is radiation therapy. In another alternative, the anti-cancer therapy is immunotherapy. In another alternative, the anti-cancer therapy is administration of an anti-cancer agent. In yet another alternative, the anti-cancer therapy is surgery.

Radiation therapy is the use of radiation to kill, destroy or treat the cancers. Exemplary radiation therapy includes, but is not limited to, gamma-radiation, neutron beam radiotherapy, electron beam radiotherapy, proton therapy, brachytherapy, and radioisotope therapy (i.e., systemic radioactive isotopes therapy), An endocrine therapy is a treatment that adds, blocks or removes hormones. For example, chemotherapeutic agents that can block the production or activity of estrogen have been used for treating breast cancer. In addition, hormonal stimulation of the immune system has been used to treat specific cancers, such as renal cell carcinoma and melanoma. In one embodiment, the endocrine therapy comprises administration of natural hormones, synthetic hormones or other synthetic molecules that may block or increase the production of the body's natural hormones. In another embodiment, the endocrine therapy includes removal of a gland that makes a certain hormone.

As use herein, a gene therapy is the insertion of genes into a subject's cell and biological tissues to treat diseases, such as cancer. Exemplary gene therapy includes, but is not limited to, a germ line gene therapy and a somatic gene therapy.

Immunotherapy (also called biological response modifier therapy, biologic therapy, biotherapy, immune therapy, or biological therapy) is treatment that uses parts of the immune system to fight disease. Immunotherapy can help the immune system recognize cancer cells, or enhance a response against cancer cells. Immunotherapies include active and passive immunotherapies. Active immunotherapies stimulate the body's own immune system while passive immunotherapies generally use immune system components created outside of the body.

Examples of active immunotherapies include, but are not limited to vaccines including cancer vaccines, tumor cell vaccines (autologous or allogeneic), dendritic cell vaccines, antigen vaccines, anti-idiotype vaccines, DNA vaccines, viral vaccines, or Tumor-Infiltrating Lymphocyte (TIL) Vaccine with Interleukin-2 (IL-2) or Lymphokine-Activated Killer (LAK) Cell Therapy.

Examples of passive immunotherapies include but are not limited to monoclonal antibodies and targeted therapies containing toxins. Monoclonal antibodies include naked antibodies and conjugated monoclonal antibodies (also called tagged, labeled, or loaded antibodies). Naked monoclonal antibodies do not have a drug or radioactive material attached whereas conjugated monoclonal antibodies are joined to, for example, a chemotherapy drug (chemolabeled), a radioactive particle (radiolabeled), or a toxin (immunotoxin). Examples of these naked monoclonal antibody drugs include, but are not limited to Rituximab (Rituxan), an antibody against the CD20 antigen used to treat, for example, B cell non-Hodgkin lymphoma; Trastuzumab (Herceptin), an antibody against the HER2 protein used to treat, for example, advanced breast cancer; Alemtuzumab (Campath), an antibody against the CD52 antigen used to treat, for example, B cell chronic lymphocytic leukemia (B-CLL); Cetuximab (Erbitux), an antibody against the EGFR protein used, for example, in combination with irinotecan to treat, for example, advanced colorectal cancer and head and neck cancers; and Bevacizumab (Avastin) which is an antiangiogenesis therapy that works against the VEGF protein and is used, for example, in combination with chemotherapy to treat, for example, metastatic colorectal cancer. Examples of the conjugated monoclonal antibodies include, but are not limited to Radiolabeled antibody Ibritumomab tiuxetan (Zevalin) which delivers radioactivity directly to cancerous B lymphocytes and is used to treat, for example, B cell non-Hodgkin lymphoma; radiolabeled antibody Tositumomab (Bexxar) which is used to treat, for example, certain types of non-Hodgkin lymphoma; and immunotoxin Gemtuzumab ozogamicin (Mylotarg) which contains calicheamicin and is used to treat, for example, acute myelogenous leukemia (AML). BL22 is a conjugated monoclonal antibody for treating, for example, hairy cell leukemia, immunotoxins for treating, for example, leukemias, lymphomas, and brain tumors, and radiolabeled antibodies such as OncoScint for example, for colorectal and ovarian cancers and ProstaScint for example, for prostate cancers.

Further examples of therapeutic antibodies that can be used include, but are not limited to, HERCEPTIN® (Trastuzumab) (Genentech, CA) which is a humanized anti-HER2 monoclonal antibody for the treatment of patients with metastatic breast cancer; REOPRO® (abciximab) (Centocor) which is an anti-glycoprotein IIb/IIIa receptor on the platelets for the prevention of clot formation; ZENAPAX® (daclizumab) (Roche Pharmaceuticals, Switzerland) which is an immunosuppressive, humanized anti-CD25 monoclonal antibody for the prevention of acute renal allograft rejection; PANOREX™ which is a murine anti-17-IA cell surface antigen IgG2a antibody (Glaxo Wellcome/Centocor); BEC2 which is a murine anti-idiotype (GD3 epitope) IgG antibody (ImClone System); IMC-C225 which is a chimeric anti-EGFR IgG antibody (ImClone System); VITAXIN™ which is a humanized anti-αVβ3 integrin antibody (Applied Molecular Evolution/MedImmune); Campath 1H/LDP-03 which is a humanized anti CD52 IgG1 antibody (Leukosite); Smart M195 which is a humanized anti-CD33 IgG antibody (Protein Design Lab/Kanebo); RITUXAN™ which is a chimeric anti-CD20 IgG1 antibody (IDEC Pharm/Genentech, Roche/Zettyaku); LYMPHOCIDE™ which is a humanized anti-CD22 IgG antibody (Immunomedics); LYMPHOCIDE™ Y-90 (Immunomedics); Lymphoscan (Tc-99m-labeled; radioimaging; Immunomedics); Nuvion (against CD3; Protein Design Labs); CM3 is a humanized anti-ICAM3 antibody (ICOS Pharm); IDEC-114 is a primatized anti-CD80 antibody (IDEC Pharm/Mitsubishi); ZEVALIN™ is a radiolabelled murine anti-CD20 antibody (IDEC/Schering AG); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (C5) antibody (Alexion Pharm); D2E7 is a humanized anti-TNF-α antibody (CAT/BASF); CDP870 is a humanized anti-TNF-α Fab fragment (Celltech); IDEC-151 is a primatized anti-CD4 IgG1 antibody (IDEC Pharm/SmithKline Beecham); MDX-CD4 is a human anti-CD4 IgG antibody (Medarex/Eisai/Genmab); CD20-sreptdavidin (+biotin-yttrium 90; NeoRx); CDP571 is a humanized anti-TNF-α IgG4 antibody (Celltech); LDP-02 is a humanized anti-α4β7 antibody (LeukoSite/Genentech); OrthoClone OKT4A is a humanized anti-CD4 IgG antibody (Ortho Biotech); ANTOVA™ is a humanized anti-CD40L IgG antibody (Biogen); ANTEGREN™ is a humanized anti-VLA-4 IgG antibody (Elan); and CAT-152 is a human anti-TGF-$\beta_2$ antibody (Cambridge Ab Tech).

Immunotherapies that can be used in the present teachings include adjuvant immunotherapies. Examples include cytokines, such as granulocyte-macrophage colony-stimulating factor (GM-CSF), granulocyte-colony stimulating factor (G-CSF), macrophage inflammatory protein (MIP)-1-alpha, interleukins (including IL-1, IL-2, IL-4, IL-6, IL-7, IL-12, IL-15, IL-18, IL-21, and IL-27), tumor necrosis factors (including TNF-alpha), and interferons (including IFN-alpha, IFN-beta, and IFN-gamma); aluminum hydroxide (alum); Bacille Calmette-Guerin (BCG); Keyhole limpet hemocyanin (KLH); Incomplete Freund's adjuvant (IFA); QS-21; DETOX; Levamisole; and Dinitrophenyl (DNP), and combinations thereof, such as, for example, combinations of, interleukins, for example, IL-2 with other cytokines, such as IFN-alpha.

Alternatively, the anti-cancer therapy described herein includes administration of an anti-cancer agent. An "anti-cancer agent" is a compound, which when administered in an effective amount to a subject with cancer, can achieve, partially or substantially, one or more of the following: arresting the growth, reducing the extent of a cancer (e.g., reducing size of a tumor), inhibiting the growth rate of a cancer, and ameliorating or improving a clinical symptom or indicator associated with a cancer (such as tissue or serum components) or increasing longevity of the subject.

The anti-cancer agent suitable for use in the methods described herein includes any anti-cancer agents that have been approved for the treatment of cancer. In one embodiment, the anti-cancer agent includes, but is not limited to, a targeted antibody, an angiogenesis inhibitor, an alkylating agent, an antimetabolite, a vinca alkaloid, a taxane, a podophyllotoxin, a topoisomerase inhibitor, a hormonal antineoplastic agent and other antineoplastic agents.

Examples of alkylating agents useful in the methods of the present teachings include but are not limited to, nitrogen mustards (e.g., mechloroethamine, cyclophosphamide, chlorambucil, melphalan, etc.), ethylenimine and methylmelamines (e.g., hexamethylmelamine, thiotepa), alkyl sulfonates (e.g., busulfan), nitrosoureas (e.g., carmustine, lomusitne, semustine, streptozocin, etc.), or triazenes (decarbazine, etc.). Examples of antimetabolites useful in the methods of the present teachings include but are not limited to folic acid analog (e.g., methotrexate), or pyrimidine analogs (e.g., fluorouracil, floxouridine, Cytarabine), purine analogs (e.g., mercaptopurine, thioguanine, pentostatin). Examples of plant alkaloids and terpenoids or derivatives thereof include, but are not limited to, vinca alkaloids (e.g., vincristine, vinblastine, vinorelbine, vindesine), podophyllotoxin, and taxanes (e.g., paclitaxel, docetaxel). Examples of a topoisomerase inhibitor include, but are not limited to, irinotecan, topotecan, amsacrine, etoposide, etoposide phosphate and teniposide. Examples of antineoplastic agents include, but are not limited to, actinomycin, anthracyclines (e.g., doxorubicin, daunorubicin, valrubicin, idarubicin, epirubicin), bleomycin, plicamycin and mitomycin.

In one embodiment, the anti-cancer agents that can be used in the present teachings include Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Yet other anti-cancer agents/drugs that can be used in the present teachings include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; beta-clamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-aminotriazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred additional anti-cancer drugs are 5-fluorouracil and leucovorin.

In one embodiment, the anti-cancer agents that can be used in methods described herein are selected from the group consisting of paclitaxel, docetaxel, 5-fluorouracil, trastuzumab, lapatinib, bevacizumab, letrozole, goserelin, tamoxifen, cetuximab, panitumumab, gemcitabine, capecitabine, irinotecan, oxaliplatin, carboplatin, cisplatin, doxorubicin, epirubicin, cyclophosphamide, methotrexate, vinblastine, vincristine, melphalan and a combination thereof.

In one embodiment, the anti-cancer agent and the compound represented by Structural Formula (I-0), (I) or (I)' are administered contemporaneously. When administered contemporaneously, the anti-cancer agent and the compound can be administered in the same formulation or in different formulations. Alternatively, the compound and the additional anti-cancer agent are administered separately. Alternatively, the compound and the additional anti-cancer agent can be administered sequentially, as separate compositions, within an appropriate time frame (e.g., a cancer treatment session/interval (e.g., about 1.5 to about 5 hours to about 10 hours to about 15 hours to about 20 hours; about 1 day to about 2 days to about 5 days to about 10 days to about 14 days)) as determined by the skilled clinician (e.g., a time sufficient to allow an overlap of the pharmaceutical effects of the therapies). The compound and the additional anti-cancer agent can be administered in a single dose or multiple doses in an order and on a schedule suitable to achieve a desired therapeutic effect (e.g., inhibition of tumor growth).

In one embodiment, the subject in the methods described herein has not been previously treated with a TTK inhibitor (e.g., the compound represented by Structural Formula (I-0), (I) or (I)').

The term "inhibiting the growth of tumor-initiating cells" refers to decreasing the rate of the proliferation and/or survival of the tumor-initiating cells.

As used herein, the term "reducing the likelihood of recurrence of a cancer" means partially or totally inhibiting, delaying the return of a cancer at or near a primary site and/or at a secondary site after a period of remission. It also means that the cancer is less likely to return with treatment described herein than in its absence.

As used herein, the term "remission" refers to a state of cancer, wherein the clinical symptoms or indicators associated with a cancer have disappeared or cannot be detected, typically after the subject has been successfully treated with an anti-cancer therapy.

As used herein, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e., not worsening) state of disease, reducing the likelihood of the spread of the disease, delay or slowing of disease progression, amelioration or palliation of the disease state, whether detectable or undetectable. "Treatment" can also mean prolonging survival as compared to expected survival if not receiving treatment. "Treatment" also includes reducing the likelihood of reoccurrence of the disease.

As used herein, "treating a subject with a cancer" includes achieving, partially or substantially, one or more of the following: arresting the growth, reducing the extent of the cancer (e.g., reducing size of a tumor), inhibiting the growth rate of the cancer, ameliorating or improving a clinical symptom or indicator associated with the cancer (such as tissue or serum components) or increasing longevity of the subject; and reducing the likelihood of recurrence of the cancer.

Generally, an effective amount of a compound taught herein varies depending upon various factors, such as the given drug or compound, the pharmaceutical formulation, the route of administration, the type of disease or disorder, the identity of the subject or host being treated, and the like, but can nevertheless be routinely determined by one skilled in the art. An effective amount of a compound of the present teachings may be readily determined by one of ordinary skill by routine methods known in the art.

The term an "effective amount" means an amount when administered to the subject which results in beneficial or desired results, including clinical results, e.g., inhibits, suppresses or reduces the cancer (e.g., as determined by clinical symptoms or the amount of cancer cells) in a subject as compared to a control.

In an embodiment, an effective amount of a compound taught herein ranges from about 0.1 to about 1000 mg/kg body weight, alternatively about 1 to about 500 mg/kg body weight, and in another alternative, from about 20 to about 300 mg/kg body weight. In another embodiment, an effective amount of a compound taught herein ranges from about 0.5 to about 5000 mg/m$^2$, alternatively about from 5 to about 2500 mg/m$^2$, and in another alternative from about 50 to about 1000 mg/m$^2$. The skilled artisan will appreciate that certain factors may influence the dosage required to effectively treat a subject suffering from cancer or reduce the likelihood of recurrence of a cancer. These factors include, but are not limited to, the severity of the disease or disorder, previous treatments, the general health and/or age of the subject and other diseases present.

Moreover, for methods described herein (including treating a subject with a cancer or reducing the likelihood of recurrence of a cancer), a "treatment" or dosing regimen of a subject with an effective amount of the compound of the present teachings may consist of a single administration, or alternatively comprise a series of applications. For example, the compound of the present teachings may be administered at least once a week. However, in another embodiment, the compound may be administered to the subject from about one time per week to once daily for a given treatment. The length of the treatment period depends on a variety of factors, such as the severity of the disease, the age of the patient, the concentration and the activity of the compounds of the present teachings, or a combination thereof. It will also be appreciated that the effective dosage of the compound used for the treatment may increase or decrease over the course of a particular treatment regime. Changes in dosage may result and become apparent by standard diagnostic assays known in the art. In some instances, chronic administration may be required.

A "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

The compounds taught herein can be administered to a patient in a variety of forms depending on the selected route of administration, as will be understood by those skilled in the art. The compounds of the present teachings may be administered, for example, by oral, parenteral, buccal, sublingual, nasal, rectal, patch, pump or transdermal administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration can be by continuous infusion over a selected period of time.

The compounds taught herein can be suitably formulated into pharmaceutical compositions for administration to a subject. The pharmaceutical compositions of the present teachings optionally include one or more pharmaceutically acceptable carriers and/or diluents therefor, such as lactose, starch, cellulose and dextrose. Other excipients, such as flavoring agents; sweeteners; and preservatives, such as methyl, ethyl, propyl and butyl parabens, can also be included. More complete listings of suitable excipients can be found in the Handbook of Pharmaceutical Excipients (5$^{th}$ Ed., Pharmaceutical Press (2005)). A person skilled in the art would know how to prepare formulations suitable for various types of administration routes. Conventional procedures and ingredients for the selection and preparation of suitable formulations are described, for example, in Remington's Pharmaceutical Sciences (2003-20th edition) and in The United States Pharmacopeia: The National Formulary (USP 24 NF19) published in 1999. The carriers, diluents and/or excipients are "acceptable" in the sense of being compatible with the other ingredients of the pharmaceutical composition and not deleterious to the recipient thereof.

Typically, for oral therapeutic administration, a compound of the present teachings may be incorporated with excipient and used in the form of ingestible tablets, buccal tablets, troches, capsules, elixirs, suspensions, syrups, wafers, and the like.

Typically for parenteral administration, solutions of a compound of the present teachings can generally be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms.

Typically, for injectable use, sterile aqueous solutions or dispersion of, and sterile powders of, a compound described herein for the extemporaneous preparation of sterile injectable solutions or dispersions are appropriate.

For nasal administration, the compounds of the present teachings can be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

For buccal or sublingual administration, the compounds of the present teachings can be formulated with a carrier such as sugar, acacia, tragacanth, or gelatin and glycerine, as tablets, lozenges or pastilles.

For rectal administration, the compounds described herein can be formulated in the form of suppositories containing a conventional suppository base such as cocoa butter.

The compounds of invention may be prepared by methods known to those skilled in the art, as illustrated by the general schemes and procedures below and by the preparative examples that follow. All starting materials are either commercially available or prepared by methods known to those skilled in the art and the procedures described below.

In accordance with another aspect of the present invention, the compounds of the invention can be prepared by processes analogues to those established in the art. General methods to synthesize the claimed compounds are elaborated below in Example A.

EXEMPLIFICATION

Example A

Synthesis

General Methods

Commercially available starting materials, reagents, and solvents were used as received. In general, anhydrous reactions were performed under an inert atmosphere such as nitrogen or Argon. PoraPak® Rxn CX refers to a commercial cation-exchange resin available from Waters. Microwave reactions were performed with a Biotage Initiator microwave reactor. Reaction progress was generally monitored by TLC using Merck silica gel plates with visualization by UV at 254 nm, by analytical HPLC or by LCMS (Bruker Exquire 4000 or Waters Acquity UPLC system). Flash column chromatographic purification of intermediates or final products was performed using 230-400 mesh silica gel 60 from EMD chemicals or Silicycle, or purified using a Biotage Isolera with KP-SIL or HP-SIL silica cartridges, or KP-NH basic modified silica and corresponding samplets. Reverse-phase HPLC purification was performed on a Varian PrepStar model SD-1 HPLC system with a Varian Monochrom 10 u C-18 reverse-phase column using a of about 5-30% MeCN or MeOH/0.05% TFA-H$_2$O to 70-90% MeCN or MeOH/0.05% TFA in H$_2$O over a 20-40-min period at a flow rate of 30-80 mL/min. Reverse phase purification was also performed using a Biotage Isolera equipped with a KP-C18-H column using a between 10-95% MeOH or CH$_3$CN/0.1% TFA in H$_2$O. Proton NMRs were recorded on a Bruker 400 MHz spectrometer, and mass spectra were obtained using a Bruker Esquire 4000 spectrometer or Waters Acquity UPLC system.

Compound names were generated using the software built into CambridgeSoft-PerkinElmer's ChemBioDraw Ultra version 11.0 or 12.0.

ABBREVIATIONS

Ac Acetyl
aq aqueous
anh anhydrous
Ar argon
BINOL 1,1'-binaphthalene-2,2'-diol
Boc tert-butoxycarbonyl
br. broad
calcd calculated
d doublet (only when used within 1H NMR spectra)
d day
DBU 1,8-Diazabicyclo[5.4.0]undec-7-ene
DCE 1,2-dichloroethane
DCC N,N'-dicyclohexylcarbodiimide
DCM dichloromethane
DEA diethylamine
de diastereomeric excess
DIPEA diisopropylethylamine
DME 1,2-dimethoxyethane
DMF N,N-dimethylformamide
DMSO dimethylsulfoxide
dppf 1,1'-bis(diphenylphosphino) ferrocene
h hour
hal halogen
HPLC high performance liquid chromatography
IPA iso-propanol
LC-MS liquid chromatography coupled to mass spectrometry
min minute
m multiplet
mCPBA meta-chloroperoxybenzoic acid
MS ESI mass spectra, electrospray ionization
NMR nuclear magnetic resonance
NBS N-Bromosuccinimide
O/N overnight
pin pinacol
PMB para-methoxybenzyl
prep preparative
PTSA para-toluenesulfonic acid
RBF round bottomed flask
rt room temperature
Rt retention time
RP reverse phase
s singlet
satd saturated
SMs starting materials
S$_N$Ar Nucleophilic Aromatic Substitution
SPE solid phase extraction
t triplet
TBTU O-(benzotriazol-1-yl)-N,N,N',N'-tetramethyluronium tetrafluoroborate
TEA triethylamine
temp. temperatureTFA trifluoroacetic acid
TLC thin layer chromatography
THF tetrahydrofuran
THP tetrahydropyranyl
xs excess By way of illustration, pyrazolotriazine compounds of Structural Formula 6 may be prepared by the methods outlined in Scheme 1. Treatment of 8-halo-4-chloro-2-(methylthio)pyrazolo[1,5-a][1,3,5]triazine 1 with suitably substituted aliphatic primary amine or alcohol in the presence of base such as DIPEA, TEA, pyridine and DBU yields the desired intermediate 2. In the case where primary amine is used in the previous step, protection of the nitrogen is performed using standard procedures well known in the art before the Suzuki-Miyaura cross coupling reaction. A detailed description of techniques applicable to the creation of protecting groups and their removal can be found in T. W. Green, "Protecting Groups in Organic Chemistry", 3rd edition, John Wiley and Sons, Inc., 1999. The subsequent Suzuki-Miyaura cross coupling is carried out in the presence of a Pd catalyst (e.g. PdCl$_2$(dppf) or Pd(PPh$_3$)$_4$), and a suitably substituted aryl boronate ester or boronic acid and a base (e.g. aq K$_3$PO$_4$, or Na$_2$CO$_3$) at high temperatures (e.g. 100-130° C.). Removal of protecting group under acidic conditions (e.g. for PG=PMB at TFA, 35-80° C.) followed by oxidation of methylsulfide using oxidants (e.g. mCPBA) afforded the desired intermediate 5. The compounds of the invention 6 can be synthesized via an nucleophilc aromatic substitution in the presence of primary/secondary amines or alcohols/phenols in the presence of a suitable base (e.g. DIPEA, TEA, DBU, NaH), at a temperature in the range of rt to 80° C.

Scheme 1

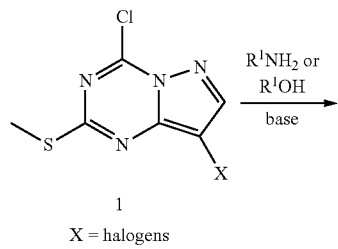

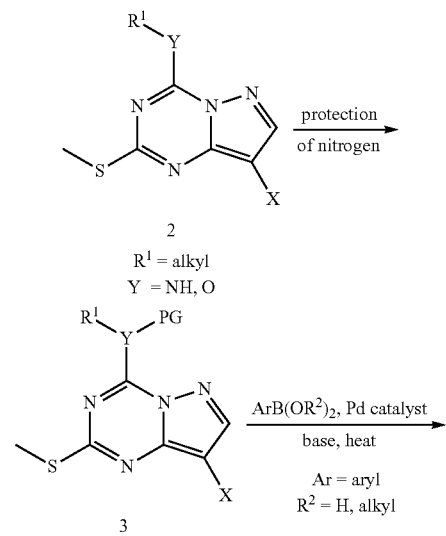

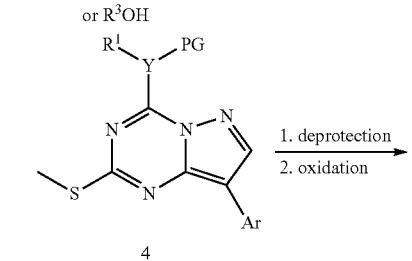

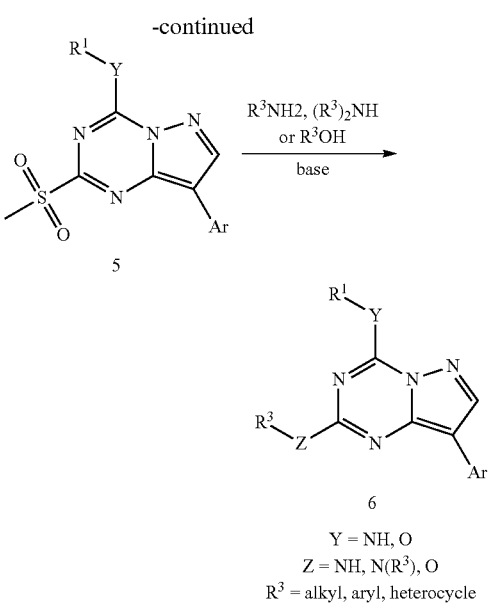

Alternatively, final compound 6 can be synthesized using the reaction sequence depicted in Scheme 2 where intermediate 4 undergoes an oxidation of methylsulfide followed by nucleophilic aromatic substitution and removal of protecting group using the reaction conditions described above.

Scheme 2

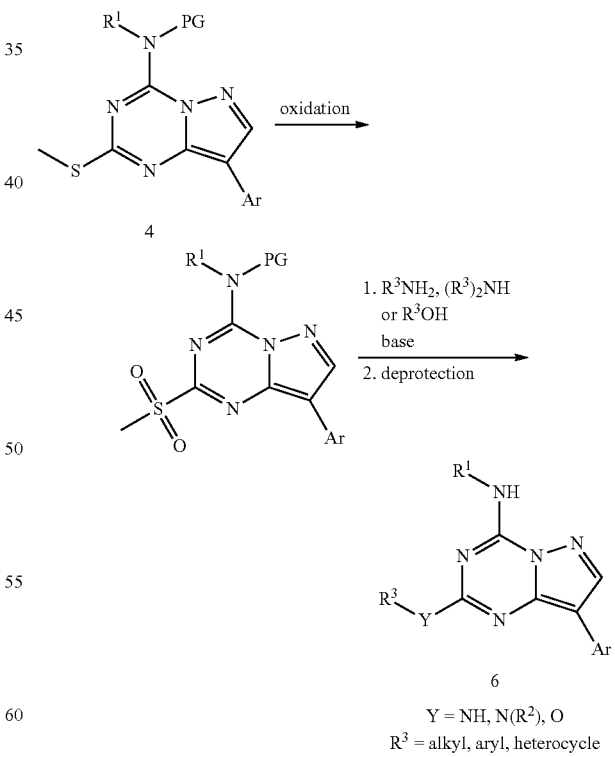

The starting materials of formula I can be synthesized using procedures analogues to those well known in the arts of heterocyclic and organic chemistry for the production of structurally analogous compounds. Thus, intermediate 7 is synthesized according to a procedure from International Patent Application Publication No. WO2011/079231. Desired intermediate 1 can be obtained by bromination of intermediate 7 using NBS or other brominating reagents.

Scheme 3

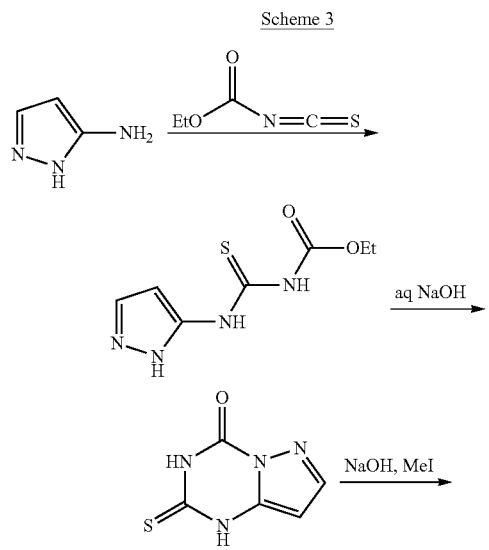

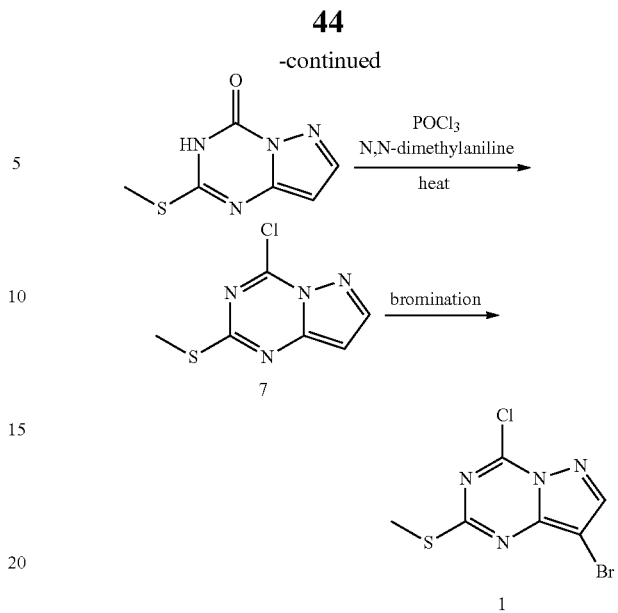

Compounds described herein can be prepared in a manner analogous to the general procedures described above or the detailed procedures described in the examples herein.

Pyrazolopyrimidine compounds of the present invention may be prepared by the methods outlined in Scheme 4.

Scheme 4

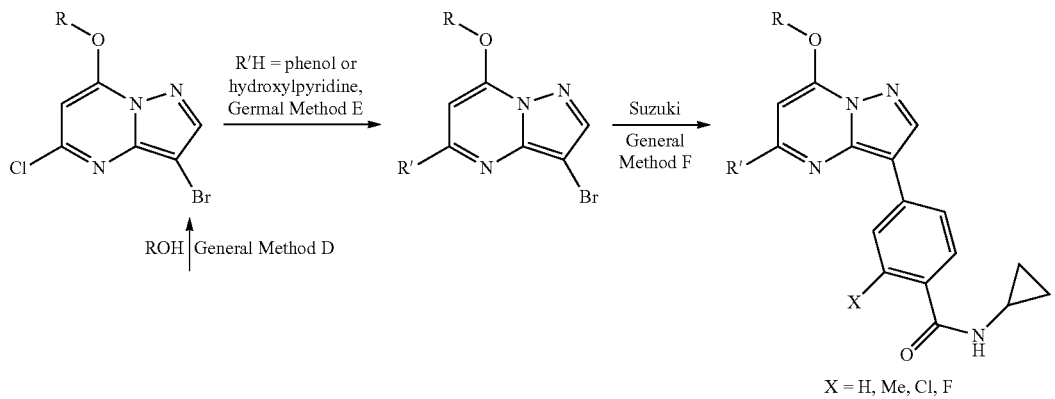

X = H, Me, Cl, F

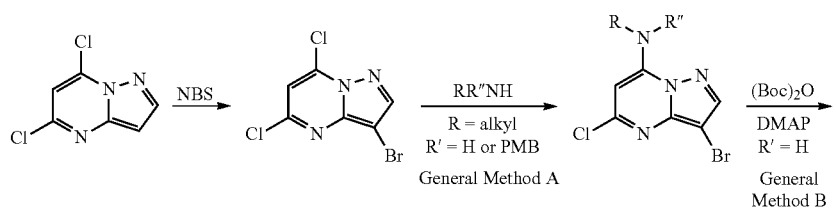

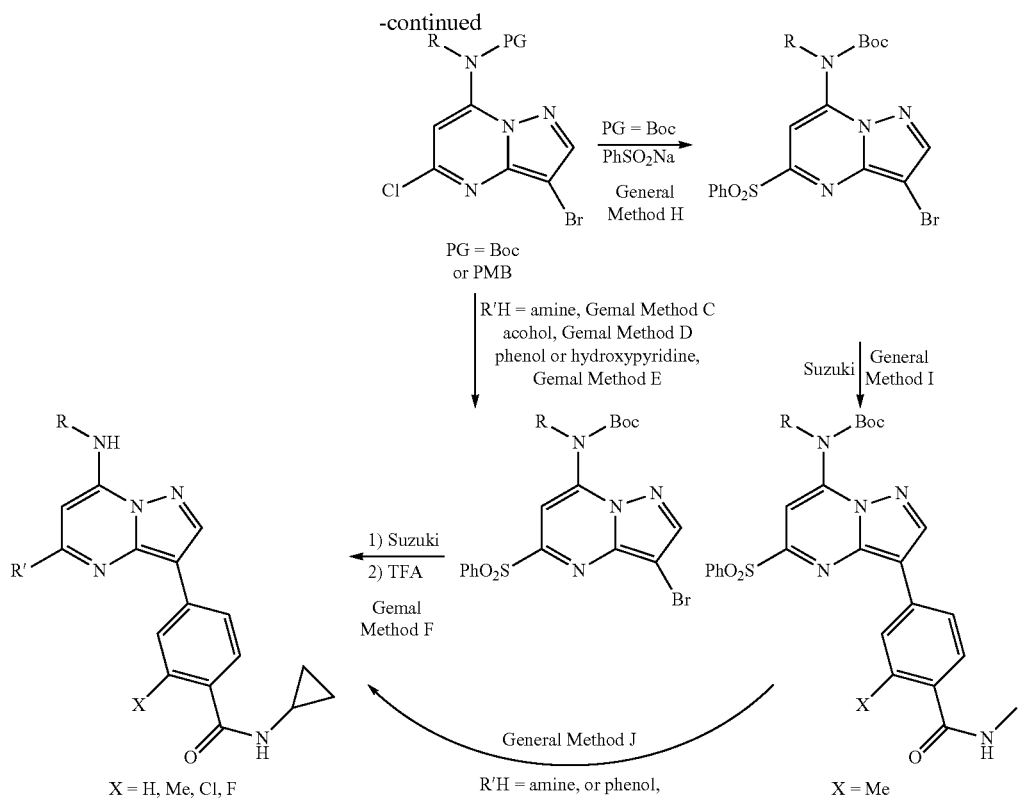

General Method A (Amination)

To a cooled (0° C.) DCM solution (0.1-1 M) of 3-bromo-5,7-dichloropyrazolo[1,5-a]pyrimidine (1 equiv) or 8-bromo-4-chloro-2-(methylthio)pyrazolo[1,5-a][1,3,5]triazine (1.0 equiv) was added primary amine (1-2 equiv) and DIPEA or TEA (1-2 equiv). Alternatively, primary amine (2-3 equiv) was added alone without DIPEA/TEA. The reaction was stirred at rt for 0.5-24 h. The product was partitioned between EtOAc or DCM and satd NaHCO$_3$ solution, dried over Na$_2$SO$_4$ or MgSO$_4$, filtered, and concentrated to dryness. In the majority of examples the crude product was used without further purification or alternatively the material was purified by flash chromatography.

General Method B (Boc Protection)

To a solution of pyrazolo[1,5-a]pyrimidin-7-amine derivative (1 equiv) in DCM was added Boc$_2$O (0.8-1.5 equiv), followed by DMAP (0.1-0.2 equiv) and Et$_3$N (1-2 equiv). The resulting mixture was stirred at rt and purified by flash chromatography (gradient: EtOAc/hex 0-100%).

General Method B2 (PMB Protection)

A solution of 8-bromo-2-(methylthio)pyrazolo[1,5-a][1,3,5]triazin-4-amine (1 equiv) in DMF (0.2-1M), 4-methoxybenzyl chloride (1.0-1.2 equiv), and K$_2$CO$_3$ (2 equiv) was heated to 60° C. for 2-4 h. The product was partitioned between EtOAc and H$_2$O, dried over Na$_2$SO$_4$ or MgSO$_4$, filtered, concentrated to dryness, and purified by flash chromatography.

General Method C (Nucleophilic Substitutions of Amines)

To a solution of pyrazolo[1,5-a]pyrimidin-5-chlorine derivative (1 equiv) or 2-(methylsulfonyl)-8-arylpyrazolo[1,5-a][1,3,5]triazin-4-amine (1.0 equiv) in THF, dioxane, DME, DMF or NMP was added amines or amine-HCl (1-2 equiv) and DIPEA (1-3 equiv). The resulting mixture was stirred at rt for 24 h or more generally the reaction was heated in a microwave reactor, an oil bath or a reaction block at temperatures from 35-130° C. for 2-12 h. Solvent was removed in vacuo and the crude product was purified by flash chromatography.

Alternatively, a solution of pyrazolo[1,5-a]pyrimidin-5-chlorine derivative (1 equiv) or 2-(methylsulfonyl)-8-arylpyrazolo[1,5-a][1,3,5]triazin-4-amine (1.0 equiv) and amine or aniline (2-22 equiv) was heated in a microwave reactor, an oil bath or a reaction block at temperatures from 35-170° C. for 2-12 h. Solvent was removed in vacuo and the crude product was purified by flash chromatography.

General Method D (Nucleophilic Substitutions of Alcohols)

To a solution of pyrazolo[1,5-a]pyrimidin-5-chlorine derivative (1 equiv) or 2-(methylsulfonyl)-8-arylpyrazolo[1,5-a][1,3,5]triazin-4-amine (1.0 equiv) and alcohol (1-3 equiv) in DMF or THF at 0° C. was added 60% NaH (1.5-6 equiv). The resulting mixture was stirred at rt for 1-4 h. After cooling to 0° C., quenching with satd NH$_4$Cl and H$_2$O, it was extracted with EtOAc and purified by flash chromatography.

General Method E (Nucleophilic Substitutions of Phenols or Hydroxylpyridine)

Using Phenol and K$_2$CO$_3$:

To a solution of pyrazolo[1,5-a]pyrimidin-5-chlorine derivative (1 equiv) and phenol (2-3 equiv) in DMF was added K$_2$CO$_3$ (3 equiv). The resulting mixture was stirred O/N at rt and quenched with H$_2$O. The precipitates were collected by suction filtration and dried to give the desired product. Alternatively, the aqueous layer was extracted with EtOAc. The organic layer was dried (Na$_2$SO$_4$ or MgSO$_4$), filtered, concentrated to dryness and purified by flash chromatography.

Using Phenol and DBU:

A mixture of pyrazolo[1,5-a]pyrimidin-5-chlorine derivative (1 equiv) or 2-(methylsulfonyl)-8-arylpyrazolo[1,5-a][1,3,5]triazin-4-amine (1.0 equiv) in DME or DMF, phenol (2-4 equiv), and DBU (2-4 equiv) was heated in a microwave reactor, an oil bath or a reaction block at temperatures 80-100° C. for 1-4 h. Solvent was removed and the crude product was purified by flash chromatography.

Using Phenoxide:

To a solution of pyrazolo[1,5-a]pyrimidin-5-chlorine derivative (1 equiv) in DMF was added sodium phenoxides (1-1.5 equiv, commercial or freshly made using phenols and NaOH in $H_2O$). The resulting mixture was stirred at rt for 30 min to O/N and quenched with $H_2O$. The precipitates were collected by suction filtration and dried to give the desired product. Alternatively the aqueous layer was extracted with EtOAc. The organic layer was dried ($Na_2SO_4$ or $MgSO_4$), filtered, concentrated to dryness and purified by flash chromatography.

General Method F (Suzuki-Miyaura Coupling; Followed by Boc or PMB Deprotection if Applicable)

A mixture of pyrazolo[1,5-a]pyrimidin-3-bromine derivative (1.0 equiv) or 8-bromo-N-(4-methoxybenzyl)-2-(methylthio)pyrazolo[1,5-a][1,3,5]triazin-4-amine (1.0 equiv), boronic acid or aryl boronate ester (1-3 equiv), aq $K_3PO_4$ (1-2 M, 3-5 equiv) and $PdCl_2dppf.DCM$ (0.05-0.2 equiv) in THF was heated under Ar in a microwave reactor, an oil bath or a reaction block at temperatures 80-130° C. for 2 h to 2 days. The product was partitioned between EtOAc and $H_2O$, dried over $Na_2SO_4$ or $MgSO_4$, filtered and concentrated to dryness, then purified by flash chromatography.

If Boc deprotection is required, the above compound was redissolved in DCM and treated with TFA and stirred O/N. After removal of TFA, it was triturated with MeOH or purified by flash chromatography or prep-HPLC.

Alternatively, the Boc deprotection can be done in microwave in mixture of $H_2O$ and DMF or NMP or EtOH at 100-140° C. for 1-4 h and purified by prep-HPLC, reversed phase or normal phase Biotage column.

For PMB deprotection: A solution of N-(4-methoxybenzyl)-2-(methylthio)-8-arylpyrazolo[1,5-a][1,3,5]triazin-4-amine (1 equiv) in a mixture of DCM and TFA (2:1 v/v) or DCE and TFA (3:1 v/v) was heated in a microwave reactor, an oil bath or a reaction block at temperatures 60-100° C. for 30 min-30 h. Solvent was removed in vacuo and the crude product was purified by chromatography.

General Method G (Borylation of Aryl Halides): Using $B_2Pin_2$/Pd

A mixture of aryliodide or arylbromide (1 equiv), $B_2pin_2$ (1.2 to 1.5 equiv), KOAc (3 equiv.) and DMF or DMSO was purged with Ar for 10 min. $PdCl_2(dppf).DCM$ (3-5 mol %) was added, the vial sealed and heated at 80-100° C. for 2-6 h. The product was partitioned between EtOAc and satd aq $NaHCO_3$, washed with brine, dried over $Na_2SO_4$ or $MgSO_4$, filtered, and concentrated to dryness. The crude product was purified by flash chromatography to give the title compound.

General Method H (Substitution with Sodium Sulfinate)

A mixture of pyrazolo[1,5-a]pyrimidin-5-chlorine derivative (1 equiv) and sodium sulfinate (1-1.2 equiv) in DMF was heated at 60° C. in oil bath or microwave for 1-2 h. After removal of solvents, it was purified by flash chromatography on $SiO_2$.

General Method I (Suzuki on pyrazolo[1,5-a]pyrimidin-5-phenylsulphonyl Derivative)

To a mixture of the pyrazolo[1,5-a]pyrimidin-5-phenylsulphonyl derivative (1 equiv) and N-cyclopropyl-4-(4,4,5,5-tetramethyl-1,3,2-dioxaborolan-2-yl)benzamide (1-1.5 equiv) in THF was added 2 M $K_3PO_4$ (3 equiv), followed by $PdCl_2dppfDCM$ (2-10 mol %). The resulting mixture was purged with Ar and then heated at 60° C. for 1.5 h to O/N. It was diluted with brine, extracted with EtOAc and combined. After removal of solvents, the residue was purified by flash chromatography on $SiO_2$.

General Method J (Nucleophilic Substitutions on Benzenesulfonate, Followed by Boc Deprotection)

To a solution of pyrazolo[1,5-a]pyrimidin-5-phenylsulphonyl derivative (1 equiv, 0.05-0.3 M) in DMF or NMP was added amines, amine-HCls (1-3 equiv) and DIPEA (1-3 equiv) or phenolates (prepared from NaOH and phenols in H2O, after drying). The resulting mixture was heated in microwave at 100-130° C. for 1-6 h.

For the Boc deprotction, after adding 0.5-2 volumes of $H_2O$, the resulting mixture was heated in microwave at 120-140° C. for 1-4 h and purified by prep-HPLC or reversed phase Biotage column.

Intermediates

Synthesis of 4-bromo-N-cyclopropyl-2-methylbenzamide

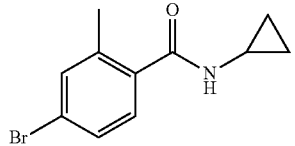

To a suspension of 4-bromo-2-methylbenzoic acid (43.0 g, 200 mmol) and oxalyl dichloride (30.5 g, 240 mmol) in DCM (300 mL) was added DMF (0.1 mL). The resulting reaction mixture was stirred at rt for 16 h. The reaction turned into a clear yellow solution slowly over 16 h. Solvent was then removed in vacuo, and the crude product was used in the next step without further purification. The crude product was redissolved in DCM (300 mL) and cooled to 0° C. A mixture of TEA (42 mL, 300 mmol) and cyclopropylamine (12.6 g, 220 mmol) in DCM (100 mL) was added slowly over 15 min, and the resulting mixture was stirred at rt for 2 h. The reaction was diluted with DCM (200 mL) and water was added. The resulting mixture was extracted with DCM and the combined organic extracts were dried over $MgSO_4$ and concentrated to give the desired product as a pale pink solid (50.1 g, 99%). $^1$H NMR (400 MHz, $CDCl_3$) δ ppm 7.37 (s, 1H), 7.31 (d, J=8.0 Hz, 1H), 7.17 (d, J=8.1 Hz, 1H), 5.93 (br, s, 1H), 2.90-2.85 (m, 1H), 2.40 (s, 3H), 0.90-0.85 (m, 2H), 0.62-0.58 (m, 2H); MS ESI [M+H]+ 253.9, calcd for $[C_{11}H_{12}BrNO+H]^+$ 254.0.

Synthesis of N-(4-bromo-2-methylphenyl)cyclopropanecarboxamide

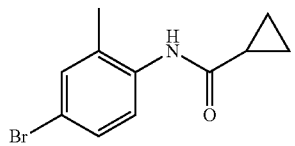

In a 100 mL RBF, 4-bromo-2-methylaniline (3.7 g, 20 mmol) and DIPEA (6.95 mL, 40 mmol) were combined with DMF (40 mL). The reaction was cooled to 0° C. in an ice bath and cyclopropanecarbonyl chloride (2.1 g, 20 mmol) was added. The mixture was stirred at 0° C. for 1 h. Water and EtOAc were added to separate the phases and the aqueous phase was extracted with EtOAc. The organic layers were combined, dried over $Na_2SO_4$, filtered, and concentrated under reduced pressure to give the title compound as a white solid (4.76 g, 94%). $^1$H NMR (400 MHz, $CDCl_3$) δ ppm 7.85-7.72 (m, 1H), 7.38-7.28 (m, 2H), 7.15-7.02 (m, 1H), 2.27 (s, 3H), 1.57-1.48 (m, 1H), 1.10 (quint, J=3.9 Hz, 2H), 0.92-0.79 (m, 2H); MS ESI [M+H] 253.9, calcd for $[C_{11}H_{12}BrNO+H]^+$ 254.0.

Synthesis of N-cyclopropyl-2-methyl-4-(4,4,5,5-tetramethyl-1,3,2-dioxaborolan-2-yl)benzamide

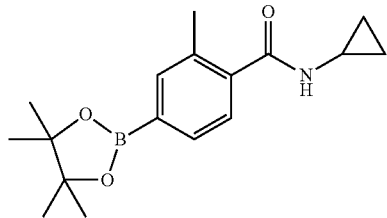 [SMILES: Cc1cc(B2OC(C)(C)C(C)(C)O2)ccc1C(=O)NC1CC1]

To a mixture of 4-bromo-N-cyclopropyl-2-methylbenzamide (3.73 g, 14 mmol), Bis(pinacolato)diboron (5.59 g, 22 mmol), anh KOAc (4.29 g, 43 mmol) in DMF (37 mL) was purged with Ar for 10 min at rt. Then $PdCl_2$(dppf).DCM (0.59 g, 5 mol %) was added and the reaction was heated at 100° C. in oil bath for 4 h. After reaction completion the reaction mass was diluted with EtOAc (200 mL) & $H_2O$ (100 mL). The combined layer filtered through celite pad and washed it with little EtOAc. The aq. layer further extracted with EtOAc (50 mL) and the combined organic layer washed with brine, dried over $Na_2SO_4$, filtered, and concentrated to give crude oily residue. The crude product was purified by flash chromatography (gradient: EtOAc/hex 0-100%) to give the title compound as a creamy solid (4.15 g, 94%). $^1$H NMR (400 MHz, $CDCl_3$) δ ppm 7.66 (s, 1H), 7.63-7.61 (d, J=7.6 Hz, 1H), 7.32-7.30 (d, J=7.6 Hz, 1H), 5.85 (s, 1H), 2.93-2.87 (m, 1H), 2.46 (s, 3H), 1.35 (s, 12H), 0.90-0.86 (m, 2H), 0.63-0.59 (m, 2H); MS ESI [M+H]$^+$ 302.2, calcd for $[C_{17}H_{24}BNO_3+H]^+$ 302.2.

The following compounds were synthesized according to the synthesis of General Method G

| IUPAC name | Structure | MS calcd; MS ESI [M + H]+ | Yield; Appearance; Salt form |
|---|---|---|---|
| N-(2-methyl-4-(4,4,5,5-tetramethyl-1,3,2-dioxaborolan-2-yl)phenyl)cyclopropane-carboxamide | 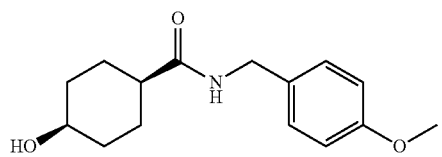 [SMILES: COc1ccc(CNC(=O)[C@H]2CC[C@@H](O)CC2)cc1] | $[C_{17}H_{24}BNO_3 + H]^+$ 302.2; 302.4 | 1.13 g (63%); white solid; free base |

SMs: N-(4-bromo-2-methylphenyl)cyclopropanecarboxamide (1.5 g, 5.9 mmol), (PinB)$_2$ (2.3 g, 8.9 mmol), $PdCl_2$dppfDCM (242 mg, 0.30 mmol).
$^1$H NMR (400 MHz, $CDCl_3$) δ ppm 8.03 (br, s, 1H), 7.70-7.60 (m, 2H), 7.36-7.29 (m, 1H), 2.31 (s, 3H), 1.58-1.48 (m, 1H), 1.34 (s, 12H), 1.15-1.05 (m, 2H), 0.90-0.80 (m, 2H).

Synthesis of (cis)-4-hydroxy-N-(4-methoxybenzyl) cyclohexanecarboxamide

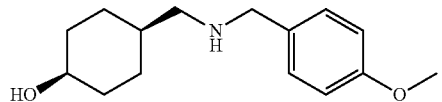 [SMILES: COc1ccc(CNC[C@H]2CC[C@@H](O)CC2)cc1]

TBTU (3.21 g, 10.0 mmol) was added in one portion to a stirred DMF (anh., 20 mL) solution of (cis)-4-hydroxycyclohexanecarboxylic acid (1.44 g, 9.9 mmol), 4-methoxybenzylamine (1.37 g, 9.9 mmol) and DIPEA (1.8 mL, 10.3 mmol) at rt. Stirring was continued for 21 h, then the reaction was diluted with $H_2O$ and taken into EtOAc (150 mL). The organic phase was washed with $H_2O$ (50 mL and 30 mL). The aq. phases were combined, concentrated under reduced pressure and purified by RP HPLC (C18, MeOH—$H_2O$) to afford the title compound as a white solid (0.83 g, 32%). $^1$H NMR (400 MHz, $CDCl_3$) δ ppm 7.21 (d, J=8.28 Hz, 2H), 6.88 (d, J=8.28 Hz, 2H), 5.69 (br. s., 1H), 4.39 (d, J=5.52 Hz, 2H), 4.01 (br. s., 1H), 3.81 (s, 3H), 2.12-2.26 (m, 1H), 1.78-1.97 (m, 4H), 1.76-1.66 (m, 2H), 1.65-1.57 (m, 2H); MS ESI [M+H]$^+$ 264.2, calcd for $[C15H_{21}NO_3+H]^+$ 264.15.

Synthesis of (cis)-4-(((4-methoxybenzyl)amino) methyl)cyclohexanol

LiAlH$_4$ (1.0 M in THF, 10.0 mL, 10 mmol) was added slowly to an anh THF (40 mL) solution of (cis)-4-hydroxy-N-(4-methoxybenzyl cyclohexanecarboxamide (0.83 g, 3.1 mmol) at 0° C. Stirring was continued with cooling for another 5 min, later the reaction was allowed to warm to rt and subsequently heated at 60° C. overnight. The reaction was cooled to rt and poured carefully to a stirred cold (0° C.) mixture of xs Na$_2$SO$_4$.10H$_2$O in DCM. The reaction was stirred for additional 2 h at rt and then filtered under vacuum. The solid was rinsed with DCM and the filtrate was concentrated under reduced pressure to give the desired material that was used without further purification (pale yellow oil, 0.79 g, quant). MS ESI [M+H]$^+$ 250.3, calcd for [C$_{15}$H$_{23}$NO$_2$+H]$^+$ 250.18.

Synthesis of 8-bromo-2-(methylthio)-N-((tetrahydro-2H-pyran-4-yl)methyl)pyrazolo[1,5-a][1,3,5]triazin-4-amine

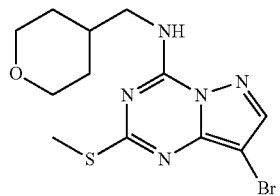 [SMILES: CSc1nc(NCC2CCOCC2)n2ncc(Br)c2n1]

The title compound was synthesized according to General Method A utilizing 8-bromo-4-chloro-2-(methylthio)pyrazolo[1,5-a][1,3,5]triazine (1.5 g, 5.4 mmol), 4-(aminomethyl)tetrahydro-2H-pyran hydrochloride (0.81 g, 534 mmol), and DIPEA (1.9 mL, 11 mmol) at 0° C.-rt for 1 h. The desired product was isolated as a beige solid (1.8 g, 95%) and was used without further purification. $^1$H NMR (400 MHz, CDCl$_3$) δ ppm 7.86 (s, 1H), 6.53 (br s, 1H), 4.01 (dd, J=11.3, 3.6 Hz, 2H), 3.58 (t, J=6.6 Hz, 2H), 3.41 (t, J=11.8 Hz, 2H), 2.61 (s, 3H), 1.94-2.00 (m, 1H), 1.68-1.73 (m, 2H), 1.38-1.49 (m, 2H); MS ESI [M+H]+ 358.2, calcd for [C$_{12}$H$_{16}$BrN$_5$OS+H]$^+$ 358.03.

Synthesis of (1r,4r)-4-(((4-methoxybenzyl)amino)methyl)cyclohexanol

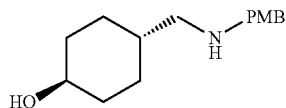

A sealed vial charged with (1r,4r)-4-hydroxycyclohexanecarboxylic acid (0.505 g, 3.20 mmol), (4-methoxyphenyl)methanamine (0.460 g, 3.35 mmol), 1H-1,2,4-trizole (44 mg, 0.2 mmol), DBU (0.100 g. 0.66 mmol) was heated with stirring at 70° C. for 3 d. The reaction was directly loaded a SiO$_2$ column and purified by flash chromatography (gradient: EtOAc/hex 0-30%) to afford (1r,4r)-4-hydroxy-N-(4-methoxybenzyl)-cyclohexanecarboxamide (705 mg, 84%) as white solid. $^1$H NMR (400 MHz, CD$_3$OD) δ ppm 7.19 (d, J=8.3 Hz, 2H), 6.87 (d, J=8.5 Hz, 2H), 4.28 (s, 2H), 3.77 (s, 3H), 3.57-3.46 (m, 1H), 2.20-2.09 (m, 1H), 2.05-1.94 (m, 2H), 1.90-1.80 (m, 2H), 1.62-1.49 (m, 2H), 1.33-1.19 (m, 2H); MS ESI [M+H]264.2, calcd for [C$_{12}$H$_{21}$NO$_3$+H]$^+$ 264.1.

A solution of the above (1r,4r)-4-hydroxy-N-(4-methoxybenzyl)cyclohexanecarboxamide (0.705 g, 2.7 mmol) in anh THF (30 mL) was treated with LiAlH$_4$ (1 M in THF, 8 mL, 8 mmol) at rt and then heated at reflux O/N under Ar. The reaction mixture was cooled to rt and added slowly to a stirred suspension of xs Na$_2$SO$_4$*10H$_2$O in DCM at 0° C. The reaction was stirred for 2 h then filtered and concentrated to provide the title compound (0.67 g, quantitative) as pale orange gum used without further purification. $^1$H NMR (400 MHz, CD$_3$OD) δ ppm 7.25 (d, J=8.53 Hz, 2H), 6.92-6.85 (d, J=8.8 Hz, 2H), 3.78 (s, 3H), 3.68 (s, 2H), 3.61-3.54 (m, 1H), 3.51-3.40 (m, 1H), 2.40 (d, J=6.8 Hz, 2H), 1.99-1.90 (m, 2H), 1.88-1.74 (m, 2H), 1.63-1.58 (m, 1H), 1.52-1.41 (m, 1H), 1.35-1.15 (m, 2H), 1.08-0.85 (m, 2H); MS ESI [M+H]$^+$ 250.2, calcd for [C$_{12}$H$_{23}$NO$_2$+H]$^+$ 250.2.

Synthesis of 3-bromo-5,7-dichloropyrazolo[1,5-a]pyrimidine

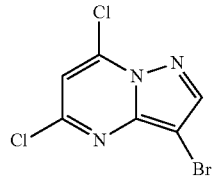 [SMILES: Clc1cc(Cl)n2ncc(Br)c2n1]

To a stirred solution of sodium ethoxide in EtOH, which was prepared from sodium (281.3 g, 12.0 mol) and EtOH (10 L) by the conventional method, were added diethyl malonate (963.7 g, 6.02 mol) at ambient temperature and then compound 1H-pyrazol-3-amine (500 g, 6.02 mol). The reaction mixture was refluxed for 12 hours. After cooled to room temperature, the precipitates were collected by filtration and dissolved in water. The aqueous solution was acidified with 2 M HCl (pH=2). The resulting precipitates were collected by filtration and dried under reduced pressure to afford pyrazolo[1,5-a]pyrimidine-5,7(4H,6H)-dione (649 g, 71%) as a yellow solid, which was used for the next reaction without further purification.

A stirred suspension of pyrazolo[1,5-a]pyrimidine-5,7(4H,6H)-dione (265 g, 1.75 mol) and N,N-dimethylaniline (335.6 mL) in POCl$_3$ (2.00 kg, 13.2 mol) was refluxed for 4 hours. After cooled to room temperature, the reaction mixture was poured into ice-water, and stirred for 30 min, neutralized with saturated aqueous sodium carbonate and extracted with EtOAc. The combined organic layers were washed with water, brine and dried over MgSO$_4$, filtered and evaporated. The residue was purified by column chromatography on silica gel (gradient: EtOAc/PE 1:10) to give 5,7-dichloropyrazolo[1,5-a]pyrimidine (287 g, 87%) as a yellow solid.

To a solution 5,7-dichloropyrazolo[1,5-a]pyrimidine (246.6 g, 1.31 mol) in CH$_3$CN (1.8 L) was added NBS (245 g, 1.38 mol). The resulting mixture was stirred at room temperature for 2 hours. After removal of the solution, the reaction mixture was purified by column chromatography on silica gel (gradient: EtOAc/PE 1:5) to give the title compound (313.5 g, 89%) as light yellow solid. $^1$H NMR (300 MHz, CDCl$_3$): δ 7.04 (s, 1H), 8.21 (s, 1H); MS ESI [M+H]$^+$ 265.9, calcd for [C$_6$H$_2$BrC$_2$N$_3$+H]$^+$ 265.9.

Synthesis of 3-bromo-5-chloro-N-((tetrahydro-2H-pyran-4-yl)methyl)pyrazolo[1,5-a]pyrimidin-7-amine

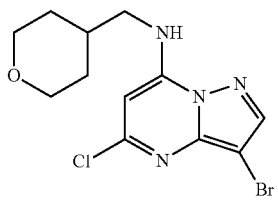

To a solution of 3-bromo-5,7-dichloropyrazolo[1,5-a]pyrimidine (2.67 g, 10 mmol) in DCM (30 mL) at 0° C. was added (tetrahydro-2H-pyran-4-yl)methan-amine (1.27 g, 11 mmol), followed by DIPEA (2.1 mL, 12 Br mmol). The resulting mixture was stirred at rt for 1 h and purified by flash chromatography (gradient: EtOAc/hex 0-90%) to give the title compound as white solid (3.46 g, quantitative yield). $^1$H NMR (400 MHz, CDCl$_3$) δ ppm 7.96 (s, 1H), 6.55-6.43 (m, 1H), 6.00 (s, 1H), 4.08-4.00 (m, 2H), 3.43 (dt, J=12.0, 1.7 Hz, 2H), 3.32 (t, J=6.6 Hz, 2H), 2.06-1.94 (m, 1H), 1.78-1.71 (m, 2H), 1.51-1.38 (m, 2H); MS ESI [M+H]$^+$ 345.1, calcd for [C$_{12}$H$_{14}$BrClN$_4$O+H]$^+$ 344.9.

The following intermediates were synthesized according to General Method A:

| IUPAC name | Structure | MS calcd; MS ESI [M + H]$^+$ | Yield; Appearance; Salt form |
|---|---|---|---|
| 8-bromo-2-(methylthio)-N-(2-morpholinoethyl)pyrazolo[1,5-a][1,3,5]triazin-4-amine | 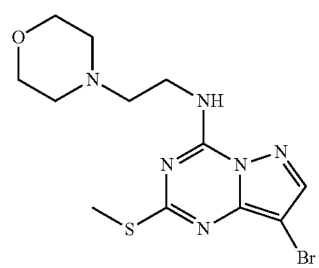 [SMILES: CSc1nc(NCCN2CCOCC2)n2ncc(Br)c2n1] | [C$_{12}$H$_{17}$BrN$_6$OS + H]$^+$ 373.0; 372.8 | 1.108 g (88%); white solid; free base |

SMs: 8-bromo-4-chloro-2-(methylthio)pyrazolo[1,5-a][1,3,5]triazine (945 mmol, 3.37 mmol), 2-morpholinoethanamine (0.47 ml, 3.61 mmol).

$^1$H NMR (400 MHz, CDCl$_3$) δ 7.87 (s, 1H), 7.05 (s, 1H), 3.85-3.65 (m, 6H), 2.75-2.55 (m, 9H).

| IUPAC name | Structure | MS calcd; MS ESI [M + H]$^+$ | Yield; Appearance; Salt form |
|---|---|---|---|
| 8-bromo-2-(methylthio)-N-(3-morpholinopropyl)pyrazolo[1,5-a][1,3,5]triazin-4-amine | | [C$_{13}$H$_{19}$BrN$_6$OS + H]$^+$ 387.1; 387.1 | 3.47 g (100%); white solid; free base |

SMs: 8-bromo-4-chloro-2-(methylthio)pyrazolo[1,5-a][1,3,5]triazine (2.5 g, 8..94 mmol), 3-morpholinopropan-1-amine (1.31 mL, 8.94 mmol).

$^1$H NMR (400 MHz, CDCl$_3$) δ ppm 9.11 (br. s., 1H), 7.85 (d, J = 0.8 Hz, 1H), 3.90 (t, J = 4.5 Hz, 4H), 3.72-3.80 (m, 2H), 2.58-2.66 (m, 5H), 2.54 (br. s., 4H), 1.80-1.91 (m, 2H).

| IUPAC name | Structure | MS calcd; MS ESI [M + H]+ | Yield; Appearance; Salt form |
|---|---|---|---|
| (cis)-4-(((8-bromo-2-(methylthio)pyrazolo[1,5-a][1,3,5]triazin-4-yl)(4-methoxybenzyl)amino)methyl)cyclohexanol | | $[C_{21}H_{26}BrN_5O_2S + H]^+$ 492.1; 492.1 | 0.39 g (64%); white foam; free base |

SMs: 8-bromo-4-chloro-2-(methylthio)pyrazolo[1,5-a][1,3,5]triazine (0.343 g, 1.23 mmol), (cis)-4-(((4-methoxybenzyl)amino)methyl)cyclohexanol (0.31 g, 1.24 mmol), DIPEA (0.22 mL, 1.24 mmol).
$^1$H NMR (400 MHz, CDCl$_3$) δ ppm 7.84 (s, 1H), 7.18 (d, J = 8.28 Hz, 2H), 6.85 (d, J = 8.53 Hz, 2H), 5.01-5.62 (br.s, 2H), 4.01 (br. s., 1H), 3.65-3.98 (br.s, 2H), 3.80 (s, 3H), 2.57 (s, 3H), 1.85-1.99 (m, 1H), 1.69-1.80 (m, 2H), 1.42-1.67 (m, 6H).

| 3-bromo-5-chloro-N-(2-methoxyethyl)pyrazolo[1,5-a]pyrimidin-7-amine | | $[C_9H_{10}BrClN_4O + H]^+$ 305.0; 304.9 | 2.94 (96%); white solid; free base |

SMs: 3-bromo-5,7-dichloropyrazolo[1,5-a]pyrimidine (2.67 g, 10 mmol), 2-methoxyethanamine (1.9 mL, 21 mmol).
$^1$H NMR (400 MHz, CDCl$_3$) δ ppm 7.98 (s, 1H), 6.70 (br, s, 1H), 6.02 (s, 1H), 3.69 (t, J = 5.2 Hz, 2H), 3.58 (t, J = 5.2 Hz, 2H), 3.44 (s, 3H).

| 3-bromo-5-chloro-N-(2-morpholinoethyl)pyrazolo[1,5-a]pyrimidin-7-amine | | $[C_{12}H_{15}BrClN_5O + H]^+$ 360.0; 359.9 | 3.21 g (89%); white solid; free base |

SMs: 3-bromo-5,7-dichloropyrazolo[1,5-a]pyrimidine (2.67 g, 10 mmol), 2-morpholinoethanamine (1.45 mL, 11 mmol), DIPEA (2.1 mL, 12 mmol).
$^1$H NMR (400 MHz, CDCl$_3$) δ ppm 7.98 (s, 1H), 7.02-7.08 (m, 1H), 5.97 (s, 1H), 3.77 (t, J = 4.6 Hz, 2H), 3.47-3.42 (m, 4H), 2.77 (t, J = 5.8 Hz, 2H), 2.55 (t, J = 4.2 Hz, 4H).

| 3-bromo-5-chloro-N-(3-morpholinopropyl)pyrazolo[1,5-a]pyrimidin-7-amine | | $[C_{13}H_{17}BrClN_5O + H]^+$ 376.0; 376.0 | 530 mg (75%); white solid; free base |

SMs: 3-bromo-5,7-dichloropyrazolo[1,5-a]pyrimidine (500 mg, 1.873 mmol), 3-morpholinopropan-1-amine (540 mg, 3.745 mmol).
$^1$H NMR (400 MHz, CDCl$_3$) δ ppm 8.97 (br, s, 1H), 7.97 (s, 1H), 5.93 (s, 1H), 3.92 (t, J = 4.6 Hz, 4H), 3.56-3.40 (m, 2H), 2.69-2.61 (m, 2H), 2.55 (br, s, 4H), 2.00-1.87 (m, 2H).

| IUPAC name | Structure | MS calcd;<br>MS ESI<br>[M + H]⁺ | Yield;<br>Appearance;<br>Salt form |
|---|---|---|---|
| 3-bromo-5-chloro-N-(2-(tetrahydro-2H-pyran-4-yl)ethyl)pyrazolo[1,5-a]pyrimidin-7-amine | 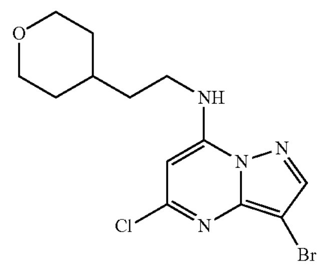 [SMILES: Clc1cc(NCCC2CCOCC2)n2ncc(Br)c2n1] | [C₁₃H₁₆BrClN₄O + H]⁺<br>361.0;<br>361.1 | 662 mg (98%);<br>white solid;<br>free base |

SMs: 3-bromo-5,7-dichloropyrazolo[1,5-a]pyrimidine (500 mg, 1.873 mmol), 2-(tetrahydro-2H-pyran-4-yl)ethanamine (266 mg, 2.06 mmol), DIPEA (0.37 mL, 2.25 mmol).
¹H NMR (400 MHz, CDCl₃) δ ppm 7.97 (s, 1H), 6.34 (br, s, 1H), 5.99 (s, 1H), 4.00 (dd, J = 11.2, 4.4 Hz, 2H), 3.52-3.34 (m, 4H), 1.77-1.63 (m, 5H), 1.48-1.33 (m, 2H).

| 3-bromo-5-chloro-N-isobutyl-pyrazolo[1,5-a]pyrimidin-7-amine | | [C₁₀H₁₂BrClN₄ + H]⁺<br>303.0;<br>303.0 | 1.10 g (96%);<br>clear oil;<br>free base |
|---|---|---|---|

SMs: 3-bromo-5,7-dichloropyrazolo[1,5-a]pyrimidine (1 g, 3.8 mmol), isobutylamine (304 mg, 4.2 mmol), DIPEA (1.44 mL, 8.34 mmol).
¹H NMR (400 MHz, CDCl₃) δ ppm 7.96 (s, 1H), 6.47 (br, s, 1H), 5.99 (s, 1H), 3.26-3.16 (m, 2H), 2.12-1.98 (m, 1H), 1.07 (d, J = 6.5 Hz, 6H).

| 1-((3-bromo-5-chloropyrazolo[1,5-a]pyrimidin-7-yl)amino)-2-methylpropan-2-ol | | [C₁₀H₁₂BrClN₄O + H]⁺<br>319.0;<br>319.0 | 910 mg (76%);<br>white solid;<br>free base |
|---|---|---|---|

SMs: 3-bromo-5,7-dichloropyrazolo[1,5-a]pyrimidine (1 g, 3.8 mmol), 1-amino-2-methylpropan-2-ol (371 mg, 4.2 mmol), DIPEA (1.3 mL, 7.56 mmol).
¹H NMR (400 MHz, CDCl₃) δ ppm 7.98 (s, 1H), 6.80 (br, s, 1H), 6.04 (s, 1H), 3.36 (d, J = 6.0 Hz, 2H), 1.61 (s, 1H), 1.39 (s, 6H).

| (1r,4r)-4-(((3-bromo-5-chloropyrazolo[1,5-a]pyrimidin-7-yl)(4-methoxybenzyl)amino)methyl)cyclohexanol | | [C₂₁H₂₄BrClN₄O₂ + H]⁺<br>479.1/481.1;<br>479.0/481.0 | 0.36 g (84%);<br>white solid;<br>free base |
|---|---|---|---|

SMs: 3-bromo-5,7-dichloropyrazolo[1,5-a]pyrimidine (239 g, 0.89 mmol), (1r,4r)-4-(((4-methoxybenzyl)amino)methyl)cyclohexanol (223 mg, 0.89 mmol).
¹H NMR (400 MHz, CDCl₃) δ ppm 8.01 (s, 1H), 7.12 (d, J = 8.28 Hz, 2H), 6.86 (d, J = 8.53 Hz, 2H), 6.02 (s, 1H), 5.05 (s, 2H), 3.80 (s, 3H), 3.59 (d, J = 6.78 Hz, 2H), 3.57-3.46 (m, 1H), 2.02-1.91 (m, 2H), 1.84-1.70 (m, 2H), 1.37 (d, J = 4.52 Hz, 1H), 1.31-1.15 (m, 2H), 1.05-0.90 (m, 2H).

| IUPAC name | Structure | MS calcd; MS ESI [M + H]⁺ | Yield; Appearance; Salt form |
|---|---|---|---|
| 3-bromo-5-chloro-N-(cyclopropylmethyl)pyrazolo[1,5-a]pyrimidin-7-amine | 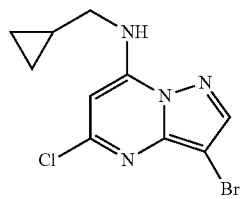 [SMILES: Clc1cc(NCC2CC2)n2ncc(Br)c2n1] | [$C_{10}H_{10}BrClN_4$ + H]⁺ 301.0; 301.0 | 5.3 g (92%); yellow solid; free base |

SMs: 3-bromo-5,7-dichloropyrazolo[1,5-a]pyrimidine (5.0 g, 19 mmol), cyclopropylmethanamine (1.5 g, 21 mmol), and DIPEA (6.6 mL 38 mmol).
¹H NMR (400 MHz, CDCl₃) δ ppm 7.97 (s, 1H), 6.50 (br. s, 1H), 5.97 (s, 1H), 3.25 (dd, J = 7.3, 5.5 Hz, 2H), 1.26-1.13 (m, 1H), 0.74-0.65 (m, 2H), 0.37 (q, J = 5.0 Hz, 2H).

| IUPAC name | Structure | MS calcd; MS ESI [M + H]⁺ | Yield; Appearance; Salt form |
|---|---|---|---|
| (1s,3s)-3-(((3-bromo-5-chloropyrazolo[1,5-a]pyrimidin-7-yl)amino)methyl)-1-methylcyclobutanol | 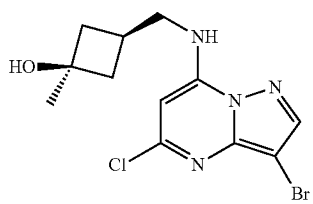 [SMILES: C[C@]1(O)C[C@@H](CNc2cc(Cl)nc3c(Br)cnn23)C1] | [$C_{12}H_{14}BrClN_4O$ + H]⁺ 345.0; 345.1 | 6.1 g (94%); yellow solid; free base |

SMs: 3-bromo-5,7-dichloropyrazolo[1,5-a]pyrimidine (5.0 g, 19 mmol), cis-hydroxy-3-methylcyclobutane-1-methylamine (2.4 g, 21 mmol), and DIPEA (6.6 mL, 38 mmol).
¹H NMR (400 MHz, CDCl₃) δ ppm 7.96 (s, 1H), 6.60-6.49 (m, 1H), 5.99 (s, 1H), 3.47 (t, J = 6.0 Hz, 2H), 2.38-2.27 (m, 3H), 1.96-1.85 (m, 2H), 1.43 (s, 3H).

| IUPAC name | Structure | MS calcd; MS ESI [M + H]⁺ | Yield; Appearance; Salt form |
|---|---|---|---|
| tert-butyl 4-(((3-bromo-5-chloropyrazolo[1,5-a]pyrimidin-7-yl)amino)methyl)-4-fluoropiperidine-1-carboxylate | 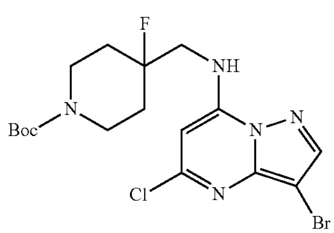 [SMILES: CC(C)(C)OC(=O)N1CCC(F)(CNc2cc(Cl)nc3c(Br)cnn23)CC1] | [$C_{17}H_{22}BrClFN_5O_2$ + H]⁺ 462.1; 462.1 | 6.0 g (100%); yellow solid; free base |

SMs: 3-bromo-5,7-dichloropyrazolo[1,5-a]pyrimidine (3.45 g, 12.9 mmol), tert-butyl 4-(aminomethyl)-4-fluoropiperidine-1-carboxylate (3.0 g, 12.9 mmol), and DIPEA (4.5 mL, 25.8 mmol).
¹H NMR (400 MHz, CDCl₃) δ ppm 8.00 (s, 1H), 6.68 (s, 1H), 6.06 (s, 1H), 4.19-3.93 (m, 2H), 3.58 (d, J = 6.5 Hz, 1H), 3.53 (d, J = 6.5 Hz, 1H), 3.10 (br. s., 2H), 2.04-1.90 (m, 2H), 1.77-1.62 (m, 2H), 1.48 (s, 9H).

| IUPAC name | Structure | MS calcd; MS ESI [M + H]⁺ | Yield; Appearance; Salt form |
|---|---|---|---|
| (R)-3-bromo-5-chloro-N-((tetrahydrofuran-3-yl)methyl)pyrazolo[1,5-a]pyrimidin-7-amine | 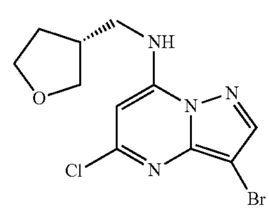 [SMILES: Clc1cc(NC[C@H]2CCOC2)n2ncc(Br)c2n1] | [$C_{11}H_{12}BrClN_4O$ + H]⁺ 331.0; 330.9 | 13.6 g (91.3%); light yellow solid; free base |

SMs: 3-bromo-5,7-dichloropyrazolo[1,5-a]pyrimidine (12 g, 45 mmol), (R)-(tetrahydrofuran-3-yl)methanamine (5 g, 49.5 mmol), DIPEA (8.9 mL, 54 mmol), DCM (150 mL).
¹H NMR (400 MHz, CDCl₃) δ ppm 7.98 (s, 1H), 6.57 (br. s., 1H), 6.02 (s, 1H), 4.01 (td, J = 8.4, 5.3 Hz, 1H), 3.87 (dd, J = 9.2, 6.7 Hz, 1H), 3.84-3.77 (m, 1H), 3.73 (dd, J = 9.0, 4.3 Hz, 1H), 3.44-3.39 (m, 2H), 2.77-2.65 (m, 1H), 2.29-2.15 (m, 1H), 1.80-1.69 (m, 1H).

| IUPAC name | Structure | MS calcd; MS ESI [M + H]+ | Yield; Appearance; Salt form |
|---|---|---|---|
| (S)-3-bromo-5-chloro-N-((tetrahydrofuran-3-yl)methyl)pyrazolo[1,5-a]pyrimidin-7-amine | 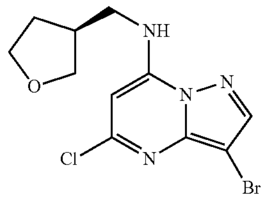 [SMILES: Clc1cc(NC[C@@H]2CCOC2)n2ncc(Br)c2n1] | $[C_{11}H_{12}BrClN_4O + H]^+$ 331.0; 331.1 | 8.05 g (92.5%); light yellow solid; free base |
| | SMs: 3-bromo-5,7-dichloropyrazolo[1,5-a]pyrimidine (7 g, 26 mmol), (S)-(tetrahydrofuran-3-yl)methanamine (2.92 g, 28 mmol), DIPEA (5.71 mL, 32 mmol), DCM (56 mL).<br>$^1$H NMR identical to (R)-isomer | | |
| 3-bromo-5-chloro-N-((1-methylpiperidin-4-yl)methyl)pyrazolo[1,5-a]pyrimidin-7-amine | 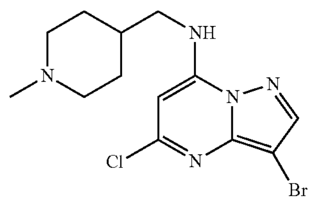 [SMILES: CN1CCC(CNc2cc(Cl)nc3c(Br)cnn23)CC1] | $[C_{13}H_{17}BrClN_5 + H]^+$ 358.0; 358.0 | 0.534 g, (78%); pale yellow foam; free base |
| | SMs: (1-methylpiperidin-4-yl)methanamine (0.247 g, 1.9 mmol), 3-bromo-5,7-dichloropyrazolo[1,5-a]pyrimidine (0.516 g, 1.9 mmol)<br>$^1$H NMR (400 MHz, CDCl$_3$) δ ppm 7.91 (s, 1H), 6.58 (t, J = 5.9 Hz, 1H), 5.95 (s, 1H), 3.30 (t, J = 6.40 Hz, 2H), 2.99 (d, J = 11.8 Hz, 2H), 2.35 (s, 3H), 2.08 (td, J = 11.9, 2.0 Hz, 2H), 1.86-1.79 (m, 2H), 1.79-1.67 (m, 1H), 1.58-1.47 (m, 2H) | | |
| 3-bromo-5-chloro-N-(2-(4-fluoropiperidin-1-yl)ethyl)pyrazolo[1,5-a]pyrimidin-7-amine | 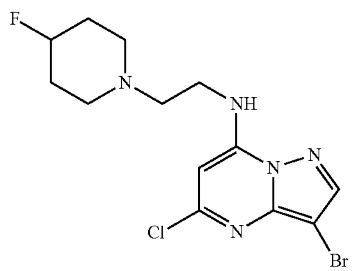 [SMILES: FC1CCN(CCNc2cc(Cl)nc3c(Br)cnn23)CC1] | $[C_{13}H_{16}BrClFN_5 + H]^+$ 376.0; 376.1 | 0.79 g, (68%); pale solid; free base |
| | SMs: 3-bromo-5,7-dichloropyrazolo[1,5-a]pyrimidine (0.92 g, 3.4 mmol), 2-(4-fluoropiperidin-1-yl)ethanamine (0.46 g, 3.1 mmol)<br>$^1$H NMR (400 MHz, CDCl$_3$) δ ppm 7.98 (s, 1H), 7.08 (br. s., 1H), 5.97 (s, 1H), 5.05-4.52 (m, 1H), 3.47-3.36 (m, 2H), 2.82-2.72 (m, 2H), 2.72-2.58 (m, 2H), 2.57-2.43 (m, 2H), 2.05-1.86 (m, 4H) | | |

Synthesis of 8-bromo-N-(4-methoxybenzyl)-2-(methylthio)-N-((tetrahydro-2H-pyran-4-yl)methyl)pyrazolo[1,5-a][1,3,5]triazin-4-amine

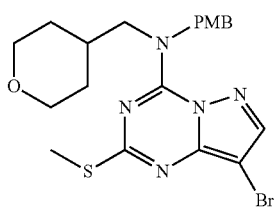

The title compound was synthesized according to General Method B2 utilizing 8-bromo-2-(methylthio)-N-((tetrahydro-2H-pyran-4-yl)methyl)pyrazolo[1,5-a][1,3,5]triazin-4-amine (1.8 g, 5.1 mmol), 4-methoxybenzyl chloride (0.83 mL, 6.1 mmol), K$_2$CO$_3$ (1.4 g, 10.1 mmol) and DMF (14 mL) at 60° C. for 4 h. The crude product was purified by flash chromatography (SiO$_2$, 0-50% EtOAc/DCM) to give the desired product as a white solid (2.2 g, 89%). $^1$H NMR (400 MHz, CDCl$_3$) δ ppm 7.84 (s, 1H), 7.20 (d, J=8.3 Hz, 2H), 6.86 (d, J=8.8 Hz, 2H), 5.31 (br. s., 2H), 3.96 (dd, J=11.7, 2.9 Hz, 3H), 3.73-3.86 (m, 3H), 3.25-3.41 (m, 2H), 2.57 (s, 3H), 2.01-2.20 (m, 1H), 1.57-1.61 (m, 3H), 1.32-1.47 (m, 2H); MS ESI [M+H]$^+$ 480.3, calcd for $[C_{20}H_{24}BrN_5O_2S+H]^+$ 480.08.

Synthesis of tert-butyl(3-bromo-5-chloropyrazolo[1,5-a]pyrimidin-7-yl)((tetrahydro-2H-pyran-4-yl)methyl)carbamate

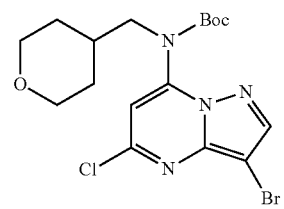 [SMILES: CC(C)(C)OC(=O)N(CC1CCOCC1)c1cc(Cl)nc2c(Br)cnn12]

To a solution of 3-bromo-5-chloro-N-((tetrahydro-2H-pyran-4-yl)methyl)pyrazolo [1,5-a]pyrimidin-7-amine (3.46 g, 10 mmol) in DCM (40 mL) was added Boc$_2$O (1.91 g, 8.8 mmol), followed by Et$_3$N (1.7 mL, 12 mmol) and DMAP (122 mg, 1 mmol). The resulting mixture was stirred at rt for 2 h. Additional Boc$_2$O (348 mg, 1.6 mmol) and Et$_3$N (0.28 mL, 2 mmol) were added and the mixture was stirred at rt for 1 h. After removal of solvents, it was purified by flash chromatography (gradient: EtOAc/hex 0-50%) to give the title compound as pale yellow foam (4.51 g, quantitative) after drying. $^1$H NMR (400 MHz, CDCl$_3$) δ ppm 8.11 (s, 1H), 6.75 (s, 1H), 3.96-3.86 (m, 2H), 3.71 (d, J=6.8 Hz, 2H), 3.29 (t, J=11.4 Hz, 2H), 1.85-1.73 (m, 1H), 1.67-1.58 (m, 2H), 1.45-1.25 (m, 11H; s, 9H at 1.34); MS ESI [M+H]$^+$ 445.0, calcd for [C$_{17}$H$_{22}$BrClN$_4$O$_3$+H]$^+$ 445.1.

The following intermediates were synthesized according to General Method B2:

| IUPAC name | Structure | MS calcd; MS ESI [M + H]$^+$ | Yield; Appearance; Salt form |
|---|---|---|---|
| 8-bromo-N-(4-methoxybenzyl)-2-(methylthio)-N-(2-morpholinoethyl)pyrazolo[1,5-a][1,3,5]triazin-4-amine | 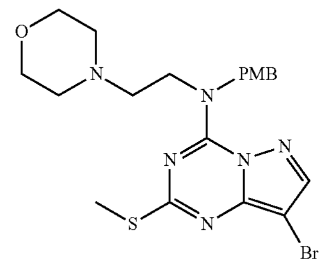 | [C$_{20}$H$_{25}$BrN$_6$O$_2$S + H]$^+$ 493.1; 493.7 | 1.10 g (75%); colorless oil; free base |

SMs: 8-bromo-2-(methylthio)-N-(2-morpholinoethyl)pyrazolo[1,5-a][1,3,5]triazin-4-amine (1.010 g, 3 mmol), 4-methoxybenzyl chloride (0.5 ml, 3.6 mmol).
$^1$H NMR (400 MHz, DMSO-d6) δ 8.10 (s, 1H), 7.25 (d, J = 8.4 Hz, 2H), 6.85 (d, J = 8.8 Hz, 2H), 5.35-5.10 (m, 2H), 4.10-3.90 (m, 2H), 3.69 (s, 3H), 3.47-3.35 (m, 7H), 2.54 (t, J = 6.4 Hz, 2H), 2.37-2.26 (m, 4H).

| 8-bromo-N-(4-methoxybenzyl)-2-(methylthio)-N-(3-morpholinopropyl)pyrazolo[1,5-a][1,3,5]triazin-4-amine | | [C$_{21}$H$_{27}$BrN$_6$O$_2$S + H]$^+$ 507.1; 507.8 | 3.25 g (84%); white solid; free base |

SMs: 8-bromo-2-(methylthio)-N-(3-morpholinopropyl)pyrazolo[1,5-a][1,3,5]triazin-4-amine (2.95 g, 7.64 mmol), 4-methoxybenzyl chloride (1.27 mL, 9.17 mmol).
$^1$H NMR (400 MHz, DMSO-d6) δ 7.82 (s, 1H), 7.25 (d, J = 8.5 Hz, 2H), 6.87 (d, J = 8.5 Hz, 2H), 5.06-5.47 (br, s, 2H), 3.98 (br. s., 2H), 3.81 (s, 3H), 3.70 (d, J = 4.3 Hz, 4H), 2.57 (s, 3H), 2.31-2.45 (m, 6H), 1.83-1.94 (m, 2H).

The following intermediates were synthesized according to General Method B:

| IUPAC name | Structure | MS calcd; MS ESI [M + H]$^+$ | Yield; Appearance; Salt form |
|---|---|---|---|
| tert-butyl (3-bromo-5-chloropyrazolo[1,5-a]pyrimidin-7-yl)(2-methoxyethyl)carbamate | 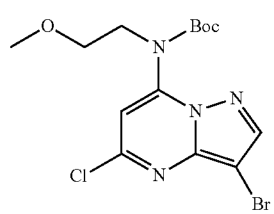 [SMILES: COCCN(C(=O)OC(C)(C)C)c1cc(Cl)nc2c(Br)cnn12] | [C$_{14}$H$_{18}$BrClN$_4$O$_3$ + H]$^+$ 405.0; 404.9 | 4.98 g (90%); light yellow solid; free base |

SMs: 3-bromo-5-chloro-N-(2-methoxyethyl)pyrazolo[1,5-a]pyrimidin-7-amine (4.19 g, 13.7 mmol)
Boc$_2$O (2.89 g, 13.3 mmol), DMAP (171 mg, 1.4 mmol).
$^1$H NMR (400 MHz, CDCl$_3$) δ ppm 8.11 (s, 1H), 6.95 (s, 1H), 3.96 (t, J = 5.0 Hz, 2H), 3.59 (t, J = 5.0 Hz, 2H), 3.22 (s, 3H), 1.37 (s, 9H).

| IUPAC name | Structure | MS calcd; MS ESI [M + H]$^+$ | Yield; Appearance; Salt form |
|---|---|---|---|
| tert-butyl (3-bromo-5-chloropyrazolo[1,5-a]pyrimidin-7-yl)(2-morpholinoethyl)carbamate | 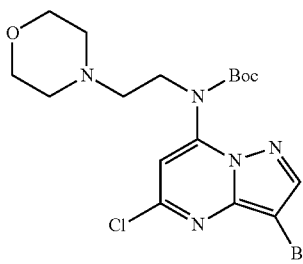 | [C$_{17}$H$_{23}$BrClN$_5$O$_3$ + H]$^+$ 460.0; 460.8 | 3.59 g (88%); off white solid; free base |

SMs: 3-bromo-5-chloro-N-(2-morpholinoethyl)pyrazolo[1,5-a]pyrimidin-7-amine (3.21 g, 8.9 mmol), Boc$_2$O (1.91 g, 8.8 mmol), DMAP (110 mg, 0.9 mmol).
$^1$H NMR (400 MHz, CDCl$_3$) δ ppm 8.08 (s, 1H), 6.90 (s, 1H), 3.94 (t, J = 5.6 Hz, 2H), 3.30-3.22 (m, 4H), 2.54 (t, J = 5.6 Hz, 2H), 2.24 (t, J = 4.4 Hz, 4H), 1.36 (s, 9H).

| IUPAC name | Structure | MS calcd; MS ESI [M + H]$^+$ | Yield; Appearance; Salt form |
|---|---|---|---|
| tert-butyl (3-bromo-5-chloropyrazolo[1,5-a]pyrimidin-7-yl)(3-morpholinopropyl)carbamate | 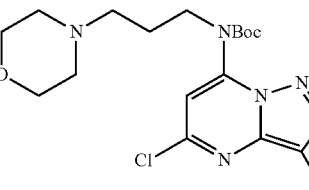 | [C$_{18}$H$_{25}$BrClN$_5$O$_3$ + H]$^+$ 474.1; 474.9 | 626 mg (94%); pale yellow solid; free base |

SMs: 3-bromo-5-chloro-N-(3-morpholinopropyl)pyrazolo[1,5-a]pyrimidin-7-amine (530 mg, 1.41 mmol), Boc$_2$O (368 mg, 2.11 mmol), DMAP (17 mg, 0.14 mmol), Et$_3$N (0.24 mL, 1.69 mmol).
$^1$H NMR (400 MHz, CDCl$_3$) δ ppm 8.11 (s, 1H), 7.27 (s, 1H), 6.83 (s, 1H), 3.88 (t, J = 7.3 Hz, 2H), 3.59 (t, J = 4.4 Hz, 4H), 2.34 (t, J = 6.9 Hz, 2H), 2.30-2.24 (m, 3H), 1.81 (quint, J = 7.2 Hz, 2H), 1.38 (s, 9H).

| IUPAC name | Structure | MS calcd; MS ESI [M + H]$^+$ | Yield; Appearance; Salt form |
|---|---|---|---|
| tert-butyl (3-bromo-5-chloropyrazolo[1,5-a]pyrimidin-7-yl)(3-morpholinopropyl)carbamate | 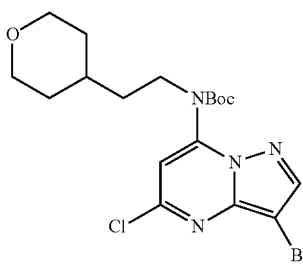 | [C$_{18}$H$_{24}$BrClN$_4$O$_3$ + H]$^+$ 459.0; 459.3 | 800 mg (95%); yellow solid; free base |

SMs: 3-bromo-5-chloro-N-(2-(tetrahydro-2H-pyran-4-yl)ethyl)pyrazolo[1,5-a]pyrimidin-7-amine (662 mg, 1.83 mmol), Boc$_2$O (480 mg, 2.21 mmol), DMAP (22 mg, 0.18 mmol), Et$_3$N (0.3 mL, 2.2 mmol).
$^1$H NMR (400 MHz, CDCl$_3$) δ ppm 8.12 (s, 1H), 6.76 (s, 1H), 3.93 (dd, J = 11.2, 3.6 Hz, 2H), 3.88-3.81 (m, 2H), 3.34 (t, J = 11.0 Hz, 2H), 1.62-1.47 (m, 5H), 1.38 (s, 9H), 1.34-1.21 (m, 2H).

| IUPAC name | Structure | MS calcd; MS ESI [M + H]$^+$ | Yield; Appearance; Salt form |
|---|---|---|---|
| tert-butyl (3-bromo-5-chloropyrazolo[1,5-a]pyrimidin-7-yl)(isobutyl)carbamate | 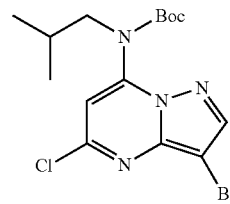 | [C$_{15}$H$_{20}$BrClN$_4$O$_2$ + H]$^+$ 403.0; 403.0 | 1.19 g (81%); white solid; free base |

SMs: 3-bromo-5-chloro-N-isobutylpyrazolo[1,5-a]pyrimidin-7-amine (1.10 g, 3.64 mmol), Boc$_2$O (869 mg, 4.01 mmol), DMAP (44 mg, 0.36 mmol), TEA (0.61 mL, 4.37 mmol).
$^1$H NMR (400 MHz, CDCl$_3$) δ ppm 8.12 (s, 1H), 6.76 (s, 1H), 3.65 (d, J = 7.3 Hz, 2H), 1.87-1.75 (m, 1H), 1.36 (s, 9H), 0.91 (d, J = 6.8 Hz, 6H).

| IUPAC name | Structure | MS calcd;<br>MS ESI<br>[M + H]+ | Yield;<br>Appearance;<br>Salt form |
|---|---|---|---|
| tert-butyl (3-bromo-5-chloropyrazolo[1,5-a]pyrimidin-7-yl)(2-((tert-butoxycarbonyl)oxy)-2-methylpropyl)carbamate | 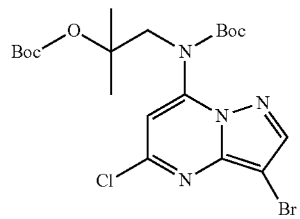 [SMILES: CC(C)(C)OC(=O)OC(C)(C)CN(C(=O)OC(C)(C)C)c1cc(Cl)nc2c(Br)cnn12] | $[C_{20}H_{28}BrClN_4O_5 + H]^+$<br>519.0;<br>519.0 | 809 mg (67%);<br>white solid;<br>free base |

SMs: 1-((3-bromo-5-chloropyrazolo[1,5-a]pyrimidin-7-yl)amino)-2-methylpropan-2-ol (744 mg, 2.34 mmol), Boc$_2$O (869 mg, 4.01 mmol), DMAP (44 mg, 0.36 mmol), TEA (0.65 mL, 4.67 mmol).

$^1$H NMR (400 MHz, CDCl$_3$) δ ppm 8.11 (s, 1H), 6.83 (s, 1H), 4.06 (s, 2H), 1.56 (s, 6H), 1.33 (s, 9H), 1.22 (s, 9H).

| IUPAC name | Structure | MS calcd;<br>MS ESI<br>[M + H]+ | Yield;<br>Appearance;<br>Salt form |
|---|---|---|---|
| tert-butyl (3-bromo-5-chloropyrazolo[1,5-a]pyrimidin-7-yl)(cyclopropylmethyl)carbamate | 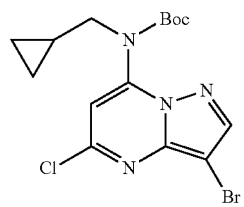 [SMILES: CC(C)(C)OC(=O)N(CC1CC1)c1cc(Cl)nc2c(Br)cnn12] | $[C_{15}H_{18}BrClN_4O_2—C_4H_8]^+$<br>345.0;<br>345.0 | 6.24 g (89%);<br>yellow solid;<br>free base |

SMs: 3-bromo-5-chloro-N-(cyclopropylmethyl)pyrazolo[1,5-a]pyrimidin-7-amine (5.25 g, 17.5 mmol), Boc$_2$O (5.70 g, 26.2 mmol), DMAP (0.21 g, 1.75 mmol), and TEA (7.3 mL, 52.5 mmol).

$^1$H NMR (400 MHz, CDCl$_3$) δ ppm 8.12 (s, 1H), 6.85 (s, 1H), 3.72 (d, J = 7.3 Hz, 2H), 1.39 (s, 9H), 1.05-0.94 (m, 1H), 0.46-0.37 (m, 2 H) 0.13-0.03 (m, 2H).

| IUPAC name | Structure | MS calcd;<br>MS ESI<br>[M + H]+ | Yield;<br>Appearance;<br>Salt form |
|---|---|---|---|
| tert-butyl (3-bromo-5-chloropyrazolo[1,5-a]pyrimidin-7-yl)(((1s,3s)-3-((tert-butoxycarbonyl)oxy)-3-methylcyclobutyl)methyl)carbamate | 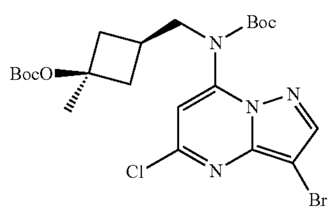 | $[C_{22}H_{30}BrClN_4O_5 + H]^+$<br>545.1;<br>545.1 | 0.90 g (40%);<br>white solid;<br>free base |

SMs: (1s,3s)-3-(((3-bromo-5-chloropyrazolo[1,5-a]pyrimidin-7-yl)amino)methyl)-1-methylcyclobutanol (1.44 g, 4.2 mmol), Boc$_2$O (2.2 g, 10.5 mmol), DMAP (0.10 g, 0.84 mmol), and TEA (1.75 mL, 12.6 mmol).

$^1$H NMR (400 MHz, CDCl$_3$) δ ppm 8.11 (s, 1H), 6.74 (s, 1H), 3.88 (d, J = 6.5 Hz, 2H), 2.17 (s, 3H), 1.99-1.88 (m, 2H), 1.47 (s, 3H), 1.45 (s, 9H), 1.35 (s, 9H).

| IUPAC name | Structure | MS calcd;<br>MS ESI<br>[M + H]+ | Yield;<br>Appearance;<br>Salt form |
|---|---|---|---|
| tert-butyl 4-(((3-bromo-5-chloropyrazolo[1,5-a]pyrimidin-7-yl)(tert-butoxycarbonyl)amino)methyl)-4-fluoropiperidine-1-carboxylate | 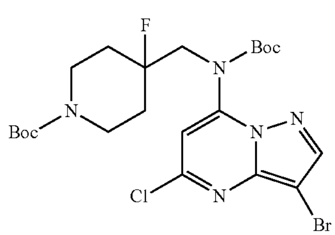 [SMILES: CC(C)(C)OC(=O)N1CCC(F)(CN(C(=O)OC(C)(C)C)c2cc(Cl)nc3c(Br)cnn23)CC1] | $[C_{22}H_{30}BrClFN_5O_4 + H]^+$<br>508.1;<br>508.1 | 7.0 g (97%);<br>yellow solid;<br>free base |

SMs: tert-butyl 4-(((3-bromo-5-chloropyrazolo[1,5-a]pyrimidin-7-yl)amino)methyl)-4-fluoropiperidine-1-carboxylate (6.0 g, 12.9 mmol), Boc$_2$O (4.36 g, 20.0 mmol), DMAP (0.33 g, 2.66 mmol), and DIPEA (4.7 mL, 26.6 mmol).

$^1$H NMR (400 MHz, CDCl$_3$) δ ppm 8.12 (s, 1H), 6.84 (s, 1H), 4.14-3.84 (m, 4H), 3.09-2.88 (m, 2H), 2.02-1.86 (m, 2H), 1.79-1.61 (m, 2H), 1.47 (s, 9H), 1.33 (s, 9H).

| IUPAC name | Structure | MS calcd; MS ESI [M + H]⁺ | Yield; Appearance; Salt form |
|---|---|---|---|
| (R)-tert-butyl (3-bromo-5-chloropyrazolo[1,5-a]pyrimidin-7-yl)((tetrahydrofuran-3-yl)methyl)carbamate | 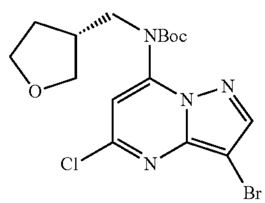 [SMILES: CC(C)(C)OC(=O)N(C[C@H]1CCOC1)c1cc(Cl)nc2c(Br)cnn12] | $[C_{16}H_{20}BrClN_4O_3 + H—Boc]^+$ 331.0; 330.9 | 16.16 g (91%); light yellow solid; free base |

SMs: (R)-3-bromo-5-chloro-N-((tetrahydrofuran-3-yl)methyl)pyrazolo[1,5-a]pyrimidin-7-amine (13.6 g, 41.1 mmol), Boc₂O (10.75 g, 49.3 mmol), DMAP (501 mg, 4.11 mmol), Et₃N (6.87 mL, 49.3 mmol), DCM (100 mL).

¹H NMR (400 MHz, CDCl₃) δ ppm 8.13 (s, 1H), 6.77 (s, 1H), 3.91-3.80 (m, 3H), 3.79-3.67 (m, 2H), 3.48 (dd, J = 8.8, 5.5 Hz, 1H), 2.53-2.40 (m, 1H), 2.02-1.90 (m, 1H), 1.65-1.54 (m, 1H), 1.36 (s, 9H).

| IUPAC name | Structure | MS calcd; MS ESI [M + H]⁺ | Yield; Appearance; Salt form |
|---|---|---|---|
| (S)-tert-butyl (3-bromo-5-chloropyrazolo[1,5-a]pyrimidin-7-yl)((tetrahydrofuran-3-yl)methyl)carbamate | | $[C_{16}H_{20}BrClN_4O_3 + H—Boc]^+$ 331.0; 331.1 | 9.8 g (93.5%); yellow solid; free base |

SMs: (S)-3-bromo-5-chloro-N-((tetrahydrofuran-3-yl)methyl)pyrazolo[1,5-a]pyrimidin-7-amine (8.05 g, 24.2 mmol), Boc₂O (5.56 g, 25.4 mmol), DMAP (295 mg, 2.4 mmol), Et₃N (4.39 mL, 31.4 mmol).

¹H NMR identical to (R)-isomer

| IUPAC name | Structure | MS calcd; MS ESI [M + H]⁺ | Yield; Appearance; Salt form |
|---|---|---|---|
| tert-butyl (3-bromo-5-chloropyrazolo[1,5-a]pyrimidin-7-yl)((1-methylpiperidin-4-yl)methyl)carbamate | | $[C_{18}H_{25}BrClN_5O_2 + H]^+$ 458.1; 458.1 | 0.483 g (70%); pale yellow solid; free base |

Sms: 3-bromo-5-chloro-N-((1-methylpiperidin-4-yl)methyl)pyrazolo[1,5-a]pyrimidin-7-amine (0.534 g, 1.5 mmol), Boc₂O (0.37 g, 1.7 mmol)

¹H NMR (400 MHz, CD₃OD) δ ppm 8.24 (s, 1H), 7.22 (s, 1H), 3.74 (d, J = 7.3 Hz, 2H), 2.91-2.84 (m, 2H), 2.27 (s, 3H), 2.05-1.96 (m, 2H), 1.83-1.76 (m, 2H), 1.63-1.49 (m, 1H), 1.32 (s, 9H), 1.31-1.17 (m, 2H)

| IUPAC name | Structure | MS calcd; MS ESI [M + H]⁺ | Yield; Appearance; Salt form |
|---|---|---|---|
| tert-butyl (3-bromo-5-chloropyrazolo[1,5-a]pyrimidin-7-yl)(2-(4-fluoropiperidin-1-yl)ethyl)carbamate | | $[C_{18}H_{24}BrClFN_5O_2 + H]^+$ 476.1; 476.1 | 1.0 g (quant.); pale foam; free base |

SMs: 3-bromo-5-chloro-N-(2-(4-fluoropiperidin-1-yl)ethyl)pyrazolo[1,5-a]pyrimidin-7-amine (0.79 g, 2.1 mmol), Boc₂O (0.91 g, 4.2 mmol)

¹H NMR (400 MHz, CDCl₃) δ ppm 8.10 (s, 1H), 6.93 (s, 1H), 4.65-4.37 (m, 1H), 3.94 (t, J = 5.6 Hz, 2H), 2.55 (t, J = 5.6 Hz, 2H), 2.45-2.32 (m, 2H), 2.30-2.14 (m, 2H), 1.59-1.45 (m, 2H), 1.46-1.29 (m, 2H), 1.37 (s, 9H)

Synthesis of N-cyclopropyl-4-(4-((4-methoxybenzyl)((tetrahydro-2H-pyran-4-yl)methyl)amino)-2-(methylthio)pyrazolo[1,5-a][1,3,5]triazin-8-yl)-2-methylbenzamide

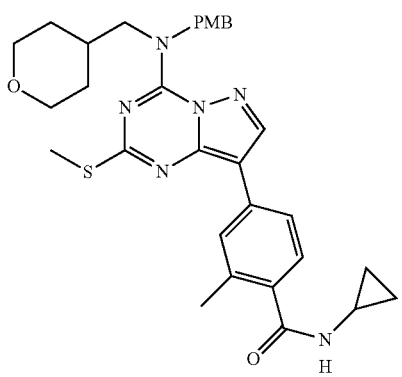

The title compound was synthesized according to General Method F utilizing 8-bromo-N-(4-methoxybenzyl)-2-(methylthio)-N-((tetrahydro-2H-pyran-4-yl)methyl)pyrazolo[1,5-a][1,3,5]triazin-4-amine (550 mg, 1.15 mmol), N-cyclopropyl-4-(4,4,5,5-tetramethyl-1,3,2-dioxaborolan-2-yl)benzamide (520 mg, 1.73 mmol), aq K$_3$PO$_4$ (2.0 mL, 4.0 mmol) and PdCl$_2$dppfDCM (94 mg, 0.110 mmol) at 130° C. for 4 h. The crude product was purified by flash chromatography (SiO$_2$, 10-40% EtOAc/DCM) to give the desired product as a yellow solid (600 mg, 92%). $^1$H NMR (400 MHz, CDCl$_3$) δ ppm 8.21 (s, 1H), 7.81-7.93 (m, 2H), 7.39 (d, J=7.8 Hz, 1H), 7.23 (d, J=8.5 Hz, 2H), 6.87 (d, J=8.8 Hz, 2H), 5.92 (br. s., 1H), 5.15-5.62 (m, 2H), 3.97 (dd, J=11.4, 2.9 Hz, 3H), 3.80 (s, 3H), 3.35 (t, J=10.8 Hz, 2H), 2.92 (td, J=7.0, 3.1 Hz, 1H), 2.61 (s, 3H), 2.53 (s, 3H), 2.08-2.23 (m, 1H), 1.57-1.61 (m, 3H), 1.34-1.49 (m, 2H), 0.85-0.93 (m, 2H), 0.56-0.68 (m, 2H); MS ESI [M+H]$^+$ 573.5, calcd for [C$_{31}$H$_{36}$N$_6$O$_3$S+H]$^+$ 573.26.

Synthesis of tert-butyl (3-bromo-5-(cyclopentylamino)pyrazolo[1,5-a]pyrimidin-7-yl)((tetrahydro-2H-pyran-4-yl)methyl)carbamate

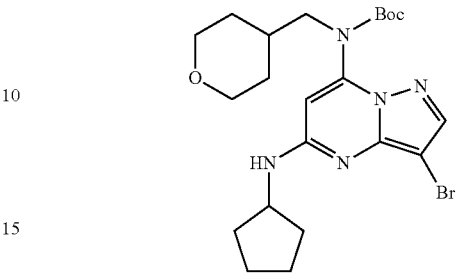

To a solution of tert-butyl (3-bromo-5-chloropyrazolo[1,5-a]pyrimidin-7-yl)((tetrahydro-2H-pyran-4-yl)methyl)carbamate (446 mg, 1 mmol) and cyclopentamine (0.11 mL, 1.1 mmol, 1.1 equiv) in THF (6 mL) was added DIPEA (0.22 mL, 1.2 mmol, 1.2 equiv). The resulting mixture was microwaved 3 h at 80° C., 1 h at 120° C. and 1 h at 130° C. The reaction was then allowed to cool to room temperature and was diluted with EtOAc and water was added. The resulting mixture was extracted with EtOAc and the combined organic extracts were dried over MgSO$_4$ and concentrated to give the crude product. Crude product was purified by flash chromatography (gradient: EtOAc/hex 5-40%) to give the title compound as a pale yellow solid (420 mg, 85%). NMR $^1$H NMR (400 MHz, CDCl3) δ ppm 7.81 (s, 1H), 5.96 (s, 1H), 5.01 (br, s, 1H), 4.43-4.15 (m, 1H), 3.95 (d, J=7.5 Hz, 2H), 3.63 (d, J=7.0 Hz, 2H), 3.43-3.20 (m, 2H), 2.21-2.08 (m, 2H), 1.88-1.60 (m, 7H), 1.56-1.49 (m, 2H), 1.33-1.23 (m, 2H); MS ESI [M+H]$^+$ 494.9, calcd for [C$_{22}$H$_{32}$BrN$_5$O$_3$+H]$^+$ 494.2.

The following intermediates were synthesized according to General Method C:

| IUPAC name | Structure | MS calcd; MS ESI [M + H]$^+$ | Yield; Appearance; Salt form |
|---|---|---|---|
| tert-butyl (3-bromo-5-((2-hydroxy-2-methylpropyl)amino)pyrazolo[1,5-a]pyrimidin-7-yl)((tetrahydro-2H-pyran-4-yl)methyl)carbamate | 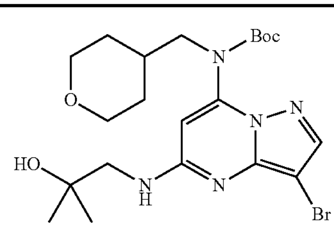 | [C$_{21}$H$_{32}$BrN$_5$O$_4$ + H]$^+$ 498.2; 498.8 | 810 mg (81%); white solid; free base |

SMs: tert-butyl (3-bromo-5-chloropyrazolo[1,5-a]pyrimidin-7-yl)((tetrahydro-2H-pyran-4-yl)methyl)carbamate (891 mg, 2 mmol), 1-amino-2-methylpropan-2-ol (356 mg, 2 mmol).

$^1$H NMR (400 MHz, CDCl$_3$) δ ppm 7.81 (s, 1H), 6.01 (s, 1H), 5.32-5.37 (m, 1H), 3.97-3.92 (m, 2H), 3.63 (d, J = 7.2 Hz, 2H), 3.55 (d, J = 5.6 Hz, 2H), 3.33 (t, J = 10.2 Hz, 2H), 1.87-1.75 (m, 1H), 1.69-1.62 (m, 2H), 1.37 (s, 9H), 1.33 (s, 6H), 1.31-1.26 (m, 2H).

| IUPAC name | Structure | MS calcd; MS ESI [M + H]⁺ | Yield; Appearance; Salt form |
|---|---|---|---|
| tert-butyl (3-bromo-5-morpholinopyrazolo[1,5-a]pyrimidin-7-yl)((tetrahydro-2H-pyran-4-yl)methyl)carbamate | 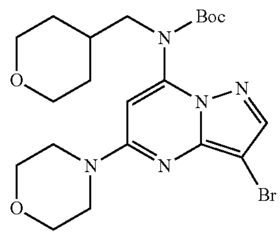 [SMILES: CC(C)(C)OC(=O)N(CC1CCOCC1)c1cc(N2CCOCC2)nc2c(Br)cnn12] | $[C_{21}H_{30}BrN_5O_4 + H]^+$ 496.1; 496.8 | 475 mg (96%); light yellow solid; free base |

SMs: tert-butyl (3-bromo-5-chloropyrazolo[1,5-a]pyrimidin-7-yl)((tetrahydro-2H-pyran-4-yl)methyl) carbamate (446 mg, 1 mmol), morpholine (0.26 mL, 3 mmol).
$^1$H NMR (400 MHz, CDCl$_3$) δ ppm 7.86 (s, 1H), 6.22 (s, 1H), 3.91-3.97 (m, 2H), 3.85 (t, J = 4.8 Hz, 4H), 3.72 (t, J = 4.6 Hz, 4H), 6.64 (d, J = 6.8 Hz, 2H), 3.32 (t, J = 11.4 Hz, 2H), 1.87-1.75 (m, 1H), 1.70-1.62 (m, 2H), 1.58 (s, 9H), 1.29 (dd, J = 12.4, 4.8 Hz, 2H).

| tert-butyl (3-bromo-5-((tetrahydro-2H-pyran-4-yl)amino)pyrazolo[1,5-a]pyrimidin-7-yl)((tetrahydro-2H-pyran-4-yl)methyl)carbamate | | $[C_{22}H_{32}BrN_5O_4 + H]^+$ 510.2; 510.9 | 122 mg (53%); white solid; free base |

SMs: tert-butyl (3-bromo-5-chloropyrazolo[1,5-a]pyrimidin-7-yl)((tetrahydro-2H-pyran-4-yl)methyl) carbamate (200 mg, 0.45 mmol), tetrahydro-2H-pyran-4-amine (55 mg, 0.54 mmol), DIPEA (0.10 mL, 0.57 mmol)
$^1$H NMR (400 MHz, CDCl$_3$) δ ppm 7.81 (s, 1H), 5.93 (s, 1H), 4.97 (d, J = 7.0 Hz, 1H), 4.15 (br, s, 1H), 4.04-3.97 (m, 2H), 3.93 (dd, J = 11.4, 2.6 Hz, 2H), 3.67-3.51 (m, 4H), 3.31 (td, J = 11.7, 1.8 Hz, 2H), 2.12-2.05 (m, 2H), 1.86-1.71 (m, 2H), 1.88-1.68 (m, 2H), 1.57-1.45 (m, 2H), 1.37 (s, 9H).

| tert-butyl (3-bromo-5-(cyclohexylamino)pyrazolo[1,5-a]pyrimidin-7-yl)((tetrahydro-2H-pyran-4-yl)methyl)carbamate | | $[C_{23}H_{34}BrN_5O_3 + H]^+$ 508.2; 508.9 | 433 mg (85%); yellow solid; free base |

SMs: tert-butyl(3-bromo-5-chloropyrazolo[1,5-a]pyrimidin-7-yl)((tetrahydro-2H-pyran-4-yl)methyl) carbamate (446 mg, 1 mmol), cyclopentamine (0.34 mL, 3 mmol).
$^1$H NMR (400 MHz, CDCl$_3$) δ ppm 7.80 (s, 1H), 5.92 (s, 1H), 4.96-4.85 (m, 1H), 3.94 (dd, J = 11.4, 2.4 Hz, 2H), 3.63 (d, J = 7.3 Hz, 2H), 3.38-3.25 (m, 2H), 2.15-2.04 (m, 2H), 1.87-1.74 (m, 3H), 1.74-1.60 (m, 4H), 1.54-1.40 (m, 2H), 1.39-1.34 (m, 9H), 1.34-1.23 (m, 5H).

| tert-butyl (3-bromo-5-((tetrahydro-2H-pyran-4-yl)amino)pyrazolo[1,5-a]pyrimidin-7-yl)(isobutyl)carbamate | | $[C_{20}H_{30}BrN_5O_3 + H]^+$ 468.2; 468.8 | 103 mg (58%); white solid; free base |

SMs: tert-butyl (3-bromo-5-chloropyrazolo[1,5-a]pyrimidin-7-yl)(isobutyl)carbamate (150 mg, 0.37 mmol), 4-aminotetrahydropyran (45 mg, 0.44 mmol), DIPEA (84 μL, 0.48 mmol)
$^1$H NMR (400 MHz, CDCl$_3$) 7.82 (s, 1H), 5.94 (s, 1H), 4.81-4.70 (m, 1H), 4.24-4.13 (m, 1H), 4.06-3.97 (m, 2H), 3.66-3.51 (m, 4H), 2.16-2.07 (m, 2H), 1.90-1.78 (m, 1H), 1.59-1.52 (m, 1H), 1.38 (s, 9H), 0.92 (d, J = 6.8 Hz, 6H).

| IUPAC name | Structure | MS calcd; MS ESI [M + H]+ | Yield; Appearance; Salt form |
|---|---|---|---|
| (R)-tert-butyl (3-bromo-5-((1-hydroxybutan-2-yl)amino)pyrazolo[1,5-a]pyrimidin-7-yl)((tetrahydro-2H-pyran-4-yl)methyl)carbamate | 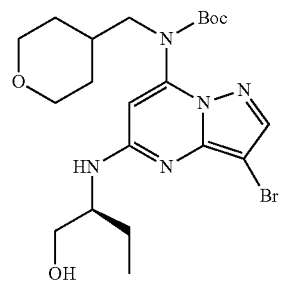 [SMILES: CC[C@@H](CO)Nc1cc(N(CC2CCOCC2)C(=O)OC(C)(C)C)n2ncc(Br)c2n1] | [C₂₁H₃₂BrN₅O₄ + H]+ 498.2; 498.8 | 115 mg (51.8%); Colorless thick oil |

SMs: tert-butyl (3-bromo-5-chloropyrazolo[1,5-a]pyrimidin-7-yl)((tetrahydro-2H-pyran-4-yl)methyl) carbamate (200 mg, 0.45 mmol), R(−)-2-aminobutan-1-ol (85 mmL, 0.90 mmol), DIPEA (156 mmL, 0.90 mmol).
¹H NMR (400 MHz, CDCl₃) δ ppm 7.79 (s, 1H), 6.00 (s, 1H), 5.22 (d, J = 6.8 Hz, 1H), 4.08-4.02 (m, 1H), 3.95-3.84 (m, 4H), 3.71-3.67 (m, 1H), 3.62 (d, J = 7.2 Hz, 2H), 3.31 (t, J = 11.6 Hz, 2H), 1.83-1.56 (m, 4H), 1.37 (s, 9H), 1.31-1.20 (m, 3H) , 1.03 (t, J = 7.4 Hz, 3H).

| IUPAC name | Structure | MS calcd; MS ESI [M + H]+ | Yield; Appearance; Salt form |
|---|---|---|---|
| tert-butyl (3-bromo-5-(((2S,3S)-2-hydroxypentan-3-yl)amino)pyrazolo[1,5-a]pyrimidin-7-yl)((tetrahydro-2H-pyran-4-yl)methyl)carbamate | | [C₂₂H₃₄BrN₅O₄ + H]+ 512.2; 512.9 | 145 mg (31.5%); White foam |

Starting materials: tert-butyl (3-bromo-5-chloropyrazolo[1,5-a]pyrimidin-7-yl)((tetrahydro-2H-pyran-4-yl)methyl)carbamate (400 mg, 0.90 mmol), (2S,3S)-3-aminopentan-2-ol hydrochloride (250 mg, 1.79 mmol), DIPEA (625 mmL, 3.59 mmol), 1,4-Dioxane (10 mL).
¹H NMR (400 MHz, CDCl₃) δ ppm 7.79 (s, 1H), 6.00 (s, 1H), 5.27 (br, s, 1H), 3.98-3.92 (m, 4H), 3.62 (d, J = 7.2 Hz, 2H), 3.35-3.29 (m, 2H), 2.96 (s, 1H), 1.84-1.72 (m, 2H), 1.70-1.61 (m, 3H), 1.37 (s, 9H), 1.30-1.25 (m, 4H), 1.00 (t, J = 7.2 Hz, 3H).

| IUPAC name | Structure | MS calcd; MS ESI [M + H]+ | Yield; Appearance; Salt form |
|---|---|---|---|
| tert-butyl (3-bromo-5-((tetrahydro-2H-pyran-4-yl)amino)pyrazolo[1,5-a]pyrimidin-7-yl)(2-((tert-butoxycarbonyl)oxy)-2-methylpropyl)carbamate | | [C₂₅H₃₈BrN₅O₆ + H]+ 584.2; 584.9 | 159 mg (70%); clear oil; free base |

SMs: tert-butyl (3-bromo-5-chloropyrazolo[1,5-a]pyrimidin-7-yl)(2-((tert-butoxycarbonyl)oxy)-2-methylpropyl)carbamate (200 mg, 0.39 mmol), 4-aminotetrahydropyran (79 mg, 0.78 mmol), DIPEA (137 µL, 0.78 mmol).

| IUPAC name | Structure | MS calcd; MS ESI [M + H]+ | Yield; Appearance; Salt form |
|---|---|---|---|
| (1r,4r)-4-(((3-bromo-5-((tetrahydro-2H-pyran-4-yl)amino)pyrazolo[1,5-a]pyrimidin-7-yl)(4-methoxybenzyl)amino)methyl)cyclohexanol | | [C₂₆H₃₄BrN₅O₃ + H]+ 544.2; 544.2 | 179 mg (73%); white solid; free base |

SMs: (1r,4r)-4-(((3-bromo-5-chloropyrazolo[1,5-a]pyrimidin-7-yl)(4-methoxybenzyl)amino)methyl) cyclohexanol (215 mg, 0.45 mmol), tetrahydro-2H-pyran-4-amine (0.453 g, 4.5 mmol) in dioxane (4 mL) at 170° C. for 8 h.
¹H NMR (400 MHz, CDCl₃) δ ppm 7.82 (s, 1H), 7.12 (d, J = 8.5 Hz, 2H), 6.83 (d, J = 8.5 Hz, 2H), 5.17 (s, 1H), 4.83 (s, 2H), 4.05-3.89 (m, 3H), 3.79 (s, 3H), 3.63-3.46 (m, 3H), 3.42 (d, J = 6.3 Hz, 2H), 2.06-1.87 (m., 4H), 1.80-1.60 (m, 3H), 1.57-1.39 (m, 2H), 1.30-1.11 (m, 2H), 1.01-0.88 (m, 2H).

| IUPAC name | Structure | MS calcd; MS ESI [M + H]+ | Yield; Appearance; Salt form |
|---|---|---|---|
| tert-butyl(3-bromo-5-(((2S,3S)-2-hydroxypentan-3-yl)amino)pyrazolo[1,5-a]pyrimidin-7-1)((tetrahydro-2H-pyran-4-yl)methyl)carbamate | 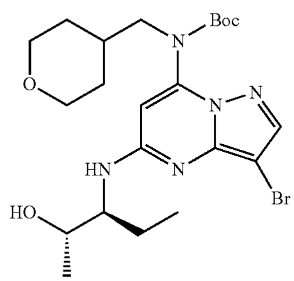 [SMILES: CC[C@H](Nc1cc(N(CC2CCOCC2)C(=O)OC(C)(C)C)n2ncc(Br)c2n1)[C@H](C)O] | [C$_{23}$H$_{34}$BrN$_5$O$_4$ + H]+ 512.2; 512.3 | 9.55 g (84%); off white solid; free base |

SMs: tert-butyl (3-bromo-5-chloropyrazolo[1,5-a]pyrimidin-7-yl)((tetrahydro-2H-pyran-4-yl)methyl) carbamate (10.0 g, 22 mmol), (2S,3S)-3-aminopentan-2-ol hydrochloride (4.7 g, 33 mmol), DIPEA (15.6 mL, 89 mmol)

$^1$H NMR (400 MHz, CDCl$_3$) δ ppm .80 (s, 1H), 5.99 (s, 1H), 5.14 (br.s, 1H), 4.00-3.93 (m, 4H), 3.62 (d, J = 7.2 Hz, 2H), 3.33 (td, J = 12 Hz, 2.0 Hz, 2H), 2.69 (br.s, 1H), 1.84-1.73 (m, 2H), 1.71-1.63 (m, 3H), 1.37 (s, 9H), 1.34-1.27 (m, 5H), 1.01 (t, J = 7.2 Hz, 3H).

| IUPAC name | Structure | MS calcd; MS ESI [M + H]+ | Yield; Appearance; Salt form |
|---|---|---|---|
| (S)-tert-butyl(3-bromo-5-((1-hydroxy-3-methylbutan-2-yl)amino)pyrazolo[1,5-a]pyrimidin-7-yl)((tetrahydro-2H-pyran-4-yl)methyl)carbamate | 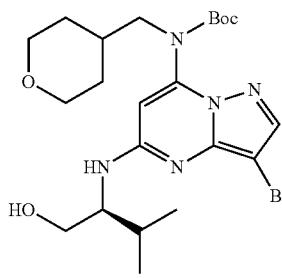 | [C$_{22}$H$_{34}$BrN$_5$O$_4$ + H]+ 512.2; 512.2 | 6.02 g (88%); off white solid; free base |

SMs: tert-butyl (3-bromo-5-chloropyrazolo[1,5-a]pyrimidin-7-yl)((tetrahydro-2H-pyran-4-yl)methyl) carbamate (6.0 g, 13.4 mmol), (S)-2-amino-3-methylbutan-1-ol (2.08 g, 20.2 mmol), DIPEA (7.02 mL, 40.3 mmol)

$^1$H NMR (400 MHz, CDCl$_3$) δ ppm 7.78 (s, 1H), 6.05 (s, 1H), 5.38 (d, J = 6.4 Hz, 1H), 3.93-3.90 (m, 2H), 3.85-3.83 (m, 2H), 3.74-3.69 (m, 1H), 3.61 (d, J = 7.6 Hz, 2H), 3.30 (t, J = 11.6 Hz, 2H), 2.02-1.92 (m, 1H), 1.83-1.75 (m, 1H), 1.65-1.58 (m, 2H), 1.37 (s, 9H), 1.31-1.27 (m, 1H), 0.99 (t, J = 6.4 Hz, 6H).

| IUPAC name | Structure | MS calcd; MS ESI [M + H]+ | Yield; Appearance; Salt form |
|---|---|---|---|
| tert-butyl (3-bromo-5-(((1S,2R)-2-hydroxycyclohexyl)amino)pyrazolo[1,5-a]pyrimidin-7-yl)((tetrahydro-2H-pyran-4-yl)methyl)carbamate | 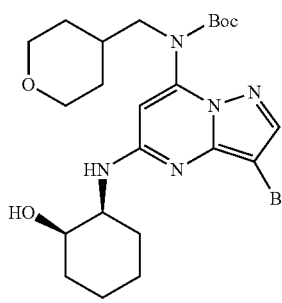 | [C$_{23}$H$_{34}$BrN$_5$O$_4$ + H]+ 524.2; 524.1 | 8.0 g (97%); cream solid; free base |

SMs: tert-butyl (3-bromo-5-chloropyrazolo[1,5-a]pyrimidin-7-yl)((tetrahydro-2H-pyran-4-yl)methyl) carbamate (7.0 g, 15.0 mmol), (1R,2S)-2-aminocyclohexanol hydrochloride (3.58 g, 23.0 mmol), DIPEA (10.95 mL, 62.0 mmol)

$^1$H NMR (400 MHz, CDCl$_3$) δ ppm 7.77 (s, 1H), 6.00 (s, 1H), 5.49 (br. s, 1H), 4.16 (br. s, 1H), 4.07-4.04 (m, 1H), 3.92 (dd, J = 11.6 Hz, 2.8 Hz, 2H), 3.60 (d, J = 7.2 Hz, 2H), 3.31 (td, J = 11.6 Hz, 2.0 Hz, 2H), 1.82-1.77 (br.m, 3H), 1.72-1.58 (br.m, 6H), 1.49-1.41 (br. m, 2H), 1.36 (s, 9H), 1.30-1.23 (m, 2H).

| IUPAC name | Structure | MS calcd; MS ESI [M + H]⁺ | Yield; Appearance; Salt form |
|---|---|---|---|
| (S)-tert-butyl(3-bromo-5-((2-hydroxy-2,4-dimethylpentan-3-yl)amino)pyrazolo[1,5-a]pyrimidin-7-yl)((tetrahydro-2H-pyran-4-yl)methyl)carbamate | 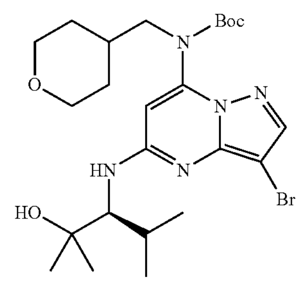 [SMILES: CC(C)[C@H](Nc1cc(N(CC2CCOCC2)C(=O)OC(C)(C)C)n2ncc(Br)c2n1)C(C)(C)O] | [$C_{24}H_{38}BrN_5O_4$ + H]⁺ 540.2; 540.2 | 5.50 g (60%); off white solid; free base |

SMs: tert-butyl (3-bromo-5-chloropyrazolo[1,5-a]pyrimidin-7-yl)((tetrahydro-2H-pyran-4-yl)methyl) carbamate (7.5 g, 16.8 mmol), (S)-3-amino-2,4-dimethylpentan-2-ol hydrochloride (4.24 g, 25.2 mmol), DIPEA (11.7 mL, 67.2 mmol)

¹H NMR (400 MHz, CDCl₃) δ ppm 7.80 (s, 1H), 6.04 (s, 1H), 3.97-3.93 (m, 2H), 3.63 (d, J = 7.2 Hz, 2H), 3.36-3.30 (m, 2H), 2.31-2.24 (m, 1H), 1.85-1.79 (m, 1H), 1.76-1.58 (m, 3H), 1.37-1.34 (m, 14H), 1.33-1.27 (m, 5H), 0.99 (d, J = 6.8 Hz, 6H).

| IUPAC name | Structure | MS calcd; MS ESI [M + H]⁺ | Yield; Appearance; Salt form |
|---|---|---|---|
| (S)-tert-butyl(3-bromo-5-((1-cyclopropyl-2-hydroxy-2-methylpropyl)amino)pyrazolo[1,5-a]pyrimidin-7-yl)((tetrahydro-2H-pyran-4-yl)methyl)carbamate | 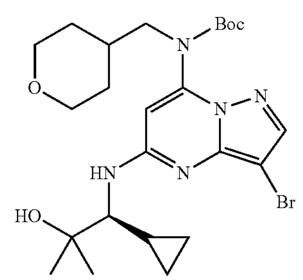 [SMILES: CC(C)(C)OC(=O)N(CC1CCOCC1)c1cc(N[C@@H](C2CC2)C(C)(C)O)nc2c(Br)cnn12] | [$C_{24}H_{36}BrN_5O_4$ + H]⁺ 538.2; 538.3 | 7.50 g (83%); cream solid; free base |

SMs: tert-butyl (3-bromo-5-chloropyrazolo[1,5-a]pyrimidin-7-yl)((tetrahydro-2H-pyran-4-yl)methyl) carbamate (7.0 g, 15.0 mmol), (S)-1-amino-1-cyclopropyl-2-methylpropan-2-ol hydrochloride (4.89 g, 25.0 mmol), DIPEA (11.7 mL, 67.3 mmol).

¹H NMR (400 MHz, CDCl₃) δ ppm 7.79 (s, 1H), 6.01 (s, 1H), 5.25 (d, J = 7.2 Hz, 1H), 3.95 (dd, J = 11.6 Hz, 2.4 Hz, 2H), 3.61 (d, J = 7.2 Hz, 2H), 3.39-3.30 (m, 3H), 1.86-1.73 (m, 1H), 1.69-1.62 (m, 2H), 1.38 (s, 14H), 1.34-1.25 (m, 4H), 1.06-0.99 (m, 1H), 0.79-0.74 (m, 1H), 0.56-0.50 (m, 2H), 0.41-0.39 (m, 1H).

| IUPAC name | Structure | MS calcd; MS ESI [M + H]⁺ | Yield; Appearance; Salt form |
|---|---|---|---|
| tert-butyl(3-bromo-5-(((1S,2R)-2-hydroxycyclohexyl)amino)pyrazolo[1,5-a]pyrimidin-7-yl)(cyclopropylmethyl)carbamate | 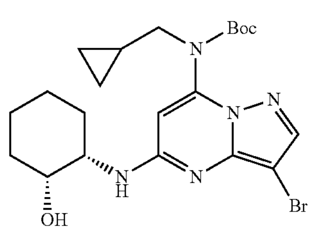 [SMILES: CC(C)(C)OC(=O)N(CC1CC1)c1cc(N[C@H]2CCCC[C@H]2O)nc2c(Br)cnn12] | [$C_{21}H_{30}BrN_5O_3$ + H]⁺ 480.2; 480.3 | 8.5 g (79%); beige solid; free base |

SMs: tert-butyl (3-bromo-5-chloropyrazolo[1,5-a]pyrimidin-7-yl)(cyclopropylmethyl)carbamate (9.0 g, 22.5 mmol), (1R,2S)-2-aminocyclohexanol·HCl (4.08 g, 27.0 mmol), DIPEA (3.47 g, 25.1 mmol).

¹H NMR (400 MHz, CDCl₃) δ ppm 7.80 (s, 1H), 6.08 (s, 1H), 5.33-5.19 (m, 1H), 4.26-4.14 (m, 1H), 4.13-4.06 (m, 1H), 3.61 (d, J = 7.3 Hz, 2H), 2.51 (br. s, 1H), 1.89-1.62 (m, 8H), 1.55-1.45 (m, 2H), 1.40 (s, 9H), 1.06-0.95 (m, 1H), 0.47-0.38 (m, 2H), 0.17-0.07 (m, 2H).

| IUPAC name | Structure | MS calcd; MS ESI [M + H]$^+$ | Yield; Appearance; Salt form |
|---|---|---|---|
| tert-butyl (3-bromo-5-(cyclopentylamino)pyrazolo[1,5-a]pyrimidin-7-yl)(((1s,3s)-3-((tert-butoxycarbonyl)oxy)-3-methylcyclobutyl)methyl)carbamate | 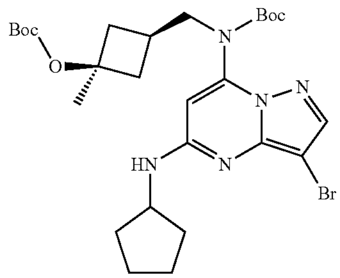 [SMILES: CC(C)(C)OC(=O)O[C@]1(C)C[C@H](CN(C(=O)OC(C)(C)C)c2cc(NC3CCCC3)nc3c(Br)cnn23)C1] | [C$_{27}$H$_{40}$BrN$_5$O$_5$ + H]$^+$ 594.2; 594.3 | 0.40 g (67%); white solid; free base |

SMs: tert-butyl (3-bromo-5-chloropyrazolo[1,5-a]pyrimidin-7-yl)(((1s,3s)-3-((tert-butoxycarbonyl)oxy)-3-methylcyclobutyl)methyl)carbamate (0.45 g, 0.83 mmol), cyclopentylamine (0.085 g, 1.0 mmol), DIPEA (0.21 g, 1.66 mmol).

$^1$H NMR (400 MHz, CDCl$_3$) δ ppm 7.79 (s, 1H), 5.94 (s, 1H), 5.08 (br. s, 1H), 4.23 (br. s, 1H), 3.85-3.72 (m, 2H), 2.28-2.06 (m, 5H), 2.02-1.89 (m, 2H), 1.81-1.61 (m, 5H), 1.48 (s, 4H), 1.44 (s, 9H), 1.36 (s, 9H).

| IUPAC name | Structure | MS calcd; MS ESI [M + H]$^+$ | Yield; Appearance; Salt form |
|---|---|---|---|
| tert-butyl (3-bromo-5-((1-(hydroxymethyl)cyclopentyl)amino)pyrazolo[1,5-a]pyrimidin-7-yl)((tetrahydro-2H-pyran-4-yl)methyl)carbamate | | [C$_{23}$H$_{34}$BrN$_5$O$_4$ + H]$^+$ 524.2; 524.3 | 10.6 g (75%); yellow solid; free base |

SMs: tert-butyl (3-bromo-5-chloropyrazolo[1,5-a]pyrimidin-7-yl)(((1s,3s)-3-((tert-butoxycarbonyl)oxy)-3-methylcyclobutyl)methyl)carbamate (12.0 g, 26.9 mmol), (1-aminocyclopentyl)methanol (4.64 g, 40 mmol), DIPEA (9.6 mL, 54 mmol).

$^1$H NMR (400 MHz, CDCl$_3$) δ ppm 7.75 (s, 1H), 6.36 (br. s, 1H), 6.06 (s, 1H), 5.96 (s, 1H), 3.89 (dd, J = 11.3, 2.8 Hz, 2H), 3.67 (d, J = 4.0 Hz, 2H), 3.59 (d, J = 7.3 Hz, 2H), 3.27 (t, J = 11.5 Hz, 2H), 1.94 (d, J = 7.8 Hz, 2H), 1.83-1.53 (m, 8H), 1.39 (s, 9H), 1.33-1.17 (m, 3H).

| IUPAC name | Structure | MS calcd; MS ESI [M + H]$^+$ | Yield; Appearance; Salt form |
|---|---|---|---|
| tert-butyl (3-bromo-5-(((1S,2R)-2-hydroxycyclohexyl)amino)pyrazolo[1,5-a]pyrimidin-7-yl)(((R)-tetrahydrofuran-3-yl)methyl)carbamate | | [C$_{22}$H$_{32}$BrN$_5$O$_4$ + H]$^+$ 510.2; 510.3 | 9.14 g (90%); white solid; free base |

SMs: (R)-tert-butyl (3-bromo-5-chloropyrazolo[1,5-a]pyrimidin-7-yl)((tetrahydrofuran-3-yl)methyl)carbamate (2.155 g, 5 mmol), (1R,2S)-2-aminocyclohexanol hydrochloride (1.137 g, 7.5 mmol), DIPEA (3.3 mL, 20 mmol), NMP (12 mL), in each vial, 4 vials in total.

$^1$H NMR (400 MHz, CDCl$_3$) δ ppm 7.81 (s, 1H), 5.99 (s, 1H), 5.31 (br. s., 1H), 4.26-4.15 (m, 1H), 4.10 (br. s., 1H), 3.90-3.66 (m, 6H), 3.50 (dd, J = 8.8, 5.5 Hz, 1H), 2.56-2.45 (m, 1H), 1.97 (dd, J = 12.5, 5.3 Hz, 1H), 1.89-1.56 (m, 7H), 1.51 (d, J = 4.3 Hz, 2H), 1.41-1.35 (m, 9H).

| IUPAC name | Structure | MS calcd;<br>MS ESI<br>[M + H]+ | Yield;<br>Appearance;<br>Salt form |
|---|---|---|---|
| tert-butyl (3-bromo-5-(((1S,2R)-2-hydroxycyclohexyl)amino)pyrazolo[1,5-a]pyrimidin-7-yl)(((S)-tetrahydrofuran-3-yl)methyl)carbamate | 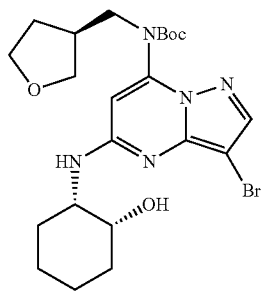 [SMILES: CC(C)(C)OC(=O)N(C[C@@H]1CCOC1)c1cc(N[C@H]2CCCC[C@H]2O)nc2c(Br)cnn12] | [C₂₂H₃₂BrN₅O₄ + H]+<br>510.2;<br>510.2 | 453 mg (89%);<br>white solid; free base |

SMs: (S)-tert-butyl (3-bromo-5-chloropyrazolo[1,5-a]pyrimidin-7-yl)((tetrahydrofuran-3-yl)methyl)carbamate
(431 mg, 1 mmol), (1R,2S)-2-aminocyclohexanol hydrochloride (303 mg, 2 mmol), DIPEA (0.66 mL, 4 mmol)
¹H NMR identical to (R)-isomer

Synthesis of tert-butyl (3-bromo-5-(cyclopentyloxy)pyrazolo[1,5-a]pyrimidin-7-yl)((tetrahydro-2H-pyran-4-yl)methyl)carbamate

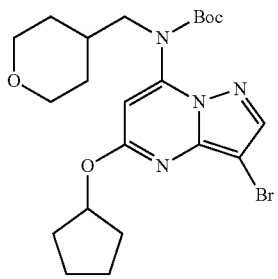 [SMILES: CC(C)(C)OC(=O)N(CC1CCOCC1)c1cc(OC2CCCC2)nc2c(Br)cnn12]

To a solution of tert-butyl (3-bromo-5-chloropyrazolo[1,5-a]pyrimidin-7-yl) ((tetrahydro-2H-pyran-4-yl)methyl)carbamate (446 mg, 1 mmol) and cyclopentan-ol (129 mg, 1.5 mmol, 1.5 equiv) in DMF (8 mL) at 0° C. was added 60% NaH (160 mg, 4 mmol, 4 equiv). The resulting mixture was stirred at rt for 1 h. After cooling to 0° C., quenching with satd NH₄Cl and H₂O, it was extracted with EtOAc and purified by flash chromatography (gradient: EtOAc/hex 0-35%) to give the title compound (224 mg, 45%) as white solid. ¹H NMR (400 MHz, CDCl₃) δ ppm 7.92 (s, 1H), 6.19 (s, 1H), 5.59-5.68 (m, 1H), 3.94 (dd, J=11.3, 3.3 Hz, 2H), 3.64 (d, J=7.3 Hz, 2H), 3.37-3.26 (m, 2H), 2.15-2.01 (m, 2H), 1.92-1.75 (m, 5H), 1.73-1.59 (m, 4H), 1.36 (s, 9H), 1.30 (dd, J=12.7, 4.1 Hz, 2H).

The following intermediates were synthesized according to General Method D:

| IUPAC name | Structure | MS calcd;<br>MS ESI<br>[M + H]+ | Yield;<br>Appearance;<br>Salt form |
|---|---|---|---|
| tert-butyl (3-bromo-5-((tetrahydro-2H-pyran-4-yl)oxy)pyrazolo[1,5-a]pyrimidin-7-yl)((tetrahydro-2H-pyran-4-yl)methyl)carbamate | 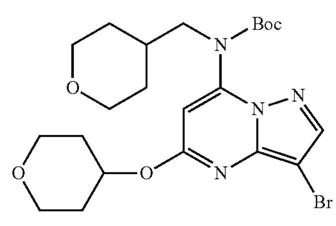 [SMILES: CC(C)(C)OC(=O)N(CC1CCOCC1)c1cc(OC2CCOCC2)nc2c(Br)cnn12] | [C₂₂H₃₁BrN₄O₅ + H]+<br>511.2;<br>511.9 | 158 mg (69%);<br>clear oil;<br>free base |

SMs: tert-butyl (3-bromo-5-chloropyrazolo[1,5-a]pyrimidin-7-yl)((tetrahydro-2H-pyran-4-yl)methyl) carbamate
(200 mg, 0.45 mmol), tetrahydro-2H-pyran-4-ol (84 mg, 0.82 mmol), 60% NaH (72 mg, 1.8 mmol).
¹H NMR (400 MHz, CDCl₃) δ ppm 7.94 (s, 1H), 6.24 (s, 1H), 5.51-5.42 (m, 1H), 4.07-3.88 (m, 4H),
3.66 (d, J = 7.3 Hz, 2H), 3.46-3.25(m, 4H), 3.08-2.96 (m, 1H), 2.22-2.12 (m, 2H), 1.92-1.79 (m, 2H),
1.64 (t, J = 13.6 Hz, 4H), 1.37 (s, 9H).

| IUPAC name | Structure | MS calcd; MS ESI [M + H]+ | Yield; Appearance; Salt form |
|---|---|---|---|
| 3-bromo-5-chloro-7-((tetrahydro-2H-pyran-4-yl)methoxy)pyrazolo[1,5-a]pyrimidine | 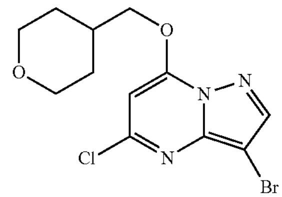 [SMILES: Clc1cc(OCC2CCOCC2)n2ncc(Br)c2n1] | [C$_{12}$H$_{13}$BrClN$_3$O$_2$ + H]+ 347.99; 348.0 | 770 mg (100%); white solid; free base |

SMs: 3-bromo-5,7-dichloropyrazolo[1,5-a]pyrimidine (585 mg, 2.2 mmol), (tetrahydro-2H-pyran-4-yl)methanol (280 mg, 2.4 mmol), 60% NaH (263 mg, 6.6 mmol).
$^1$H NMR (400 MHz, CDCl$_3$) δ ppm 8.11 (s, 1H), 6.25 (s, 1H), 4.23 (d, J = 7.0 Hz, 2H), 4.06 (dd, J = 11.2, 4.1 Hz, 2H), 3.48 (td, J = 12.0, 2.0 Hz, 2H), 2.47-2.28 (m, 1H), 1.87 (d, J = 11.8 Hz, 2H), 1.55-1.45 (m, 2H).

| tert-butyl (3-bromo-5-(cyclohexyloxy)pyrazolo[1,5-a]pyrimidin-7-yl)((tetrahydro-2H-pyran-4-yl)methyl)carbamate | | [C$_{23}$H$_{33}$BrN$_4$O$_4$ + H]+ 509.2; 509.9 | 281 mg (62%); white solid; free base |

SMs tert-butyl (3-bromo-5-chloropyrazolo[1,5-a]pyrimidin-7-yl)((tetrahydro-2H-pyran-4-yl)methyl)carbamate (400 mg, 0.89 mmol), cyclohexanol (134 mg, 1.34 mmol), 60% NaH (72 mg, 2 mmol).
$^1$H NMR (400 MHz, CDCl$_3$) δ ppm 7.92 (s, 1H), 6.21 (s, 1H), 5.23-5.33 (m, 1H), 3.94 (d, J = 11.0 Hz, 2H), 3.65 (d, J = 7.0 Hz, 2H), 3.39-3.26 (m, 2H), 2.06 (br, s, 2H), 1.82 (dd, J = 7.3, 3.8 Hz, 3H), 1.70-1.44 (m, 8H), 1.42-1.23 (m, 11H).

Synthesis of tert-butyl (3-bromo-5-phenoxypyrazolo[1,5-a]pyrimidin-7-yl)((tetrahydro-2H-pyran-4-yl)methyl)carbamate

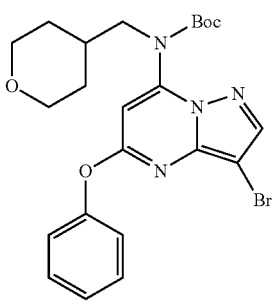 [SMILES: CC(C)(C)OC(=O)N(CC1CCOCC1)c1cc(Oc2ccccc2)nc2c(Br)cnn12]

Using Phenol:

To a solution of tert-butyl (3-bromo-5-chloropyrazolo[1,5-a]pyrimidin-7-yl)((tetrahydro-2H-pyran-4-yl)methyl)carbamate (2.01 g, 4.51 mmol) and phenol (1.27 g, 13.53 mmol, 3 equiv) in DMF (15 mL) was added K$_2$CO$_3$ (1.84 g, 13.53 mmol, 3 equiv). The resulting mixture was stirred O/N at rt and quenched with H$_2$O (150 mL). After extracting with EtOAc (60 mL×2), it was concentrated to dryness and purified by flash chromatography twice (gradient: EtOAc/DCM 0-50%; EtOAc/hex 30-80%) to give the desired product (2.09 g, 92%) as white foam. $^1$H NMR (400 MHz, CDCl$_3$) δ ppm 7.97 (s, 1H), 7.49-7.44 (m, 2H), 7.33-7.28 (m, 3H), 6.44 (s, 1H), 3.98-3.92 (m, 2H), 3.70 (d, J=7.2 Hz, 2H), 3.33 (t, J=11.8 Hz, 2H), 1.90-1.78 (m, 1H), 1.70-1.62 (m, 2H), 1.37 (s, 9H), 1.32 (dd, J=12.8, 4.8 Hz, 2H).

Using Phenoxide:

To a solution of tert-butyl (3-bromo-5-chloropyrazolo[1,5-a]pyrimidin-7-yl)((tetrahydro-2H-pyran-4-yl)methyl)carbamate (4.55 g, not very dry, assuming 10 mmol) in DMF (20 mL) in was added PhONa (1.22 g, 10.5 mmol). The resulting mixture was stirred at rt for 30 min and quenched with H$_2$O (200 mL). The precipitates were collected by suction filtration and dried to give the desired product (3.88 g) as white solid.

The following intermediates were synthesized according to General Method E:

| IUPAC name | Structure | MS calcd; MS ESI [M + H]⁺ | Yield; Appearance; Salt form |
|---|---|---|---|
| tert-butyl (3-bromo-5-phenoxypyrazolo[1,5-a]pyrimidin-7-yl)(2-methoxyethyl)carbamate | 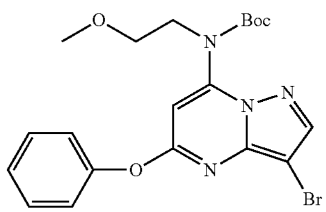 [SMILES: COCCN(C(=O)OC(C)(C)C)c1cc(Oc2ccccc2)nc2c(Br)cnn12] | [$C_{20}H_{23}BrN_4O_4$ + H]⁺ 463.1; 463.6 | 3.20 g (quantitative); white solid; free base |

SMs: tert-butyl (3-bromo-5-chloropyrazolo[1,5-a]pyrimidin-7-yl)(2-methoxyethyl)carbamate (2.71 g, 6.69 mmol), PhOH (1.23 g, 13.4 mmol).

¹H NMR (400 MHz, CDCl₃) δ ppm 7.97 (s, 1H), 7.49-7.43 (m, 2H), 7.32-7.27 (m, 3H), 6.61 (s, 1H), 3.94 (t, J = 5.0 Hz, 2H), 3.59 (t, J = 5.0 Hz, 2H), 3.22 (s, 3H), 1.38 (s, 9H).

| IUPAC name | Structure | MS calcd; MS ESI [M + H]⁺ | Yield; Appearance; Salt form |
|---|---|---|---|
| tert-butyl (3-bromo-5-(pyridin-3-yloxy)pyrazolo[1,5-a]pyrimidin-7-yl)(2-methoxyethyl)carbamate | | [$C_{19}H_{22}BrN_5O_4$ + H]⁺ 464.1; 464.7 | 261 mg (56%); light brown oil; free base |

SMs: tert-butyl (3-bromo-5-chloropyrazolo[1,5-a]pyrimidin-7-yl)(2-methoxyethyl)carbamate (406 mg, 1 mmol), 3-hydroxypyridine (190 mg, 2 mmol).

¹H NMR (400 MHz, CDCl₃) δ ppm 8.61 (d, J = 2.8 Hz, 1H), 8.49 (dd, J = 4.8, 1.2 Hz, 1H), 7.94 (s, 1H), 7.74-7.69 (m, 1H), 7.37 (dd, J = 8.4, 4.8 Hz, 1H), 6.68 (s, 1H), 3.92 (t, J = 5.2 Hz, 2H), 3.58 (t, J = 5.0 Hz, 2H), 3.22 (s, 3H), 1.35 (s, 9H).

| IUPAC name | Structure | MS calcd; MS ESI [M + H]⁺ | Yield; Appearance; Salt form |
|---|---|---|---|
| tert-butyl (3-bromo-5-(pyridin-3-yloxy)pyrazolo[1,5-a]pyrimidin-7-yl)((tetrahydro-2H-pyran-4-yl)methyl)carbamate | | [$C_{22}H_{26}BrN_5O_4$ + H]⁺ 504.1; 504.8 | 485 mg (96%); light brown foam; free base |

SMs: tert-butyl (3-bromo-5-chloropyrazolo[1,5-a]pyrimidin-7-yl)((tetrahydro-2H-pyran-4-yl)methyl) carbamate (446 mg, 1 mmol), 3-hydroxypyridine (190 mg, 2 mmol).

¹H NMR (400 MHz, CDCl₃) δ ppm 8.63 (d, J = 2.4 Hz, 1H), 8.51 (dd, J = 4.8, 1.2 Hz, 1H), 7.95 (s, 1H), 7.76-7.72 (m, 1H), 7.39 (dd, J = 8.6, 4.8 Hz, 1H), 6.51 (s, 1H), 3.98-3.88 (m, 2H), 3.70 (d, J = 7.2 Hz, 2H), 3.30 (t, J = 7.2 Hz, 2H), 1.88-1.76 (m, 1H), 1.68-1.61 (m, 2H), 1.40-1.25 (m, 11H; s, 9H at 1.34 and m, 2H).

| IUPAC name | Structure | MS calcd; MS ESI [M + H]+ | Yield; Appearance; Salt form |
|---|---|---|---|
| tert-butyl (3-bromo-5-(3-fluorophenoxy)pyrazolo[1,5-a]pyrimidin-7-yl)((tetrahydro-2H-pyran-4-yl)methyl)carbamate | 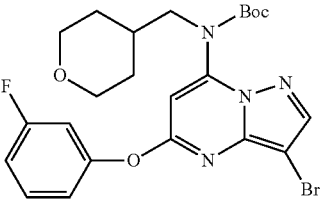 | [$C_{23}H_{26}BrFN_4O_4$ + H]+ 521.1; 521.8 | 487 mg (94%); white solid; free base |

SMs: tert-butyl (3-bromo-5-chloropyrazolo[1,5-a]pyrimidin-7-yl)((tetrahydro-2H-pyran-4-yl)methyl) carbamate (446 mg, 1 mmol), 3-fluorophenol (224 mg, 2 mmol).
1H NMR (400 MHz, CDCl3) δ ppm 7.99 (s, 1H), 7.45-7.39 (m, 1H), 7.15-7.09 (m, 2H), 7.06-6.99 (m, 1H), 6.46 (s, 1H), 3.98-3.82 (m, 2H), 3.71 (d, J = 6.8 Hz, 2H), 3.33 (t, J = 7.2 Hz, 2H), 1.90-1.78 (m, 1H), 1.70-1.63 (m, 2H) 1.38 (s, 9H), 1.32 (dd, J = 12.6, 3.8 Hz, 2H).

| | | | |
|---|---|---|---|
| tert-butyl (3-bromo-5-phenoxypyrazolo[1,5-a]pyrimidin-7-yl)(2-morpholinoethyl)carbamate | 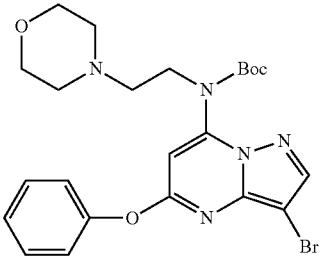 [SMILES: CC(C)(C)OC(=O)N(CCN1CCOCC1)c1cc(Oc2ccccc2)nc2c(Br)cnn12] | [$C_{23}H_{28}BrN_5O_4$ + H]+ 518.1; 518.8 | 3.60 g (99%); white foam; free base |

SMs: tert-butyl (3-bromo-5-chloropyrazolo[1,5-a]pyrimidin-7-yl)(2-morpholinoethyl)carbamate (3.22 g, 7.0 mmol), PhONa (893 mg, 0.77 mmol).
1H NMR (400 MHz, CDCl3) δ ppm 7.96 (s, 1H), 7.50-7.44 (m, 2H), 7.32-7.26 (m, 3H), 6.52 (s, 1H), 3.94 (t, J = 6.0 Hz, 2H), 3.40-3.33 (m, 4H), 2.56 (t, J = 6.0 Hz, 2H), 2.33-2.27 (m, 4H), 1.38 (s, 9H).

| | | | |
|---|---|---|---|
| 3-bromo-5-phenoxy-7-((tetrahydro-2H-pyran-4-yl)methoxy)pyrazolo[1,5-a]pyrimidine | 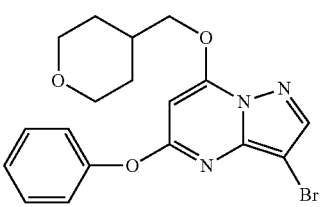 [SMILES: Brc1cnn2c(OCC3CCOCC3)cc(Oc3ccccc3)nc12] | [$C_{18}H_{18}BrN_3O_3$ + H]+ 404.1; 404.6 | 241 mg (83%); white solid; free base |

SMs: 3-bromo-5-chloro-7-((tetrahydro-2H-pyran-4-yl)methoxy)pyrazolo[1,5-a]pyrimidine (250 mg, 0.72 mmol), sodium phenoxide (92 mg, 0.79 mmol)
1H NMR (400 MHz, CDCl3) δ ppm 7.98 (s, 1H), 7.49-7.40 (m, 2H), 7.31-7.27 (m, 3H), 5.88 (s, 1H), 4.17 (d, J = 6.5 Hz, 2H), 4.06 (dd, J = 11.5, 3.3 Hz, 2H), 3.48 (t, J = 11.3 Hz, 2H), 2.45-2.29 (m, 1H), 1.87 (d, J = 11.3 Hz, 2H), 1.54-1 45 (m, 2H).

| | | | |
|---|---|---|---|
| tert-butyl (3-bromo-5-phenoxypyrazolo[1,5-a]pyrimidin-7-yl)(3-morpholinopropyl)carbamate | 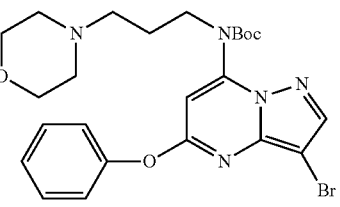 | [$C_{24}H_{30}BrN_5O_4$ + H]+ 534.2; 534.1 | 374 mg (quantitative); white solid; free base |

SMs: tert-butyl (3-bromo-5-chloropyrazolo[1,5-a]pyrimidin-7-yl)(3-morpholinopropyl)carbamate (200 mg, 0.42 mmol), PhONa (53 mg, 0.46 mmol).
1H NMR (400 MHz, CDCl3) δ ppm 7.97 (s, 1H), 7.51-7.42 (m, 2H), 7.35-7.21 (m, 3H), 6.47 (s, 1H), 3.86 (t, J = 7.3 Hz, 2H), 3.63 (t, J = 4.5 Hz, 4H), 2.41-226 (m, 6H), 1.88-1.74 (m, 2H), 1.38 (s, 9H).

| IUPAC name | Structure | MS calcd; MS ESI [M + H]⁺ | Yield; Appearance; Salt form |
|---|---|---|---|
| tert-butyl (3-bromo-5-phenoxypyrazolo[1,5-a]pyrimidin-7-yl)(2-(tetrahydro-2H-pyran-4-yl)ethyl)carbamate | 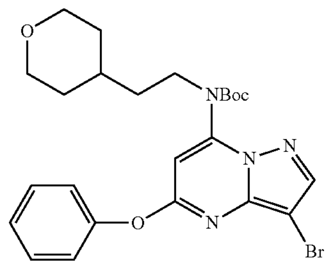 [SMILES: CC(C)(C)OC(=O)N(CCC1CCOCC1)c1cc(Oc2ccccc2)nc2c(Br)cnn12] | [C$_{24}$H$_{29}$BrN$_4$O$_4$ + H]⁺ 517.1; 517.9 | 192 mg (85%); white solid; free base |

SMs: tert-butyl (3-bromo-5-chloropyrazolo[1,5-a]pyrimidin-7-yl)(2-(tetrahydro-2H-pyran-4-yl)ethyl)carbamate (200 mg, 0.44 mmol), PhONa (56 mg, 0.48 mmol).
¹H NMR (400 MHz, CDCl$_3$) δ ppm 7.98 (s, 1H), 7.51-7.43 (m, 2H), 7.33-7.28 (m, 3H), 6.43 (s, 1H), 3.94 (dd, J = 11.7, 3.9 Hz, 2H), 3.87-3.80 (m, 2H), 3.35 (t, J = 11.2 Hz, 2H), 1.62-1.49 (m, 5H), 1.39 (s, 9H), 1.35-1.25 (m, 2H).

| IUPAC name | Structure | MS calcd; MS ESI [M + H]⁺ | Yield; Appearance; Salt form |
|---|---|---|---|
| tert-butyl (3-bromo-5-(pyridin-3-yloxy)pyrazolo[1,5-a]pyrimidin-7-yl)(2-(tetrahydro-2H-pyran-4-yl)ethyl)carbamate | 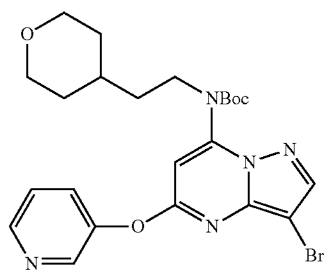 [SMILES: CC(C)(C)OC(=O)N(CCC1CCOCC1)c1cc(Oc2cccnc2)nc2c(Br)cnn12] | [C$_{23}$H$_{28}$BrN$_5$O$_4$ + H]⁺ 518.1; 518.8 | 190 mg (84%); off-white solid; free base |

SMs: tert-butyl (3-bromo-5-chloropyrazolo[1,5-a]pyrimidin-7-yl)(2-(tetrahydro-2H-pyran-4-yl)ethyl)carbamate (200 mg, 0.44 mmol), pyridin-3-ol (124 mg, 1.31 mmol), K$_2$CO$_3$ (241 mg, 1.747 mmol).
¹H NMR (400 MHz, CDCl$_3$) δ ppm 8.66 (d, J = 2.5 Hz, 1H), 8.56 (dd, J = 4.8, 1.3 Hz, 1H), 7.99 (s, 1H), 7.77 (ddd, J = 8.2, 2.7, 1.4 Hz, 1H), 7.43 (dd, J = 8.3, 4.8 Hz, 1H), 6.52 (s, 1H), 3.94 (dd, J = 11.0, 3.8 Hz, 2H), 3.89-3.80 (m, 2H), 3.35 (t, J = 11.0 Hz, 2H), 1.68-1.49 (m, 5H), 1.44-1.37 (m, 9H), 1.37-1.21 (m, 2H).

| IUPAC name | Structure | MS calcd; MS ESI [M + H]⁺ | Yield; Appearance; Salt form |
|---|---|---|---|
| tert-butyl (3-bromo-5-phenoxypyrazolo[1,5-a]pyrimidin-7-yl)(2-((tert-butoxycarbonyl)oxy)-2-methylpropyl)carbamate | 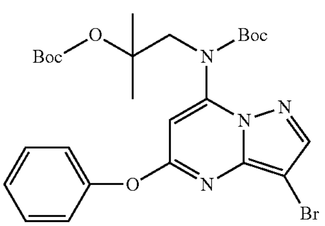 [SMILES: CC(C)(C)OC(=O)OC(C)(C)CN(C(=O)OC(C)(C)C)c1cc(Oc2ccccc2)nc2c(Br)cnn12] | [C$_{26}$H$_{33}$BrN$_4$O$_6$ + H]⁺ 577.2; 577.9 | 115 mg (54%); light brown solid; free base |

SMs: tert-butyl (3-bromo-5-chloropyrazolo[1,5-a]pyrimidin-7-yl)(2-((tert-butoxycarbonyl)oxy)-2-methylpropyl)carbamate (190 mg, 0.37 mmol), NaOPh (51 mg, 0.44 mmol).
¹H NMR (400 MHz, CDCl$_3$) δ ppm 7.96 (s, 1H), 7.47-7.40 (m, 2H), 7.33-7.24 (m, 3H), 6.51 (s, 1H), 4.07 (s, 2H), 1.57 (s, 6H), 1.34 (s, 9H) 1.25 (s, 9H).

| IUPAC name | Structure | MS calcd; MS ESI [M + H]⁺ | Yield; Appearance; Salt form |
|---|---|---|---|
| tert-butyl (3-bromo-5-(pyridin-3-yloxy)pyrazolo[1,5-a]pyrimidin-7-yl)(isobutyl)carbamate | 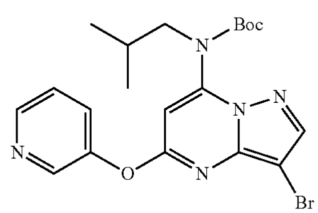 [SMILES: CC(C)CN(C(=O)OC(C)(C)C)c1cc(Oc2cccnc2)nc2c(Br)cnn12] | [C$_{20}$H$_{24}$BrN$_5$O$_3$ + H]⁺ 462.1; 462.8 | 132 mg (77%); light brown oil; free base |

SMs: tert-butyl (3-bromo-5-chloropyrazolo[1,5-a]pyrimidin-7-yl)(isobutyl)carbamate (150 mg, 0.37 mmol), 3-hydroxypyridine (176 mg, 1.85 mmol), DBU (281 mg, 1.85 mmol).
¹H NMR (400 MHz, CDCl$_3$) δ ppm 8.65 (s, 1H), 8.57-8.51 (m, 1H), 7.99 (s, 1H), 7.79-7.72 (m, 1H), 7.45-7.39 (m, 1H), 6.53 (s, 1H), 3.65 (d, J = 7.3 Hz, 2H), 1.93-1.82 (m, 1H), 1.43-1.30 (m, 9H), 0.95 (d, J = 6.8 Hz, 6H).

| IUPAC name | Structure | MS calcd; MS ESI [M + H]+ | Yield; Appearance; Salt form |
|---|---|---|---|
| tert-butyl (3-bromo-5-(pyridin-3-yloxy)pyrazolo[1,5-a]pyrimidin-7-yl)(2-((tert-butoxycarbonyl)oxy)-2-methylpropyl)carbamate | | [$C_{25}H_{32}BrN_5O_6$ + H]+ 578.2; 578.9 | 120 mg (53%); light brown oil; free base |
| (1r,4r)-4-(((3-bromo-5-phenoxy-pyrazolo[1,5-a]pyrimidin-7-yl)(4-methoxy-benzyl)amino)methyl)cyclohexanol | | [$C_{27}H_{29}BrN_4O_3$ + H]+ 537.1/539.1; 537.1/539.1 | 0.18 g (89%); clear film; free base |
| tert-butyl(3-bromo-5-(pyridin-3-yloxy)pyrazolo[1,5-a]pyrimidin-7-yl)(((1s,3s)-3-((tert-butoxycarbonyl)oxy)-3-methylcyclobutyl)methyl)carbamate | | [$C_{27}H_{34}BrN_5O_6$ + H]+ 604.2; 604.3 | 0.23 g (46%); yellow solid; free base |

SMs: tert-butyl (3-bromo-5-chloropyrazolo[1,5-a]pyrimidin-7-yl)(2-((tert-butoxycarbonyl)oxy)-2-methylpropyl)carbamate (200 mg, 0.39 mmol), 3-hydroxypyridine (183 mg, 1.93 mmol), DBU (293 mg, 1.93 mmol).

1H NMR (400 MHz, CDCl3) δ ppm 8.65 (s, 1H), 8.56-8.50 (m, 1H), 7.97 (s, 1H), 7.79-7.71 (m, 1H), 7.44-7.37 (m, 1H), 6.59 (s, 1H), 4.07 (s, 2H), 1.58 (s, 6H), 1.34 (s, 9H), 1.21 (s, 9H).

SMs: (1r,4r)-4-(((3-bromo-5-chloropyrazolo[1,5-a]pyrimidin-7-yl)(4-methoxybenzyl)amino)methyl)-cyclohexanol (180 mg, 0.37 mmol) and PhONa (108 mg, 0.93 mmol), 50° C., 70 min.

1H NMR (400 MHz, CDCl3) δ ppm 7.93 (s, 1H), 7.40 (t, J = 8.30 Hz, 2H), 7.24-7.17 (m, 3H), 7.10 (d, J = 8.30 Hz, 2H), 6.84 (d, J = 8.8 Hz, 2H), 5.56 (s, 1H), 4.96 (s, 2H), 3.80 (s, 3H), 3.55-3.475 (m, 1H), 3.48 (d, J = 6.8 Hz, 2H), 2.00-1.88 (m, 2H), 1.80-1.60 (m, 3H), 1.26-1.10 (m, 2H), 1.05-0.84 (m, 2H)

SMs: tert-butyl (3-bromo-5-chloropyrazolo[1,5-a]pyrimidin-7-yl)(((1s,3s)-3-((tert-butoxycarbonyl)oxy)-3-methylcyclobutyl)methyl)carbamate (0.45 g, 0.83 mmol), 3-hydroxypyridine (0.39 g, 4.14 mmol), DBU (0.63 g, 4.14 mmol)

1H NMR (400 MHz, CDCl3) δ ppm 8.65 (d, J = 2.8 Hz, 1H), 8.55 (dd, J = 4.6, 1.4 Hz, 1H), 7.98 (s, 1H), 7.78-7.73 (m, 1H), 7.46-7.40 (m, 1H), 6.50 (s, 1H), 3.89 (d, J = 6.8 Hz, 2H), 2.30-2.15 (m, 3H), 2.02-1.93 (m, 2H), 1.50 (s, 3H), 1.45 (s, 9H), 1.38 (s, 9H).

| IUPAC name | Structure | MS calcd; MS ESI [M + H]⁺ | Yield; Appearance; Salt form |
|---|---|---|---|
| tert-butyl 4-(((3-bromo-5-(3-fluorophenoxy)pyrazolo[1,5-a]pyrimidin-7-yl)(tert-butoxycarbonyl)amino)methyl)-4-fluoropiperidine-1-carboxylate | 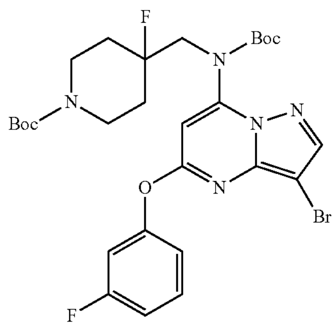 [SMILES: CC(C)(C)OC(=O)N1CCC(F)(CN(C(=O)OC(C)(C)C)c2cc(Oc3cccc(F)c3)nc3c(Br)cnn23)CC1] | [$C_{28}H_{34}BrF_2N_5O_5$ + H]⁺ 638.2; 638.2 | 7.8 g (97%); pale yellow solid; free base |

SMs: tert-butyl 4-(((3-bromo-5-chloropyrazolo[1,5-a]pyrimidin-7-yl)(tert-butoxycarbonyl)amino)methyl)-4-fluoropiperidine-1-carboxylate (7.04 g, 12.6 mmol), 3-fluorophenol (2.0 g, 17.6 mmol), K₂CO₃ (3.47 g, 25.1 mmol).

¹H NMR (400 MHz, CDCl₃) δ ppm 7.98 (s, 1H), 7.46-7.37 (m, 1H), 7.16-7.07 (m, 2H), 7.05-6.95 (m, 1H), 6.55 (s, 1H), 4.14-3.85 (m, 4H), 3.11-2.92 (m, 2H), 2.02-1.86 (m, 2H), 1.81-1.62 (m, 2H), 1.47 (s, 9H), 1.35 (s, 9H).

| IUPAC name | Structure | MS calcd; MS ESI [M + H]⁺ | Yield; Appearance; Salt form |
|---|---|---|---|
| tert-butyl (3-bromo-5-(3-fluorophenoxy)pyrazolo[1,5-a]pyrimidin-7-yl)(2-morpholinoethyl)carbamate | 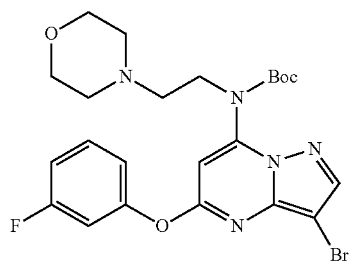 [SMILES: CC(C)(C)OC(=O)N(CCN1CCOCC1)c1cc(Oc2cccc(F)c2)nc2c(Br)cnn12] | [$C_{23}H_{27}BrFN_5O_4$ + H]⁺ 536.1; 536.2 | 5.42 g (quant.); light brown foam; free base |

SMs: tert-butyl (3-bromo-5-chloropyrazolo[1,5-a]pyrimidin-7-yl)(2-morpholinoethyl)carbamate (4.61 g, 10 mmol), 3-fluorophenol (2.24 g, 20 mmol), K₂CO₃ (2.76 g, 20 mmol).

¹H NMR (400 MHz, CDCl₃) δ ppm 7.94 (s, 1H), 7.42-7.35 (m, 1H), 7.10-7.02 (m, 2H), 7.00-6.95 (m, 1H), 6.54 (s, 1H), 3.92 (t, J = 5.8 Hz, 2H), 3.35-3.28 (m, 4H), 2.55 (t, J = 5.8 Hz, 2H), 2.27 (t, J = 4.2 Hz, 4H), 1.36 (s, 9H).

| IUPAC name | Structure | MS calcd; MS ESI [M + H]⁺ | Yield; Appearance; Salt form |
|---|---|---|---|
| tert-butyl (3-bromo-5-(2,3-difluorophenoxy)pyrazolo[1,5-a]pyrimidin-7-yl)(2-morpholinoethyl)carbamate | 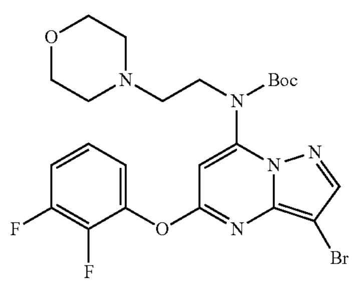 [SMILES: CC(C)(C)OC(=O)N(CCN1CCOCC1)c1cc(Oc2cccc(F)c2F)nc2c(Br)cnn12] | [$C_{23}H_{26}BrF_2N_5O_4$ + H]⁺ 554.1; 554.1 | 532 mg (100%); white solid; free base |

SMs: tert-butyl (3-bromo-5-chloropyrazolo[1,5-a]pyrimidin-7-yl)(2-morpholinoethyl)carbamate (mg, 1 mmol), 2,3-difluorophenol (390 mg, 3 mmol), K₂CO₃ (552 mg, 4 mmol).

¹H NMR (400 MHz, CDCl₃) δ ppm 7.96 (s, 1H), 7.18-7.18 (m, 3H), 6.64 (s, 1H), 3.97 (t, J = 5.6 Hz, 2H), 3.32 (br. s., 4H), 2.58 (t, J = 5.8 Hz, 2H), 2.29 (t, J = 4.4 Hz, 4H), 1.39 (s, 9H).

| IUPAC name | Structure | MS calcd; MS ESI [M + H]+ | Yield; Appearance; Salt form |
|---|---|---|---|
| tert-butyl (3-bromo-5-(3-fluorophenoxy)pyrazolo[1,5-a]pyrimidin-7-yl)((1-methyl-piperidin-4-yl)methyl)carbamate | 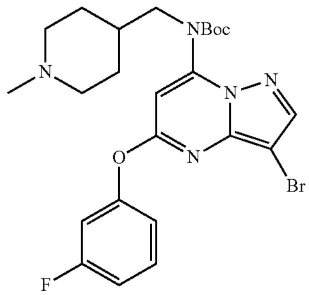 [SMILES: CN1CCC(CN(C(=O)OC(C)(C)C)c2cc(Oc3cccc(F)c3)nc3c(Br)cnn23)CC1] | [C$_{24}$H$_{29}$BrFN$_5$O$_3$ + H]+ 533.1 534.1 | 0.338 g (60%); light grey solid; free base |
| Sms: (General Method E)_tert-butyl (3-bromo-5-chloropyrazolo[1,5-a]pyrimidin-7-yl)((1-methylpiperidin-4-yl)methyl)carbamate (0.483 g, 1.05 mmol), 3-fluorophenol (0.413 g, 3.7 mmol), K$_2$CO$_3$ (0.44 g, 3.2 mmol) $^1$H NMR (400 MHz, CD$_3$OD) δ ppm 8.05 (s, 1H), 7.55-7.39 (m, 1H), 7.20-7.13 (m, 2H), 7.07 (dd, J = 2.5, 0.8 Hz, 1H), 6.83 (s, 1H), 3.72 (d, J = 7.3 Hz, 2H), 2.84 (d, J = 11.8 Hz, 2H), 2.23 (s, 3H), 2.00-1.88 (m., 2H), 1.85-1.76 (m, 2H), 1.65-1.50 (m, 1H), 1.35 (s, 9H), 1.33-1.22 (m, 2H) | | | |
| tert-butyl (3-bromo-5-(2,3-difluorophenoxy)pyrazolo[1,5-a]pyrimidin-7-yl)(2-(4-fluoro-piperidin-1-yl)ethyl)carbamate | 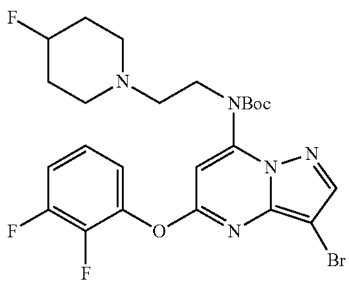 [SMILES: CC(C)(C)OC(=O)N(CCN1CCC(F)CC1)c1cc(Oc2cccc(F)c2F)nc2c(Br)cnn12] | [C$_{24}$H$_{27}$BrF$_3$N$_5$O$_3$ + H]+ 570.1 570.3 | 0.289 g (68%); pale foam; free base |
| Sms: (General Method E)_tert-butyl (3-bromo-5-chloropyrazolo[1,5-a]pyrimidin-7-yl)(2-(4-fluoropiperidin-1-yl)ethyl)carbamate (0.354 g, 0.74 mmol), 2,3-difluorophenol (0.288 g, 2.2 mmol), K$_2$CO$_3$ (0.31 g, 2.2 mmol) $^1$H NMR (400 MHz, CDCl$_3$) δ ppm 7.97 (s, 1H), 7.21-7.07 (m, 3H), 6.66 (s, 1H), 4.65-4.43 (m, 1H), 3.95 (t, J = 5.8 Hz, 2H), 2.58 (t, J = 5.9 Hz, 2H), 2.48-2.36 (m, 2H), 2.31-2.20 (m, 2H), 1.45-1.34 (m, 4H), 1.39 (s, 9H) | | | |

The following intermediates were synthesized according to General Method F (Suzuki):

| IUPAC name | Structure | MS calcd; MS ESI [M + H]+ | Yield; Appearance; Salt form |
|---|---|---|---|
| 2-chloro-N-cyclopropyl-4-(4-((4-methoxybenzyl)((tetrahydro-2H-pyran-4-yl)methyl)amino)-2-(methylthio)pyrazolo[1,5-a][1,3,5]triazin-8-yl)benzamide | 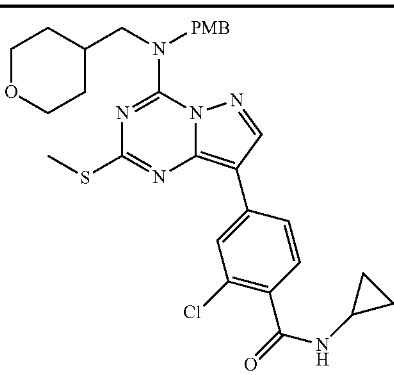 | [C$_{30}$H$_{33}$ClN$_6$O$_3$S + H]+ 593.2; 593.7 | 1.3 g (68%); yellow solid; free base |
| SMs: 8-bromo-N-(4-methoxybenzyl)-2-(methylthio)-N-((tetrahydro-2H-pyran-4-yl)methyl)pyrazolo[1,5-a][1,3,5]triazin-4-amine (1.6 g, 3.3 mmol), (3-chloro-4-(cyclopropylcarbamoyl)phenyl)boronic acid (0.87 g, 3.6 mmol). | | | |

| IUPAC name | Structure | MS calcd; MS ESI [M + H]+ | Yield; Appearance; Salt form |
|---|---|---|---|

¹H NMR (400 MHz, CDCl₃) δ ppm 8.21 (s, 1H), 8.19 (d, J = 1.5 Hz, 1H), 7.94 (dd, J = 8.0, 2.0 Hz, 1H), 7.80 (d, J = 8.3 Hz, 1H), 7.23 (d, J = 8.8 Hz, 2H), 6.88 (d, J = 8.5 Hz, 2H), 6.50 (br. s., 1H), 5.32 (br. s, 2H), 3.97 (d, J = 11.0 Hz, 2H), 3.81 (s, 3H), 3.29-3.41 (m, 2H), 2.92-3.00 (m, 1H), 2.62 (s, 3H), 2.09-2.19 (m, 1H), 1.58-1.66 (m, 4H), 1.36-1.49 (m, 2H), 0.87-0.95 (m, 2H), 0.64-0.72 (m, 2H).

| N-cyclopropyl-4-(4-((4-methoxybenzyl)(2-morpholinoethyl)amino)-2-(methylthio)pyrazolo[1,5-a][1,3,5]triazin-8-yl)benzamide | 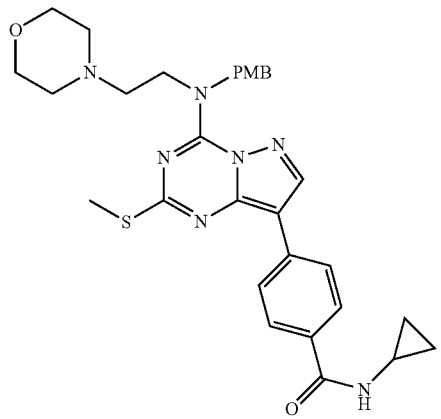 | [C₃₀H₃₅IN₇O₃S + H]+ 574.3; 574.5 | 1.3 g (68%); yellow solid; free base |
|---|---|---|---|

SMs: 8-bromo-N-(4-methoxybenzyl)-2-(methylthio)-N-(2-morpholinoethyl)pyrazolo[1,5-a][1,3,5]triazin-4-amine (1.10 g, 2.28 mmol), N-cyclopropyl-4-(4,4,5,5-tetramethyl-1,3,2-dioxaborolan-2-yl)benzamide (982 mg, 3.42 mmol).

¹H NMR (400 MHz, CDCl₃) δ 8.17 (s, 1H), 8.03 (d, J = 8.4 Hz, 2H), 7.78 (d, J = 8.4 Hz, 2H), 7.26 (d, J = 8.4 Hz, 2H), 6.85 (d, J = 8.4 Hz, 2H), 5.38-5.22 (m, 2H), 4.15-4.00 (m, 2H), 3.78 (s, 3H), 3.68-3.57 (m, 4H), 2.96-2.86 (m, 1H), 2.64 (t, J = 6.6 Hz, 2H), 2.56 (s, 3H), 2.52-2.38 (m, 4H), 0.90-0.80 (m, 2H), 0.66-0.60 (m, 2H).

| N-cyclopropyl-4-(4-((4-methoxybenzyl)(3-morpholinopropyl)amino)-2-(methylthio)pyrazolo[1,5-a][1,3,5]triazin-8-yl)benzamide | 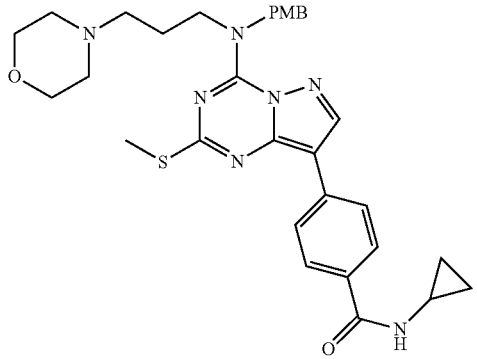 | [C₃₁H₃₇N₇O₃S + H]+ 588.3; 588.2 | 1.3 g (68%); pale solid; free base |
|---|---|---|---|

SMs: 8-bromo-N-(4-methoxybenzyl)-2-(methylthio)-N-(3-morpholinopropyl)pyrazolo[1,5-a][1,3,5]triazin-4-amine (1.6 g, 3.156 mmol), N-cyclopropyl-4-(4,4,5,5-tetramethyl-1,3,2-dioxaborolan-2-yl)benzamide (1.359 g, 4.734 mmol).

¹H NMR (400 MHz, CDCl₃) δ 8.22 (s, 1H), 8.10 (d, J = 8.5 Hz, 2H), 7.80 (d, J = 8.5 Hz, 2H), 7.29 (d, J = 8.8 Hz, 2H), 6.88 (d, J = 8.8 Hz, 2H), 6.25 (br. s., 1H), 5.15-5.52 (br. s., 2H), 3.88-4.11 (br. s., 2H), 3.81 (s, 3H), 3.70 (t, J = 4.6 Hz, 4H), 2.89-2.99 (m, 1H), 2.61 (s, 3H), 2.32-2.47 (m, 6H), 1.87-1.97 (m, 2H), 0.86-0.94 (m, 2H), 0.61-0.68 (m, 2H).

| IUPAC name | Structure | MS calcd; MS ESI [M + H]+ | Yield; Appearance; Salt form |
|---|---|---|---|
| N-cyclopropyl-4-(4-((4-methoxybenzyl)((tetrahydro-2H-pyran-4-yl)methyl)amino)-2-(methylthio)pyrazolo[1,5-a][1,3,5]triazin-8-yl)benzamide | 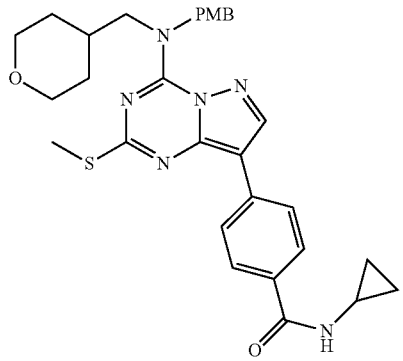 | [C30H34N6O3S + H]+ 559.2; 559.5 | 815 mg (70%); white solid; free base |

SMs: 8-bromo-N-(4-methoxybenzyl)-2-(methylthio)-N-((tetrahydro-2H-pyran-4-yl)methyl)pyrazolo[1,5-a][1,3,5]triazin-4-amine (1.0 g, 2.09 mmol), N-cyclopropyl-4-(4,4,5,5-tetramethyl-1,3,2-dioxaborolan-2-yl)benzamide (900 mg, 3.14 mmol).

$^1$H NMR (400 MHz, CDCl$_3$) δ ppm 8.24 (s, 1H), 8.09 (d, J = 8.3 Hz, 2H), 7.80 (d, J = 8.3 Hz, 2H), 7.23 (d, J = 8.5 Hz, 2H), 6.87 (d, J = 8.5 Hz, 2H), 6.26 (br. s., 1H), 5.36 (br. s., 1H), 3.97 (dd, J = 11.2, 3.1 Hz, 3H), 3.80 (s, 3H), 3.35 (t, J = 11.2 Hz, 1H), 2.93 (s, 1H), 2.61 (s, 3H), 2.06-2.20 (m, 1H), 1.54-1.66 (m, 2H), 1.35-1.48 (m, 2H), 0.83-0.93 (m, 2H), 0.61-0.68 (m, 2H).

| IUPAC name | Structure | MS calcd; MS ESI [M + H]+ | Yield; Appearance; Salt form |
|---|---|---|---|
| N-cyclopropyl-4-(4-((((cis)-4-hydroxycyclohexyl)methyl)(4-methoxybenzyl)amino)-2-(methylthio)pyrazolo[1,5-a][1,3,5]triazin-8-yl)-2-methylbenzamide | 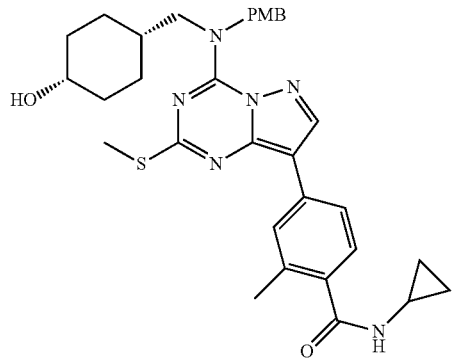 | [C32H38N6O3S + H]+ 587.3; 587.2, | 0.347 g (74%); a cream colored solid; free base |

SMs: (cis)-4-(((8-bromo-2-(methylthio)pyrazolo[1,5-a][1,3,5]triazin-4-yl)(4-methoxybenzyl)amino)methyl)cyclohexanol (0.39 g, 0.80 mmol), N-cyclopropyl-2-methyl-4-(4,4,5,5-tetramethyl-1,3,2-dioxaborolan-2-yl)benzamide (0.37 g, 1.2 mmol).

$^1$H NMR (400 MHz, CDCl$_3$) δ ppm 8.11 (s, 1H), 7.69-7.81 (m, 2H), 7.27 (d, J = 8.00 Hz, 1H), 7.13 (d, J = 7.28 Hz, 2H), 6.77 (d, J = 8.53 Hz, 2H), 5.05-5.50 (br. s., 2H), 3.85 (br. s., 1H), 3.70 (s, 3H), 3.55-4.05 (br.s. 2H), 2.73-2.84 (m, 1H), 2.50 (s, 3H), 2.39 (s, 3H), 1.87 (br. s., 1H), 1.64 (br. s., 2H), 1.33-1.49 (m, 6H), 0.71-0.80 (m, 2H), 0.53 (br. s., 2H).

| IUPAC name | Structure | MS calcd; MS ESI [M + H]+ | Yield; Appearance; Salt form |
|---|---|---|---|
| N-cyclopropyl-4-(4-((4-methoxybenzyl)(2-morpholinoethyl)amino)-2-(methylthio)pyrazolo[1,5-a][1,3,5]triazin-8-yl)-2-methylbenzamide | 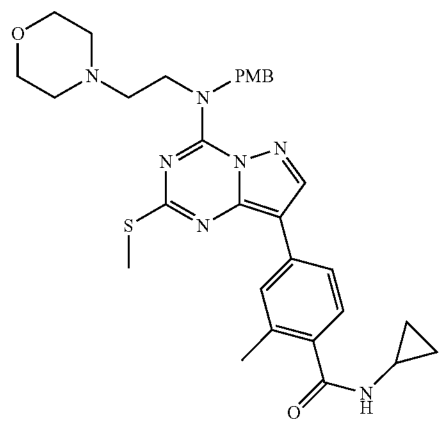 | [$C_{31}H_{37}N_7O_3S$ + H]+ 588.3; 588.2 | 0.34 g (94%); light yellow solid; free base |

SMs: 8-bromo-N-(4-methoxy benzyl)-2-(methylthio)-N-(2-morpholinoethyl)pyrazolo[1,5-a][1,3,5]triazin-4-amine (0.30 g, 0.61 mmol), N-cyclopropyl-2-methyl-4-(4,4,5,5-tetramethyl-1,3,2-dioxaborolan-2-yl)benzamide (0.26 g, 0.85 mmol).
$^1$H NMR (400 MHz, CD$_3$OD) δ ppm 8.36-8.43 (m, 1H), 7.98-8.03 (m, 1H), 7.94 (d, J = 7.50 Hz, 1H), 7.36 (d, J = 8.00 Hz, 1H), 7.33 (d, J = 8.50 Hz, 2H), 6.91 (d, J = 8.50 Hz, 2H), 5.31-5.37 (br.s., 2H), 4.13-4.20 (m, 2H), 3.79 (s, 3H), 3.54-3.60 (m, 4H), 2.82-2.92 (m, 1H), 2.64-2.73 (m, 2H), 2.60 (s, 3H), 2.47-2.53 (m, 4H), 2.46 (s, 3H), 0.78-0.86 (m, 2H), 0.58-0.67 (m, 2H).

Synthesis of N-cyclopropyl-2-methyl-4-(2-(methylthio)-4-(((tetrahydro-2H-pyran-4-yl)methyl)amino)pyrazolo[1,5-a][1,3,5]triazin-8-yl)benzamide

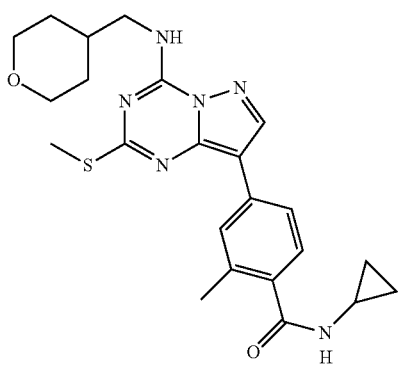

The title compound was synthesized according to General Method F utilizing N-cyclopropyl-4-(4-((4-methoxybenzyl)((tetrahydro-2H-pyran-4-yl)methyl)amino)-2-(methylthio)pyraz-olo[1,5-a][1,3,5]triazin-8-yl)-2-methylbenzamide (410 mg, 0.72 mmol) in DCM/TFA (2:1, 6 mL) at 60° C. for 30 h. The crude product was purified by flash chromatography (SiO$_2$, 20-100% EtOAc/DCM) to give the desired product as a yellow solid (320 mg, 100%). $^1$H NMR (400 MHz, CDCl$_3$) δ ppm 8.22 (s, 1H), 7.83-7.90 (m, 2H), 7.40 (d, J=8.0 Hz, 1H), 6.56 (t, J=6.6 Hz, 1H), 5.90 (br s, 1H), 4.02 (dd, J=11.4, 3.6 Hz, 2H), 3.59 (t, J=6.9 Hz, 2H), 3.42 (t, J=11.7 Hz, 2H), 2.91-2.94 (m, 1H), 2.64 (s, 3H), 2.53 (s, 3H), 1.96-1.99 (m, 1H), 1.73 (d, J=11.8 Hz, 2H), 1.41-1.49 (m, 2H), 0.87-0.92 (m, 2H), 0.62-0.65 (m, 2H); MS ESI [M+H]$^+$ 453.5, calcd for [$C_{23}H_{28}N_6O_2S$+H]$^+$ 453.20.

The following intermediates were synthesized according to General Method F (deprotection):

| IUPAC name | Structure | MS calcd; MS ESI [M + H]⁺ | Yield; Appearance; Salt form |
|---|---|---|---|
| 2-chloro-N-cyclopropyl-4-(2-(methylthio)-4-(((tetrahydro-2H-pyran-4-yl)methyl)amino)pyrazolo[1,5-a][1,3,5]triazin-8-yl)benzamide | 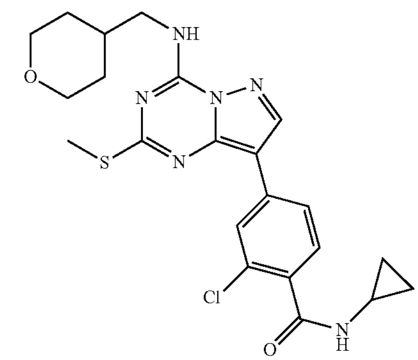 [SMILES: CSc1nc(NCC2CCOCC2)n2ncc(-c3ccc(C(=O)NC4CC4)c(Cl)c3)c2n1] | $[C_{22}H_{25}ClN_6O_2S + H]^+$ 473.1; 473.7 | 1.1 g (100%); brown solid; free base |
| | SMs: 2-chloro-N-cyclopropyl-4-(4-((4-methoxybenzyl)((tetrahydro-2H-pyran-4-yl)methyl)amino)-2-(methylthio)pyrazolo[1,5-a][1,3,5]triazin-8-yl)benzamide (1.3 g, 2.3 mmol). | | |
| N-cyclopropyl-4-(2-(methylthio)-4-((3-morpholinopropyl)amino)pyrazolo[1,5-a][1,3,5]triazin-8-yl)benzamide | 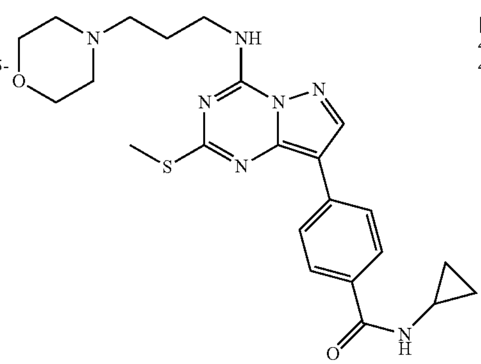 | $[C_{23}H_{29}N_7O_2S + H]^+$ 468.3; 468.2 | 724 mg (79%); yellow solid; free base |
| | SMs: N-cyclopropyl-4-(4-((4-methoxybenzyl)(3-morpholinopropyl)amino)-2-(methylthio)pyrazolo[1,5-a][1,3,5]triazin-8-yl)benzamide(1.15 g, 1.96 mmol). ¹H NMR (400 MHz, CDCl₃) δ 9.11 (br. s., 1H), 8.27 (s, 1H), 8.09 (d, J = 8.8 Hz, 2H), 7.80 (d, J = 8.5 Hz, 2H), 6.25 (br. s., 1H), 3.93 (t, J = 4.4 Hz, 4H), 3.79 (d, J = 5.5 Hz, 2H), 2.90-2.97 (m, 1H), 2.62-2.68 (m, 5H), 2.57 (br. s., 4H), 1.88 (br. s., 2H), 0.86-0.94 (m, 2H), 0.61-0.67 (m, 2H). | | |
| N-cyclopropyl-4-(2-(methylthio)-4-(((tetrahydro-2H-pyran-4-yl)methyl)amino)pyrazolo[1,5-a][1,3,5]triazin-8-yl)benzamide | 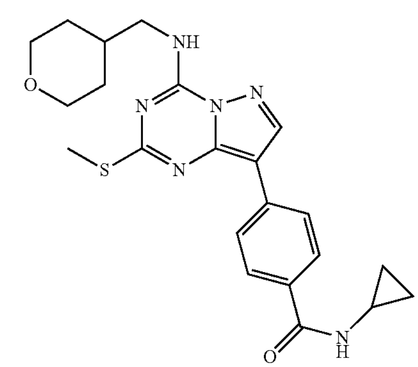 [SMILES: CSc1nc(NCC2CCOCC2)n2ncc(-c3ccc(C(=O)NC4CC4)cc3)c2n1] | $[C_{22}H_{26}N_6O_2S + H]^+$ 439.2; 439.6 | 561 mg (90%); beige solid; free base |
| | SMs: N-cyclopropyl-4-(4-((4-methoxybenzyl)((tetrahydro-2H-pyran-4-yl)methyl)amino)-2-(methylthio)pyrazolo[1,5-a][1,3,5]triazin-8-yl)benzamide (800 mg, 1.43 mmol). ¹H NMR (400 MHz, CDCl₃) δ ppm 8.25 (s, 1H), 8.07 (d, J = 8.5 Hz, 2H), 7.80 (d, J = 8.5 Hz, 2H), 6.54-6.62 (m, 1H), 6.27 (br. s., 1H), 4.02 (dd, J = 11.0, 3.8 Hz, 2H), 3.59 (t, J = 6.8 Hz, 2H), 3.42 (t, J = 12.0 Hz, 2H), 2.89-2.98 (m, 1H), 2.64 (s, 3H), 1.91-2.05 (m, 1H), 1.68-1.77 (m, 2H), 1.37-1.52 (m, 2H), 0.85-0.93 (m, 2H), 0.61-0.68 (m, 2H). | | |

The following intermediates were synthesized according to General Method K:

| IUPAC name | Structure | MS calculated; MS ESI [M + H]⁺ | Yield; Appearance; Salt form |
|---|---|---|---|
| N-cyclopropyl-4-(4-((4-methoxybenzyl)((tetrahydro-2H-pyran-4-yl)methyl)amino)-2-(methylsulfonyl)pyrazolo[1,5-a][1,3,5]triazin-8-yl)-2-methylbenzamide | 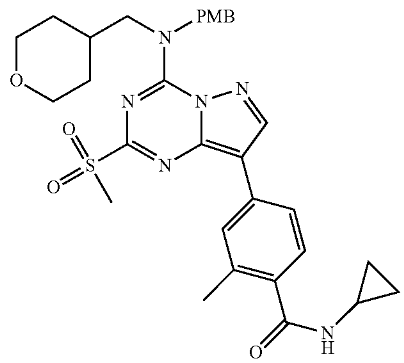 | $[C_{31}H_{36}N_6O_5S + H]^+$ 605.25; 605.4 | 140 mg (89%); yellow solid; free base |

SMs: N-cyclopropyl-4-(4-((4-methoxybenzyl)((tetrahydro-2H-pyran-4-yl)methyl)amino)-2-(methylthio)pyrazolo[1,5-a][1,3,5]triazin-8-yl)-2-methylbenzamide (150 mg, 0.26 mmol), mCPBA (180 mg, 0.79 mmol).
¹H NMR (400 MHz, CDCl₃) δ ppm 8.38 (s, 1H), 7.82 (d, J = 7.3 Hz, 1H), 7.77 (s, 1H), 7.58 (s, 1H), 7.42 (d, J = 8.0 Hz, 2H), 6.89 (d, J = 8.8 Hz, 2H), 5.91 (br. s., 1H), 4.97-5.19 (m, 2H), 4.31-4.53 (m, 2H), 3.99 (d, J = 8.3 Hz, 2H), 3.81 (s, 3H), 3.26-3.45 (m, 5H), 2.85-3.02 (m, 1H), 2.53 (s, 3H), 1.46-1.71 (m, 5H), 0.82-0.99 (m, 2H), 0.59-0.69 (m, 2H).

| | | | |
|---|---|---|---|
| 2-chloro-N-cyclopropyl-4-(2-(methylsulfonyl)-4-(((tetrahydro-2H-pyran-4-yl)methyl)amino)pyrazolo[1,5-a][1,3,5]triazin-8-yl)benzamide | | $[C_{22}H_{25}ClN_6O_4S + H]^+$ 505.1; 505.6 | 1.2 g (100%); yellow solid; free base |

SMs: 2-chloro-N-cyclopropyl-4-(2-(methylthio)-4-(((tetrahydro-2H-pyran-4-yl)methyl) amino)pyrazolo[1,5-a][1,3,5]triazin-8-yl)benzamide (1.0 g, 2.1 mmol), mCPBA (1.4 g, 6.3 mmol).
¹H NMR (400 MHz, CDCl₃) δ ppm 8.39 (s, 1H), 7.95 (s, 1H), 7.85 (dd, J = 8.1, 1.5 Hz, 1H), 7.75 (d, J = 8.1 Hz, 1H), 7.10 (t, J = 6.3 Hz, 1H), 6.51 (br s, 1H), 4.05 (dd, J = 11.0, 3.2 Hz, 2H), 3.74 (t, J = 6.6 Hz, 2H), 3.38-3.47 (m, 5H), 2.94-3.00 (m, 1H), 2.02-2.08 (m, 1H), 1.75 (d, J = 11.7 Hz, 2H), 1.44-1.53 (m, 2H), 0.87-0.96 (m, 2H), 0.66-0.72 (m, 2H).

| | | | |
|---|---|---|---|
| N-cyclopropyl-4-(2-(methylsulfonyl)-4-((3-morpholinopropyl)amino)pyrazolo[1,5-a][1,3,5]triazin-8-yl)benzamide | | $[C_{23}H_{29}N_7O_4S + H]^+$ 500.2; 500.1 | 126 mg (16%); pale solid; free base |

SMs: N-cyclopropyl-4-(2-(methylthio)-4-((3-morpholinopropyl)amino)pyrazolo[1,5-a][1,3,5]triazin-8-yl)benzamide (724 mg, 1.55 mmol), mCPBA (1042 mg, 4.65 mmol).

| IUPAC name | Structure | MS calculated; MS ESI [M + H]+ | Yield; Appearance; Salt form |
|---|---|---|---|
| | 1H NMR (400 MHz, CDCl3) δ 12.28-12.38 (m, 1H), 8.29 (s, 1H), 7.91 (d, J = 8.3 Hz, 2H), 7.69 (d, J = 8.3 Hz, 2H), 6.52-6.60 (m, 1H), 4.53-4.59 (m, 2H), 3.93 (br. s., 2H), 3.82 (d, J = 12.0 Hz, 2H), 3.68 (br. s., 2H), 3.34 (br. s., 4H), 2.92-3.04 (m, 4H), 2.36 (br. s., 2H), 0.87-0.92 (m, 2H), 0.71 (br. s., 2H). | | |
| N-cyclopropyl-4-(2-(methylsulfonyl)-4-(((tetrahydro-2H-pyran-4-yl)methyl)amino)pyrazolo[1,5-a][1,3,5]triazin-8-yl)benzamide | 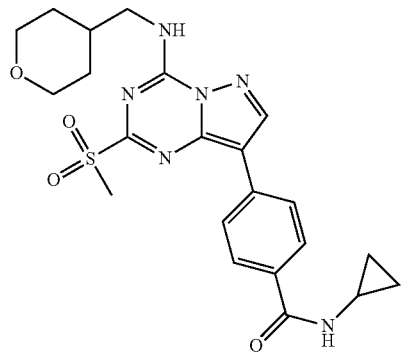 [SMILES: CS(=O)(=O)c1nc(NCC2CCOCC2)n2ncc(-c3ccc(C(=O)NC4CC4)cc3)c2n1] | [C22H26N6O4S + H]+ 471.2; 471.5 | 412 mg (69%); white solid; free base |
| | SMs: N-cyclopropyl-4-(2-(methylthio)-4-(((tetrahydro-2H-pyran-4-yl)methyl)amino)pyrazolo[1,5-a][1,3,5]triazin-8-yl)benzamide (535 mg, 1.27 mmol), mCPBA (849 mg, 3.8 mmol) | | |
| N-cyclopropyl-4-(4-((((cis)-4-hydroxycyclohexyl)methyl)(4-methoxybenzyl)amino)-2-(methylsulfonyl)pyrazolo[1,5-a][1,3,5]triazin-8-yl)-2-methylbenzamide | 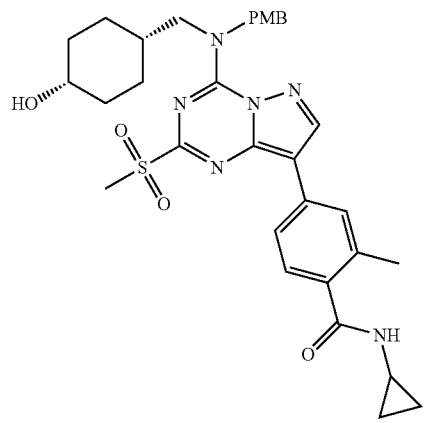 | [C32H38N6O5S + H]+ 619.3; 619.2 | 0.279 g (76%); white powder; free base |
| | SMs: N-cyclopropyl-4-(4-(((((cis)-4-hydroxycyclohexyl)methyl)(4-methoxybenzyl)amino)-2-(methylthio)pyrazolo[1,5-a][1,3,5]triazin-8-yl)-2-methylbenzamide (0.347 g, 0.59 mmol), mCPBA (0.397 g, 1.8 mmol). | | |
| | 1H NMR (400 MHz, CDCl3) δ ppm 8.37 (s, 1H), 7.83 (d, J = 7.03 Hz, 1H), 7.77 (s, 1H), 7.25-7.46 (br. m. 1H), 7.42 (d, J = 8.03 Hz, 2H), 6.88 (d, J = 8.28 Hz, 2H), 5.87-4.98 (m, 2H), 5.03-5.14 (br. s., 1H), 4.34-4.49 (m, 1H), 3.96-4.13 (m, 2H), 3.80 (s, 3H), 3.35 (br. S., 3H), 2.87-2.98 (m, 1H), 2.53 (s, 3H), 1.79 (br. S., 2H), 1.56 (br. s, 9H), 0.84-0.96 (m, 2H), 0.54-0.71 (m, 2H). | | |

Synthesis of N-cyclopropyl-4-(2-(methylsulfonyl)-4-((2-morpholinoethyl)amino)pyrazolo[1,5-a][1,3,5]triazin-8-yl)benzamide

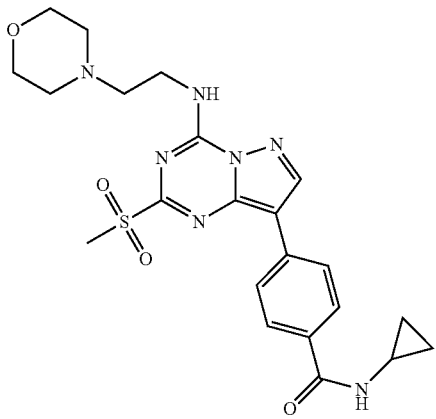 [SMILES: CS(=O)(=O)c1nc(NCCN2CCOCC2)n2ncc(-c3ccc(C(=O)NC4CC4)cc3)c2n1]

The title compound was synthesized according to General Method F followed by General Method K. A solution of N-cyclopropyl-4-(4-((4-methoxybenzyl)(2-morpholinoethyl)amino)-2-(methylthio)pyrazolo[1,5-a][1,3,5]triazin-8-yl)benz-amide (701 mg, 1.22 mmol) in TFA/DCM (5 ml/10 ml) was heated in microwave for 2 h at 80° C. After removal of solvent, it was redissovled DCM (20 ml) and treated with mMCPBA (3 eq). After stirring for 3 h at rt, additional mCPBA (2 eq) was added and it was stirred for 2 h. Solvents were removed and the crude product was purified by flash chromatography (SiO$_2$, 10-80% EtOAc/DCM then 10-90% MeOH/DCM) to give the desired product as a yellow solid (345 mg, TFA salt, 47%). NMR $^1$H NMR (400 MHz, CDCl$_3$) δ ppm 9.79 (brs, 1H), 9.01 (s, 1H), 8.46 (d, J=4.0 Hz, 1H), 8.15 (d, J=8.4 Hz, 2H), 9.26 (d, J=8.4 Hz, 2H), 4.13-3.00 (m, 15H), 2.90-2.82 (m, 1H), 0.75-0.68 (m, 2H), 0.62-0.56 (m, 2H); MS ESI [M+H]$^+$ 486.4, calcd for [C$_{22}$H$_{27}$N$_7$O$_4$S+H]$^+$ 486.2.

Synthesis of N-cyclopropyl-4-(4-((4-methoxybenzyl)((tetrahydro-2H-pyran-4-yl)methyl)amino)-2-phenoxypyrazolo[1,5-a][1,3,5]triazin-8-yl)-2-methylbenzamide

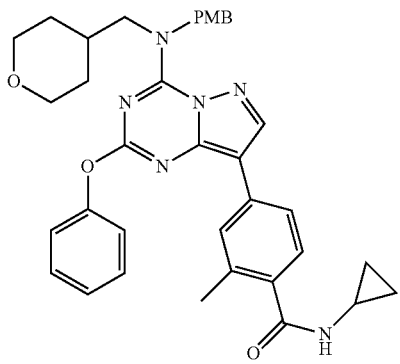

The title compound was synthesized according to General Method E utilizing N-cyclopropyl-4-(4-((4-methoxybenzyl)((tetrahydro-2H-pyran-4-yl)methyl)amino)-2-(methylsulfonyl)pyrazolo[1,5-a][1,3,5]triazin-8-yl)-2-methylbenzamide (87 mg, 0.14 mmol), phenol (68 mg, 0.72 mmol), and DBU (0.11 mL, 0.72 mmol) in DME (2 mL) at 100° C. to rt for 1 h. The crude product was purified by flash chromatography (SiO$_2$, 10-80% EtOAc/DCM) to give the desired product as a white solid (70 mg, 79%). $^1$H NMR (400 MHz, CDCl$_3$) δ ppm 8.22 (s, 1H), 7.74 (s, 1H), 7.69 (d, J=7.8 Hz, 1H), 7.37-7.46 (m, 2H), 7.30 (d, J=8.0 Hz, 1H), 7.22-7.28 (m, 3H), 7.16 (d, J=8.5 Hz, 2H), 6.86 (d, J=8.3 Hz, 2H), 5.91 (br. s., 1H), 5.66 (d, J=15.8 Hz, 2H), 4.07 (t, J=6.7 Hz, 1H), 3.93 (d, J=9.3 Hz, 2H), 3.80 (s, 3H), 3.29 (t, J=11.2 Hz, 2H), 2.90 (td, J=7.0, 3.4 Hz, 1H), 2.42 (s, 3H), 1.96-2.10 (m, 2H), 1.33-1.65 (m, 4H), 0.82-0.91 (m, 2H), 0.55-0.65 (m, 2H); MS ESI [M+H]$^+$ 619.5, calcd for [C$_{36}$H$_{38}$N$_6$O$_4$+H]$^+$ 619.30.

Synthesis of N-cyclopropyl-4-(2-(dimethylamino)-4-((4-methoxybenzyl)((tetrahydro-2H-pyran-4-yl)methyl)amino)pyrazolo[1,5-a][1,3,5]triazin-8-yl)-2-methylbenzamide

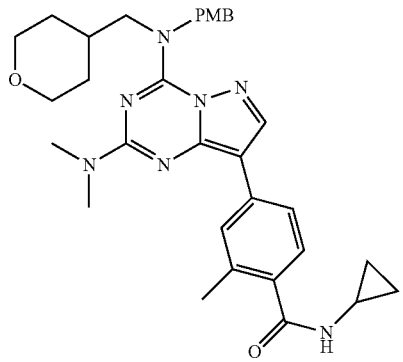

The title compound was synthesized according to General Method C utilizing N-cyclopropyl-4-(4-((4-methoxybenzyl)((tetrahydro-2H-pyran-4-yl)methyl)amino)-2-(methylsulfonyl)pyrazolo[1,5-a][1,3,5]triazin-8-yl)-2-methylbenzamide (50 mg, 0.083 mmol) and 2,2,2-trifluoro-1,1-dimethyl-ethylamine hydrochloride (20 mg, 0.12 mmol) and DIPEA (0.020 mL, 0.12 mmol) in DMF (2 mL) at 100° C. for 18 h. The crude product was purified by RP chromatography (C18 column, 10-90% MeCN/H$_2$O) to give the desired product as a pale yellow solid (23 mg, 58%). $^1$H NMR (400 MHz, CD$_3$OD) δ ppm 8.21 (s, 1H), 7.96 (s, 1H), 7.91 (d, J=8.3 Hz, 1H), 7.31 (d, J=7.8 Hz, 1H), 7.24 (d, J=8.5 Hz, 2H), 6.87 (d, J=8.5 Hz, 2H), 5.34 (br. s., 2H), 3.90 (dd, J=11.2, 3.4 Hz, 4H), 3.76 (s, 3H), 3.21 (s, 6H), 2.84-2.87 (m, 1H), 2.44 (s, 3H), 2.07-2.30 (m, 1H), 1.59 (d, J=12.5 Hz, 2H), 1.19-1.43 (m, 4H), 0.75-0.87 (m, 2H), 0.55-0.69 (m, 2H); MS ESI [M+H]$^+$ 570.5, calcd for [C$_{32}$H$_{39}$N$_7$O$_3$+H]$^+$ 570.31.

Synthesis of N-cyclopropyl-2-methyl-4-(2-(methylsulfonyl)-4-(((tetrahydro-2H-pyran-4-yl)methyl)amino)pyrazolo[1,5-a][1,3,5]triazin-8-yl)benzamide

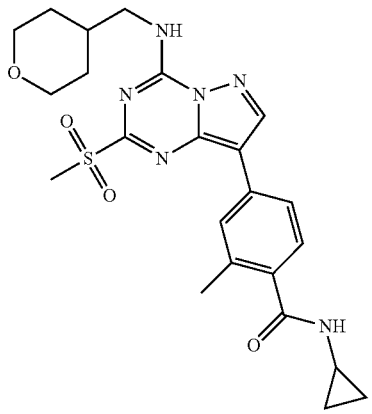 [SMILES: Cc1cc(-c2cnn3c(NCC4CCOCC4)nc(S(C)(=O)=O)nc23)ccc1C(=O)NC1CC1]

The title compound was synthesized according to General Method K utilizing N-cyclopropyl-2-methyl-4-(2-(methylthio)-4-(((tetrahydro-2H-pyran-4-yl)methyl)amino)pyrazolo[1,5-a][1,3,5]triazin-8-yl)benzamide (360 mg, 0.80 mmol) and mCPBA (540 mg, 2.39 mmol) in DCM (12 mL) 0° C. to rt for 2 h. The crude product was purified by flash chromatography (SiO$_2$, 40-100% EtOAc/DCM) to give the desired product as a pale yellow solid (185 mg, 48%). MS ESI [M+H]$^+$ 485.4, calcd for [C$_{23}$H$_{28}$N$_6$O$_4$S+H]$^+$ 485.19.

Synthesis of tert-butyl (3-(4-(cyclopropylcarbamoyl)-3-methylphenyl)-5-(phenylsulfonyl)pyrazolo[1,5-a]pyrimidin-7-yl)((tetrahydro-2H-pyran-4-yl)methyl)carbamate

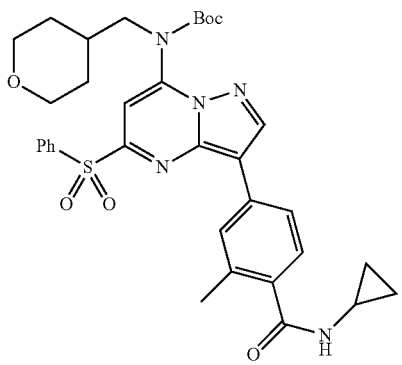 [SMILES: Cc1cc(-c2cnn3c(N(CC4CCOCC4)C(=O)OC(C)(C)C)cc(S(=O)(=O)c4ccccc4)nc23)ccc1C(=O)NC1CC1]

According to General method H, a mixture of sodium benzenesulfinate (1.968 g, 12 mmol, 1.2 equiv) and tert-butyl (3-bromo-5-chloropyrazolo[1,5-a]pyrimidin-7-yl)((tetrahydro-2H-pyran-4-yl)methyl)carbamate (4.455 g, 10 mmol) in DMF (40 mL) was heated at 60° C. for 2 h. After removal of solvents, it was purified by flash chromatography (gradient: EtOAc/hex 0-80%) to give tert-butyl (3-bromo-5-(phenylsulfonyl)pyrazolo[1,5-a]pyrimidin-7-yl)((tetrahydro-2H-pyran-4-yl) methyl)carbamate (5.37 g, 97%) as yellow solid. $^1$H NMR (400 MHz, CDCl$_3$) δ ppm 8.23 (s, 1H), 8.19-8.15 (m, 2H), 7.73-7.69 (m, 1H), 7.65-7.60 (m, 2H), 7.55 (s, 1H), 3.95-3.89 (m, 2H), 3.79 (d, J=7.6 Hz, 2H), 3.33-3.25 (m, 2H), 1.82-1.72 (m, 2H), 1.64-1.57 (m, 2H), 1.36 (s, 9H), 1.30-1.24 (m, 2H). MS ESI [M+H]$^+$ 551.1, calcd for [C$_{23}$H$_{27}$BrN$_4$O$_5$S+H]$^+$ 551.1.

According to General method I, to a mixture of the above compound (5.37 g, 9.75 mmol) and N-cyclopropyl-4-(4,4,5,5-tetramethyl-1,3,2-dioxaborolan-2-yl)benzamide (4.11 g, 13.65 mmol, 1.4 equiv) in THF (60 mL) was added 2 M K$_3$PO$_4$ (14.6 mL, 29.2 mmol, 3 equiv), followed by PdCl$_2$dppfDCM (318 mg, 0.39 mmol, 4 mol %). The resulting mixture was purged with Ar and then heated at 60° C. for 1.5 h. It was diluted with brine (30 mL), extracted with EtOAc and combined. After removal of solvents, the residue was purified by flash chromatography (gradient: EtOAc/hex 0-80%) to give the title compound (6.02 g) as yellow foam. $^1$H NMR (400 MHz, CDCl$_3$) δ ppm 8.54 (s, 1H), 8.20-8.17 (m, 2H), 7.77-7.72 (m, 2H), 7.70-7.62 (m, 3H), 7.56 (s, 1H), 7.36 (d, J=8.0 Hz, 1H), 5.96 (d, J=2.8 Hz, 1H), 3.96-3.91 (m, 2H), 3.83 (d, J=7.2 Hz, 2H), 3.31 (td, J=11.6, 1.8 Hz, 2H), 2.97-2.91 (m, 1H), 2.50 (s, 3H), 1.87-1.67 (m, 1H), 1.68-1.63 (m, 2H), 1.38 (s, 9H), 1.34-1.27 (m, 2H), 0.96-0.89 (m, 2H), 0.68-0.63 (m, 2H). MS ESI [M+H]$^+$ 646.2, calcd for [C$_{34}$H$_{39}$N$_5$O$_6$S+H]$^+$ 646.3.

Preparation of Exemplary Compounds of the Invention

Example A1

N-Cyclopropyl-4-(2-(dimethylamino)-4-(((tetrahydro-2H-pyran-4-yl)methyl)amino)pyrazolo[1,5-a][1,3,5]triazin-8-yl)-2-methylbenzamide

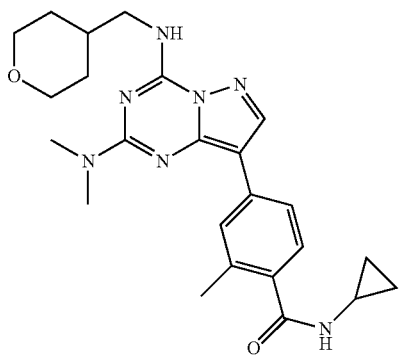 [SMILES: Cc1cc(-c2cnn3c(NCC4CCOCC4)nc(N(C)C)nc23)ccc1C(=O)NC1CC1]

The title compound was synthesized according to General Method F utilizing N-cyclopropyl-4-(2-(dimethylamino)-4-((4-methoxybenzyl)((tetrahydro-2H-pyran-4-yl)methyl)amino)pyrazolo[1,5-a][1,3,5]triazin-8-yl)-2-methylbenzamide (23 mg, 0.040 mmol) in DCM:TFA (1 mL:3 mL) at 100° C. for 30 min. Purification by prep-HPLC, followed by trituration with MeOH gave the title compound as a free base (white solid, 8.1 mg, 45%). $^1$H NMR (400 MHz, CDCl$_3$) δ ppm 8.11 (s, 1H), 7.77-7.93 (m, 2H), 7.37 (d, J=8.5 Hz, 1H), 6.39 (t, J=6.1 Hz, 1H), 5.90 (br. s., 1H), 4.02 (dd, J=11.8, 3.5 Hz, 2H), 3.52 (t, J=6.7 Hz, 2H), 3.41 (t, J=11.5 Hz, 2H), 3.27 (s, 6H), 2.82-2.97 (m, 1H), 2.52 (s, 3H), 1.87-2.06 (m, 1H), 1.73 (d, J=12.8 Hz, 2H), 1.39-1.49 (m, 2H), 0.81-0.96 (m, 2H), 0.56-0.66 (m, 2H); MS ESI [M+H]$^+$ 450.5, calcd for [C$_{24}$H$_{31}$N$_7$O$_2$+H]$^+$ 450.25.

Example A2

4-(2-(Cyclopentylamino)-4-(((tetrahydro-2H-pyran-4-yl)methyl)amino)pyrazolo[1,5-a][1,3,5]triazin-8-yl)-N-cyclopropyl-2-methylbenzamide

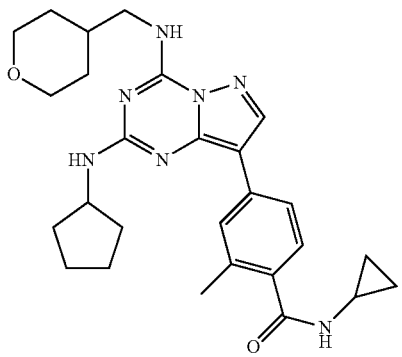 [SMILES: Cc1cc(-c2cnn3c(NCC4CCOCC4)nc(NC4CCCC4)nc23)ccc1C(=O)NC1CC1]

The title compound was synthesized according to General Method C utilizing N-cyclopropyl-2-methyl-4-(2-(methylsulfonyl)-4-(((tetrahydro-2H-pyran-4-yl)methyl)amino)pyrazolo[1,5-a][1,3,5]triazin-8-yl)benzamide (88 mg, 0.18 mmol) and cyclopentylamine (0.040 mL, 0.40 mmol) in THF (5 mL) at 35° C. for 6 h. The crude product was purified by RP chromatography (C18 column, 20-90% MeCN/H$_2$O) to give the desired product as a white solid (68 mg, 76%). $^1$H NMR (400 MHz, CDCl$_3$) δ ppm 8.08 (s, 1H), 7.66-7.96 (m, 2H), 7.34 (d, J=7.8 Hz, 1H), 6.45 (br. s., 1H), 5.98 (br. s., 1H), 5.89-6.33 (m, 1H), 5.09 (br. s., 1H), 4.26-4.42 (m, 1H), 4.00 (dd, J=11.2, 3.4 Hz, 2H), 3.45 (br. s., 2H), 3.39 (td, J=11.7, 1.9 Hz, 2H), 2.86-2.93 (m, 1H), 2.50 (s, 3H), 2.12 (br. s., 2H), 1.83-1.99 (m, 2H), 1.69-1.81 (m, 5H), 1.56 (d, J=5.8 Hz, 2H), 1.33-1.47 (m, 2H), 0.78-0.94 (m, 2H), 0.56-0.65 (m, 2H); MS ESI [M+H]$^+$ 490.5, calcd for [C$_{27}$H$_{35}$N$_7$O$_2$+H]$^+$ 490.29.

Example A4

2-Chloro-N-cyclopropyl-4-(2-phenoxy-4-(((tetrahydro-2H-pyran-4-yl)methyl)amino) pyrazolo[1,5-a][1,3,5]triazin-8-yl)benzamide

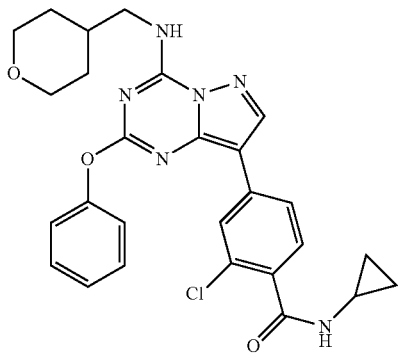 [SMILES: O=C(NC1CC1)c1ccc(-c2cnn3c(NCC4CCOCC4)nc(Oc4ccccc4)nc23)cc1Cl]

The title compound was synthesized according to General Method E utilizing 2-chloro-N-cyclopropyl-4-(2-(methylsulfonyl)-4-(((tetrahydro-2H-pyran-4-yl)methyl)amino) pyrazolo[1,5-a][1,3,5]triazin-8-yl)benzamide (100 mg, 0.20 mmol), phenol (75 mg, 0.79 mmol), and DBU (0.12 mL, 0.79 mol) in DME (4 mL) at 100° C. for 1 h. The crude product was purified by flash chromatography (C18 column, 20-90% MeCN/H$_2$O) followed by trituration with MeOH to give the desired product as a white solid (34 mg, 33%). $^1$H NMR (400 MHz, CDCl$_3$) δ ppm 8.23 (br. s., 1H), 7.89 (br. s., 1H), 7.69 (br. s., 2H), 7.41-7.54 (m, 2H), 7.28-7.37 (m, 3H), 6.74 (br. s., 1H), 6.46 (br. s., 1H), 4.03 (d, J=8.0 Hz, 2H), 3.58 (br. s., 2H), 3.41 (t, J=10.2 Hz, 2H), 2.84-3.03 (m, 1H), 1.91-2.11 (m, 1H), 1.71 (d, J=11.8 Hz, 2H), 1.34-1.51 (m, 2H), 0.89 (d, J=6.5 Hz, 2H), 0.57-0.73 (m, 2H); MS ESI [M+H]$^+$ 519.6, calcd for [C$_{27}$H$_{27}$ClN$_6$O$_3$+H]$^+$ 519.18.

Example A5

2-chloro-4-(2-(cyclopentyloxy)-4-(((tetrahydro-2H-pyran-4-yl)methyl)amino)pyrazolo[1,5-a][1,3,5]triazin-8-yl)-N-cyclopropylbenzamide

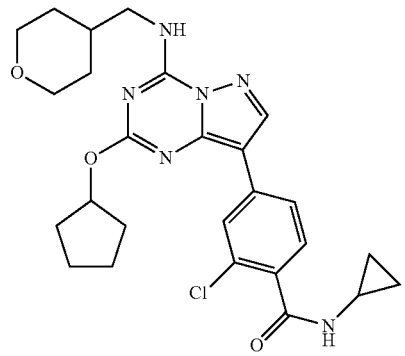 [SMILES: O=C(NC1CC1)c1ccc(-c2cnn3c(NCC4CCOCC4)nc(OC4CCCC4)nc23)cc1Cl]

The title compound was synthesized according to General Method D utilizing 2-chloro-N-cyclopropyl-4-(2-(methylsulfonyl)-4-(((tetrahydro-2H-pyran-4-yl)methyl)amino) pyrazolo[1,5-a][1,3,5]triazin-8-yl)benzamide (100 mg, 0.20 mmol), NaH (100 mg, 60% in mineral oil, 2.5 mmol), and cyclopentanol (0.040 mL, 0.44 mol) in DMF (4 mL) at 0° C. to rt for 1 h. The crude product was purified by RP chromatography (C18 column, 20-90% MeCN/H$_2$O) followed by trituration with MeOH to give the desired product as a white solid (48 mg, 48%). $^1$H NMR (400 MHz, CDCl$_3$) δ ppm 8.20 (s, 1H), 8.11 (s, 1H), 7.89 (d, J=9.3 Hz, 1H), 7.79 (d, J=8.3 Hz, 1H), 6.58 (br. s., 1H), 6.48 (br. s., 1H), 5.39-5.62 (m, 1H), 4.02 (d, J=8.0 Hz, 2H), 3.59 (t, J=6.4 Hz, 2H), 3.42 (t, J=10.8 Hz, 2H), 2.96 (d, J=3.5 Hz, 1H), 2.06-2.19 (m, 2H), 1.93-2.05 (m, 3H), 1.81-1.92 (m, 2H), 1.63-1.78 (m, 4H), 1.38-1.51 (m, 2H), 0.84-0.97 (m, 2H), 0.61-0.74 (m, 2H); MS ESI [M+H]$^+$ 511.7, calcd for [C$_{26}$H$_{31}$ClN$_6$O$_3$+H]$^+$ 511.21.

Example C1

N-cyclopropyl-4-(4-((3-morpholinopropyl)amino)-2-phenoxypyrazolo[1,5-a][1,3,5]triazin-8-yl)benzamide

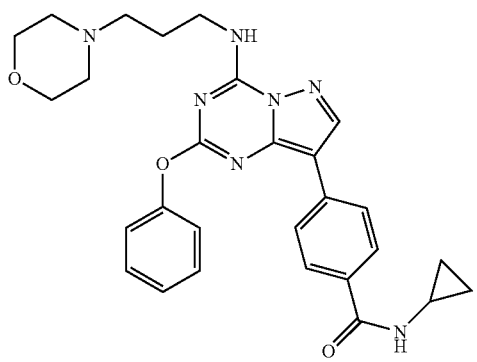 [SMILES: O=C(NC1CC1)c1ccc(-c2cnn3c(NCCCN4CCOCC4)nc(Oc4ccccc4)nc23)cc1]

4-(3-((8-(4-(cyclopropylcarbamoyl)phenyl)-2-phenoxypyrazolo[1,5-a][1,3,5]triazin-4-yl)amino)propyl)-4-hydroxymorpholin-4-ium 2,2,2-trifluoroacetate (42 mg, 0.065 mmol) was converted into free base by running through PoraPak. The resulting free base was dissolved in CDCl3 before the solution of (pinB)2 (17 mg, 0.065 mmol) in DCM was added dropwise at rt. The resulting reaction mixture was stirred at rt for 5 min followed by removal of solvent. The residue was purified by HPLC to give the title compound (30 mg, 70% yield) as light yellow solid. 1H NMR (400 MHz, CD3OD) δ ppm 8.39 (s, 1H), 7.85 (d, J=8.5 Hz, 2H), 7.69 (d, J=8.3 Hz, 2H), 7.42-7.54 (m, 2H), 7.24-7.36 (m, 3H), 4.07 (d, J=12.3 Hz, 2H), 3.81 (t, J=12.3 Hz, 2H), 3.67 (t, J=6.4 Hz, 2H), 3.54 (d, J=12.3 Hz, 2H), 3.21-3.29 (m, 2H), 3.14 (t, J=10.9 Hz, 2H), 2.79-2.90 (m, 1H), 2.08-2.22 (m, 2H), 0.76-0.85 (m, 2H), 0.59-0.68 (m, 2H); MS ESI [M+H]+ 514.3, calcd for [$C_{28}H_{31}N_7O_3$+H]+ 514.3.

The following exemplary compounds were synthesized according to General Methods C, D, E or F, as indicated:

| Example/IUPAC name | Structure | MS calculated MS ESI [M + H]$^+$ | Yield; Appearance; Salt form |
|---|---|---|---|
| A3: N-cyclopropyl-2-methyl-4-(2-phenoxy-4-(((tetrahydro-2H-pyran-4-yl)methyl)amino)pyrazolo[1,5-a][1,3,5]triazin-8-yl)benzamide | 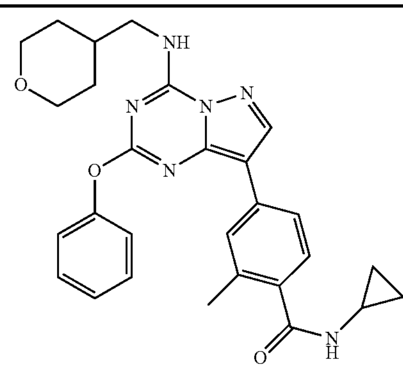 | [$C_{28}H_{30}N_6O_3$ + H]$^+$ 499.2 499.5 | 131 mg (46%); white solid; free base |

SMs (method F): N-cyclopropyl-4-(4-((4-methoxybenzyl)((tetrahydro-2H-pyran-4-yl)methyl)amino)-2-phenoxypyrazolo[1,5-a][1,3,5]triazin-8-yl)-2-methylbenzamide (354 mg, 0.57 mmol).
1H NMR (400 MHz, CDCl3) δ ppm 8.15 (s, 1H), 7.64 (s, 1H), 7.49 (d, J = 8.0 Hz, 1H), 7.39-7.45 (m, 2H), 7.25-7.31 (m, 3H), 7.21 (d, J = 8.0 Hz, 1H), 6.87 (t, J = 6.1 Hz, 1H), 6.11 (br. s., 1H), 3.96 (dd, J = 11.4, 3.4 Hz, 2H), 3.50 (t, J = 6.7 Hz, 2H), 3.35 (td, J = 11.7, 1.6 Hz, 2H), 2.87-2.92 (m, 1H), 2.32 (s, 3H), 1.87-2.01 (m, 1H), 1.61-1.70 (m, 2H), 1.38-1.45 (m, 2H), 0.79-0.86 (m, 2H), 0.55-0.61 (m, 2H).

| Example/IUPAC name | Structure | MS calculated MS ESI [M + H]$^+$ | Yield; Appearance; Salt form |
|---|---|---|---|
| A10: N-cyclopropyl-4-(2-phenoxy-4-(((tetrahydro-2H-pyran-4-yl)methyl)amino)pyrazolo[1,5-a][1,3,5]triazin-8-yl)benzamide | | [$C_{27}H_{28}N_6O_3$ + H]$^+$ 485.2 485.5 | 46 mg (45%); white solid; free base |

SMs (method E): N-cyclopropyl-4-(2-(methylthio)-4-(((tetrahydro-2H-pyran-4-yl)methyl)amino)pyrazolo[1,5-a][1,3,5]triazin-8-yl)benzamide (100 mg, 0.21 mmol), phenol (79 mg, 0.84 mmol), DBU (0.13 mL, 0.84 mmol).

| Example/IUPAC name | Structure | MS calculated<br>MS ESI<br>[M + H]+ | Yield;<br>Appearance;<br>Salt form |
|---|---|---|---|
| | ¹H NMR (400 MHz, CDCl₃) δ 8.26 (s, 1H), 7.86 (d, J = 9.3 Hz, 2H), 7.67 (d, J = 8.5 Hz, 2H), 7.45 (t, J = 7.8 Hz, 2H), 7.26-7.33 (m, 3H), 6.84 (br. s., 1H), 6.24 (br. s., 1H), 4.01 (dd, J = 11.3, 3.3 Hz, 2H), 3.51-3.58 (m, 2H), 3.40 (td, J = 11.8, 2.0 Hz, 2H), 2.86-2.95 (m, 1H), 1.92-2.06 (m, 1H), 1.63-1.75 (m, 2H), 1.31-1.49 (m, 2H), 0.82-0.92 (m, 2H), 0.56-0.69 (m, 2H). | | |
| A11: 4-(2-(cyclopentyloxy)-4-(((tetrahydro-2H-pyran-4-yl)methyl)amino)pyrazolo[1,5-a][1,3,5]triazin-8-yl)-N-cyclopropylbenzamide | 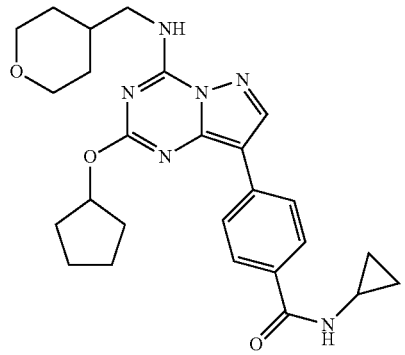 [SMILES: O=C(NC1CC1)c1ccc(-c2cnn3c(NCC4CCOCC4)nc(OC4CCCC4)nc23)cc1] | [C₂₆H₃₂N₆O₃ + H]+<br>477.25<br>477.5 | 39 mg<br>(39%);<br>white solid;<br>free base |
| | SMs (method D): N-cyclopropyl-4-(2-(methylthio)-4-(((tetrahydro-2H-pyran-4-yl)methyl)amino)pyrazolo[1,5-a][1,3,5]triazin-8-yl)benzamide (100 mg, 0.21 mmol), NaH (44 mg, 60% in mineral oil, 1.11 mmol), and cyclopentanol (0.049 g, 0.57 mol)<br>¹H NMR (400 MHz, CDCl₃) δ ppm 8.23 (s, 1H), 8.04 (d, J = 8.5 Hz, 2H), 7.79 (d, J = 8.5 Hz, 2H), 6.53-6.60 (m, 1H), 6.24 (br. s., 1H), 5.47-5.55 (m, 1H), 4.01 (dd, J = 11.0, 4.0 Hz, 2H), 3.59 (t, J = 6.4 Hz, 2H), 3.35-3.46 (m, 2H), 2.88-2.97 (m, 1H), 2.04-2.14 (m, 2H), 1.92-2.02 (m, 3H), 1.81-1.90 (m, 2H), 1.69-1.77 (m, 2H), 1.62-1.69 (m, 2H), 1.37-1.51 (m, 2H), 0.85-0.92 (m, 2H), 0.60-0.67 (m, 2H). | | |
| A13: N-cyclopropyl-4-(2-(pyridin-3-yloxy)-4-(((tetrahydro-2H-pyran-4-yl)methyl)amino)-pyrazolo[1,5-a][1,3,5]triazin-8-yl)benzamide | 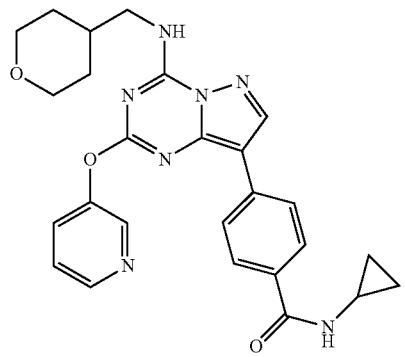 [SMILES: O=C(NC1CC1)c1ccc(-c2cnn3c(NCC4CCOCC4)nc(Oc4cccnc4)nc23)cc1] | [C₂₆H₂₇N₇O₃ + H]+<br>486.2<br>486.4 | 18 mg<br>(18%);<br>white solid;<br>free base |
| | SMs (method E): N-cyclopropyl-4-(2-(methylthio)-4-(((tetrahydro-2H-pyran-4-yl)methyl)amino)pyrazolo[1,5-a][1,3,5]triazin-8-yl)benzamide (100 mg, 0.21 mmol), 3-hydroxypyridine (79 mg, 0.84 mmol), DBU (0.13 mL, 0.84 mmol). | | |

| Example/IUPAC name | Structure | MS calculated MS ESI [M + H]+ | Yield; Appearance; Salt form |
|---|---|---|---|

1H NMR (400 MHz, CDCl3) δ ppm 8.68 (s, 1H), 8.56 (d, J = 4.8 Hz, 1H), 8.28 (d, J = 1.3 Hz, 1H), 7.82 (d, J = 7.3 Hz, 2H), 7.63-7.73 (m, 3H), 7.42 (dd, J = 8.3, 4.8 Hz, 1H), 6.78 (br. s., 1H), 6.23 (br. s., 1H), 3.97-4.06 (m, 2H), 3.57 (d, J = 6.5 Hz, 2H), 3.41 (t, J = 11.4, Hz, 2H), 2.85-2.97 (m, 1H), H), 1.92-2.06 (m, 1H), 1.71 (d, J = 12.0 Hz, 2H), 1.35-1.51 (m, 2H), 0.83-0.92 (m, 2H), 0.58-0.68 (m, 2H).

| A6: 2-chloro-N-cyclopropyl-4-(2-morpholino-4-(((tetrahydro-2H-pyran-4-yl)methyl)amino)pyrazolo[1,5-a][1,3,5]triazin-8-yl)benzamide | 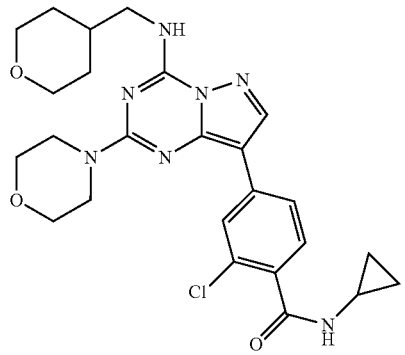 [SMILES: O=C(NC1CC1)c1ccc(-c2cnn3c(NCC4CCOCC4)nc(N4CCOCC4)nc23)cc1Cl] | [C25H30ClN7O3 + H]+ 512.2 512.7 | 46 mg (46%); beige solid; free base |

SMs (method C): 2-chloro-N-cyclopropyl-4-(2-(methylsulfonyl)-4-(((tetrahydro-2H-pyran-4-yl)methyl)amino) pyrazolo[1,5-a][1,3,5]triazin-8-ylbenzamide (100 mg, 0.20 mmol), morpholine (0.46 mmol)

1H NMR (400 MHz, CDCl3) δ ppm 8.11 (s, 1H), 8.03 (s, 1H), 7.87 (d, J = 6.8 Hz, 1H), 7.78 (d, J = 7.3 Hz, 1H), 6.53 (s, 1H), 6.43 (s, 1H), 3.98-4.08 (m, 2H), 3.82-3.98 (m, 4H), 3.75-3.87 (m, 4H), 3.48-3.59 (m, 2H), 3.42 (t, J = 10.0 Hz, 2H), 2.92-3.04 (m, 1H), 1.93-1.98 (m, 1H), 1.58-1.77 (m, 2H), 1.36-1.52 (m, 2H), 0.75-0.95 (m, 2H), 0.61-0.73 (m, 2H).

| A9: N-cyclopropyl-4-(2-(4-hydroxypiperidin-1-yl)-4-((2-morpholinoethyl)amino)pyrazolo[1,5-a][1,3,5]triazin-8-yl)benzamide | 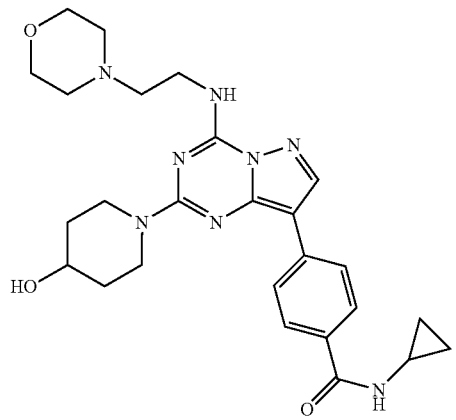 [SMILES: O=C(NC1CC1)c1ccc(-c2cnn3c(NCCN4CCOCC4)nc(N4CCC(O)CC4)nc23)cc1] | [C26H34N8O3 + H]+ 507.3 507.5 | 25.3 mg (31%); white solid; free base |

SMs (method C): N-cyclopropyl-4-(2-(methylsulfonyl)-4-((2-morpholinoethyl)amino)pyrazolo[1,5-a][1,3,5]triazin-8-yl)benzamide TFA salt (97 mg, 0.16 mmol), piperidin-4-ol hydrochloride (55 mg, 0.4 mmol), DIPEA (0.14 ml, 0.8 mmol).

1H NMR (400 MHz, CDCl3) δ ppm 8.14 (s, 1H), 8.02 (d, J = 8.4 Hz, 2H), 7.77 (d, J = 8.4 Hz, 2H), 6.85-6.78 (m, 1H), 6.32 (s, 1H), 4.54-4.43 (m, 2H), 4.03-3.94 (m, 1H), 3.8-3.65 (m, 6H), 3.48-3.38 (m, 2H), 2.97-2.88 (m, 1H), 2.68 (t, J = 6.0 Hz, 2H), 2.60-2.48 (m, 4H), 2.05-1.94 (m, 2H), 1.65-1.53 (m, 2H), 0.93-0.83 (m, 2H), 0.66-0.57 (m, 2H).

| Example/IUPAC name | Structure | MS calculated MS ESI [M + H]+ | Yield; Appearance; Salt form |
|---|---|---|---|
| A7: N-cyclopropyl-4-(4-((2-morpholinoethyl)amino)-2-phenoxypyrazolo [1,5-a][1,3,5]triazin-8-yl) benzamide | 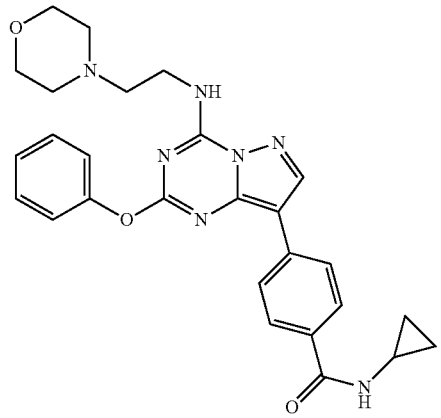 | [C$_{27}$H$_{29}$N$_7$O$_3$ + H]+ 500.2 500.5 | 25.4 mg (32%); yellow solid; free base |

SMs (method E): N-cyclopropyl-4-(2-(methylsulfonyl)-4-((2-morpholinoethyl)amino)pyrazolo[1,5-a][1,3,5]triazin-8-yl)benzamide TFA salt (97 mg, 0.16 mmol), phenol (38 mg, 0.4 mmol), DBU (0.06 ml, 0.4 mmol).

$^1$H NMR (400 MHz, CDCl$_3$) δ ppm 8.26 (s, 1H), 7.83 (d, J = 8.4 Hz, 2H), 7.65 (d, J = 8.4 Hz, 2H), 7.47-7.41 (m, 2H), 7.32-7.23 (m, 4H), 6.29 (s, 1H), 3.80-3.68 (m, 6H), 2.94-2.87 (m, 1H), 2.69 (t, J = 6.0 Hz, 2H), 2.57-2.49 (m, 4H), 0.90-0.83 (m, 2H), 0.55-0.49 (m, 2H).

| A8: N-cyclopropyl-4-(4-((2-morpholinoethyl)amino)-2-(pyridin-3-yloxy)pyrazolo[1,5-a][1,3,5]triazin-8-yl)benzamide | 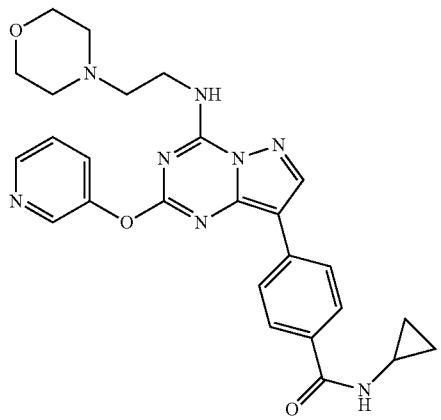 [SMILES: O=C(NC1CC1)c1ccc(-c2cnn3c(NCCN4CCOCC4)nc(Oc4cccnc4)nc23)cc1] | [C$_{26}$H$_{28}$N$_8$O$_3$ + H]+ 501.2 501.3 | 22.5 mg (28%); white solid; free base |

SMs (method E): N-cyclopropyl-4-(2-(methylsulfonyl)-4-((2-morpholinoethyl)amino)pyrazolo[1,5-a][1,3,5]triazin-8-yl)benzamide TFA salt (97 mg, 0.16 mmol), 3-hydroxypyridine (38 mg, 0.2 mmol), DBU (0.06 ml, 0.4 mmol).

$^1$H NMR (400 MHz, CDCl$_3$) δ ppm 8.67 (d, J = 2.8 Hz, 1H), 8.55 (dd, J = 4.8, 1.2 Hz, 1H), 8.28 (s, 1H), 7.81 (d, J = 8.4 Hz, 2H), 7.70-7.65 (m, 3H), 7.41 (dd, J = 8.2, 4.6 Hz, 1H), 7.37-7.33 (m, 1H),

| Example/IUPAC name | Structure | MS calculated MS ESI [M + H]+ | Yield; Appearance; Salt form |
|---|---|---|---|
| | 6.33 (s, 1H), 3.80-3.69 (m, 6H), 2.95-2.87 (m, 1H), 2.71 (t, J = 6.0 Hz, 2H), 2.58-2.51 (m, 4H), 0.90-0.84 (m, 2H), 0.66-0.61 (m, 2H). | | |
| A12: N-cyclopropyl-4-(2-(methylsulfonyl)-4-((3-morpholinopropyl)amino)pyrazolo[1,5-a][1,3,5]triazin-8-yl)benzamide | 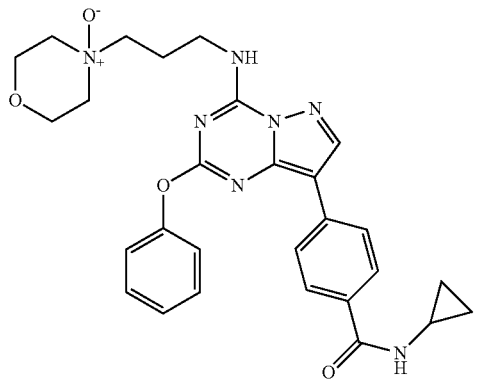 [SMILES: O=C(NC1CC1)c1ccc(-c2cnn3c(NCCC[N+]4([O-])CCOCC4)nc(Oc4ccccc4)nc23)cc1] | [$C_{28}H_{31}N_7O_4$ + H]+ 530.2 530.3 | 62 mg (48%); off white solid; TFA salt |

SMs: (method E)N-cyclopropyl-4-(2-(methylsulfonyl)-4-((3-morpholinopropyl)amino)pyrazolo[1,5-a][1,3,5]triazin-8-yl)benzamide (100 mg, 0.2 mmol), phenol (75 mg, 0.820 mmol), DBU (122 mg, 0.802 mmol), small amount of peroxide carried over from previous step (sulfide → sulfone oxidation).

$^1$H NMR (400 MHz, CD$_3$OD) δ 8.35 (s, 1H), 7.82 (d, J = 8.5 Hz, 2H), 7.66 (d, J = 8.5 Hz, 2H), 7.43-7.52 (m, 2H), 7.25-7.35 (m, 3H), 4.06-4.18 (m, 2H), 3.93-4.02 (m, 2H), 3.63-3.85 (m, 8H), 2.83 (tt, J = 7.4, 3.8 Hz, 1H), 2.26-2.37 (m, 2H), 0.77-0.85 (m, 2H), 0.62-0.68 (m 2H).

| Example/IUPAC name | Structure | MS calculated MS ESI [M + H]+ | Yield; Appearance; Salt form |
|---|---|---|---|
| A14: 2-chloro-N-cyclopropyl-4-(4-(((tetrahydro-2H-pyran-4-yl)methyl)amino)-2-((tetrahydro-2H-pyran-4-yl)oxy)pyrazolo[1,5-a][1,3,5]triazin-8-yl)benzamide | 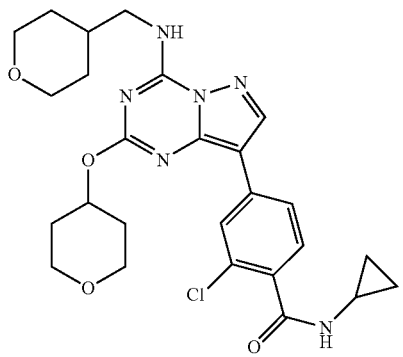 [SMILES: O=C(NC1CC1)c1ccc(-c2cnn3c(NCC4CCOCC4)nc(OC4CCOCC4)nc23)cc1Cl] | [$C_{26}H_{31}ClN_6O_4$ + H]+ 527.2 527.7 | 69 mg (69%); white solid; free base |

SMs (method D): 2-chloro-N-cyclopropyl-4-(2-(methylsulfonyl)-4-(((tetrahydro-2H-pyran-4-yl)methyl)amino) pyrazolo[1,5-a][1,3,5]triazin-8-yl)benzamide (100 mg, 0.20 mmol), NaH (100 mg, 60% in mineral oil, 2.5 mmol), and tetrahydro-2H-pyran-4-ol (0.044 g, 0.44 mol)

$^1$H NMR (400 MHz, CDCl$_3$) δ 8.21 (s, 1H), 8.14 (s, 1H), 7.79 (s, 2H), 6.63 (t, J = 6.1 Hz, 1H), 6.50 (br. s., 1H), 5.27-5.33 (m, 1H), 4.09 (dt, J = 11.6, 3.9 Hz, 2H), 4.02 (dd, J = 11, 3.9 Hz, 2H), 3.59-

| Example/IUPAC name | Structure | MS calculated<br>MS ESI<br>[M + H]+ | Yield;<br>Appearance;<br>Salt form |
|---|---|---|---|
| | 3.67 (m, 4H), 3.42 (t, J = 10.3 Hz, 2H), 2.93-2.99 (m, 1H), 2.21-2.25 (m, 2H), 1.91-2.02 (m, 3H),<br>1.74 (d, J = 11.8 Hz, 2H), 1.40-1.50 (m, 2H), 0.91 (q, J =7.1 Hz, 2H), 0.68 (q, J = 8.0 Hz, 2H). | | |
| A15: 4-(2-(cyclopentylamino)-4-<br>(((tetrahydro-2H-pyran-4-<br>yl)methyl)amino)pyrazolo[1,5-<br>a][1,3,5]triazin-8-yl)-N-<br>cyclopropylbenzamide | | [C₂₆H₃₃N₇O₂ + H]+<br>476.3<br>476.5 | 45 mg<br>(45%);<br>white solid;<br>free base |
| | SMs (method C): N-cyclopropyl-4-(2-(methylthio)-4-(((tetrahydro-2H-pyran-4-<br>yl)methyl)amino)pyrazolo[1,5-a][1,3,5]triazin-8-yl)benzamide (100 mg, 0.21 mmol),<br>cyclopentylamine (0.046 g, 0.47 mol).<br>¹H NMR (400 MHz, CDCl₃) δ ppm 8.12 (s, 1H), 8.05 (br. s., 2H), 7.77 (d, J = 8.3 Hz, 2H), 6.41<br>(br. s., 1H), 6.28 (br. s., 1H), 5.11 (br. s., 1H), 4.30-4.42 (m, 1H), 4.01 (dd, J = 11.5, 3.0 Hz, 2H),<br>3.29-3.56 (m, 4H), 2.87-2.96 (m, 1H), 2.02-2.22 (m, 2H), 1.87-2.00 (m, 1H), 1.62-1.83 (m,<br>6H), 1.49-1.61 (m, 2H), 1.35-1.48 (m, 2H), 0.84-0.91 (m, 2H), 0.58-0.67 (m, 2H). | | |

The following exemplary compounds were synthesized according to General Methods C, D, E or F, as indicated:

| Structure | Example number<br>MS calcd;<br>MS ESI [M + H]+;<br>HPLC purity | ¹H NMR |
|---|---|---|
| | C2<br>[C₂₇H₃₀N₆O₃ + H]+<br>487.2;<br>487.5;<br>95% at 254 nm | (400 MHz, CDCl₃) δ ppm 8.26 (s, 1H), 7.86 (d,<br>J = 8.5 Hz, 2H), 7.69 (d, J = 8.3 Hz, 2H), 7.45 (t,<br>J = 8.0 Hz, 2H), 7.25-7.35 (m, 3H), 5.92 (d, J = 7.5<br>Hz, 1H), 4.30 (dq, J = 13.7, 6.8 Hz, 1H), 4.01 (dd,<br>J = 11.3, 3.5 Hz, 2H), 3.54 (d, J = 7.0 Hz, 2H), 3.39<br>(t, J = 11.0 Hz, 2H), 1.90-2.04 (m, 1H), 1.69 (d,<br>J = 12.0 Hz, 2H), 1.33-1.48 (m, 2H), 1.27 (d, J = 6.5<br>Hz, 6H). |
| | C3<br>[C₂₇H₃₀N₆O₃ + H]+<br>487.2;<br>487.5;<br>95% at 254 nm | (400 MHz, CDCl₃) δ ppm 8.29 (s, 1H), 7.85 (d,<br>J = 8.3 Hz, 2H), 7.57 (d, J = 8.0 Hz, 2H), 7.51 (t,<br>J = 8.0 Hz, 2H), 7.31-7.41 (m, 3H), 6.78 (br. s, 1H),<br>4.09 (m, J = 7.3 Hz, 2H), 3.61 (d, J = 6.8 Hz, 2H),<br>3.47 (t, J = 11.4 Hz, 2H), 2.53-2.64 (m, 1H),<br>2.05 (br. s., 1H), 1.77 (d, J = 12.8 Hz, 2H), 1.41-<br>1.55 (m, 2H), 1.34 (d, J = 6.8 Hz, 6H). |

| Structure | Example number MS calcd; MS ESI [M + H]+; HPLC purity | 1H NMR |
|---|---|---|
| | C4<br>[C26H34N6O3 + H]+<br>479.3;<br>479.6;<br>95% at 254 nm | (400 MHz, CDCl3) δ ppm 8.22 (s, 1H), 8.03 (d, J = 8.3 Hz, 2H), 7.79 (d, J = 8.3 Hz, 2H), 6.61-6.68 (m, 1H), 6.05 (d, J = 7.5 Hz, 1H), 5.47-5.55 (m, 1H), 5.11 (br. s, 1H), 4.24-4.38 (m, 1H), 4.01 (dd, J = 11.4, 3.4 Hz, 2H), 3.57 (t, J = 6.5 Hz, 2H), 3.40 (t, J = 10.9 Hz, 2H), 2.04-2.14 (m, 2H), 1.92-2.01 (m, 2H), 1.78-1.90 (m, 2H), 1.60-1.76 (m, 4H), 1.36-1.49 (m, 2H), 1.22-1.32 (m, 6H). |
| | C5<br>[C26H34N6O3 + H]+<br>479.3;<br>479.6;<br>95% at 254 nm | (400 MHz, CDCl3) δ ppm 9.17 (br. s, 1H), 8.16 (s, 1H), 7.83 (d, J = 8.3 Hz, 2H), 7.56 (d, J = 8.5 Hz, 2H), 7.50 (s, 1H), 6.93-7.04 (m, 1H), 5.45-5.58 (m, 1H), 4.05 (d, J = 11.5, 3.5 Hz, 2H), 3.59 (t, J = 6.5 Hz, 2H), 3.44 (t, J = 11.3 Hz, 2H), 2.52-2.65 (m, 1H), 1.58-2.12 (m, 10H), 1.38-1.53 (m, 2H), 1.22-1.32 (m, 6H). |
| | C6<br>[C24H24N6O3 + H]+<br>445.2;<br>445.4;<br>95 % at 254 nm | (400 MHz, CDCl3) δ ppm 8.25 (s, 1H), 7.82 (d, J = 8.3 Hz, 2H), 7.64 (d, J = 8.0 Hz, 2H), 7.39-7.51 (m, 2H), 7.25-7.36 (m, 3H), 7.06 (br. s, 1H), 6.23 (br. s., 1H), 3.85 (q, J = 5.4 Hz, 2H), 3.66 (t, J = 4.8 Hz, 2H), 3.44 (s, 3H), 2.81-2.99 (m, 1H), 0.78-0.98 (m, 2H), 0.53-0.72 (m, 2H). |
| | C7<br>[C27H27FN6O3 + H]+<br>503.2;<br>503.5;<br>95% at 254 nm | (400 MHz, CDCl3) δ ppm 8.22 (s, 1H), 8.03 (t, J = 8.4 Hz, 1H), 7.54-7.68 (m, 2H), 7.46 (t, J = 7.8 Hz, 2H), 7.23-7.35 (m, 3H), 6.82 (d, J = 12.5 Hz, 1H), 4.00 (d, J = 8.3 Hz, 2H), 3.55 (d, J = 6.5 Hz, 2H), 3.39 (t, J = 11.5 Hz, 2H), 2.94 (br. d, J = 3.0 Hz, 1H), 1.98 (br. s., 1H), 1.68 (d, J = 11.5 Hz, 2H), 1.33-1.48 (m, 2H), 0.80-0.92 (m, 2H), 0.57-0.67 (m, 2H). |

| Structure | Example number MS calcd; MS ESI [M + H]+; HPLC purity | 1H NMR |
|---|---|---|
| 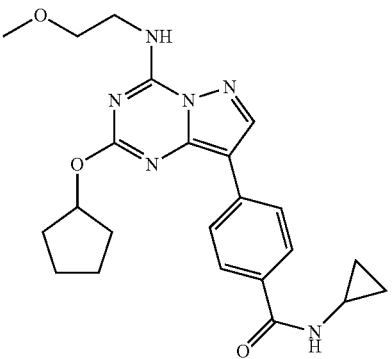 [SMILES: COCCNc1nc(OC2CCCC2)nc2c(-c3ccc(C(=O)NC4CC4)cc3)cnn12] | C8 [C23H28N6O3 + H]+ 437.2; 437.2; 95% at 254 nm | (400 MHz, CDCl3) δ ppm 8.13 (s, 1H), 7.93 (d, J = 8.3 Hz, 2H), 7.72 (d, J = 8.3 Hz, 2H), 7.05-7.15 (m, 1H), 6.66 (br. s., 1H), 5.46-5.51 (m, 1H), 3.84 (q, J = 5.2 Hz, 2H), 3.63-3.71 (m, 2H), 3.42 (s, 3H), 2.94 (m, J = 6.9, 3.4 Hz, 1H), 2.02-2.14 (m, 2H), 1.91-2.00 (m, 2H), 1.79-1.90 (m, 2H), 1.58-1.72 (m, 2H), 0.83-0.95 (m, 2H), 0.64-0.74 (m, 2H). |
| 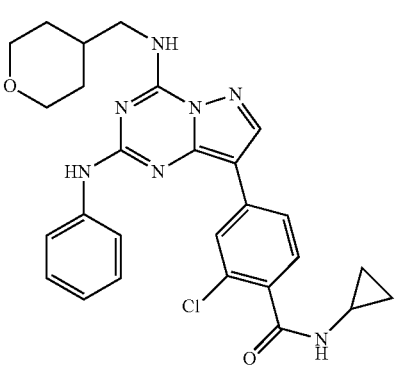 [SMILES: Cc1cc(-c2cnn3c(NCC4CCOCC4)nc(Nc4ccccc4)nc23)ccc1C(=O)NC1CC1] | C9 [C27H28ClN7O2 + H]+ 445.2; 445.4; 96.4 % at 254 nm | (400 MHz, CDCl3) δ ppm 8.27 (s, 1H), 8.17 (s, 1H), 7.81 (s, 2H), 7.77 (d, J = 8.0 Hz, 2H), 7.42 (t, J = 7.9 Hz, 2H), 7.13 (t, J = 1.0 Hz, 1H), 7.06 (s, 1H), 6.55 (br. s., 2H), 4.04 (d, J = 7.3 Hz, 2H), 3.55 (t, J = 6.8 Hz, 2H), 3.43 (t, J = 11.7 Hz, 2H), 2.92-3.00 (m, 1H), 1.91-2.13 (m, 1H), 1.74 (d, J = 12.3 Hz, 2H), 1.36-1.53 (m, 2H), 0.91 (s, 2H), 0.62-0.80 (m, 2H). |
| 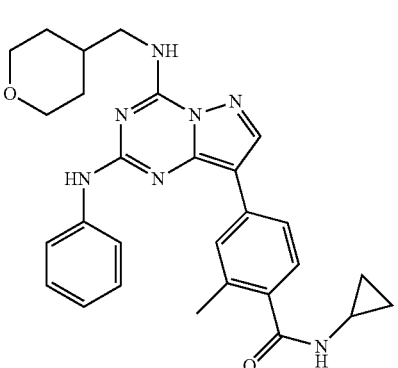 | C10 [C28H31N7O2 + H]+ 498.6; 498.5; 98.5% at 254 nm | (400 MHz, CDCl3) δ 8.17 (s, 1H), 8.00 (s, 1H), 7.79 (d, J = 8.3 Hz, 2H), 7.74 (d, J = 7.5 Hz, 1H), 7.34-7.44 (m, 3H), 7.11 (t, J = 7.4 Hz, 1H), 7.02 (s, 1H), 6.54 (t, J = 6.0 Hz, 1H), 5.90 (br. s., 1H), 4.04 (dd, J = 11.3, 3.8 Hz, 2H), 3.54 (t, J = 6.7 Hz, 2H), 3.43 (t, J = 11.0 Hz, 2H), 2.88-2.99 (m, 1H), 2.56 (s, 3H), 1.93-2.10 (m, 1H), 1.76 (d, J = 10.5 Hz, 2H), 1.38-1.53 (m, 2H), 0.84-0.96 (m, 2H), 0.58-0.68 (m, 2H). |
| 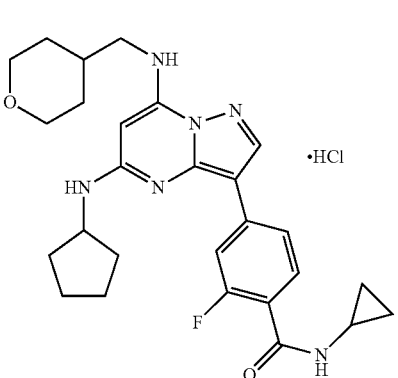 | C11 [C26H32FN7O2 + H]+ 494.3; 494.5; 95% at 254 nm | (400 MHz, CDCl3) δ ppm 14.23 (br. s., 1H), 9.86 (br. s., 1H), 7.91-8.32 (m, 2H), 7.30-7.79 (m, 3H), 6.87 (br. s., 1H), 4.38 (br. s, 1H), 3.94-4.16 (m, 2H), 3.54-3.81 (m, 2H), 3.30-3.54 (m, 2H), 2.87-3.05 (m, 1H), 1.39-2.20 (m, 12H), 0.76-0.96 (m, 2H), 0.55-0.73 (m, 2H). |

| Structure | Example number<br>MS calcd;<br>MS ESI [M + H]+;<br>HPLC purity | 1H NMR |
|---|---|---|
| | C12<br>[C28H29FN6O4 + H]+<br>533.2;<br>533.5;<br>95% at 254 nm | (400 MHz, CDCl3) δ ppm 8.22 (s, 1H), 8.03 (t, J = 8.4 Hz, 1H), 7.56-7.70 (m, 2H), 7.34 (t, J = 8.8 Hz, 1H), 6.79-6.93 (m, 5H), 5.94 (br. s., 1H), 4.00 (dd, J = 11.3, 3.3 Hz, 2H), 3.83 (s, 3H), 3.54 (t, J = 6.5 Hz, 2H), 3.39 (t, J = 11.3 Hz, 2H), 2.88-2.98 (m, 1H), 1.89-2.04 (m, 1H), 1.68 (d, J = 11.5 Hz, 2H), 1.33-1.48 (m, 2H), 0.82-0.92 (m, 2H), 0.58-0.67 (m, 2H). |
| | C13<br>[C27H34N6O3 +H]+<br>491.3;<br>491.2;<br>96.8% at 254 nm | (400 MHz, CDCl3) δ ppm 8.18 (s, 1H), 7.72-7.89 (m, 2H), 7.36 (d, J = 8.0 Hz, 1H), 6.61 (t, J = 6.0 Hz, 1H), 6.00 (br. s., 1H), 5.39-5.56 (m, 1H), 4.01 (dd, J = 11.3, 3.5 Hz, 2H), 3.57 (t, J = 6.5 Hz, 2H), 3.30-3.45 (m, 2H), 2.83-2.98 (m, 1H), 2.51 (s, 3H), 2.03-2.18 (m, 2H), 1.92-2.00 (m, 2H), 1.60-1.90 (m, 6H), 1.34-1.51 (m, 2H), 0.81-0.93 (m, 2H), 0.54-0.68 (m, 2H). |
| | C14<br>[C28H28F2N6O3 + H]+<br>535.2;<br>535.5;<br>95.4% at 254 nm | (400 MHz, CDCl3) δ ppm 8.21 (s, 1H), 7.63 (s, 1H), 7.52 (d, J = 8.0 Hz, 1H), 7.26 (d, J = 8.8 Hz, 1H), 7.05-7.20 (m, 2H), 5.96 (br. s., 1H), 4.00 (dd, J = 11.2, 3.4 Hz, 2H), 3.53 (d, J = 7.0 Hz, 2H), 3.39 (t, J = 11.2 Hz, 2H), 2.79-2.96 (m, 1H), 2.36 (s, 3H), 1.89-2.06 (m, 1H), 1.68 (d, J = 11.5 Hz, 2H), 1.30-1.47 (m, 2H), 0.73-0.95 (m, 2H), 0.49-0.68 (m, 2H). |
| | C15<br>[C28H36FN7O2 + H]+<br>·TFA<br>522.3;<br>522.5;<br>95% at 254 nm | (400 MHz, CDCl3) δ ppm 10.67 (br. s., 1H), 8.02-8.15 (m, 2H), 7.82-7.93 (m, 1H), 7.71 (d, J = 8.3 Hz, 1H), 7.04 (d, J = 13.3 Hz, 1H), 6.81 (br. s., 1H), 4.54-4.67 (m, 1H), 4.05 (dd, J = 11.5, 3.0 Hz, 2H), 3.52 (t, J = 6.5 Hz, 2H), 3.43 (t, J = 10.9 Hz, 2H), 3.14 (s, 3H), 2.92-3.01 (m, 1H), 1.96-2.08 (m, 1H), 1.92 (d, J = 12.3 Hz, 2H), 1.69-1.87 (m, 5H), 1.39-1.61 (m, 6H), 1.13-1.31 (m, 1H), 0.84-0.95 (m, 2H), 0.62-0.72 (m, 2H). |

-continued

| Structure | Example number<br>MS calcd;<br>MS ESI [M + H]+;<br>HPLC purity | 1H NMR |
|---|---|---|
| | C16<br>[C26H32ClN7O2 + H]+<br>510.2;<br>510.2;<br>97.0% at 254 nm | (400 MHz, CDCl3) δ ppm 8.06 (d, J = 9.0 Hz, 2H), 7.91 (d, J = 8.0 Hz, 1H), 7.78 (d, J = 8.3 Hz, 1H), 6.53 (br. s., 1H), 6.36 (br. s., 1H), 4.02 (d, J = 8.5 Hz, 2H), 3.88 (br. s., 4H), 3.51 (t, J = 6.5 Hz, 2H), 3.41 (t, J = 11.7 Hz, 2H), 2.85-3.03 (m, 1H), 1.87-2.04 (m, 1H), 1.55-1.79 (m, 8H), 1.36-1.52 (m, 2H), 0.81-0.97 (m, 2H), 0.60-0.73 (m, 2H). |
| | C17<br>[C28H30N6O3 + H]+<br>499.2;<br>499.5;<br>95% at 254nm | (400 MHz, CDCl3) δ ppm 8.20 (s, 1H), 7.64-7.86 (m, 2H), 7.50-7.60 (m, 1H), 7.40-7.49 (m, 2H), 7.24-7.36 (m, 3H), 7.17 (br. s., 1H), 6.72-6.82 (m, 1H), 4.02 (dd, J = 11.3, 3.5 Hz, 2H), 3.56 (t, J = 6.5 Hz, 2H), 3.32-3.45 (m, 2H), 2.20 (s, 3H), 1.91-2.05 (m, 1H), 1.71 (d, J = 12.5 Hz, 2H), 1.53 (br. s., 1H), 1.34-1.48 (m, 2H), 1.02-1.18 (m, 2H), 0.66-0.93 (m, 2H). |
| | C18<br>[C27H35N7O2 + H]+<br>490.3;<br>490.5;<br>95% at 254 nm<br>·TFA | (400 MHz, MeOD-d4) δ ppm 8.14 (br. s., 1H), 7.23-7.51 (m, 3H), 4.41 (br. s., 1H), 3.97 (d, J = 8.5 Hz, 2H), 3.55 (d, J = 6.5 Hz, 2H), 3.41 (t, J = 11.7 Hz,H), 2.31 (s, 3H), 2.00-2.16 (m, 3H), 1.57-1.94 (m, 9H), 1.31-1.48 (m, 2H), 0.80-1.03 (m, 4 H). |
| | C19<br>[C30H33N7O4 + H]+<br>556.3;<br>556.5;<br>95% at 254 nm | (400 MHz, CDCl3) δ ppm 8.25 (s, 1H), 8.14 (s, 1H), 7.61 (s, 2H), 7.48 (d, J = 7.8 Hz, 1H), 7.33-7.40 (m, 1H), 7.25-7.33 (m, 1H), 7.20 (d, J = 8.0 Hz, 1H), 6.98 (d, J = 7.8 Hz, 1H), 6.84 (t, J = 6.1 Hz, 1H), 6.22 (d, J = 3.0 Hz, 1H), 3.97 (dd, J = 11.4, 3.1 Hz, 2H), 3.44-3.54 (m, 2H), 3.37 (t, J = 11.3 Hz, 2H), 2.79-2.92 (m, 1H), 2.31 (s, 3H), 2.10 (s, 3H), 1.94 (s, 1H), 1.66 (d, J = 11.5 Hz, 2H), 1.27-1.44 (m, 2H), 0.76-0.88 (m, 2H), 0.54-0.65 (m, 2H). |

| Structure | Example number  MS calcd;  MS ESI [M + H]+;  HPLC purity | ¹H NMR |
|---|---|---|
| | C20  [C₂₈H₂₉FN₆O₃ + H]+  517.2;  517.5;  99.1% at 254 nm | (400 MHz, CDCl₃) δ ppm 8.21 (s, 1H), 7.64 (s, 1H), 7.53 (d, J = 8.0 Hz, 1H), 7.15-7.38 (m, 5H), 6.82 (t, J = 6.1 Hz, 1H), 5.93 (br. s., 1H), 4.00 (dd, J = 11.5, 3.5 Hz, 2H), 3.53 (t, J = 6.5 Hz, 2H), 3.39 (t, J = 11.0 Hz, 2H), 2.80-2.97 (m, 1H), 2.34 (s, 3H), 1.88-2.06 (m, 1H), 1.68 (d, J = 13.1 Hz, 2H), 1.31-1.49 (m, 2H), 0.77-0.96 (m, 2H), 0.49-0.67 (m, 2H). |
| | C21  [C₂₈H₂₉FN₆O₃ + H]+  517.2;  517.5;  98.2% at 254 nm | (400 MHz, CDCl₃) δ ppm 8.22 (s, 1H), 7.68 (s, 1H), 7.56 (d, J = 8.0 Hz, 1H), 7.40 (td, J = 8.3, 6.5 Hz, 1H), 7.23-7.31 (m, 1H), 7.07-7.15 (m, 2H), 7.01 (t, J = 8.2 Hz, 1H), 6.81 (t, J = 6.1 Hz, 1H), 5.94 (d, J = 2.3 Hz, 1H), 4.01 (dd, J = 11.3, 3.3 Hz, 2H), 3.55 (d, (t, J = 6.7 Hz, 2H), 3.40 (td, J = 11.7, 1.6 Hz, 2H), 2.83-2.94 (m, 1H), 2.38 (s, 3H), 1.93-2.07 (m, 1H), 1.65-1.73 (m, 2H), 1.33-1.50 (m, 2H), 0.80-0.95 (m, 2H), 0.50-0.68 (m, 2H). |
| | C22  [C₂₈H₃₇N₇O₂ + H]+  504.3;  504.6;  95% at 254 nm | (400 MHz, CDCl₃) δ ppm 13.88 (br. s., 1H), 9.82 (br. s., 1H), 7.79-8.20 (m, 1H), 7.50 (br. s., 3H), 5.92-6.25 (m, 1H), 4.02 (br. s., 3H), 3.63 (br. s., 2H), 3.30-3.52 (m, 2H), 2.81-3.01 (m, 1H), 2.55 (br. s., 3H), 1.29-2.18 (m, 15H), 0.80-0.97 (m, 2H), 0.49-0.74 (m, 2H). |
| | C23  [C₂₇H₃₅N₇O₃ + H]+  506.3;  506.5;  97.4% at 254 nm | (400 MHz, CDCl₃) δ ppm 10.33 (br. s., 1H), 8.00 (br. s., 1H), 7.31-7.47 (m, 2H), 7.16 (br. s., 1H), 5.95 (br. s., 1H), 4.13 (br. s., 1H), 4.05 (d, J = 11.3 Hz, 4H), 3.29-3.70 (m, 8H), 2.85-2.98 (m, 1H), 2.49 (s, 3H), 1.79-2.07 (m, 4H), 1.73 (d, J = 10.3 Hz, 2H), 1.37-1.55 (m, 2H), 0.80-0.96 (m, 2H), 0.53-0.68 (m, 2H). |

| Structure | Example number MS calcd; MS ESI [M + H]⁺; HPLC purity | ¹H NMR |
|---|---|---|
| 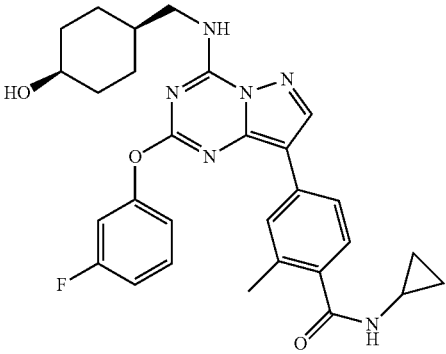 [SMILES: Cc1cc(-c2cnn3c(NC[C@H]4CC[C@@H](O)CC4)nc(Oc4cccc(F)c4)nc23)ccc1C(=O)NC1CC1] | C24 [C$_{29}$H$_{31}$FN$_6$O$_3$ + H]⁺ 531.2; 531.2; 95 % at 254 nm | (400 MHz, CDCl$_3$) δ ppm 8.34 (s, 1H), 7.77 (s, 1H), 7.62 (dd, J = 8.03, 1.25 Hz, 1H), 7.46 (td, J = 8.34, 6.65 Hz, 1H), 7.24 (d, J = 8.03 Hz, 1H), 7.09-7.18 (m, 2H), 7.05 (tdd, J = 8.50, 8.50, 2.50, 0.80 Hz, 1H), 3.90 (br. s., 1H), 3.41 (d, J = 7.03 Hz, 2H), 2.85 (tt, J = 7.37, 3.80 Hz, 1H), 2.33 (s, 3H), 1.69-1.84 (m, 3H), 1.42-1.60 (m, 6H), 0.77-0.84 (m, 2H), 0.59-0.65 (m, 2H). |
| 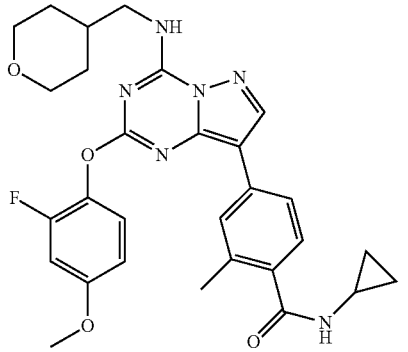 [SMILES: COc1ccc(Oc2nc(NCC3CCOCC3)n3ncc(-c4ccc(C(=O)NC5CC5)c(C)c4)c3n2)c(F)c1] | C25 [C$_{29}$H$_{31}$FN$_6$O$_4$ + H]⁺ 547.2; 547.5; 95% at 254 nm | (400 MHz, CDCl$_3$) δ ppm 8.22 (s, 1H), 7.68 (s, 1H), 7.54 (d, J = 8.0 Hz, 1H), 7.25-7.31 (m, 2H), 7.22 (t, J = 8.8 Hz, 1H), 6.70-6.84 (m, 3H), 5.87 (br. s., 1H), 4.01 (dd, J = 11.2, 3.4 Hz, 2H), 3.84 (s, 3H), 3.56 (t, J = 6.5 Hz, 2H), 3.34-3.45 (m, 2H), 2.89 (s, 1H), 2.37 (s, 3H), 1.93-2.04 (m, 1H), 1.70 (d, J = 11.3 Hz, 2H), 1.35-1.49 (m, 2H), 0.83-0.91 (m, 2H), 0.54-0.65 (m, 2H). |
| 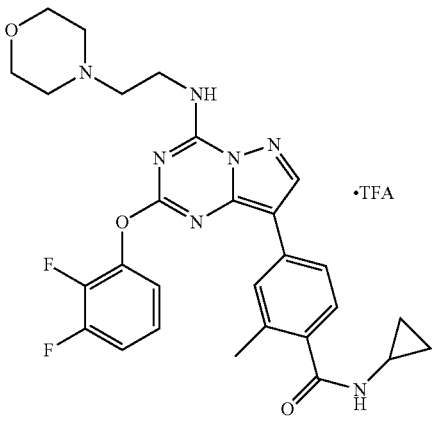 [SMILES: Cc1cc(-c2cnn3c(NCCN4CCOCC4)nc(Oc4cccc(F)c4F)nc23)ccc1C(=O)NC1CC1] | C26 [C$_{28}$H$_{29}$F$_2$N$_7$O$_3$ + H]⁺ 550.2; 550.3; 98.5% at 254 nm | (400 MHz, CD$_3$OD) δ ppm 8.46 (s, 1H), 7.72 (s, 1H), 7.54-7.63 (m, 1H), 7.29-7.38 (m, 2H), 7.17-7.29 (m, 2H), 4.08-4.21 (m, 2H), 4.05 (t, J = 5.65 Hz, 2H), 3.70-3.91 (m, 4H), 3.55 (t, J = 5.52 Hz, 2H), 3.15-3.30 (m, 2H), 2.78-2.88 (m, 1H), 2.29 (s, 3H), 0.76-0.85 (m, 2H), 0.56-0.64 (m, 2H). |

| Structure | Example number<br>MS calcd;<br>MS ESI [M + H]+;<br>HPLC purity | 1H NMR |
|---|---|---|
| (structure shown) ·TFA | C27<br>[C28H30FN7O3 + H]+<br>532.2;<br>532.3;<br>99.5% at 254 nm | (400 MHz, CD3OD) δ ppm 8.45 (s, 1H), 7.80 (s, 1H), 7.64 (dd, J = 8.00, 1.80 Hz, 1H), 7.48-7.56 (m, 1H), 7.25 (d, J = 8.03 Hz, 1H), 7.09-7.22 (m, 3H), 4.04-4.20 (m, 2H), 4.01 (t, J = 5.50 Hz, 2H), 3.67-3.89 (m, 4H), 3.53 (t, J = 5.50 Hz, 2H), 3.12-3.29 (m, 2H), 3.00 (s, 1H), 2.81-2.89 (m, 1H), 2.32 (s, 3H), 0.77-0.85 (m, 2H), 0.57-0.65 (m, 2H). |

Example B1

Synthesis of tert-butyl tert-butyl (3-bromo-5-phenoxypyrazolo[1,5-a]pyrimidin-7-yl)((tetrahydro-2H-pyran-4-yl)methyl)carbamate

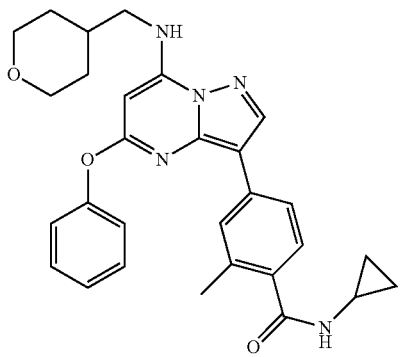 [SMILES: Cc1cc(-c2cnn3c(NCC4CCOCC4)cc(Oc4ccccc4)nc23)ccc1C(=O)NC1CC1]

To a solution of tert-butyl (3-bromo-5-phenoxypyrazolo[1,5-a]pyrimidin-7-yl)((tetrahydro-2H-pyran-4-yl)methyl)carbamate (1.51 g, 3 mmol) and N-cyclopropyl-2-methyl-4-(4,4,5,5-tetramethyl-1,3,2-dioxaborolan-2-yl)benzamide (2.71 g, 3 equiv) in THF (12 mL) was added 2 M $K_3PO_4$ (3 mL, 6 mmol, 2 equiv), followed by $PdCl_2$dppfDCM (122 mg, 0.15 mmol, 5 mol %). The resulting mixture was purged with Ar, and then microwaved 2 h at 120° C. After repeating the reaction on the same scale, both reactions were combined, diluted with $H_2O$ (30 mL) and extracted with EtOAc (30 mL×2). It was concentrated and purified by purified by flash chromatography (EtOAc/hex 0-60%) to give the intermediate as light yellow foam.

The above light yellow foam was redissolved in DCM (20 mL) and treated with TFA (4 mL). After stirring O/N, it was concentrated to dryness and purified by flash chromatography (gradient: EtOAc/hex 0-100%) and triturated with MeOH to give the title compound (1.819 g, 61% over 2 steps) as white solid. 1H NMR (400 MHz, CDCl3) δ ppm 8.23 (s, 1H), 7.77 (s, 1H), 7.59 (d, J=8.0 Hz, 1H), 7.46 (t, J=8.0 Hz, 2H), 7.32-7.27 (m, 3H), 7.24 (d, J=8.0 Hz, 1H), 6.39 (t, J=6.2 Hz, 1H), 5.84-5.82 (m, 1H), 5.69 (s, 1H), 4.05 (dd, J=11.6, 3.2 Hz, 2H), 3.44 (dt, J=12.0, 1.6 Hz, 2H), 3.32 (t, J=6.4 Hz, 2H), 2.92-2.76 (m, 1H), 2.34 (s, 1H), 2.09-1.97 (m, 1H), 1.82-1.75 (m, 2H), 1.53-1.40 (m, 2H), 0.90-0.84 (m, 2H), 0.63-0.58 (m, 1H); MS ESI [M+H]+ 498.5, calcd for [$C_{29}H_{31}N_5O_3$+H]+ 498.2.

The following final compounds were synthesized according to the synthesis of Example B1

| IUPAC name | Structure | MS calcd; MS ESI [M + H]⁺ | Yield; Appearance; Salt form |
|---|---|---|---|
| B2: N-cyclopropyl-4-(7-((2-methoxyethyl)amino)-5-phenoxypyrazolo[1,5-a]pyrimidin-3-yl)benzamide | | [C$_{25}$H$_{25}$N$_5$O$_3$ + H]⁺ 444.2; 444.4 | 308 mg (70%, 2 steps); white solid; free base |
| | SMs: tert-butyl (3-bromo-5-phenoxypyrazolo[1,5-a]pyrimidin-7-yl)(2-methoxyethyl)carbamate (464 mg, 1 mmol), N-cyclopropyl-4-(4,4,5,5-tetramethyl-1,3,2-dioxaborolan-2-yl)benzamide (335 mg, 1.2 mmol), PdCl$_2$dppfDCM (82 mg, 0.1 mmol, 10 mol %); TFA (3 mL). ¹H NMR (400 MHz, CDCl$_3$) δ ppm 8.29 (s, 1H), 7.91 (d, J = 8.4 Hz, 2H), 7.63 (d, J = 8.8 Hz, 2H), 7.46 (t, J = 7.8 Hz, 2H), 7.32-7.26 (m, 3H), 6.59 (t, J = 5.2 Hz, 1H), 6.18 (br, s, 1H), 5.68 (s, 1H), 3.72 (t, J = 5.2 Hz, 2H), 3.57 (q, J = 5.3 Hz, 2H), 3.45 (s, 3H), 2.95-2.87 (m, 1H), 0.90-0.85 (m, 2H), 0.66-0.60 (m, 2H). | | |
| B3: N-cyclopropyl-4-(5-phenoxy-7-(((tetrahydro-2H-pyran-4-yl)methyl)amino)pyrazolo[1,5-a]pyrimidin-3-yl)benzamide | | [C$_{28}$H$_{29}$N$_5$O$_3$ + H]⁺ 484.2; 484.5 | 152 mg (52%, 2 steps); off white solid; free base |
| | SMs: tert-butyl (3-bromo-5-phenoxypyrazolo[1,5-a]pyrimidin-7-yl)((tetrahydro-2H-pyran-4-yl)methyl)carbamate (302 mg, 0.6 mmol), N-cyclopropyl-4-(4,4,5,5-tetramethyl-1,3,2-dioxaborolan-2-yl)benzamide (207 mg, 0.72 mmol), PdCl$_2$dppfDCM (49 mg, 0.06 mmol, 10 mol %); TFA (3 mL). ¹H NMR (400 MHz, CDCl$_3$) δ ppm 8.27 (s, 1H), 7.90 (d, J = 8.0 Hz, 2H), 7.63 (d, J = 8.4 Hz, 2H), 7.47 (t, J = 7.8 Hz, 2H), 7.33-7.26 (m, 3H), 6.41 (t, J = 5.8 Hz, 1H), 6.19 (br, s, 1H), 5.68 (s, 1H), 4.08-4.02 (m, 2H), 3.40 (t, J = 11.2 Hz, 2H), 3.31 (t, J = 6.4 Hz, 2H), 2.95-2.87 (m, 1H), 2.09-1.97 (m, 1H), 1.81-1.73 (m, 2H), 1.52-1.40 (m, 2H), 0.91-0.85 (m, 2H), 0.66-0.60 (m, 2H). | | |
| B4: N-cyclopropyl-4-(7-((2-methoxyethyl)amino)-5-(pyridin-3-yloxy)pyrazolo[1,5-a]pyrimidin-3-yl)benzamide | | [C$_{24}$H$_{24}$N$_6$O$_3$ + H]⁺ 445.2; 445.6 | 133 mg (43%, 2 steps); beige solid; TFA salt |
| | SMs: tert-butyl (3-bromo-5-(pyridin-3-yloxy)pyrazolo[1,5-a]pyrimidin-7-yl)(2-methoxyethyl)carbamate (261 mg, 0.56 mmol), N-cyclopropyl-4-(4,4,5,5-tetramethyl-1,3,2-dioxaborolan-2-yl)benzamide (178 mg, 0.62 mmol), PdCl$_2$dppfDCM (46 mg, 0.056 mmol, 10 mol %); TFA (2 mL). ¹H NMR (400 MHz, CDCl$_3$) δ ppm 8.91 (d, J = 2.0 Hz, 1H), 8.69 (d, J = 9.2 Hz, 1H), 8.37-8.32 (m, 2H), 7.96 (dd, J = 8.6, 5.4 Hz, 1H), 7.76 (d, J = 8.4 Hz, 2H), 7.65 (d, J = 8.0 Hz, 2H), 5.98 (s, 1H), | | |

| IUPAC name | Structure | MS calcd; MS ESI [M + H]+ | Yield; Appearance; Salt form |
|---|---|---|---|
| | 3.72 (t, J = 5.0 Hz, 2H), 3.64 (t, J = 4.8 Hz, 2H), 3.44 (s, 3H), 2.88-2.81 (m, 1H), 0.85-0.78 (m, 2H), 0.67-0.62 (m, 2H). | | |
| B5: N-cyclopropyl-2-methyl-4-(7-((2-morpholinoethyl)amino)-5-phenoxypyrazolo[1,5-a]pyrimidin-3-yl)benzamide | 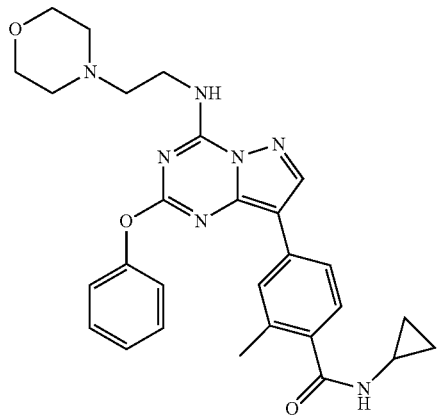 [SMILES: Cc1cc(-c2cnn3c(NCCN4CCOCC4)nc(Oc4ccccc4)nc23)ccc1C(=O)NC1CC1] | [C29H32N6O3 + H]+ 513.3; 513.6 | 2.943 g (68%, 2 steps); light pink solid; TFA salt |

SMs: tert-butyl (3-bromo-5-phenoxypyrazolo[1,5-a]pyrimidin-7-yl)(2-morpholinoethyl)carbamate (1.80 g, 3.47 mmol), N-cyclopropyl-2-methyl-4-(4,4,5,5-tetramethyl-1,3,2-dioxaborolan-2-yl)benzamide (3.14 g, 10.42 mmol), PdCl2dppfDCM (142 mg, 0.174 mmol, 5 mol %)—identical two reactions on the same scale; TFA (6 mL).

1H NMR (400 MHz, CDCl3) δ ppm 8.31 (s, 1H), 7.78 (s, 1H), 7.58 (d, J = 8.0 Hz, 1H), 7.48-7.42 (m, 2H), 7.30-7.23 (m, 3H), 7.17 (d, J = 8.0 Hz, 1H), 5.90 (s, 1H), 4.10-3.70 (m, 6H), 3.70-3.10 (m, 6H), 2.87-2.79 (m, 1H), 2.24 (s, 3H), 0.83-0.77 (m, 2H), 0.63-0.58 (m, 2H).

| B6: N-cyclopropyl-4-(7-((2-morpholinoethyl)amino)-5-phenoxypyrazolo[1,5-a]pyrimidin-3-yl)benzamide | 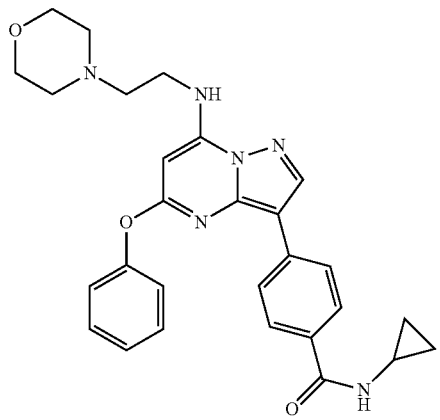 [SMILES: O=C(NC1CC1)c1ccc(-c2cnn3c(NCCN4CCOCC4)cc(Oc4ccccc4)nc23)cc1] | [C28H30N6O3 + H]+ 499.2; 499.5 | 56 mg (13%, 2 steps); white solid; TFA salt |

SMs: tert-butyl (3-bromo-5-phenoxypyrazolo[1,5-a]pyrimidin-7-yl)(2-morpholinoethyl)carbamate (0.35 g, 0.68 mmol), N-cyclopropyl-4-(4,4,5,5-tetramethyl-1,3,2-dioxaborolan-2-yl)benzamide (215 mg, 0.75 mmol), PdCl2dppfDCM (55 mg, 0.07 mmol, 10 mol %); TFA (2 mL).

1H NMR (400 MHz, CDCl3) δ ppm 8.27 (s, 1H), 7.88 (d, J = 8.5 Hz, 2H), 7.63 (d, J = 8.5 Hz, 2H), 7.50-7.36 (m, 2H), 7.33-7.21 (m, 3H), 6.90 (t, J = 4.5 Hz, 1H), 6.33 (br, s, 1H), 5.60 (s, 1H), 3.79 (t, J = 4.5 Hz, 4H), 3.44 (q, J = 5.7 Hz, 2H), 2.89 (tq, J = 7.0, 3.5 Hz, 1H), 2.80 (t, J = 5.8 Hz, 2H), 2.60 (br, s, 4H), 0.89-0.81 (m, 2H), 0.65-0.57 (m, 2H).

| IUPAC name | Structure | MS calcd; MS ESI [M + H]+ | Yield; Appearance; Salt form |
|---|---|---|---|
| B7: 2-chloro-N-cyclopropyl-4-(5-phenoxy-7-(((tetrahydro-2H-pyran-4-yl)methyl)amino)pyrazolo[1,5-a]pyrimidin-3-yl)benzamide | | [C$_{28}$H$_{28}$ClN$_5$O$_3$ + H]$^+$ 518.2; 518.7 | 141 mg (54%, 2 steps); white solid; free base |
| B8: N-cyclopropyl-2-fluoro-4-(5-phenoxy-7-(((tetrahydro-2H-pyran-4-yl)methyl)amino)pyrazolo[1,5-a]pyrimidin-3-yl)benzamide | | [C$_{28}$H$_{28}$FN$_5$O$_3$ + H]$^+$ 502.2; 502.5 | 173 mg (69%, 2 steps); white solid; free base |
| B9: N-cyclopropyl-2-methyl-4-(5-(pyridin-3-yloxy)-7-(((tetrahydro-2H-pyran-4-yl)methyl)amino)pyrazolo[1,5-a]pyrimidin-3-yl)benzamide | | [C$_{28}$H$_{30}$N$_6$O$_3$ + H]$^+$ 499.2; 499.2 | 118 mg (39%, 2 steps); brown solid; TFA salt |

SMs: tert-butyl (3-bromo-5-phenoxypyrazolo[1,5-a]pyrimidin-7-yl)((tetrahydro-2H-pyran-4-yl)methyl)carbamate (252 g, 0.5 mmol), (3-chloro-4-(cyclopropylcarbamoyl)phenyl)boronic acid (132 g, 0.55 mmol, 1.1 equiv), PdCl$_2$dppfDCM (20.4 mg, 0.025 mmol, 5 mol %); TFA (1 mL).
$^1$H NMR (400 MHz, CDCl$_3$) δ ppm 8.23 (s, 1H), 7.96 (s, 1H), 7.73-7.66 (m, 2H), 7.48 (t, J = 7.8 Hz, 2H), 7.32-7.26 (m, 3H), 6.49 (br, s, 1H), 6.40 (t, J = 6.2 Hz, 1H), 5.72 (s, 1H), 4.09-4.02 (m, 2H), 3.44 (t, J = 11.6 Hz, 2H), 3.33 (t, J = 6.4 Hz, 2H), 2.97-2.89 (m, 1H), 2.10-1.97 (m, 1H), 1.82-1.75 (m, 2H), 1.53-1.41 (m, 2H), 0.91-0.85 (m, 2H), 0.68-0.62 (m, 2H).

SMs: tert-butyl(3-bromo-5-phenoxypyrazolo[1,5-a]pyrimidin-7-yl)((tetrahydro-2H-pyran-4-yl)methyl)carbamate (252 g, 0.5 mmol), (4-(cyclopropylcarbamoyl)-3-fluorophenyl)boronic acid (123 g, 0.55 mmol, 1.1 equiv), PdCl$_2$dppfDCM (20.4 mg, 0.025 mmol, 5 mol %); TFA (1 mL).
$^1$H NMR (400 MHz, CDCl$_3$) δ ppm 8.25 (s, 1H), 8.01 (t, J = 8.4 Hz, 1H), 7.69 (d, J = 14.8 Hz, 1H), 7.63 (d, J = 8.4 Hz, 1H), 7.48 (t, J = 7.6 Hz, 2H), 7.35-7.26 (m, 3H), 6.85-6.78 (m, 1H), 6.42 (t, J = 6.0 Hz, 1H), 5.72 (s, 1H), 4.09-4.02 (m, 2H), 3.44 (t, J = 11.8 Hz, 2H), 3.33 (t, J = 6.4 Hz, 2H), 2.98-2.90 (m, 1H), 2.10-1.98 (m, 1H), 1.81-1.75 (m, 2H), 1.53-1.41 (m, 2H), 0.91-0.85 (m, 2H), 0.67-0.60 (m, 2H).

SMs: tert-butyl (3-bromo-5-(pyridin-3-yloxy)pyrazolo[1,5-a]pyrimidin-7-yl)((tetrahydro-2H-pyran-4-yl)methyl)carbamate (232 mg, 0.5 mmol), N-cyclopropyl-2-methyl-4-(4,4,5,5-tetramethyl-1,3,2-dioxaborolan-2-yl)benzamide (166 mg, 0.55 mmol, 1.1 equiv), PdCl$_2$dppfDCM (20.4 mg, 0.025 mmol, 5 mol %); TFA (2 mL).

| IUPAC name | Structure | MS calcd; MS ESI [M + H]+ | Yield; Appearance; Salt form |
|---|---|---|---|
| | ¹H NMR (400 MHz, CDCl₃) δ ppm 8.98 (d, J = 2.5 Hz, 1H), 8.67 (d, J = 5.3 Hz, 1H), 8.26 (s, 1H), 8.17 (d, J = 8.0 Hz, 1H), 7.81 (dd, J = 7.9, 5.4 Hz, 1H), 7.59-7.51 (m, 2H), 7.29 (s, 1H), 6.61 (t, J = 6.4 Hz, 1H), 6.18 (br, s, 1H), 5.78 (s, 1H), 4.07 (dd, J = 11.0, 4.0 Hz, 2H), 3.46 (t, J = 11.4 Hz, 2H), 3.38 (t, J = 6.5 Hz, 2H), 2.96-2.86 (m, 1H), 2.39 (s, 3H), 2.13-2.00 (m, 1H), 1.85-1.76 (m, 2H), 1.50 (qd, J = 12.2, 4.1 Hz, 2H), 0.88 (q, J = 6.3 Hz, 2H), 0.69-0.60 (m, 2H). | | |
| B10: N-cyclopropyl-4-(5-((2-hydroxy-2-methylpropyl)amino)-7-(((tetrahydro-2H-pyran-4-yl)methyl)amino)pyrazolo[1,5-a]pyrimidin-3-yl)-2-methylbenzamide | 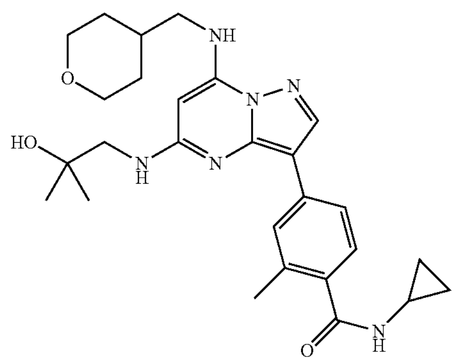 [SMILES: Cc1cc(-c2cnn3c(NCC4CCOCC4)cc(NCC(C)(C)O)nc23)ccc1C(=O)NC1CC1] | [C₂₇H₃₆N₆O₃ + H]+ 493.3; 493.3 | 98 mg (32%, 2 steps); light brown solid; TFA salt |

SMs: tert-butyl (3-bromo-5-((2-hydroxy-2-methylpropyl)amino)pyrazolo[1,5-a]pyrimdin-7-yl)((tetrahydro-2H-pyran-4-yl)methyl)carbamate (249 mg, 0.5 mmol), N-cyclopropyl-2-methyl-4-(4,4,5,5-tetramethyl-1,3,2-dioxaborolan-2-yl)benzamide (166 mg, 0.55 mmol, 1.1 equiv), PdCl₂dppfDCM (20.4 mg, 0.025 mmol, 5 mol %); TFA (2 mL).

¹H NMR (400 MHz, CDCl₃) δ ppm 9.23 (br, s, 1H), 7.94 (br, s, 1H), 7.44-7.19 (m, 4H), 6.90 (br, s, 1H), 6.26 (br, s, 1H), 5.37 (br, s, 1H), 4.04 (d, J = 8.8 Hz, 2H), 3.56-3.24 (m, 6H), 3.00-2.86 (m, 1H), 2.45 (s, 3H), 2.10-1.96 (m, 1H), 1.73-1.68 (m, 2H), 1.55-1.41 (m, 2H), 1.34 (s, 6H), 0.96-0.78 (m, 2H), 0.72-0.57 (m, 2H).

| IUPAC name | Structure | MS calcd; MS ESI [M + H]+ | Yield; Appearance; Salt form |
|---|---|---|---|
| B11: N-cyclopropyl-2-methyl-4-(5-morpholino-7-(((tetrahydro-2H-pyran-4-yl)methyl)amino)pyrazolo[1,5-a]pyrimidin-3-yl)benzamide | | [C₂₇H₃₄N₆O₃ + H]+ 491.3; 491.2 | 68 mg (22%, 2 steps); brown solid; TFA salt |

SMs: tert-butyl (3-bromo-5-morpholinopyrazolo[1,5-a]pyrimidin-7-yl)((tetrahydro-2H-pyran-4-yl)methyl)carbamate (248 mg, 0.5 mmol), N-cyclopropyl-2-methyl-4-(4,4,5,5-tetramethyl-1,3,2-dioxaborolan-2-yl)benzamide (166 mg, 0.55 mmol, 1.1 equiv), PdCl₂dppfDCM (20.4 mg, 0.025 mmol, 5 mol %); TFA (2 mL).

¹H NMR (400 MHz, CDCl₃) δ ppm 8.18 (s, 1H), 7.87 (d, J = 8.3 Hz, 1H), 7.83 (s, 1H), 7.38 (d, J = 7.8 Hz, 1H), 6.28 (t, J = 6.3 Hz, 1H), 5.97 (br, s, 1H), 5.35 (s, 1H), 4.05 (dd, J = 12.0, 3.5 Hz, 2H), 3.91-3.82 (m, 4H), 3.74-3.67 (m, 4H), 3.49-3.38 (m, 2H), 3.26 (t, J = 6.3 Hz, 2H), 2.97-2.88 (m, 1H), 2.52 (s, 3H), 2.06-1.92 (m, 1H), 1.79 (d, J = 12.8 Hz, 2H), 1.53-1.39 (m, 2H), 0.93-0.84 (m, 2H), 0.67-0.58 (m, 2H).

| IUPAC name | Structure | MS calcd; MS ESI [M + H]+ | Yield; Appearance; Salt form |
|---|---|---|---|
| B12: N-cyclopropyl-4-(5-(3-fluorophenoxy)-7-(((tetrahydro-2H-pyran-4-yl)methyl)amino)pyrazolo[1,5-a]pyrimidin-3-yl)-2-methylbenzamide | 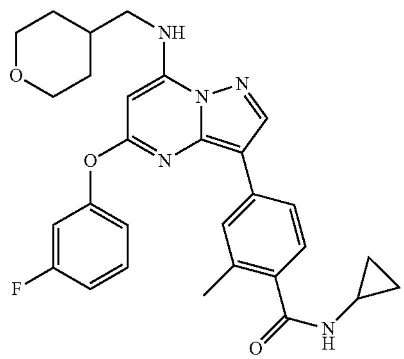 [SMILES: Cc1cc(-c2cnn3c(NCC4CCOCC4)cc(Oc4cccc(F)c4)nc23)ccc1C(=O)NC1CC1] | $[C_{29}H_{30}FN_5O_3 + H]^+$ 516.2; 516.5 | 130 mg (50%, 2 steps); off white solid; free base |

SMs: tert-butyl (3-bromo-5-(3-fluorophenoxy)pyrazolo[1,5-a]pyrimidin-7-yl)((tetrahydro-2H-pyran-4-yl)methyl)carbamate (261 mg, 0.5 mmol), N-cyclopropyl-2-methyl-4-(4,4,5,5-tetramethyl-1,3,2-dioxaborolan-2-yl)benzamide (166 mg, 0.55 mmol, 1.1 equiv), PdCl$_2$dppfDCM (20.4 mg, 0.025 mmol, 5 mol %); TFA (2 mL).
$^1$H NMR (400 MHz, CDCl$_3$) δ ppm 8.24 (s, 1H), 7.78 (s, 1H), 7.59 (d, J = 8.0 Hz, 1H), 7.41 (dd, J = 15.0, 7.8 Hz, 1H), 7.26 (d, J = 8.4 Hz, 1H), 7.10 (d, J = 7.6 Hz, 2H), 7.05-6.97 (m, 1H), 6.43 (t, J = 6.4 Hz, 1H), 5.83 (br, s, 1H), 5.69 (s, 1H), 4.09-4.02 (m, 2H), 3.44 (t, J = 12.0 Hz, 2H), 3.33 (t, J = 6.6 Hz, 2H), 2.93-2.86 (m, 1H), 2.37 (s, 3H), 2.10-1.98 (m, 1H), 1.82-1.75 (m, 2H), 1.53-1.42 (m, 2H), 0.91-0.85 (m, 2H), 0.63-0.58 (m, 2H).

| IUPAC name | Structure | MS calcd; MS ESI [M + H]+ | Yield; Appearance; Salt form |
|---|---|---|---|
| B13: N-cyclopropyl-4-(7-((2-methoxyethyl)amino)-5-phenoxypyrazolo[1,5-a]pyrimidin-3-yl)-2-methylbenzamide | | $[C_{26}H_{27}N_5O_3 + H]^+$ 458.2; 458.4 | 81 mg (35%, 2 steps); white solid; free base |

SMs: tert-butyl (3-bromo-5-phenoxypyrazolo[1,5-a]pyrimidin-7-yl)(2-methoxyethyl)carbamate (232 mg, 0.5 mmol), N-cyclopropyl-2-methyl-4-(4,4,5,5-tetramethyl-1,3,2-dioxaborolan-2-yl)benzamide (166 mg, 0.55 mmol, 1.1 equiv), PdCl$_2$dppfDCM (20.4 mg, 0.025 mmol, 5 mol %); TFA (2 mL).
$^1$H NMR (400 MHz, CDCl$_3$) δ ppm 8.25 (s, 1H), 7.78 (s, 1H), 7.60 (d, J = 8.4 Hz, 1H), 7.46 (d, J = 8.0 Hz, 2H), 7.32-7.26 (m, 4H), 7.24 (d, J = 8.0 Hz, 1H), 6.57 (t, J = 5.4 Hz, 1H), 5.81 (br, s, 1H), 5.70 (s, 1H), 3.72 (t, J = 5.2 Hz, 2H), 3.58 (t, J = 5.4 Hz, 2H), 3.45 (s, 3H), 2.92-2.87 (m, 1H), 2.35 (s, 3H), 0.90-0.85 (m, 2H), 0.63-0.57 (m, 2H).

| IUPAC name | Structure | MS calcd; MS ESI [M + H]+ | Yield; Appearance; Salt form |
|---|---|---|---|
| B14: 4-(5-(cyclopentylamino)-7-(((tetrahydro-2H-pyran-4-yl)methyl)amino)pyrazolo[1,5-a]pyrimidin-3-yl)-N-cyclopropyl-2-methylbenzamide | | $[C_{28}H_{36}N_6O_2 + H]^+$ 489.3; 489.5 | 93 mg (38%, 2 steps); white solid; TFA salt |

SMs: tert-butyl (3-bromo-5-(cyclopentylamino)pyrazolo[1,5-a]pyrimidin-7-yl)((tetrahydro-2H-pyran-4-yl)methyl)carbamate (200 mg, 0.41 mmol), N-cyclopropyl-2-methyl-4-(4,4,5,5-tetramethyl-1,3,2-dioxaborolan-2-yl)benzamide (365 mg, 1.21 mmol), PdCl$_2$dppfDCM (33 mg, 0.040 mmol); TFA (2 mL).

| IUPAC name | Structure | MS calcd; MS ESI [M + H]+ | Yield; Appearance; Salt form |
|---|---|---|---|

¹H NMR (400 MHz, CDCl₃) δ ppm 8.93 (br, s, 1H), 7.89 (s, 1H), 7.32 (d, J = 7.5 Hz, 1H), 7.26-7.16 (m, 2H), 7.03 (t, J = 5.6 Hz, 1H), 6.43 (d, J = 2.5 Hz, 1H), 5.11 (s, 1H), 4.05 (dd, J = 11.4, 3.6 Hz, 2H), 3.89 (br, s, 1H), 3.44 (t, J = 11.4 Hz, 2H), 3.35 (t, J = 6.3 Hz, 2H), 2.93-2.91 (m, 1H), 2.42 (s, 3H), 2.04 (m, 3H), 1.89-1.60 (m, 8H), 1.54-1.37 (m, 2H), 0.95-0.78 (m, 2H), 0.72-0.58 (m, 2H).

| B15: N-(4-(5-(cyclopentylamino)-7-(((tetrahydro-2H-pyran-4-yl)methyl)amino)pyrazolo[1,5-a]pyrimidin-3-yl)-2-methylphenyl)cyclopropane carboxamide | | [C₂₈H₃₆N₆O₂ + H]⁺ 489.3; 489.5 | 37 mg (14%, 2 steps); white solid; TFA salt |

SMs: tert-butyl (3-bromo-5-(cyclopentylamino)pyrazolo[1,5-a]pyrimidin-7-yl)((tetrahydro-2H-pyran-4-yl)methyl)carbamate (220 mg, 0.44 mmol), N-(2-methyl-4-(4,4,5,5-tetramethyl-1,3,2-dioxaborolan-2-yl)phenyl)cyclopropanecarboxamide (200 mg, 0.66 mmol), PdCl₂dppfDCM (36 mg, 0.044 mmol); TFA (2 mL).

¹H NMR (400 MHz, CDCl₃) δ ppm 9.29 (br, s, 1H), 8.92 (br, s, 1H), 7.90 (br, s, 1H), 7.76 (br, s, 1H), 7.50 (br, s, 1H), 7.33 (br, s, 2H), 7.22 (br, s, 1H), 6.97 (br, s, 1H), 5.11 (s, 1H), 4.07 (dd, J = 11.4, 3.6 Hz, 2H), 3.89 (t, J = 5.5 Hz, 1H), 3.46 (t, J = 11.5 Hz, 2H), 3.34 (t, J = 6.0 Hz, 2H), 2.31 (br, s, 3H), 2.13-1.95 (m, 3), 1.90-1.59 (m, 8H), 1.55-1.39 (m, 2H), 1.11 (br, s, 2H), 0.96-0.78 (m, 2H).

| B16: N-(2-methyl-4-(7-(((tetrahydro-2H-pyran-4-yl)methyl)amino)-5-((tetrahydro-2H-pyran-4-yl)oxy)pyrazolo[1,5-a]pyrimidin-3-yl)phenyl)cyclopropanecarboxamide | | [C₂₈H₃₅N₅O₄ + H]⁺ 506.3; 506.5 | 56 mg (36%, 2 steps); white solid; free base |

SMs: tert-butyl(3-bromo-5-((tetrahydro-2H-pyran-4-yl)oxy)pyrazolo[1,5-a]pyrimidin-7-yl)((tetrahydro-2H-pyran-4-yl)methyl)carbamate (160 mg, 0.31 mmol), N-(2-methyl-4-(4,4,5,5-tetramethyl-1,3,2-dioxaborolan-2-yl)phenyl)cyclopropanecarboxamide (110 mg, 0.37 mmol), PdCl₂dppfDCM (25 mg, 0.031 mmol); TFA (2 mL).

¹H NMR (400 MHz, CDCl₃) δ ppm 8.21 (s, 1H), 7.93 (s, 1H), 7.78 (d, J = 8.3 Hz, 1H), 7.36 (d, J = 8.0 Hz, 1H), 6.29 (t, J = 6.1 Hz, 1H), 5.99 (br, s, 1H), 5.47 (s, 1H), 5.43-5.33 (m, 1H), 4.11-3.95 (m, 4H), 3.65 (t, J = 9.5 Hz, 2H), 3.41 (t, J = 11.7 Hz, 2H), 3.26 (t, J = 6.5 Hz, 2H), 2.97-2.84 (m, 1H), 2.51 (s, 3H), 2.27-2.10 (m, 3H), 1.93-1.82 (m, 2H), 1.75 (d, J = 12.3 Hz, 2H), 1.51-1.34 (m, 2H), 0.96-0.79 (m, 2H), 0.67-0.54 (m, 2H).

| IUPAC name | Structure | MS calcd; MS ESI [M + H]+ | Yield; Appearance; Salt form |
|---|---|---|---|
| B17: N-(2-methyl-4-(5-((tetrahydro-2H-pyran-4-yl)amino)-7-(((tetrahydro-2H-pyran-4-yl)methyl)amino)pyrazolo[1,5-a]pyrimidin-3-yl)phenyl)cyclopropanecarboxamide | 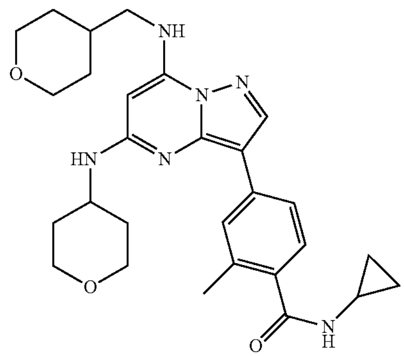 | [C28H36N6O3 + H]+ 505.3; 505.5 | 35 mg (23%, 2 steps); white solid; TFA salt |

SMs: tert-butyl (3-bromo-5-((tetrahydro-2H-pyran-4-yl)amino)pyrazolo[1,5-a]pyrimidin-7-yl)((tetrahydro-2H-pyran-4-yl)methyl)carbamate (72 mg, 0.18 mmol), N-(2-methyl-4-(4,4,5,5-tetramethyl-1,3,2-dioxaborolan-2-yl)phenyl)cyclopropanecarboxamide (66 mg, 0.21 mmol), PdCl2dppfDCM (15 mg, 0.018 mmol); TFA (2 mL).
1H NMR (400 MHz, CDCl3) δ ppm 9.65 (br. s, 2H), 7.96 (s, 1H), 7.43-7.30 (m, 3H), 6.83 (br, s, 1H), 6.06 (br, s, 1H), 5.08 (s, 1H), 4.13-3.97 (m, 4H), 3.66 (br, s, 1H), 3.54 (t, J = 11.0 Hz, 2H), 3.46 (t, J = 11.0 Hz, 2H), 3.35 (t, J = 6.4 Hz, 2H), 2.99-2.85 (m, 1H), 2.48 (s, 3H), 2.12-1.95 (m, 3H), 1.93-1.73 (m, 4H), 1.58-1.42 (m, 2H), 0.94-0.81 (m, 2H), 0.70-0.55 (m, 2H).

| IUPAC name | Structure | MS calcd; MS ESI [M + H]+ | Yield; Appearance; Salt form |
|---|---|---|---|
| B18: N-(2-methyl-4-(5-phenoxy-7-((tetrahydro-2H-pyran-4-yl)methoxy)pyrazolo[1,5-a]pyrimidin-3-yl)phenyl)cyclopropanecarboxamide | | [C29H30N4O4 + H]+ 499.2; 499.5 | 12 mg (4%, 2 steps); beige solid; free base |

SMs: 3-bromo-5-phenoxy-7-((tetrahydro-2H-pyran-4-yl)methoxy) pyrazolo[1,5-a]pyrimidine (241 mg, 0.60 mmol), N-(2-methyl-4-(4,4,5,5-tetramethyl-1,3,2-dioxaborolan-2-yl)phenyl)cyclopropane carboxamide (216 mg, 0.72 mmol), PdCl2dppfDCM (49 mg, 0.060 mmol).
1H NMR (400 MHz, CDCl3) δ ppm 8.33 (br, s, 1H), 7.74 (br, s, 1H), 7.62-7.42 (m, 3H), 7.39-7.14 (m, 4H), 5.97 (br, s, 1H), 5.85 (br, s, 1H), 4.22 (d, J = 6.3 Hz, 2H), 4.07 (d, J = 9.3 Hz, 2H), 3.50 (t, J = 11.8 Hz, 2H), 2.89 (br, s, 1H), 2.40(br, s, 1H), 2.32 (br, s, 3H), 1.90 (d, J = 11.5 Hz, 2H), 1.57-1.45 (m, 2H), 0.87 (d, J = 6.0 Hz, 2H), 0.60 (br, s, 2H).

| IUPAC name | Structure | MS calcd; MS ESI [M + H]+ | Yield; Appearance; Salt form |
|---|---|---|---|
| B19: N-cyclopropyl-2-methyl-4-(7-((3-morpholinopropyl)amino)-5-phenoxypyrazolo[1,5-a]pyrimidin-3-yl)benzamide | | [C30H34N6O3 + H]+ 527.3; 527.3 | 142 mg (72%, 2 steps); pinkish-white solid; TFA salt |

SMs: tert-butyl (3-bromo-5-phenoxypyrazolo[1,5-a]pyrimidin-7-yl)(3-morpholinopropyl)carbamate (200 mg, 0.375 mmol), N-cyclopropyl-2-methyl-4-(4,4,5,5-tetramethyl-1,3,2-dioxaborolan-2-yl)benzamide (124 mg, 1.1 equiv), PdCl2dppfDCM (31 mg, 0.0375 mmol, 10 mol %); TFA (1 mL).
1H NMR (400 MHz, CD3OD) δ ppm 8.35 (s, 1H), 7.82 (s, 1H), 7.61 (d, J = 8.3 Hz, 1H), 7.48 (t, J = 7.7 Hz, 2H), 7.35-7.23 (m, 3H), 7.18 (d, J = 8.0 Hz, 1H), 5.89 (s, 1H), 4.14-4.00 (m, 2H), 3.84-3.71

-continued

| IUPAC name | Structure | MS calcd; MS ESI [M + H]+ | Yield; Appearance; Salt form |
|---|---|---|---|
| | (m, 2H), 3.63-3.44 (m, 4H), 3.38-3.27 (m, 4H), 3.23-3.09 (m, 2H), 2.88-2.78 (m, 1H), 2.31-2.10 (m, 5H), 0.86-0.74 (m, 2H), 0.65-0.55 (m, 2H). | | |
| B20: N-cyclopropyl-2-methyl-4-(5-phenoxy-7-((2-(tetrahydro-2H-pyran-4-yl)ethyl)amino)pyrazolo[1,5-a]pyrimidin-3-yl)benzamide | 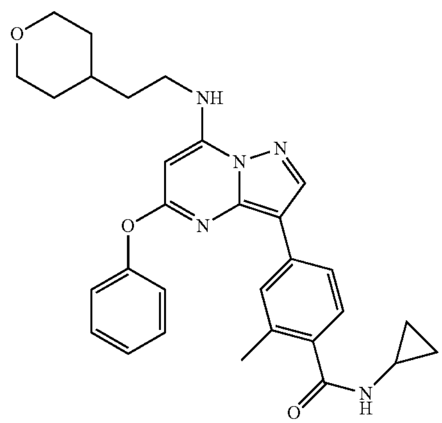 [SMILES: Cc1cc(-c2cnn3c(NCCC4CCOCC4)cc(Oc4ccccc4)nc23)ccc1C(=O)NC1CC1] | $[C_{30}H_{33}N_5O_3 + H]^+$ 512.3; 512.2 | 100 mg (53%, 2 steps); white solid; free base |

SMs: tert-butyl (3-bromo-5-phenoxypyrazolo[1,5-a]pyrimidin-7-yl)(2-(tetrahydro-2H-pyran-4-yl)ethyl)carbamate (192 mg, 0.371 mmol), N-cyclopropyl-2-methyl-4-(4,4,5,5-tetramethyl-1,3,2-dioxaborolan-2-yl)benzamide (123 mg, 0.409 mmol), PdCl$_2$dppfDCM (30 mg, 0.037 mmol, 10 mol %);TFA (1 mL).

$^1$H NMR (400 MHz, CDCl$_3$) δ ppm 8.24 (s, 1H), 7.78 (s, 1H), 7.60 (d, J = 7.8 Hz, 1H), 7.41-7.50 (m, 2H), 7.32-7.28 (m, 3H), 7.24 (d, J = 7.8 Hz, 1H), 6.24 (t, J = 5.8 Hz, 1H), 5.83 (br, s, 1H), 5.67 (s, 1H), 4.00 (dd, J = 11.2, 3.6 Hz, 2H), 3.50-3.36 (m, 4H), 2.96-2.83 (m, 1H), 2.34 (s, 3H), 1.76 (t, J = 6.5 Hz, 3H), 1.68 (d, J = 13.8 Hz, 2H), 1.47-1.34 (m, 2H), 0.92-0.82 (m, 2H), 0.60 (br, s, 2H).

| B21: 4-(5-(cyclopentyloxy)-7-(((tetrahydro-2H-pyran-4-yl)methyl)amino)pyrazolo[1,5-a]pyrimidin-3-yl)-N-cyclopropyl-2-methylbenzamide | | $[C_{28}H_{35}N_5O_3 + H]^+$ 490.3; 490.5 | 70 mg (32%, 2 steps); white solid; free base |

SMs: tert-butyl (3-bromo-5-(cyclopentyloxy)pyrazolo[1,5-a]pyrimidin-7-yl)((tetrahydro-2H-pyran-4-yl)methyl)carbamate (224 mg, 0.453 mmol), N-cyclopropyl-2-methyl-4-(4,4,5,5-tetramethyl-1,3,2-dioxaborolan-2-yl)benzamide (150 mg, 0.499 mmol), PdCl$_2$dppfDCM (37 mg, 0.045 mmol, 10 mol %); TFA (1 mL).

$^1$H NMR (400 MHz, CDCl$_3$) δ ppm 8.22 (s, 1H), 7.97 (s, 1H), 7.89 (d, J = 7.8 Hz, 1H), 7.39 (d, J = 8.0 Hz, 1H), 6.24 (t, J = 5.6 Hz, 1H), 5.94 (br, s, 1H), 5.61-5.51 (m, 1H), 5.44 (s, 1H), 4.03 (dd, J = 11.3, 3.3 Hz, 2H), 3.42 (t, J = 11.0 Hz, 2H), 3.25 (t, J = 6.7 Hz, 2H), 2.98-2.85 (m, 1H), 2.54 (s, 3H), 2.16-1.60 (m, 11H), 1.50-1.34 (m, 2H), 0.94-0.83 (m, 2H), 0.63 (br, s, 2H).

| IUPAC name | Structure | MS calcd; MS ESI [M + H]+ | Yield; Appearance; Salt form |
|---|---|---|---|
| B22: N-cyclopropyl-2-methyl-4-(5-(pyridin-3-yloxy)-7-((2-(tetrahydro-2H-pyran-4-yl)ethyl)amino)pyrazolo[1,5-a]pyrimidin-3-yl)benzamide | 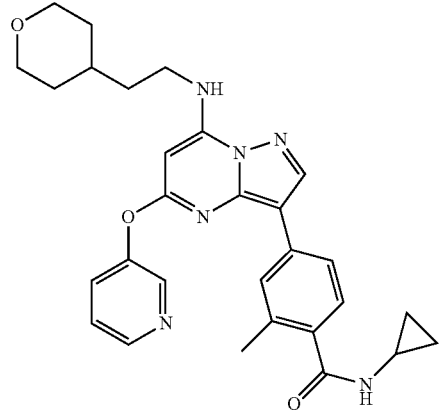 | [$C_{29}H_{32}N_6O_3$ + H]+ 513.3; 513.5 | 92 mg (40%, 2 steps); yellow solid; TFA salt |

SMs: tert-butyl (3-bromo-5-(pyridin-3-yloxy)pyrazolo[1,5-a]pyrimidin-7-yl)(2-(tetrahydro-2H-pyran-4-yl)ethyl)carbamate (190 mg, 0.367 mmol), N-cyclopropyl-2-methyl-4-(4,4,5,5-tetramethyl-1,3,2-dioxaborolan-2-yl)benzamide (121 mg, 0.403 mmol), PdCl$_2$dppfDCM (30 mg, 0.0367 mmol, 10 mol %); TFA (1 mL).

$^1$H NMR (400 MHz, CD$_3$OD) δ ppm 8.81 (br, s, 1H), 8.68-8.62 (m, 1H), 8.38 (s, 1H), 8.27-8.20 (m, 1H), 7.91-7.84 (m, 1H), 7.72 (s, 1H), 7.64-7.55 (m, 1H), 7.25-7.17 (m, 1H), 5.96 (s, 1H), 4.02-3.91 (m, 2H), 3.54 (t, J = 6.5 Hz, 2H), 3.45 (t, J = 11.3 Hz, 2H), 2.89-2.79 (m, 1H), 2.28 (s, 3H), 1.81-1.69 (m, 5H), 1.44-1.29 (m, 2H), 0.81 (d, J = 6.3 Hz, 2H), 0.61 (br, s, 2H). HPLC purity: 99.3% at 254 nm.

| B23: 4-(5-(cyclohexyloxy)-7-(((tetrahydro-2H-pyran-4-yl)methyl)amino)pyrazolo[1,5-a]pyrimidin-3-yl)-N-cyclopropyl-2-methylbenzamide | 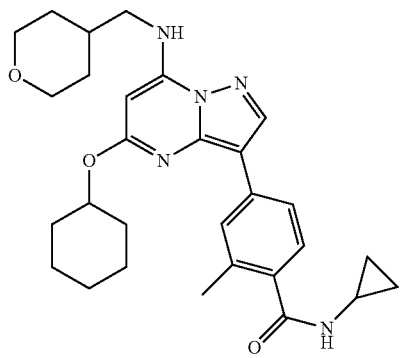 [SMILES: Cc1cc(-c2cnn3c(NCC4CCOCC4)cc(OC4CCCCC4)nc23)ccc1C(=O)NC1CC1] | [$C_{29}H_{37}N_5O_3$ + H]+ 504.3; 504.5 | 146 mg (57%, 2 steps); white solid; TFA salt |

SMs: tert-butyl (3-bromo-5-(cyclohexyloxy)pyrazolo[1,5-a]pyrimidin-7-yl)((tetrahydro-2H-pyran-4-yl)methyl)carbamate (281 mg, 0.553 mmol), N-cyclopropyl-2-methyl-4-(4,4,5,5-tetramethyl-1,3,2-dioxaborolan-2-yl)benzamide (183 mg, 0.608 mmol), PdCl$_2$dppfDCM (45 mg, 0.055 mmol, 10 mol %); TFA (1 mL).

$^1$H NMR (400 MHz, CDCl$_3$) δ ppm 8.22 (s, 1H), 8.01 (s, 1H), 7.81 (d, J = 7.3 Hz, 1H), 7.37 (d, J = 8.0 Hz, 1H), 6.24 (t, J = 6.1 Hz, 1H), 5.93 (br, s, 1H), 5.45 (s, 1H), 5.28-5.12 (m, 1H), 4.03 (dd, J = 11.4, 3.6 Hz, 2H), 3.41 (t, J = 12.0 Hz, 2H), 3.25 (t, J = 6.4 Hz, 2H), 2.92 (td, J = 7.2, 3.8 Hz, 1H), 2.54 (s, 3H), 2.23-2.13 (m, 2H), 2.05-1.92 (m, 1H), 1.91-1.81 (m, 2H), 1.75 (d, J = 13.6 Hz, 2H), 1.70-1.22 (m, 8H), 0.90 (q, J = 6.5 Hz, 2H), 0.67-0.59 (m, 2H). HPLC purity: 95.7 % at 254 nm.

| IUPAC name | Structure | MS calcd; MS ESI [M + H]+ | Yield; Appearance; Salt form |
|---|---|---|---|
| B24: 4-(5-(cyclohexylamino)-7-(((tetrahydro-2H-pyran-4-yl)methyl)amino)pyrazolo[1,5-a]pyrimidin-3-yl)-N-cyclopropyl-2-methylbenzamide | 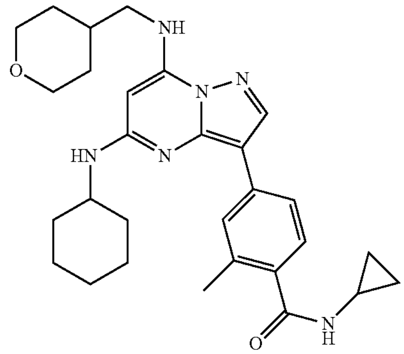 [SMILES: Cc1cc(-c2cnn3c(NCC4CCOCC4)cc(NC4CCCCC4)nc23)ccc1C(=O)NC1CC1] | $[C_{29}H_{38}N_6O_2 + H]^+$ 503.3; 503.5 | 61 mg (20%, 2 steps); white solid; TFA salt |

SMs: (250 mg, 0.493 mmol), N-cyclopropyl-2-methyl-4-(4,4,5,5-tetramethyl-1,3,2-dioxaborolan-2-yl)benzamide (178 mg, 0.692 mmol), PdCl$_2$dppfDCM (40 mg, 0.049 mmol, 10 mol %); TFA (1 mL).
$^1$H NMR (400 MHz, CD$_3$OD) δ ppm 8.19 (s, 1H), 7.51-7.46 (m, 1H), 7.43 (s, 2H), 4.89 (br, s, 1H), 4.03-3.95 (m, 2H), 3.83-3.72 (m, 1H), 3.51-3.42 (m, 4H), 2.93-2.83 (m, 1H), 2.47 (s, 3H), 2.12-2.01 (m, 3H), 1.87-1.29 (m, 12H), 0.87-0.80 (m, 2H), 0.67-0.60 (m, 2H). HPLC purity: 96.3% at 254 nm.

| IUPAC name | Structure | MS calcd; MS ESI [M + H]+ | Yield; Appearance; Salt form |
|---|---|---|---|
| B25: N-cyclopropyl-4-(7-(isobutylamino)-5-(pyridin-3-yloxy)pyrazolo[1,5-a]pyrimidin-3-yl)-2-methylbenzamide | 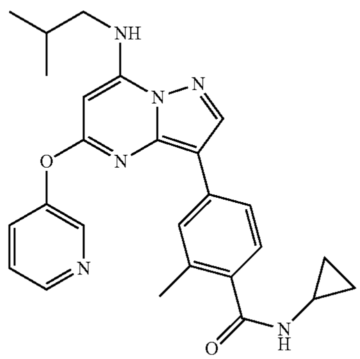 [SMILES: Cc1cc(-c2cnn3c(NCC(C)C)cc(Oc4cccnc4)nc23)ccc1C(=O)NC1CC1] | $[C_{26}H_{28}N_6O_2 + H]^+$ 457.2; 457.4 | 78 mg (51%, 2 steps); yellow solid; TFA salt |

SMs: tert-butyl (3-bromo-5-(pyridin-3-yloxy)pyrazolo[1,5-a]pyrimidin-7-yl)(isobutyl)carbamate (125 mg, 0.27 mmol), N-cyclopropyl-2-methyl-4-(4,4,5,5-tetramethyl-1,3,2-dioxaborolan-2-yl)benzamide (98 mg, 0.32 mmol), PdCl$_2$dppfDCM (22 mg, 0.027 mmol, 10 mol %); TFA (3 mL).
$^1$H NMR (400 MHz, CD$_3$OD) δ ppm 8.84 (s, 1H), 8.67 (d, J = 5.3 Hz, 1H), 8.36 (s, 1H), 8.33-8.27 (m, 1H), 7.95-7.88 (m, 1H), 7.68 (s, 1H), 7.57 (d, J = 7.8 Hz, 1H), 7.20 (d, J = 8.0 Hz, 1H), 5.94 (s, 1H), 3.30-3.27 (m, 2H), 2.86-2.78 (m, 1H), 2.27 (s, 3H), 2.14-2.05 (m, 1H), 1.06 (d, J = 6.8 Hz, 6H), 0.83-0.75 (m, 2H), 0.62-0.55 (m, 2H).

| IUPAC name | Structure | MS calcd; MS ESI [M + H]+ | Yield; Appearance; Salt form |
|---|---|---|---|
| B26: N-cyclopropyl-4-(7-(isobutylamino)-5-((tetrahydro-2H-pyran-4-yl)amino)pyrazolo[1,5-a]pyrimidin-3-yl)-2-methylbenzamide | 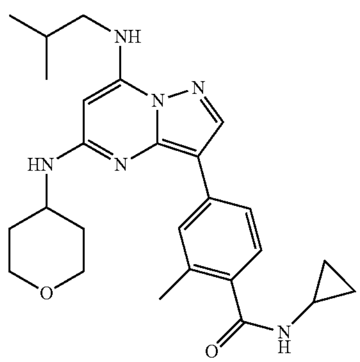 [SMILES: Cc1cc(-c2cnn3c(NCC(C)C)cc(NC4CCOCC4)nc23)ccc1C(=O)NC1CC1] | $[C_{26}H_{34}N_6O2 + H]^+$ 463.3; 463.5 | 43 mg (36%, 2 steps); white solid; TFA salt |

SMs: tert-butyl(3-bromo-5-((tetrahydro-2H-pyran-4-yl)amino)pyrazolo[1,5-a]pyrimidin-7-yl)(isobutyl)carbamate (100 mg, 0.21 mmol), N-cyclopropyl-2-methyl-4-(4,4,5,5-tetramethyl-1,3,2-dioxaborolan-2-yl)benzamide (76 mg, 0.25 mmol), PdCl$_2$dppfDCM (17 mg, 0.021 mmol, 10 mol %); TFA (3 mL).
$^1$H NMR (400 MHz, CDCl$_3$) δ ppm 7.97 (s, 1H), 7.42-7.33 (m, 3H), 6.82 (br, s, 1H), 6.03 (br, s, 1H), 5.07 (s, 1H), 4.09-4.00 (m, 2H), 3.66 (br, s, 1H), 3.58-3.51 (m, 2H), 3.27 (t, J = 6.4 Hz, 2H), 2.94 (s, 1H), 2.49 (s, 3H), 2.16-2.07 (m, 1H), 2.04-1.94 (m, 2H), 1.93-1.80 (m, 2H), 1.13 (d, J = 6.8 Hz, 6H), 0.92-0.84 (m, 2H), 0.67-0.60 (m, 2H).

-continued

| IUPAC name | Structure | MS calcd; MS ESI [M + H]+ | Yield; Appearance; Salt form |
| --- | --- | --- | --- |
| B27: N-cyclopropyl-4-(7-((2-hydroxy-2-methylpropyl)amino)-5-phenoxypyrazolo[1,5-a]pyrimidin-3-yl)-2-methylbenzamide | 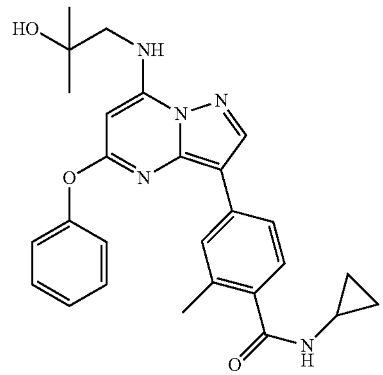 [SMILES: Cc1cc(-c2cnn3c(NCC(C)(C)O)cc(Oc4ccccc4)nc23)ccc1C(=O)NC1CC1] | [$C_{27}H_{29}N_5O_3$ + H]+ 472.2; 472.4 | 14 mg (15%, 2 steps); white solid; free base |

SMs: tert-butyl(3-bromo-5-phenoxypyrazolo[1,5-a]pyrimidin-7-yl)(2-((tert-butoxycarbonyl)oxy)-2-methylpropyl)carbamate (115 mg, 0.20 mmol), N-cyclopropyl-2-methyl-4-(4,4,5,5-tetramethyl-1,3,2-dioxaborolan-2-yl)benzamide (72 mg, 0.24 mmol), PdCl$_2$dppfDCM (16 mg, 0.02 mmol, 10 mol %); TFA (3 mL).
$^1$H NMR (400 MHz, CDCl$_3$) δ ppm 8.21 (s, 1H), 7.75 (s, 1H), 7.57 (d, J = 8.0 Hz, 1H), 7.45 (t, J = 7.5 Hz, 2H), 7.31-7.25 (m, 4H), 7.22 (d, J = 8.3 Hz, 1H), 6.69-6.62 (m, 1H), 5.85 (br, s, 1H), 5.72 (s, 1H), 3.36 (d, J = 6.0 Hz, 2H), 2.89 (br, s, 1H), 2.33 (s, 3H), 1.41 (s, 6H), 0.87 (s, 2H), 0.64-0.55 (m, 2H).

| B28: N-cyclopropyl-4-(7-((2-hydroxy-2-methylpropyl)amino)-5-(pyridin-3-yloxy)pyrazolo[1,5-a]pyrimidin-3-yl)-2-methylbenzamide | | [$C_{26}H_{28}N_6O_3$ + H]+ 473.2; 473.4 | 42 mg (34%, 2 steps); white solid; TFA salt |

SMs: tert-butyl (3-bromo-5-(pyridin-3-yloxy)pyrazolo[1,5-a]pyrimidin-7-yl)(2-((tert-butoxycarbonyl)oxy)-2-methylpropyl)carbamate (120 mg, 0.21 mmol), N-cyclopropyl-2-methyl-4-(4,4,5,5-tetramethyl-1,3,2-dioxaborolan-2-yl)benzamide (75 mg, 0.25 mmol), PdCl$_2$dppfDCM (17 mg, 0.02 mmol, 10 mol %); TFA (3 mL).
$^1$H NMR (400 MHz, CD$_3$OD) δ ppm 8.80-8.76 (m, 1H), 8.63 (d, J = 5.0 Hz, 1H), 8.39 (s, 1H), 8.23-8.16 (m, 1H), 7.88-7.82 (m, 1H), 7.72 (s, 1H), 7.60 (d, J = 7.8 Hz, 1H), 7.21 (d, J = 8.0 Hz, 1H), 6.09 (s, 1H), 3.46 (s, 2H), 2.87-2.79 (m, 1H), 2.27 (s, 3H), 1.35 (s, 6H), 0.84-0.76 (m, 2H), 0.63-0.56 (m, 2H).

| B29: (R)-N-cyclopropyl-4-(5-((1-hydroxybutan-2-yl)amino)-7-(((tetrahydro-2H-pyran-4-yl)methyl)amino)pyrazolo[1,5-a]pyrimidin-3-yl)-2-methylbenzamide | | [$C_{27}H_{36}N_6O_3$ + H]+ 493.3; 493.5 | 12 mg (11%, 2 steps); cream solid free base |

SMs: (R)-tert-butyl (3-bromo-5-((1-hydroxybutan-2-yl)amino)pyrazolo[1,5-a]pyrimidin-7-yl)((tetrahydro-2H-pyran-4-yl)methyl)carbamate (115 mg, 0.23 mmol), N-cyclopropyl-2-methyl-4-

| IUPAC name | Structure | MS calcd; MS ESI [M + H]⁺ | Yield; Appearance; Salt form |
|---|---|---|---|

(4,4,5,5-tetramethyl-1,3,2-dioxaborolan-2-yl)benzamide (209 mg, 0.69 mmol), PdCl₂dppfDCM (19 mg, 0.023 mmol, 10 mol %); TFA (3 mL)

¹H NMR (400 MHz, CD₃OD) δ ppm 8.18 (s, 1H), 7.98 (s, 1H), 7.90 (d, J = 6.4 Hz, 1H), 7.32 (d, J = 8.0 Hz, 1H), 5.41 (s, 1H), 4.11-4.08 (br, s, 1H), 3.98-3.95 (m, 2H), 3.75-3.69 (m, 2H), 3.46-3.40 (m, 2H), 3.23 (d, J = 6.4 Hz, 2H), 2.88-2.82 (m, 1H), 2.45 (s, 3H), 2.01-1.82 (m, 1H), 1.84-1.74 (m, 3H), 1.67-1.60 (m, 1H), 1.43-1.34 (m, 2H), 1.05 (t, J = 7.6 Hz, 3H), 0.84-0.79 (m, 2H), 0.63-0.60 (m, 2H).

| B30: N-cyclopropyl-4-(5-(((2S,3S)-2-hydroxypentan-3-yl)amino)-7-(((tetrahydro-2H-pyran-4-yl)methyl)amino)pyrazolo[1,5-a]pyrimidin-3-yl)-2-methylbenzamide | | [C₂₈H₃₈N₆O₃ + H]⁺ 507.3 507.5 | 2.25 g, 11% (2 steps); off white solid; free base |
|---|---|---|---|

SMs: tert-butyl (3-bromo-5-(((2S,3S)-2-hydroxypentan-3-yl)amino)pyrazolo[1,5-a]pyrimidin-7-yl)((tetrahydro-2H-pyran-4-yl)methyl)carbamate (9.0 g, 17.5 mmol), N-cyclopropyl-2-methyl-4-(4,4,5,5-tetramethyl-1,3,2-dioxaborolan-2-yl)benzamide (8.46 g, 28 mmol), PdCl₂dppfDCM (1.35 g, 1.65 mmol, 9.5 mol %), 2M K₃PO₄ (17.6 mL, 35 mmol); TFA (14.6 mL).

¹H NMR (400 MHz, CD₃OD) δ ppm 8.17 (s, 1H), 7.98 (s, 1H), 7.89 (dd, J = 7.6, 1.6 Hz, 1H), 7.31 (d, J = 8.0 Hz, 1H), 5.44 (s, 1H), 4.07-3.96 (m, 4H), 3.47-3.41 (m, 2H), 3.24 (d, J = 6.8 Hz, 2H), 2.87-2.82 (m, 1H), 2.45 (s, 3H), 2.06-1.99 (m, 1H), 1.81-1.67 (m, 3H), 1.65-1.61 (m, 1H), 1.45-1.34 (m, 2H), 1.22 (d, J = 6.0 Hz, 3H), 1.03 (t, J = 7.2 Hz, 3H), 0.74-0.79 (m, 2H), 0.64-0.60 (m, 2H). HPLC Purity: 97.6% at 254 nM

| B31: N-cyclopropyl-4-(7-((((1r,4r)-4-hydroxycyclohexyl)methyl)amino)-5-phenoxypyrazolo[1,5-a]pyrimidin-3-yl)-2-methylbenzamide | | [C₃₀H₃₃N₅O₃ + H]⁺ 512.2; 512.2 | 49 mg (24%, 2 steps); white solid; free base |
|---|---|---|---|

SMs: (1r,4r)-4-(((3-bromo-5-phenoxypyrazolo[1,5-a]pyrimidin-7-yl)(4-methoxybenzyl)amino-)methyl)cyclohexanol (179 mg, 0.33 mmol) and N-cyclopropyl-2-methyl-4-(4,4,5,5-tetramethyl-1,3,2-dioxaborolan-2-yl)benzamide (99 mg, 0.35 mmol); DCE (12 mL), TFA (5 mL), 80° C., 1 h.

¹H NMR (400 MHz, CDCl₃) δ ppm 8.18 (s, 1H), 7.70 (s, 1H), 7.52 (d, J = 7.8 Hz, 1H), 7.43-7.35 (m, 2H), 7.25-7.19 (m, 3H), 7.17 (d, J = 8.03 Hz, 1H), 6.57-6.49 (m, 1H), 5.60 (s, 1H), 3.58-3.47 (m, 1H), 3.26-3.14 (m, 2H), 2.83-2.75 (m, 1H), 2.26 (s, 3H), 2.03-1.95 (m, 2H), 1.92-1.84 (m, 2H), 1.76-1.56 (br, s, 2H), 1.33-1.19 (m, 2H), 1.15-1.00 (m, 2H), 0.83-0.74 (m, 2H), 0.60-0.46 (m, 2H); HPLC purity: 97.1% at 254 nm.

| IUPAC name | Structure | MS calcd; MS ESI [M + H]+ | Yield; Appearance; Salt form |
|---|---|---|---|
| B32: N-cyclopropyl-4-(7-((2-hydroxy-2-methylpropyl)amino)-5-((tetrahydro-2H-pyran-4-yl)amino)pyrazolo[1,5-a]pyrimidin-3-yl)-2-methylbenzamide | 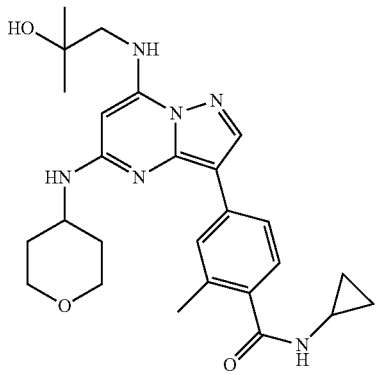 [SMILES: Cc1cc(-c2cnn3c(NCC(C)(C)O)cc(NC4CCOCC4)nc23)ccc1C(=O)NC1CC1] | [$C_{26}H_{34}N_6O_3$ + H]+ 479.3; 479.5 | 78 mg (20%, 2 steps); beige solid; TFA salt |

SMs: tert-butyl (3-bromo-5-((tetrahydro-2H-pyran-4-yl)amino)pyrazolo[1,5-a]pyrimidin-7-yl)(2-((tert-butoxycarbonyl)oxy)-2-methylpropyl)carbamate (228 mg, 0.39 mmol), N-cyclopropyl-2-methyl-4-(4,4,5,5-tetramethyl-1,3,2-dioxaborolan-2-yl)benzamide (141 mg, 0.47 mmol), PdCl$_2$dppfDCM (32 mg, 0.039 mmol, 10 mol %); TFA (3 mL).

$^1$H NMR (400 MHz, CDCl$_3$) δ ppm 7.85 (s, 1H), 7.37-7.27 (m, 3H), 7.03 (br, s, 1H), 6.31 (br, s, 1H), 5.05 (s, 1H), 4.09-3.96 (m, 2H), 3.63 (br, s, 1H), 3.56-3.48 (m, 2H), 3.23-3.13 (m, 2H), 2.99-2.86 (m, 1H), 2.45 (s, 3H), 2.01-1.92 (m, 2H), 1.83-1.68 (m, 2H), 1.38 (s, 6H), 0.94-0.83 (m, 2H), 0.66-0.59 (m, 2H).

| B33: N-cyclopropyl-4-(7-((((1r,4r)-4-hydroxycyclohexyl)methyl)amino)-5-((tetrahydro-2H-pyran-4-yl)amino)pyrazolo[1,5-a]pyrimidin-3-yl)-2-methylbenzamide | 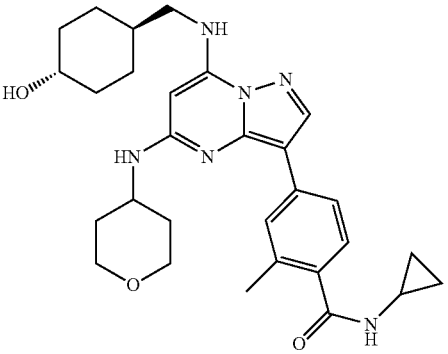 [SMILES: Cc1cc(-c2cnn3c(NC[C@H]4CC[C@H](O)CC4)cc(NC4CCOCC4)nc23)ccc1C(=O)NC1CC1] | [$C_{29}H_{38}N_6O_3$ + H]+ 519.3; 519.2 | 71 mg (42%, 2 steps) white solid TFA salt |

SMs: SMs: (1r,4r)-4-(((3-bromo-5-((tetrahydro-2H-pyran-4-yl)amino)pyrazolo[1,5-a]pyrimidin-7-yl)(4-methoxybenzyl)amino)methyl)cyclohexanol (0.179 g, 0.328 mmol) and N-cyclopropyl-2-methyl-4-(4,4,5,5-tetramethyl-1,3,2-dioxaborolan-2-yl)benzamide (0.282 g, 1.06 mmol); DCE (22 mL), TFA (5 mL), 80° C., 1 h.

$^1$H NMR (400 MHz, CD$_3$OD) δ ppm 8.20 (s, 1H), 7.48 (s, 1H), 7.46-7.40 (m, 2H), 5.60 (s, 1H), 4.06-3.95 (m, 3H), 3.67-3.58 (m, 2H), 3.57-3.49 (m, 1H), 3.42 (d, J = 7.03 Hz, 2H), 2.92-2.85 (m, 1H), 2.47 (s, 3H), 2.1-1.97 (m, 4H), 1.86-1.69 (m, 2H), 1.85-1.71 (m, 1H), 1.71-1.58 (m, 2H), 1.35-1.10 (m, 4H), 0.89-0.79 (m, 2H), 0.67-0.60 (m, 2H).

Example C28

Synthesis of tert-butyl tert-butyl (3-bromo-5-phenoxypyrazolo[1,5-a]pyrimidin-7-yl)((tetrahydro-2H-pyran-4-yl)methyl)carbamate

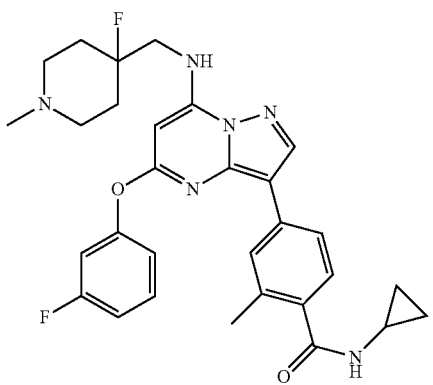 [SMILES: Cc1cc(-c2cnn3c(NCC4(F)CCN(C)CC4)cc(Oc4cccc(F)c4)nc23)ccc1C(=O)NC1CC1]

According to general Method F, using tert-butyl 4-(((3-bromo-5-(3-fluorophenoxy)pyrazolo[1,5a]pyrimidin-7-yl)(tert-butoxycarbonyl)amino)methyl)-4-fluoropiperidine-1-carboxylate (7.78 g, 12.2 mmol), N-cyclopropyl-2-methyl-4-(4,4,5,5-tetramethyl-1,3,2-dioxaborolan-2-yl)benzamide (5.14 g, 17.1 mmol), PdCl$_2$dppfDCM (1.0 g, 1.22 mmol), 2M K$_3$PO$_4$ (15 mL, 30 mmol) and THF (60 mL) by heating at reflux in an oil bath for 6 h, crude tert-butyl 4-(((tert-butoxycarbonyl)(3-(4-(cyclopropylcarbamoyl)-3-methylphenyl)-5-(3-fluorophenoxyl)pyrazolo[1,5-a]pyrimidin-7-yl)amino)methyl)-4-fluoropiperidine-1-carboxylate was obtained as a yellow solid (8.93 g, 100%). MS ESI 677.3 [M–C$_4$H$_8$]$^+$, calcd for [C$_{39}$H$_{46}$F$_2$N$_6$O$_6$—C$_4$H$_8$]$^+$ 677.3.

The above compound (8.93 g) was dissolved in DCM (50 mL) and treated with TFA (20 mL) at rt for 19 h. After reaction completion, solvent was removed in vacuo and the crude was redissolved in DCM (2 mL), neutralized with saturated aqueous sodium bicarbonate and extracted with EtOAc. The combined organic extracts were dried over MgSO$_4$, filtered and concentrated. The crude product was purified by flash chromatography (gradient: 100% EtOAc then MeOH/DCM 0-20%) using three columns in parallel to give N-cyclopropyl-4-(5-(3-fluorophenoxy)-7-(((4-fluoropiperidin-4-yl)methyl)amino)pyrazolo[1,5-a]pyrimidin-3-yl)-2-methylbenzamide as a yellow solid (4.25 g, 65% over 2 steps). $^1$H NMR (400 MHz, CDCl$_3$) δ ppm 9.65-9.45 (m, 1H), 8.26 (s, 1H), 7.78 (s, 1H), 7.59 (d, J=8.0 Hz, 1H), 7.46-7.36 (m, 1H), 7.09 (d, J=7.3 Hz, 2H), 7.04-6.94 (m, 1H), 6.62 (t, J=6.8 Hz, 1H), 5.86 (br, s, 1H), 5.76 (s, 1H), 3.58 (d, J=6.8 Hz, 1H), 3.53 (d, J=6.5 Hz, 1H), 2.99 (dd, J=8.3, 2.8 Hz, 4H), 2.89 (dd, J=7.0, 3.8 Hz, 1H), 2.37 (s, 3H), 2.08-1.94 (m, 2H), 1.80-1.64 (m, 3H), 0.94-0.82 (m, 2H), 0.66-0.55 (m, 2H); MS ESI 533.3 [M+H]$^+$, calcd for [C$_{29}$H$_{30}$F$_2$N$_6$O$_2$+H]$^+$ 533.2.

A solution of formaldehyde solution (1 mL, 11.97 mmol, 37 wt. % in H$_2$O), N-cyclopropyl-4-(5-(3-fluorophenoxy)-7-(((4-fluoropiperidin-4-yl)methyl)amino)pyrazolo[1,5-a]pyrimidin-3-yl)-2-methylbenz-amide (4.25 g, 7.98 mmol), and AcOH (1 mL) was stirred at rt for 30 min. NaBH(OAc)$_3$ (3.38 g, 15.96 mmol) was then added and the resulting mixture was stirred at rt for 1 h. Sat. NaHCO$_3$ and DCM were added to separate the phases and the aqueous phase was extracted with DCM. The combined organic extracts were dried over MgSO$_4$, filtered and concentrated. The crude product was purified by RP flash chromatography (gradient: EtOAc/hex 5-100%) using three columns in parallel, followed by Water PoraPak Rxn cartridge (three cartridges in parallel) to give the free base as a white solid (2.13 g, 49%). The free base was dissolved in a mixture of DCM (20 mL) and MeOH (40 mL), HCl (4.7 mL, 4.7 mmol, 1M Et$_2$O) was then added slowly. Solvent was removed in vacuo to give a HCl salt as a pale yellow solid (2.25 g, 49%). $^1$H NMR (400 MHz, CD$_3$OD) δ ppm 8.39 (s, 1H), 7.84 (s, 1H), 7.63 (d, J=8.0 Hz, 1H), 7.54-7.40 (m, 1H), 7.21 (d, J=8.0 Hz, 1H), 7.16-6.98 (m, 3H), 6.05 (s, 1H), 3.80 (d, J=18.1 Hz, 2H), 3.54 (d, J=12.3 Hz, 2H), 3.29-3.23 (m, 2H), 2.94 (s, 3H), 2.88-2.79 (m, 1H), 2.42-2.29 (m, 2H), 2.28 (s, 3H), 2.19 (br, s, 2H), 0.87-0.73 (m, 2H), 0.68-0.55 (m, 2H); MS ESI 547.2 [M+H]$^+$, calcd for [C$_{30}$H$_{32}$F$_2$N$_6$O$_2$+H]$^+$ 547.3; HPLC purity: 100% at 254 nm.

Example C29

(S)—N-cyclopropyl-2-methyl-4-(7-(((tetrahydro-2H-pyran-4-yl)methyl)amino)-5-(((tetrahydrofuran-2-yl)methyl)amino)pyrazolo[1,5-a]pyrimidin-3-yl)benzamide

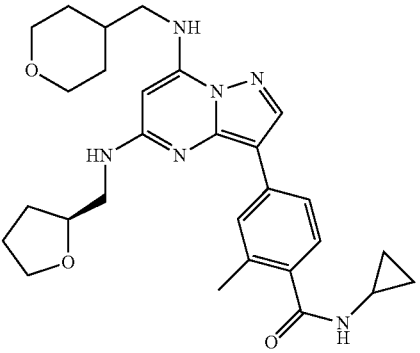 [SMILES: Cc1cc(-c2cnn3c(NCC4CCOCC4)cc(NC[C@@H]4CCCO4)nc23)ccc1C(=O)NC1CC1]

According to General Method J, to a mixture of (S)-(tetrahydrofuran-2-yl)methanamine (51 mg, 0.5 mmol) and iPr$_2$NEt (0.175 mL, 1 mmol) was added 0.2 M solution of tert-butyl (3-(4-(cyclopropylcarbamoyl)-3-methylphenyl)-5-(phenylsulfonyl)pyrazolo[1,5-a]pyrimidin-7-yl)((tetrahydro-2H-pyran-4-yl)methyl)carbamate in NMP (2 mL, 0.4 mmol). The resulting mixture was heated in microwave at 120° C. for 2 h.

2 mL of H$_2$O was added to the above reaction and the mixture was heated in microwave at 140° C. for 2 h. After passing through porapak, it was purified by RP Biotage C18 column (gradient: CH$_3$CN/H$_2$O (0.1% TFA) 0-60%) and porapak to give the title compound as a white solid. It was redissoved in MeOH (10 mL) and 0.4 mL of 1 M HCl in Et$_2$O (0.4 mmol) was added. After removal of solvents, it was redissovled in MeOH and repeated twice to give the HCl salt of the title compound as light yellow solid (98.7 mg, 46%). $^1$H NMR (400 MHz, CD$_3$OD) δ ppm 8.21 (s, 1H), 7.55-7.35 (m, 3H), 4.30-4.12 (m, 1H), 4.05-3.35 (m, 10H), 2.92-2.85 (m, 1H), 2.47 (s, 3H), 2.20-1.92 (m, 4H), 1.86-1.68 (m, 3H), 1.55-1.38 (m, 2H), 0.85-0.78 (m, 2H), 0.70-0.60 (m, 2H); MS ESI 505.3 [M+H]$^+$, [C$_{28}$H$_{36}$N$_6$O$_3$+H]$^+$ 505.3; HPLC purity: 98.5% at 254 nm

Example C30

3-((3-(4-(cyclopropylcarbamoyl)-3-methylphenyl)-7-((((tetrahydro-2H-pyran-4-yl)methyl)amino)pyrazolo[1,5-a]pyrimidin-5-yl)oxy)pyridine-1-oxide

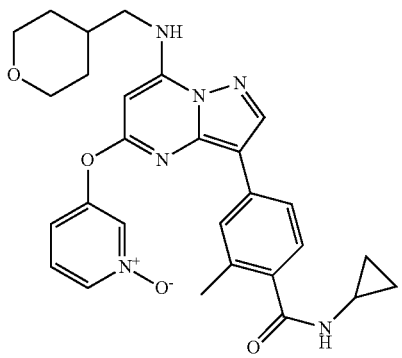 [SMILES: Cc1cc(-c2cnn3c(NCC4CCOCC4)cc(Oc4ccc[n+]([O-])c4)nc23)ccc1C(=O)NC1CC1]

The N-cyclopropyl-2-methyl-4-(5-(pyridin-3-yloxy)-7-((((tetrahydro-2H-pyran-4-yl)methyl)amino) pyrazolo[1,5-a]pyrimidin-3-yl)benzamide hydrochloride (100 mg, 0.186 mmol) was dissolved in MeOH and turned into free base by running through PoraPak. The resulting free base was dissolved in DCM (4 mL) and was added mCPBA (75%, 126 mg, 0.56 mmol) at 0° C. The ice bath was removed and the reaction mixture was stirred at rt for 3.5 h. The solvent was removed under reduced pressure and the residue was purified by flash chromatography (MeOH/DCM 0-10%) to give the intermediate as brown solid. $^1$H NMR (400 MHz, CD$_3$OD) δ ppm 8.50 (s, 1H), 8.33 (s, 1H), 8.29 (dt, J=4.8, 2.1 Hz, 1H), 7.70 (s, 1H), 7.63-7.56 (m, 3H), 7.22 (d, J=8.0 Hz, 1H), 5.87 (s, 1H), 3.97 (dd, J=11.4, 3.1 Hz, 2H), 3.42 (td, J=11.7, 1.9 Hz, 2H), 3.31 (d, J=4.8 Hz, 2H), 2.85 (td, J=7.3, 3.6 Hz, 1H), 2.32 (s, 3H), 2.01 (d, J=11.8 Hz, 1H), 1.74 (d, J=11.0 Hz, 2H), 1.45-1.32 (m, 2H), 0.85-0.77 (m, 2H), 0.65-0.57 (m, 2H). HPLC purity: 99.1% at 254 nm.

The following final compounds were synthesized according to the synthesis of Example B1 or C28 using General Method F:

| IUPAC name | Structure | MS calcd; MS ESI [M + H]$^+$ | Yield; Appearance; Salt form |
|---|---|---|---|
| C31: N-cyclopropyl-4-(5-(3-fluorophenoxy)-7-((2-morpholinoethyl)amino)pyrazolo[1,5-a]pyrimidin-3-yl)-2-methylbenzamide | 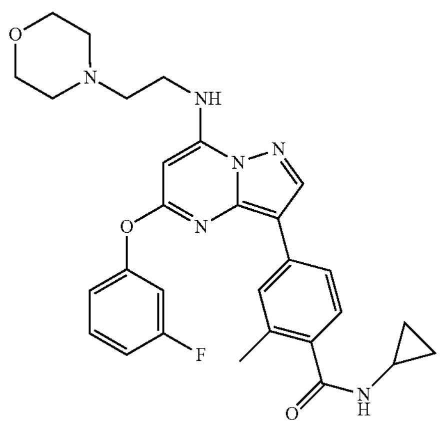 [SMILES: Cc1cc(-c2cnn3c(NCCN4CCOCC4)cc(Oc4cccc(F)c4)nc23)ccc1C(=O)NC1CC1] | [C$_{29}$H$_{31}$FN$_6$O$_3$ + H]$^+$ 531.3; 531.3 | 3.332 g, 59% (2 steps); white solid; HCl salt |

SMs: tert-butyl (5-(3-fluorophenoxy)pyrazolo[1,5-a]pyrimidin-7-yl)(2-morpholinoethyl)carbamate (5.42 g, 10 mmol), N-cyclopropyl-2-methyl-4-(4,4,5,5-tetramethyl-1,3,2-dioxaborolan-2-yl)benzamide (6.33 g, 21 mmol), PdCl$_2$dppfDCM (408 mg, 0.5 mmol, 5 mol %), 2M K$_3$PO$_4$ (15 mL, 30 mmol); TFA (10 mL).
$^1$H NMR (400 MHz, CD$_3$OD) δ ppm 8.42 (s, 1H), 7.84 (s, 1H), 7.64 (dd, J = 8.0, 1.6 Hz, 1H), 7.53-7.47 (m, 1H), 7.21 (d, J = 8.0 Hz, 1H), 7.16-7.06 (m, 3H), 6.08 (s, 1H), 4.17-4.08 (m, 2H), 3.97 (t, J = 6.2 Hz, 2H), 3.94 (t, J = 11.8 Hz, 2H), 3.65 (d, J = 12.0 Hz, 2H), 3.57 (t, J = 6.2 Hz, 2H), 3.35-3.27 (m, 2H), 2.38-2.31 (m, 3H), 2.27 (s, 3H), 0.84-0.78 (m, 2H), 0.63-0.58 (m, 2H). HPLC purity: 98.9% at 254 nm

| IUPAC name | Structure | MS calcd; MS ESI [M + H]⁺ | Yield; Appearance; Salt form |
|---|---|---|---|
| C32: N-cyclopropyl-4-(5-(2,3-difluorophenoxy)-7-((2-morpholinoethyl)amino)pyrazolo[1,5-a]pyrimidin-3-yl)-2-methylbenzamide | 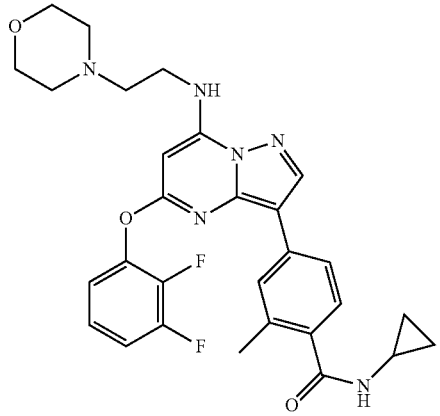 [SMILES: Cc1cc(-c2cnn3c(NCCN4CCOCC4)cc(Oc4cccc(F)c4F)nc23)ccc1C(=O)NC1CC1] | $[C_{29}H_{30}F_2N_6O_3 + H]^+$ 549.2; 549.2 | 2.84 g, 45% (2 steps); white solid; TFA salt |

SMs: tert-butyl (3-bromo-5-(2,3-difluorophenoxy)pyrazolo[1,5-a]pyrimidin-7-yl)(2-morpholinoethyl)carbamate (5.31 g, 9.54 mmol), N-cyclopropyl-2-methyl-4-(4,4,5,5-tetramethyl-1,3,2-dioxaborolan-2-yl)benzamide (4.32 g, 14.31 mmol), PdCl₂dppfDCM (390 mg, 0.477 mmol, 5 mol %), 2M K₃PO₄ (11.46 mL, 22.92 mmol); TFA (10 mL).

¹H NMR (400 MHz, CD₃OD) δ ppm 8.41 (s, 1H), 7.75 (s, 1H), 7.57 (d, J = 8.0 Hz, 1H), 7.29 (t, J = 6.3 Hz, 2H), 7.19 (d, J = 7.3 Hz, 2H), 6.14 (s, 1H), 4.18-3.76 (m, 6H), 3.59 (t, J = 5.5 Hz, 4H), 3.42-3.25 (m, 2H), 2.89-2.78 (m, 1H), 2.24 (s, 3H), 0.85-0.76 (m, 2H), 0.66-0.55 (m, 2H). HPLC purity: 98.3% at 254 nm

| IUPAC name | Structure | MS calcd; MS ESI [M + H]⁺ | Yield; Appearance; Salt form |
|---|---|---|---|
| C33: 2-chloro-N-cyclopropyl-4-(5-(2,3-difluorophenoxy)-7-((2-morpholinoethyl)amino)pyrazolo[1,5-a]pyrimidin-3-yl)benzamide | 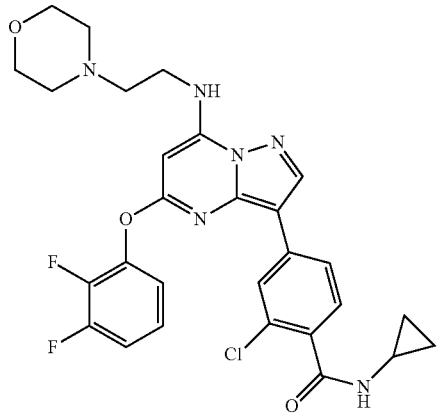 [SMILES: O=C(NC1CC1)c1ccc(-c2cnn3c(NCCN4CCOCC4)cc(Oc4cccc(F)c4F)nc23)cc1Cl] | $[C_{28}H_{27}ClF_2N_6O_3 + H]^+$ 569.2; 569.3 | 3.08 g, 51% (2 steps); white solid; HCl salt |

SMs: tert-butyl (3-bromo-5-(2,3-difluorophenoxy)pyrazolo[1,5-a]pyrimidin-7-yl)(2-morpholinoethyl)carbamate (5.82 g, 10 mmol), (3-chloro-4-(cyclopropylcarbamoyl)phenyl)boronic acid (5.88 g, 24.5 mmol), PdCl₂dppfDCM (272 mg, 0.333 mmol), 2M K₃PO₄ (5 mL, 10 mmol); TFA (10 mL).

¹H NMR (400 MHz, CD₃OD) δ ppm 8.41 (s, 1H), 7.99 (d, J = 1.5 Hz, 1H), 7.70 (dd, J = 8.0, 1.8 Hz, 1H), 7.29-7.24 (m, 3H), 7.21-7.15 (m, 1H), 6.01 (s, 1H), 3.76-3.74 (m, 4H), 3.62 (t, J = 6.3 Hz, 2H), 2.85 (tt, J = 7.3, 3.5 Hz, 1H), 2.78 (t, J = 6.3 Hz, 2H), 2.64-2.56 (m, 4H), 0.84-0.77 (m, 2H), 0.66-0.60 (m, 2H). HPLC purity: 98.2% at 254 nm

| IUPAC name | Structure | MS calcd; MS ESI [M + H]⁺ | Yield; Appearance; Salt form |
|---|---|---|---|
| C34: 2-chloro-N-cyclopropyl-4-(5-(3-fluorophenoxy)-7-((2-morpholinoethyl)amino)pyrazolo[1,5-a]pyrimidin-3-yl)benzamide | | $[C_{28}H_{28}ClFN_6O_3 + H]^+$ 551.2; 551.2 | 218 mg, 33% (2 steps); white solid; TFA salt |
| SMs: tert-butyl (5-(3-fluorophenoxy)pyrazolo[1,5-a]pyrimidin-7-yl)(2-morpholinoethyl)carbamate (540 mg, 1 mmol), (3-chloro-4-(cyclopropylcarbamoyl)phenyl)boronic acid (335 mg, 1.4 mmol), PdCl₂dppfDCM (41 mg, 0.05 mmol, 5 mol %), 2M K₃PO₄ (1.5 mL, 3 mmol); TFA (3 mL). ¹H NMR (400 MHz, CD₃OD) δ ppm 8.26 (s, 1H), 7.94 (d, J = 1.6 Hz, 1H), 7.62 (dd, J = 8.2, 1.4 Hz, 1H), 7.47-7.41 (m, 1H), 7.25 (d, J = 8.0 Hz, 1H), 7.09-7.00 (m, 3H), 5.90 (s, 1H), 4.10-3.80 (m, 6H), 3.70-3.51 (m, 4H), 3.35-3.20 (m, 2H), 2.89-2.83 (m, 3H), 0.84-0.78 (m, 2H), 0.67-0.62 (m, 2H). HPLC purity: 97.7% at 254 nm | | | |
| C35: N-cyclopropyl-4-(5-(((1S,2R)-2-hydroxycyclohexyl)amino)-7-((((R)-tetrahydrofuran-3-yl)methyl)amino)pyrazolo[1,5-a]pyrimidin-3-yl)-2-methylbenzamide | | $[C_{28}H_{36}N_6O_3 + H]^+$ 505.3; 505.4 | 4.2 g, 46% (2 steps); white solid; free base |
| SMs: tert-butyl (3-bromo-5-(((1S,2R)-2-hydroxycyclohexyl)amino)pyrazolo[1,5-a]pyrimidin-7-yl)(((R)-tetrahydrofuran-3-yl)methyl)carbamate (9.14 g, 17.96 mmol), N-cyclopropyl-2-methyl-4-(4,4,5,5-tetramethyl-1,3,2-dioxaborolan-2-yl)benzamide (8.11 g, 26.94 mmol), PdCl₂dppfDCM (1466 mg, 1.796 mmol, 10 mol %), 2M K₃PO₄ (31 mL, 62.85 mmol), THF (100 mL); TFA (18 mL), DCM (18 mL). ¹H NMR (400 M Hz, CD₃OD) δ ppm 8.18 (s, 1H), 8.06 (s, 1H), 7.83 (dd, J = 8.0, 1.3 Hz, 1H), 7.31 (d, J = 8.0 Hz, 1H), 5.45 (d, J = 0.8 Hz, 1H), 4.23-4.11 (m, 2H), 3.93 (td, J = 8.2, 5.5 Hz, 1H), 3.85 (m, J = 7.3 Hz, 1H), 3.77 (q, J = 7.9 Hz, 1H), 3.65 (dd, J = 8.4, 5.1 Hz, 1H), 3.31-3.28 (m, 2H), 2.90-2.81 (m, 1H), 2.75-2.65 (m, 1H), 2.46 (s, 3H), 2.20-2.07 (m, 1H), 1.94-1.61 (m, 7H), 1.48 (d, J = 9.0 Hz, 2H), 0.85-0.78 (m, 2H), 0.66-0.60 (m, 2H). HPLC purity: 99.1% at 254 nm | | | |
| C36: N-cyclopropyl-4-(5-(((1S,2R)-2-hydroxycyclohexyl)amino)-7-((((S)-tetrahydrofuran-3-yl)methyl)amino)pyrazolo[1,5-a]pyrimidin-3-yl)-2-methylbenzamide | | $[C_{28}H_{36}N_6O_3 + H]^+$ 505.2; 505.4 | 3.10 g, 16% (2 steps); pale yellow solid; free base |
| SMs: tert-butyl (3-bromo-5-(((1S,2R)-2-hydroxycyclohexyl)amino)pyrazolo[1,5-a]pyrimidin-7-yl)(((S)-tetra hydrofuran-3-yl)methyl)carbamate (10.5 g, 20.5 mmol), N-cyclopropyl-2-methyl-4-(4,4,5,5-tetramethyl-1,3,2-dioxaborolan-2-yl)benzamide (9.29 g, 30.8 mmol), PdCl₂dppfDCM | | | |

| IUPAC name | Structure | MS calcd; MS ESI [M + H]+ | Yield; Appearance; Salt form |
|---|---|---|---|

(1.69 g, 2.05 mmol, 10 mol %), 2M K₃PO₄ (20.6 mL, 41.1 mmol); TFA (13 mL).

¹H NMR identical to C8. 402237. HPLC purity: 98.3% at 254 nM.

C37:
N-cyclopropyl-4-(5-(((1S,2R)-2-hydroxycyclohexyl)amino)-7-((oxetan-3-ylmethyl)amino)pyrazolo[1,5-a]pyrimidin-3-yl)-2-methylbenzamide

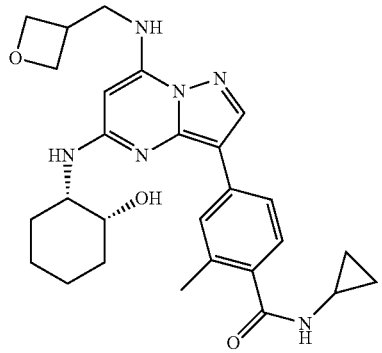 [SMILES: Cc1cc(-c2cnn3c(NCC4COC4)cc(N[C@H]4CCCC[C@H]4O)nc23)ccc1C(=O)NC1CC1]

[C₂₇H₃₄N₆O₃ + H]⁺
491.3;
491.2

75 mg, 69% (2 steps); white solid; free base

SMs: tert-butyl(3-bromo-5-(((1S,2R)-2-hydroxycyclohexyl)amino)pyrazolo[1,5-a]pyrimidin-7-yl)(oxetan-3-ylmethyl)carbamate (338 mg, 0.681 mmol), N-cyclopropyl-2-methyl-4-(4,4,5,5-tetramethyl-1,3,2-dioxaborolan-2-yl)benzamide (226 mg, 0.749 mmol), PdCl₂dppfDCM (56 mg, 0.068 mmol, 10 mol %), 2M K₃PO₄ (1 mL, 2.04 mmol); TFA (1 mL).

¹H NMR (400 MHz, CD₃OD) δ ppm 8.18 (s, 1H), 8.06 (s, 1H), 7.83 (dd, J = 7.9, 1.6 Hz, 1H), 7.31 (d, J = 8.0 Hz, 1H), 5.46 (s, 1H), 4.88-4.83 (m, 2H), 4.52 (t, J = 6.0 Hz, 2H), 4.11-4.22 (m, 2H), 3.64 (d, J = 7.3 Hz, 2H), 3.46-3.37 (m, 1H), 2.90-2.81 (m, 1H), 2.46 (s, 3H), 1.92-1.62 (m, 6H), 1.54-1.43 (m, 2H), 0.86-0.78 (m, 2H), 0.66-0.60 (m, 2H). HPLC purity: 99.2% at 254 nm C38:
(S)-N-cyclopropyl-4-(5-((1-hydroxy-3-methylbutan-2-yl)amino)-7-(((tetrahydro-2H-pyran-4-yl)methyl)amino)pyrazolo[1,5-a]pyrimidin-3-yl)-2-methylbenzamide

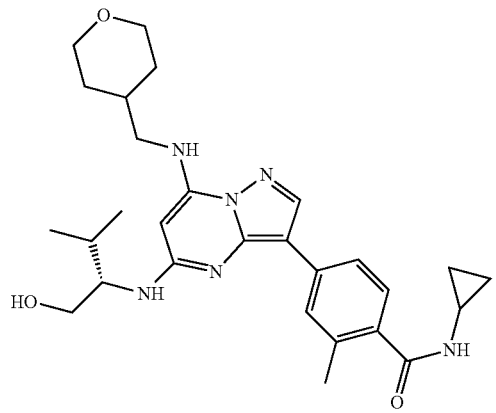 [SMILES: Cc1cc(-c2cnn3c(NCC4CCOCC4)cc(N[C@H](CO)C(C)C)nc23)ccc1C(=O)NC1CC1]

[C₂₈H₃₈N₆O₃ + H]⁺
507.3;
507.5

1.98 g, 48% (2 steps); cream solid; free base

SMs: (S)-tert-butyl (3-bromo-5-((1-hydroxy-3-methylbutan-2-yl)amino)pyrazolo[1,5-a]pyrimidin-7-yl)((tetrahydro-2H-pyran-4-yl)methyl)carbamate (6.0 g, 11.7 mmol), N-cyclopropyl-2-methyl-4-(4,4,5,5-tetramethyl-1,3,2-dioxaborolan-2-yl)benzamide (5.28 g, 17.5 mmol), PdCl₂dppfDCM (0.956 g, 1.75 mmol, 10 mol %), 2M K₃PO₄ (11.72 mL, 23.4 mmol); TFA (10.5 mL).

¹H NMR (400 MHz, CD₃OD) δ ppm 8.21 (s, 1H), 7.49 (s, 1H), 7.46-7.41 (m, 2H), 5.69 (s, 1H), 3.98 (dd, J = 11.2, 3.2 Hz, 2H), 3.84 (br, s, 1H), 3.76-3.68 (m, 2H), 3.46-3.41 (m, 4H), 2.91-2.85 (m, 1H), 2.47 (s, 3H), 2.09-2.03 (m, 2H), 1.76-1.73 (m, 2H), 1.47-1.37 (m, 2H), 1.08 (t, J = 7.2 Hz, 6H), 0.86-0.81 (m, 2H), 0.65-0.61 (m, 2H). HPLC Purity (HCl salt): 99.0% at 254 nM.

| IUPAC name | Structure | MS calcd; MS ESI [M + H]+ | Yield; Appearance; Salt form |
|---|---|---|---|
| C39: N-cyclopropyl-4-(5-((((1S,2R)-2-hydroxycyclohexyl)amino)-7-(((tetrahydro-2H-pyran-4-yl)methyl)amino)pyrazolo[1,5-a]pyrimidin-3-yl)-2-methylbenzamide | 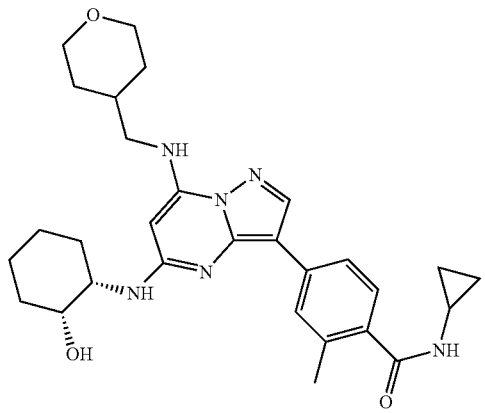 [SMILES: Cc1cc(-c2cnn3c(NCC4CCOCC4)cc(N[C@H]4CCCC[C@H]4O)nc23)ccc1C(=O)NC1CC1] | [C29H38N6O3 + H]+ 519.3; 519.3 | 1.98 g, 20% (2 steps); cream solid; free base |

SMs: tert-butyl (3-bromo-5-(((1S,2R)-2-hydroxycyclohexyl)amino)pyrazolo[1,5-a]pyrimidin-7-yl)((tetrahydro-2H-pyran-4-yl)methyl)carbamate (7.95 g, 15 mmol), N-cyclopropyl-2-methyl-4-(4,4,5,5-tetramethyl-1,3,2-dioxaborolan-2-yl)benzamide (6.84 g, 23 mmol), PdCl2dppfDCM (1.21 g, 1.50 mmol, 10 mol %), 2M K3PO4 (15.14 mL, 30 mmol); TFA (17 mL).

$^1$H NMR (400 MHz, CD3Cl3) δ ppm 8.10 (s, 1H), 7.91 (s, 1H), 7.78-7.76 (m, 1H), 7.35 (s, 1H), 7.34 (s, 1H), 6.09 (t, J = 6.0 Hz, 1H), 5.98 (d, J = 2.4 Hz, 1H), 5.12 (s, 1H), 4.98 (d, J = 6.8 Hz, 1H), 4.20-4.15 (m, 2H), 4.00 (dd, J = 11.6, 3.6 Hz, 2H), 3.42-3.36 (m, 2H), 3.15 (t, J = 6.8 Hz, 2H), 2.93-2.87 (m, 1H), _2.51 (s, 3H), 1.97-1.88 (m, 3H), 1.85-1.51 (m, 6H), 1.50-1.41 (m, 2H), 1.39-1.33 (m, 2H), 0.90-0.85 (m, 2H), 0.63-0.59 (m, 2H). HPLC Purity (HCl salt): 98.3% at 254 nM.

| IUPAC name | Structure | MS calcd; MS ESI [M + H]+ | Yield; Appearance; Salt form |
|---|---|---|---|
| C40: (S)-N-cyclopropyl-4-(5-((2-hydroxy-2,4-dimethylpentan-3-yl)amino)-7-(((tetrahydro-2H-pyran-4-yl)methyl)amino)pyrazolo[1,5-a]pyrimidin-3-yl)-2-methylbenzamide | 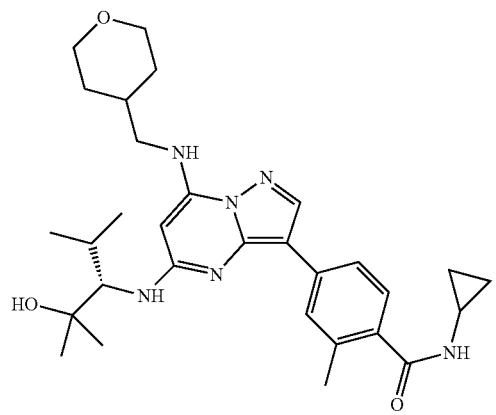 [SMILES: Cc1cc(-c2cnn3c(NCC4CCOCC4)cc(N[C@@H](C(C)C)C(C)(C)O)nc23)ccc1C(=O)NC1CC1] | [C30H42N6O3 + H]+ 535.3; 535.3 | 1.45 g, 12% (2 steps); cream solid; free base |

SMs: (S)-tert-butyl (3-bromo-5-((2-hydroxy-2,4-dimethylpentan-3-yl)amino)pyrazolo[1,5-a]pyrimidin-7-yl) ((tetrahydro-2H-pyran-4-yl)methyl)carbamate (5.50 g, 10.1 mmol), N-cyclopropyl-2-methyl-4-(4,4,5,5-tetramethyl-1,3,2-dioxaborolan-2-yl)benzamide (4.59 g, 15.2 mmol), PdCl2dppfDCM (0.825 g, 1.01 mmol, 10 mol %), 2M K3PO4 (10.18 mL, 20.2 mmol); TFA (8.4 mL).

$^1$H NMR (400 MHz, CD3OD) δ ppm 8.18 (s, 1H), 8.02 (s, 1H), 7.88 (dd, J = 8.0, 1.2 Hz, 1H), 7.31 (d, J = 8.0 Hz, 1H), 5.53 (s, 1H), 4.33 (s, 1H), 3.92 (dd, J = 11.2, 3.2 Hz, 2H), 3.45-3.35 (m, 2H), 3.32-3.31 (m, 1H), 3.18-3.16 (m, 2H), 2.87-2.82 (m, 1H), 2.45 (s, 3H), 2.31-2.24 (m, 1H), 1.95-1.85 (m, 1H), 1.85-1.67 (m, 2H), 1.37-1.30 (m, 4H), 1.27 (s, 3H), 1.07-1.03 (m, 6H), 0.82-0.78 (m, 2H), 0.64-0.60 (m, 2H). HPLC Purity (HCl salt): 99.1% at 254 nM.

| IUPAC name | Structure | MS calcd; MS ESI [M + H]+ | Yield; Appearance; Salt form |
|---|---|---|---|
| C41: (S)-N-cyclopropyl-4-(5-((1-cyclopropyl-2-hydroxy-2-methylpropyl)amino)-7-(((tetrahydro-2H-pyran-4-yl)methyl)amino)pyrazolo[1,5-a]pyrimidin-3-yl)-2-methylbenzamide | 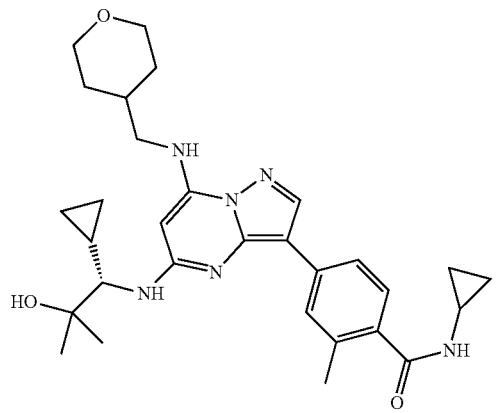 [SMILES: Cc1cc(-c2cnn3c(NCC4CCOCC4)cc(N[C@@H](C4CC4)C(C)(C)O)nc23)ccc1C(=O)NC1CC1] | $[C_{30}H_{40}N_6O_3 + H]^+$ 533.3; 533.4 | 2.10 g, 17% (2 steps); pale yellow solid; free base |

SMs: (S)-tert-butyl (3-bromo-5-((1-cyclopropyl-2-hydroxy-2-methylpropyl)amino)pyrazolo [1,5-a]pyrimidin-7-yl)((tetrahydro-2H-pyran-4-yl)methyl)carbamate (7.50 g, 13.9 mmol), N-cyclopropyl-2-methyl-4-(4,4,5,5-tetramethyl-1,3,2-dioxaborolan-2-yl)benzamide (6.27 g, 20.8 mmol), PdCl$_2$dppfDCM (1.13 g, 1.39 mmol, 10 mol %), 2M K$_3$PO$_4$ sol (13.9 mL, 27.8 mmol).
$^1$H NMR (400 MHz, CD$_3$OD) δ ppm 8.16 (s, 1H), 7.96 (s, 1H), 7.77 (dd, J = 8.4, 1.6 Hz , 1H), 7.31 (d, J = 8.0 Hz, 1H), 5.46 (s, 1H), 3.96 (dd, J = 11.2, 3.2 Hz, 2H), 3.61-3.58 (m, 1H), 3.41 (t, J = 11.6 Hz, 2H), 3.22-3.20 (m, 2H), 2.88-2.82 (m, 1H), 2.45 (s, 3H), 2.02-1.96 (m, 1H), 1.75-1.72 (m, 2H), 1.42-1.32 (m, 8H), 1.16-1.09 (m, 1H), 0.83-0.78 (m, 2H), 0.73-0.68 (m, 1H), 0.64-0.60 (m, 2H), 0.50-0.39 (m, 3H). HPLC Purity: 98.2% at 254 nM.

| C42: N-cyclopropyl-4-(7-((cyclopropylmethyl)amino)-5-(((1S,2R)-2-hydroxycyclohexyl)amino)pyrazolo[1,5-a]pyrimidin-3-yl)-2-methylbenzamide | 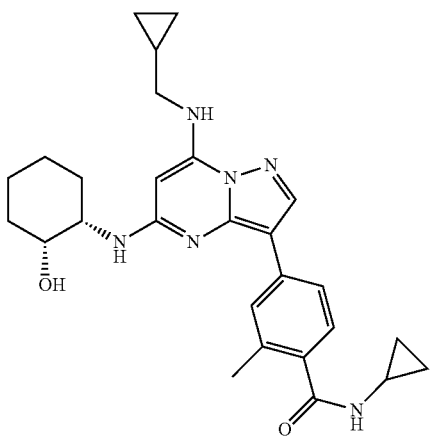 [SMILES: Cc1cc(-c2cnn3c(NCC4CC4)cc(N[C@H]4CCCC[C@H]4O)nc23)ccc1C(=O)NC1CC1] | $[C_{27}H_{34}N_6O_2 + H]^+$ 475.3; 475.3 | 2.09 g, 25% (2 steps); pale yellow solid; HCl salt |

SMs: tert-butyl (3-bromo-5-(((1S,2R)-2- hydroxycyclohexyl)amino)pyrazolo[1,5-a]pyrimidin-7-yl)(cyclopropylmethyl)carbamate (8.48 g, 17.7 mmol), N-cyclopropyl-2-methyl-4-(4,4,5,5-tetramethyl-1,3,2-dioxaborolan-2-yl)benzamide (6.92 g, 23.0 mmol), PdCl$_2$dppfDCM (1.44 g, 1.76 mmol), 2M K$_3$PO$_4$ (26.6 mL, 106.2 mmol); TFA (20 mL).
$^1$H NMR (400 MHz, CD$_3$OD) δ ppm 8.21 (s, 1H), 7.51-7.37 (m, 3H), 5.67 (br, s, 1H), 4.04-3.82 (m, 2H), 3.46-3.37 (m, 2H), 2.93-2.82 (m, 1H), 2.47 (s, 3H), 1.89-1.64 (m, 6H), 1.61-1.42 (m, 2H), 1.31-1.21 (m, 1H), 0.88-0.78 (m, 2H), 0.70-0.58 (m, 4H), 0.46-0.36 (m, 2H). HPLC purity: 98% at 254 nm.

| IUPAC name | Structure | MS calcd; MS ESI [M + H]+ | Yield; Appearance; Salt form |
| --- | --- | --- | --- |
| C43: N-cyclopropyl-4-(7-((((1s,3s)-3-hydroxy-3-methylcyclobutyl)methyl)amino)-5-(pyridin-3-yloxy)pyrazolo[1,5-a]pyrimidin-3-yl)-2-methylbenzamide | 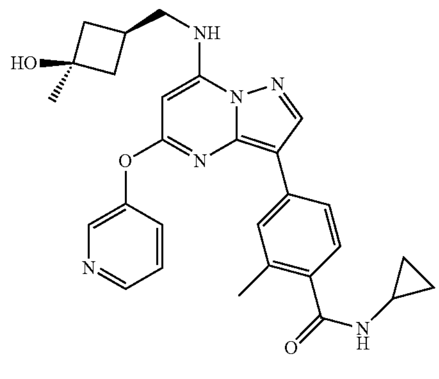 [SMILES: Cc1cc(-c2cnn3c(NC[C@H]4C[C@@](C)(O)C4)cc(Oc4cccnc4)nc23)ccc1C(=O)NC1CC1] | [$C_{28}H_{30}N_6O_3$ + H]+ 499.2; 499.3 | 96 mg, 47% (2 steps); beige solid; HCl salt |

SMs: tert-butyl (3-bromo-5-(pyridin-3-yloxy)pyrazolo[1,5-a]pyrimidin-7-yl)(((1s,3s)-3-((tert-butoxycarbonyl)oxy)-3-methylcyclobutyl)methyl)carbamate (0.23 g, 0.38 mmol), N-cyclopropyl-2-methyl-4-(4,4,5,5-tetramethyl-1,3,2-dioxaborolan-2-yl)benzamide (0.15 g, 0.49 mmol), PdCl$_2$dppfDCM (0.031 g, 0.038 mmol), 2M K$_3$PO$_4$ (0.57 mL, 1.14 mmol); TFA (3 mL).
$^1$H NMR (400 MHz, CD$_3$OD) δ ppm 9.14 (br, s, 1H), 8.89-8.82 (m, 1H), 8.79-8.71 (m, 1H), 8.40 (s, 1H), 8.31-8.21 (m, 1H), 7.68 (s, 1H), 7.59 (d, J = 9.5 Hz, 1H), 7.23 (d, J = 8.0 Hz, 1H), 6.06 (s, 1H), 3.56 (d, J = 6.5 Hz, 2H), 2.88-2.79 (m, 1H), 2.40-2.31 (m, 1H), 2.29 (s, 3H), 2.26-2.18 (m, 2H), 1.99-1.89 (m, 2H), 1.37 (s, 3H), 0.85-0.76 (m, 2H), 0.63-0.53 (m, 2H). HPLC: 99.5% at 254 nm.

| IUPAC name | Structure | MS calcd; MS ESI [M + H]+ | Yield; Appearance; Salt form |
| --- | --- | --- | --- |
| C44: 4-(5-(cyclopentylamino)-7-((((1s,3s)-3-hydroxy-3-methylcyclobutyl)methyl)amino)pyrazolo[1,5-a]pyrimidin-3-yl)-N-cyclopropyl-2-methylbenzamide | 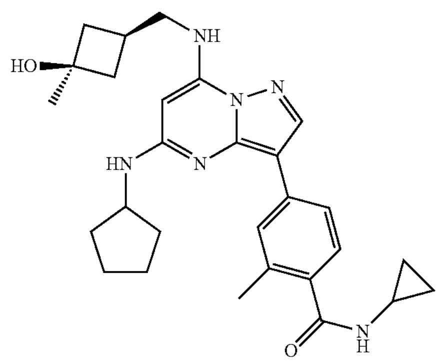 [SMILES: Cc1cc(-c2cnn3c(NC[C@H]4C[C@@](C)(O)C4)cc(NC4CCCC4)nc23)ccc1C(=O)NC1CC1] | [$C_{28}H_{36}N_6O_2$ + H]+ 489.3; 489.4 | 75 mg, 21% (2 steps); light orange solid; HCl salt |

SMs: tert-butyl (3-bromo-5-(cyclopentylamino)pyrazolo[1,5-a]pyrimidin-7-yl)(((1s,3s)-3-((tert-butoxycarbonyl)oxy)-3-methylcyclobutyl)methyl)carbamate (0.40 g, 0.67 mmol), N-cyclopropyl-2-methyl-4-(4,4,5,5-tetramethyl-1,3,2-dioxaborolan-2-yl)benzamide (0.26 g, 0.88 mmol), PdCl$_2$dppfDCM (0.055 g, 0.067 mmol), 2M K$_3$PO$_4$ (1 mL, 2.01 mmol); TFA (3 mL).
$^1$H NMR (400 MHz, CD$_3$OD) δ ppm 8.18 (s, 1H), 7.42 (s, 3H), 5.52 (br, s, 1H), 4.23-4.11 (m, 1H), 3.68-3.54 (m, 2H), 2.93-2.81 (m, 1H), 2.46 (s, 3H), 2.38-2.27 (m, 1H), 2.26-2.07 (m, 4H), 1.99-1.89 (m, 2H), 1.88-1.59 (m, 6H), 1.35 (s, 3H), 0.86-0.79 (m, 2H), 0.66-0.58 (m, 2H). HPLC purity: 99% at 254 nm.

| IUPAC name | Structure | MS calcd; MS ESI [M + H]+ | Yield; Appearance; Salt form |
| --- | --- | --- | --- |
| C45: N-cyclopropyl-4-(5-((1-(hydroxymethyl)cyclopentyl)amino-7-(((tetrahydro-2H-pyran-4-yl)methyl)amino)pyrazolo[1,5-a]pyrimidin-3-yl)-2-methylbenzamide | | [$C_{29}H_{38}N_6O_3$ + H]+ 519.3; 519.5 | 83 mg, 16 mg (2 steps); white solid; TFA salt |

SMs: tert-butyl(3-bromo-5-((1(hydroxymethyl)cyclopentyl)amino) pyrazolo[1,5-a]pyrimidin-7-yl)((tetrahydro-2H-pyran-4-yl) methyl) carbamate (437 mg, 0.83 mmol), N-cyclopropyl-2-methyl-4-(4,4,5,5-tetramethyl-1,3,2-dioxaborolan-2-yl)benzamide (350 mg, 1.2 mmol), PdCl$_2$dppfDCM (68 mg, 0.0.083 mmol), and 2M K$_3$PO$_4$ (1.3 mL, 2.5 mmol); TFA (6 mL).
$^1$H NMR (400 MHz, CDCl$_3$) δ ppm 8.51 (br, s, 1H), 7.94 (s, 1H), 7.39 (d, J = 8.3 Hz, 1H), 7.26-7.20

| IUPAC name | Structure | MS calcd; MS ESI [M + H]+ | Yield; Appearance; Salt form |
|---|---|---|---|
| | (m, 2H), 6.78 (br, s, 1H), 5.73 (br, s, 1H), 3.97 (dd, J = 11.2, 3.4 Hz, 2H), 3.66 (s, 2H), 3.37 (t, J = 11.2 Hz, 2H), 3.19 (t, J = 5.9 Hz, 2H), 2.92-2.79 (m, 1H), 2.44 (s, 3H), 2.04-1.53 (m, 11H), 1.43-1.23 (m, 2H), 0.91-0.75 (m, 2H), 0.70-0.56 (m, 2H). HPLC purity: 99.5% at 254 nm | | |
| C46: N-cyclopropyl-4-(5-(3-fluorophenoxy)-7-(((1-methylpiperidin-4-yl)methyl)amino)pyrazolo[1,5-a]pyrimidin-3-yl)-2-methylbenzamide | 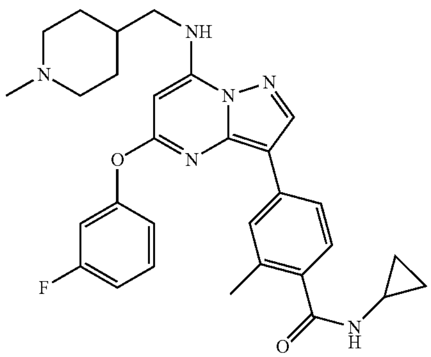 [SMILES: Cc1cc(-c2cnn3c(NCC4CCN(C)CC4)cc(Oc4cccc(F)c4)nc23)ccc1C(=O)NC1CC1] | $[C_{30}H_{33}FN_6O_2 + H]^+$ 529.3 529.3 | 116 mg, 29% (2 steps); off white powder; TFA salt |

SMs: tert-butyl (3-bromo-5-(3-fluorophenoxy)pyrazolo[1,5-a]pyrimidin-7-yl)((1-methylpiperidin-4-yl)methyl)carbamate (0.338, 0.63 mmol), N-cyclopropyl-2-methyl-4-(4,4,5,5-tetramethyl-1,3,2-dioxaborolan-2-yl)benzamide (0.381 g, 1.3 mmol)

$^1$H NMR (400 MHz, CD$_3$OD) δ ppm 8.39 (s, 1H), 7.85 (s, 1H), 7.64 (d, J = 7.8 Hz, 1H), 7.53-7.45 (m, 1H), 7.21 (d, J = 7.80 Hz, 1H), 7.14-7.04 (m, 3H), 5.95 (s, 1H), 3.61-3.54 (m, 2H), 3.46 (d, J = 6.0 Hz, 2H), 3.09-2.98 (m, 2H), 2.89 (s, 3H), 2.86-2.79 (m, 1H), 2.28 (s, 3H), 2.10-2.22 (m, 3H), 1.66-1.48 (m, 2H), 0.84-0.72 (m, 2H), 0.67-0.55 (m, 2H). HPLC Purity (HCl salt): 97.7% at 254 nM

| C47: N-cyclopropyl-4-(5-(2,3-difluorophenoxy)-7-((2-(4-fluoropiperidin-1-yl)ethyl)amino)pyrazolo[1,5-a]pyrimidin-3-yl)-2-methylbenzamide | | $[C_{30}H_{31}F_3N_6O_2 + H]^+$ 565.2 565.4 | 86 mg, 23% (2 steps); white powder; TFA salt |

SMs: tert-butyl (3-bromo-5-(2,3-difluorophenoxy)pyrazolo[1,5-a]pyrimidin-7-yl)(2-(4-fluoropiperidin-1-yl)ethyl)carbamate (315 mg, 0.55 mmol), N-cyclopropyl-2-methyl-4-(4,4,5,5-tetramethyl-1,3,2-dioxaborolan-2-yl)benzamide (0.244 g, 0.81 mmol)

$^1$H NMR (400 MHz, CDCl$_3$) δ ppm 8.20 (s, 1H), 7.66 (s, 1H), 7.46 (d, J = 6.5 Hz, 1H), 7.33 (br. s., 1H), 7.21 (d, J = 8.0 Hz, 1H), 7.19-7.08 (m, 3H), 5.99 (d, J = 2.5 Hz, 1H), 5.10-4.93 (m, 1H), 3.94 (q, J = 5.8 Hz, 2H), 3.64 (br. s., 2H), 3.44 (t, J = 6.0 Hz, 2H), 3.15 (br. s., 2H), 2.95-2.85 (m, 1H), 2.45-2.15 (m, 4H), 2.30 (s, 3H), 0.99-0.82 (m, 2H), 0.67-0.57 (m, 2H). HPLC Purity: 99.7% at 254 nM The following final compounds were synthesized according to the synthesis of Example B1, C28 or C29 using General Method F or J:

| Structure | Example number<br>MS calcd;<br>MS ESI [M + H]+<br>Salt Form;<br>HPLC purity | ¹H NMR |
|---|---|---|
| | C48<br>[$C_{29}H_{38}N_6O_3$ + H]+<br>519.3; 519.5<br>TFA salt;<br>93.9% at 254 nm | (400 MHz, CD$_3$OD) δ ppm 8.18 (s, 1H), 7.52-7.36 (m, 3H), 5.58 (s, 1H), 3.99 (dd, J = 11.2, 3.4 Hz, 2H), 3.81-3.71 (m, 1H), 3.70-3.60 (m, 1H), 3.52-3.39 (m, 4H), 2.87 (dq, J = 7.3, 3.7 Hz, 1H), 2.46 (s, 3H), 2.18-1.95 (m, 5H), 1.75 (d, J = 12.3 Hz, 2H), 1.59-1.36 (m, 6H), 0.87-0.77 (m, 2H), 0.67-0.59 (m, 2H). |
| | C49<br>[$C_{28}H_{31}N_7O_2$ + H]+<br>498.3; 498.4;<br>di-TFA salt;<br>99.4% at 254 nm | (400 MHz, CD$_3$OD) δ ppm 8.92 (br, s, 1H), 8.80 (d, J = 5.5 Hz, 1H), 8.63-8.52 (m, 1H), 8.23 (s, 1H), 8.07-7.96 (m, 1H), 7.73-7.45 (m, 2H), 7.38 (d, J = 8.0 Hz, 1H), 5.55 (s, 1H), 3.96 (d, J = 11.8 Hz, 3H), 3.61-3.49 (m, 2H), 3.36-3.29 (s, 2H), 2.88 (tt, J = 7.3, 3.8 Hz, 1H), 2.46 (s, 3H), 1.98 (d, J = 12.0 Hz, 2H), 1.67-1.50 (m, 2H), 0.88-0.78 (m, 2H), 0.68-0.60 (m, 2H). |
| | C50<br>[$C_{28}H_{30}N_6O_3$ + H]+<br>499.3; 499.5;<br>TFA salt;<br>98.3% at 254 nm | (400 MHz, CD$_3$OD) δ ppm 8.97 (d, J = 7.8 Hz, 1H), 8.57-8.55 (m, 1H), 8.01-7.97 (m, 1H), 7.94 (s, 1H), 7.39 (d, J = 8.0 Hz, 1H), 6.94 (d, J = 7.8 Hz, 2H), 6.59 (s, 1H), 3.99 (dd, J = 11.0, 3.3 Hz, 2H), 3.51-3.41 (m, 5H), 2.88 (tt, J = 7.3, 3.8 Hz, 1H), 2.47 (s, 3H), 2.16-2.07 (m, 1H), 1.83-1.76 (m, 2H), 1.51-1.39 (m, 2H), 0.87-0.80 (m, 2H), 0.66-0.62 (m, 2H). |

-continued

| Structure | Example number<br>MS calcd;<br>MS ESI [M + H]⁺<br>Salt Form;<br>HPLC purity | ¹H NMR |
|---|---|---|
| (structure) | C51<br>[C₂₈H₃₁N₇O₃ + H]⁺<br>514.3; 514.2<br>di-TFA salt;<br>98% at 254 nm | (400 MHz, CD₃OD) δ ppm 8.73 (br, s, 1H), 8.62 (d, J = 4.8 Hz, 1H), 8.42 (s, 1H), 8.11 (d, J = 7.8 Hz, 1H), 7.84-7.77 (m, 1H), 7.72 (s, 1H), 7.60 (d, J = 7.5 Hz, 1H), 7.22 (d, J = 8.0 Hz, 1H), 6.14 (s, 1H), 4.19-3.77 (m, 6H), 3.73-3.51 (m, 4H), 3.25-3.41 (m, 2H), 2.88-2.80 (m, 1H), 2.28 (s, 3H), 0.88-0.74 (m, 2H), 0.66-0.56 (m, 2H). |
| (structure) | C52<br>[C₂₈H₃₀N₆O₃ + H]⁺<br>499.3; 499.2<br>TFA salt;<br>96.7% at 254 nm | (400 MHz, CD₃OD) δ ppm 8.91 (s, 1H), 8.79 (d, J = 5.8 Hz, 1H), 8.64 (d, J = 8.3 Hz, 1H), 8.39 (s, 1H), 8.06 (dd, J = 8.0, 5.8 Hz, 1H), 8.02 (s, 1H), 7.86 (d, J = 8.0 Hz, 1H), 7.34 (d, 8.0 Hz, 1H), 5.58 (s, 1H), 5.34 (tt, J = 8.5, 4.3 Hz, 1H), 4.89 (s, 2H), 3.97 (dt, J = 11.6, 4.5 Hz, 2H), 3.63 (ddd, J = 11.6, 9.2, 2.5 Hz, 2H), 2.87 (tt, J = 7.3, 3.7 Hz, 1H), 2.45 (s, 3H), 2.20-2.12 (m, 2H), 1.84-1.72 (m, 2H), 0.86-0.79 (m, 2H), 0.66-0.61 (m, 2H). |
| (structure) | C53<br>[C₂₈H₃₇N₇O₃ + H]⁺<br>520.3; 502.3<br>di-TFA salt;<br>98.1% at 254 nm | (400 MHz, CD₃OD) δ ppm 8.21 (s, 1H), 7.79-7.65 (m, 1H), 7.64-7.53 (m, 1H), 7.38 (d, J = 13 Hz, 1H), 5.65 (br, s, 1H), 4.18-3.82 (m, 8H), 3.70-3.50 (m, 5H), 3.22-3.42 (m, 4H), 2.92-2.82 (m, 1H), 2.46 (s, 3H), 2.16-2.03 (m, 2H), 1.72-1.58 (m, 2H), 0.89-0.78 (m, 2H), 0.68-0.60 (m, 2H). |

-continued

| Structure | Example number<br>MS calcd;<br>MS ESI [M + H]+<br>Salt Form;<br>HPLC purity | 1H NMR |
|---|---|---|
| (structure) | C54<br>[C29H30F2N6O3 + H]+2H]+<br>549.2; 549.2<br>TFA salt;<br>99.6% at 254 nm | (400 MHz, CD3OD) δ ppm 8.84 (d, J = 5.5 Hz, 2H), 8.27 (s, 1H), 8.08 (d, J = 6.8 Hz, 2H), 7.77-7.65 (m, 1H), 7.64-7.54 (m, 1H), 7.39 (d, J = 8.0 Hz, 1H), 5.54-5.41 (m, 1H), 5.08 (br, s, 2H), 4.01-3.90 (m, 3H), 3.53 (td, J = 11.4, 2.0 Hz, 2H), 2.88 (tt, J = 7.3, 3.8 Hz, 1H), 2.47 (s, 3H), 2.02-1.93 (m, 2H), 1.64-1.51 (m, 2H), 0.88-0.80 (m, 2H), 0.67-0.61 (m, 2H). |
| (structure) | C55<br>[C28H29FN6O3 + H]+<br>517.2; 517.2<br>TFA salt;<br>99.6% at 254 nm | (400 MHz, CD3OD) δ ppm 8.20 (s, 1H), 7.38-7.54 (m, 3H), 5.50 (s, 1H), 4.12-4.03 (m, 1H), 3.99 (dd, J = 10.9, 4.1 Hz, 2H), 3.49-3.39 (m, 4H), 2.88 (tt, J = 7.4, 3.8 Hz, 1H), 2.47 (s, 3H), 2.13-2.00 (m, 1H), 1.79-1.71 (m, 2H), 1.50-1.38 (m, 2H), 1.35 (d, J = 6.5 Hz, 6H), 0.88-0.79 (m, 2H), 0.67-0.61 (m, 2H). |
| (structure) | C56<br>[C28H29FN6O3 + H]+<br>517.2; 517.2<br>free base;<br>97.9% at 254 nm | 1H NMR (400 MHz, CDCl3) δ ppm 8.50 (d, J = 2.3 Hz, 1H), 8.44 (d, J = 2.3 Hz, 1H), 8.26 (s, 1H), 7.72 (s, 1H), 7.61-7.55 (m, 2H), 7.30-7.28 (m, 1H), 6.54-6.49 (m, 1H), 5.85 (br, s, 1H), 5.75 (s, 1H), 4.06 (dd, J = 10.9, 4.1 Hz, 2H), 3.45 (td, J = 12.0, 2.1 Hz, 2H), 3.36 (t, J = 6.5 Hz, 2H), 2.93-2.87 (m, 1H), 2.40 (s, 3H), 2.12-1.99 (m, 1H), 1.80 (d, J = 11.0 Hz, 2H), 1.50 (td, J = 12.1, 3.9 Hz, 2H), 0.92-0.84 (m, 2H), 0.65-0.58 (m, 2H). |
| (structure) | C57<br>[C29H38N6O3 + H]+<br>519.3; 519.3<br>TFA salt;<br>96.6% at 254 nm | (400 MHz, CD3OD) δ ppm 8.20 (s, 1H), 7.55-7.37 (m, 3H), 4.05-3.94 (m, 4H), 3.51-3.35 (m, 8H), 2.88 (tt, J = 7.3, 3.7 Hz, 1H), 2.47 (s, 3H), 2.13-1.91 (m, 2H), 1.81-1.72 (m, 4H), 1.43 (qd, J = 12.3, 4.6 Hz, 4H), 0.88-0.80 (m, 2H), 0.67-0.61 (m, 2H). |

| Structure | Example number<br>MS calcd;<br>MS ESI [M + H]+<br>Salt Form;<br>HPLC purity | 1H NMR |
|---|---|---|
| | C58<br>[C29H38N6O2 + H]+<br>503.3; 503.3<br>free base;<br>98.2% at 254 nm | (400 MHz, CDCl3) δ ppm 8.15 (s, 1H), 8.01 (s, 1H), 7.86 (d, J = 6.8 Hz, 1H), 7.37 (d, J = 8.3 Hz, 1H), 6.11 (t, J = 5.8 Hz, 1H), 5.94 (br, s, 1H), 5.29 (s, 1H), 5.05 (t, J = 8.4 Hz, 1H), 4.04 (dd, J = 11.4, 3.6 Hz, 2H), 3.43 (td, J = 11.8, 2.0 Hz, 2H), 3.25 (t, J = 6.3 Hz, 2H), 3.03 (s, 3H), 2.92 (tq, J = 6.9, 3.7 Hz, 1H), 2.53 (s, 3H), 2.17-2.05 (m, 2H), 2.05-1.94 (m, 2H), 1.84-1.75 (m, 4H), 1.74-1.59 (m, 3H), 1.53-1.39 (m, 2H), 0.92-0.84 (m, 2H), 0.66-0.59 (m, 2H). |
| | C59<br>[C28H31N7O2 + H]+<br>498.3; 498.4<br>TFA salt;<br>98% at 254 nm | (400 MHz, CD3OD) δ ppm 9.69 (br, s, 1H), 8.64 (d, J = 8.5 Hz, 1H), 8.38 (d, J = 5.5 Hz, 1H), 8.32 (s, 1H), 7.96 (dd, J = 8.9, 5.9 Hz, 1H), 7.82-7.86 (m, 2H), 7.41 (d, J = 7.8 Hz, 1H), 5.68 (s, 1H), 4.00 (dd, J = 11.3, 3.8 Hz, 2H), 3.45 (t, J = 10.8 Hz, 2H), 3.37-3.27 (m, 2H), 2.89 (tt, J = 7.3, 3.9 Hz, 1H), 2.48 (s, 3H), 2.10-2.04 (m, 1H), 1.80-1.78 (m, 2H), 1.48-1.38 (m, 2H), 0.69-0.84 (m, 2H), 0.62-0.69 (m, 2H). |
| | C60<br>[C29H33N7O2 + H]+<br>512.3; 512.2<br>TFA salt;<br>99.8% at 254 nm | (400 MHz, CD3OD) δ ppm 8.32 (s, 1H), 8.15 (s, 1H), 7.84-7.80 (m, 3H), 7.40-7.34 (m, 3H), 7.09-7.05 (m, 1H), 5.68 (s, 1H), 4.15-3.95 (m, 2H), 3.85 (br, s, 4H), 3.56 (br, s, 4H), 3.37-3.26 (m, 2H), 2.90-2.86 (m, 1H), 2.49 (s, 3H), 0.86-0.81 (m, 2H), 0.69-0.61 (m, 2H). |
| | C61<br>[C29H29N7O2 + H]+<br>508.2; 508.2<br>free base;<br>97.5% at 254 nm | (400 MHz, CD3OD) δ ppm 8.32 (s, 1H), 7.80 (s, 1H), 7.76 (s, 1H), 7.60 (dd, J = 7.9, 1.4 Hz, 1H), 7.49-7.41 (m, 2H), 7.32-7.23 (m, 3H), 7.21-7.15 (m, 2H), 7.03 (s, 1H), 5.68 (s, 1H), 4.17 (t, J = 6.9 Hz, 2H), 3.37 (t, J = 6.9 Hz, 2H), 2.83 (tt, J = 7.3, 3.7 Hz, 1H), 2.24 (s, 3H), 2.20 (t, J = 7.0 Hz, 2H), 0.83-0.76 (m, 2H), 0.63-0.57 (m, 2H). |

| Structure | Example number MS calcd; MS ESI [M + H]+ Salt Form; HPLC purity | 1H NMR |
|---|---|---|
| 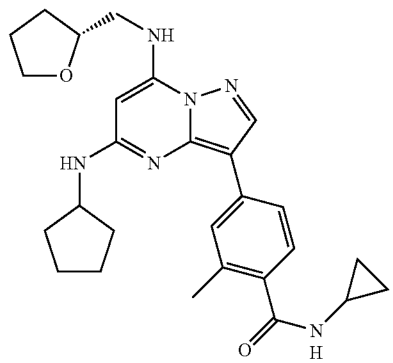 | C62 [C27H34N6O2 + H]+ 475.3; 475.3 free base; 97.3% at 254 nm | (400 MHz, CD3OD) δ ppm 8.16 (s, 1H), 8.09 (s, 1H), 7.89 (dd, J = 8.0, 1.5 Hz, 1H), 7.29 (d, J = 8.3 Hz, 1H), 5.37 (s, 1H), 4.32 (quint, J = 6.3 Hz, 1H), 4.16 (qd, J = 6.8, 4.4 Hz, 1H), 3.95-3.86 (m, 1H), 3.81-3.73 (m, 1H), 3.43-3.36 (m, 1H), 3.31-3.25 (m, 1H), 2.85 (tt, J = 7.3, 3.7 Hz, 1H), 2.44 (s, 3H), 2.19-1.86 (m, 5H), 1.84-1.52 (m, 7H), 0.84-0.77 (m, 2H), 0.66-0.60 (m, 2H). |
| 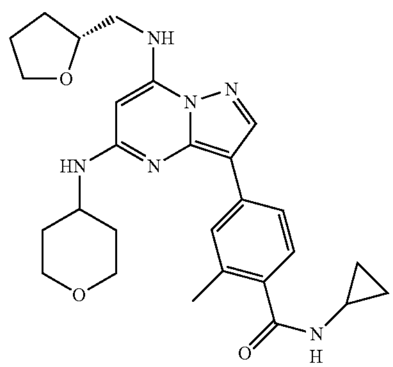 | C63 [C27H34N6O3 + H]+ 491.3; 491.3 free base; 99.0% at 254 nm | (400 MHz, CD3OD) δ ppm 8.18 (s, 1H), 8.09 (s, 1H), 7.84 (d, J = 7.8 Hz, 1H), 7.30 (d, J = 8.0 Hz, 1H), 5.38 (s, 1H), 4.24-4.12 (m, 2H), 4.06-3.98 (m, 2H), 3.97-3.88 (m, 1H), 3.83-3.75 (m, 1H), 3.60 (td, J = 11.5, 2.0 Hz, 2H), 3.47-3.39 (m, 1H), 3.37-3.32 (m, 1H), 2.86 (tt, J = 7.3, 3.9 Hz, 1H), 2.45 (s, 3H), 2.19-1.87 (m, 5H), 1.75 (s, 1H), 1.60 (dd, J = 12.7, 4.4 Hz, 2H), 0.86-0.78 (m, 2H), 0.67-0.60 (m, 2H). |
| 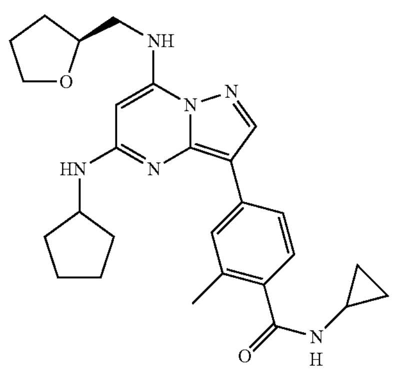 | C64 [C27H34N6O2 + H]+ 475.3; 475.3 free base; 98.0% at 254 nm | (400 MHz, CD3OD) δ ppm 8.16 (s, 1H), 8.09 (s, 1H), 7.89 (dd, J = 8.0, 1.5 Hz, 1H), 7.29 (d, J = 8.3 Hz, 1H), 5.37 (s, 1H), 4.32 (quint, J = 6.3 Hz, 1H), 4.16 (qd, J = 6.8, 4.4 Hz, 1H), 3.95-3.86 (m, 1H), 3.81-3.73 (m, 1H), 3.43-3.36 (m, 1H), 3.31-3.25 (m, 1H), 2.85 (tt, J = 7.3, 3.7 Hz, 1H), 2.44 (s, 3H), 2.19-1.86 (m, 5H), 1.84-1.52 (m, 7H), 0.84-0.77 (m, 2H), 0.66-0.60 (m, 2H). |
| 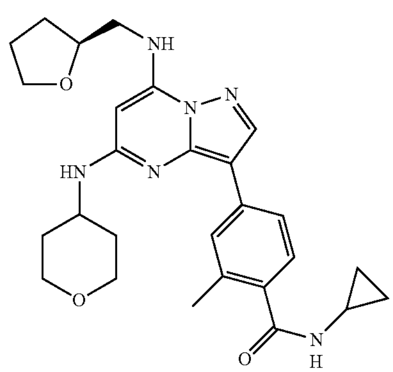 | C65 [C27H34N6O3 + H]+ 491.3; 491.3 free base; 98.0% at 254 nm | (400 MHz, CD3OD) δ ppm 8.18 (s, 1H), 8.09 (s, 1H), 7.84 (d, J = 7.8 Hz, 1H), 7.30 (d, J = 8.0 Hz, 1H), 5.38 (s, 1H), 4.24-4.12 (m, 2H), 4.06-3.98 (m, 2H), 3.97-3.88 (m, 1H), 3.83-3.75 (m, 1H), 3.60 (td, J = 11.5, 2.0 Hz, 2H), 3.47-3.39 (m, 1H), 3.37-3.32 (m, 1H), 2.86 (tt, J = 7.3, 3.9 Hz, 1H), 2.45 (s, 3H), 2.19-1.87 (m, 5H), 1.75 (s, 1H), 1.60 (dd, J = 12.7, 4.4 Hz, 2H), 0.86-0.78 (m, 2H), 0.67-0.60 (m, 2H). |

| Structure | Example number<br>MS calcd;<br>MS ESI [M + H]+<br>Salt Form;<br>HPLC purity | ¹H NMR |
|---|---|---|
| | C66<br>[C₃₀H₃₈N₆O₃ + H]+<br>531.3; 531.6<br>free base;<br>98.5% at 254 nm | (400 MHz, CDCl₃) δ ppm 8.15 (s, 1H), 7.94 (s, 1H), 7.91 (d, J = 7.5 Hz, 1H), 7.37 (d, J = 7.8 Hz, 1H), 6.08 (t, J = 6.0 Hz, 1H), 5.92 (br, s, 1H), 4.60 (br, s, 2H), 4.13 (s, 1H), 4.04 (dd, J = 11.0, 3.3 Hz, 2H), 3.43 (td, J = 11.9, 1.9 Hz, 2H), 3.23 (t, J = 6.4 Hz, 2H), 2.91 (td, J = 7.1, 3.4 Hz, 1H), 2.53 (s, 3H), 2.41-2.30 (m, 4H), 2.16-2.09 (m, 2H), 2.03-1.92 (m, 1H), 1.79 (d, J = 14.6 Hz, 4H), 1.52-1.38 (m, 2H), 0.92-0.85 (m, 2H), 0.65-0.59 (m, 2H). |
| | C67<br>[C₂₈H₃₆N₆O₃ + H]+<br>505.3; 505.3<br>free base;<br>98.5% at 254 nm | (400 MHz, CDCl₃ & drops of CD₃OD) δ ppm 8.12 (s, 1H), 7.89-7.84 (m, 2H), 7.34 (d, J = 8.5 Hz, 1H), 5.37 (s, 1H), 4.22-4.13 (m, 2H), 4.01 (dd, J = 11.2, 3.9 Hz, 2H), 3.97-3.90 (m, 1H), 3.46-3.37 (m, 2H), 3.30 (ddd, J = 13.2, 9.9, 3.0 Hz, 2H), 3.21 (d, J = 6.8 Hz, 2H), 2.82-2.90 (m, 1H), 2.48 (s, 3H), 2.03-1.93 (m, 3H), 1.81-1.73 (m, 2H), 1.66-1.54 (m, 2H), 1.49-1.36 (m, 2H), 0.90-0.81 (m, 2H), 0.59 (d, J = 2.5 Hz, 2H). |
| | C68<br>[C₂₆H₃₂N₆O₃ + H]+<br>477.3; 477.2<br>free base;<br>99.6% at 254 nm | (400 MHz, CD₃OD) δ ppm 8.19 (s, 1H), 8.05 (s, 1H), 7.91 (dd, J = 8.2, 1.6 Hz, 1H), 7.32 (d, J = 8.0 Hz, 1H), 5.35 (s, 1H), 4.44 (quint, J = 7.0 Hz, 1H), 3.98 (dd, J = 11.4, 3.6 Hz, 2H), 3.56 (d, J = 7.8 Hz, 2H), 3.40-3.45 (m, 2H), 3.23 (d, J = 7.0 Hz, 2H), 2.86 (tt, J = 7.4, 3.8 Hz, 1H), 2.62-2.52 (m, 1H), 2.45 (s, 3H), 2.27-2.19 (m, 2H), 2.13-1.96 (m, 3H), 1.80-1.73 (m, 2H), 1.46-1.34 (m, 2H), 0.85-0.79 (m, 2H), 0.66-0.61 (m, 2H). |
| | C69<br>[C₂₆H₃₂N₆O₃ + H]+<br>477.3; 477.2<br>free base;<br>99.8% at 254 nm | (400 MHz, CDCl₃) δ ppm 8.13 (s, 1H), 7.90 (s, 1H), 7.86 (d, J = 8.0 Hz, 1H), 7.33 (d, J = 8.0 Hz, 1H), 6.12 (t, J = 5.9 Hz, 1H), 5.98 (br. s., 1H), 4.95 (s, 1H), 4.83-4.75 (m, 1H), 4.38 (dd, J = 9.2, 6.9 Hz, 2H), 4.03 (dd, J = 11.7, 3.9 Hz, 2H), 3.97 (dd, J = 9.5, 4.3 Hz, 2H), 3.42 (td, J = 11.9, 1.9 Hz, 2H), 3.20 (t, J = 6.4 Hz, 2H), 2.90 (tq, J = 7.1, 3.7 Hz, 1H), 2.50 (s, 3H), 1.89-2.02 (m, 1H), 1.76 (d, J = 3.1 Hz, 2H), 1.64 (br, s, 1H), 1.50-1.37 (m, 2H), 0.92-0.84 (m, 2H), 0.65-0.58 (m, 2H). |

| Structure | Example number<br>MS calcd;<br>MS ESI [M + H]+<br>Salt Form;<br>HPLC purity | ¹H NMR |
|---|---|---|
| 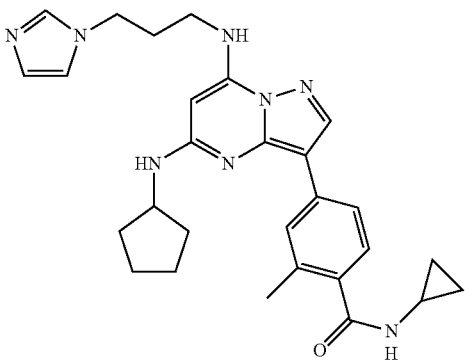 | C70<br>[$C_{28}H_{34}N_8O$ + H]+<br>499.3; 499.2<br>free base;<br>97.4% at 254 nm | (400 MHz, CDCl₃) δ ppm 8.12 (s, 1H), 7.96 (s, 1H), 7.85 (dd, J = 8.2, 1.1 Hz, 1H), 7.46 (s, 1H), 7.34 (d, J = 8.0 Hz, 1H), 7.09 (s, 1H), 6.92 (s, 1H), 6.13-5.98 (m, 2H), 4.99-4.91 (m, 2H), 4.22 (d, J = 5.8 Hz, 1H), 4.08 (t, J = 6.7 Hz, 2H), 3.21 (q, J = 6.5 Hz, 2H), 2.90 (tq, J = 7.1, 3.6 Hz, 1H), 2.50 (s, 3H), 2.20-2.07 (m, 4H), 1.82-1.60 (m, 4H), 1.54 (dq, J = 12.7, 6.6 Hz, 2H), 0.90-0.82 (m, 2H), 0.65-0.57 (m, 2H). |
| 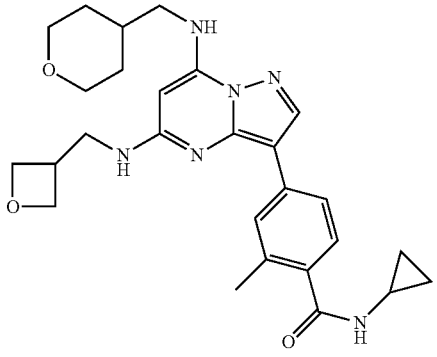 [SMILES: Cc1cc(-c2cnn3c(NCC4CCOCC4)cc(NCC4COC4)nc23)ccc1C(=O)NC1CC1] | C71<br>[$C_{27}H_{34}N_6O_3$ + H]+<br>491.3; 491.4<br>free base;<br>98.2% at 254 nm | (400 MHz, DMSO-d₆) δ ppm 8.33 (s, 1H), 8.17 (d, J = 4.3 Hz, 1H), 8.01-7.97 (m, 1H), 7.92 (d, J = 6.8 Hz, 1H), 7.45 (t, J = 5.5 Hz, 1H), 7.26 (d, J = 8.0 Hz, 1H), 7.10 (t, J = 5.4 Hz, 1H), 5.33 (s, 1H), 4.67 (dd, J = 7.7, 5.9 Hz, 2H), 4.39 (t, J = 5.9 Hz, 2H), 3.85 (dd, J = 10.7, 2.9 Hz, 2H), 3.67 (t, J = 6.3 Hz, 2H), 3.30-3.22 (m, 3H), 3.12 (t, J = 6.5 Hz, 2H), 2.85-2.76 (m, 1H), 2.36 (s, 3H), 2.00-1.86 (m, 1H), 1.60 (d, J = 12.0 Hz, 2H), 1.30-1.16 (m, 2H), 0.69-0.62 (m, 2H), 0.52 (m, 2H). |
| 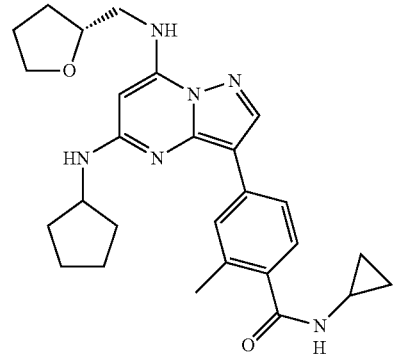 | C72<br>[$C_{27}H_{34}N_6O_2$ + H]+<br>475.3; 475.4<br>free base;<br>99.3% at 254 nm | (400 MHz, CD₃OD) δ ppm 8.16 (s, 1H), 8.09 (s, 1H), 7.88 (dd, J = 8.2, 1.4 Hz, 1H), 7.29 (d, J = 8.0 Hz, 1H), 5.31 (s, 1H), 4.37-4.27 (m, 1H), 3.90 (td, J = 8.2, 5.4 Hz, 1H), 3.82 (dd, J = 8.8, 6.8 Hz, 1H), 3.70-3.77 (m, 1H), 3.62 (dd, J = 8.8, 5.0 Hz, 1H), 3.24 (d, J = 7.3 Hz, 2H), 2.88-2.81 (m, 1H), 2.71-2.58 (m, 1H), 2.43 (s, 3H), 2.18-2.04 (m, 3H), 1.84-1.49 (m, 7H), 0.85-0.77 (m, 2H), 0.65-0.59 (m, 2H). |
| 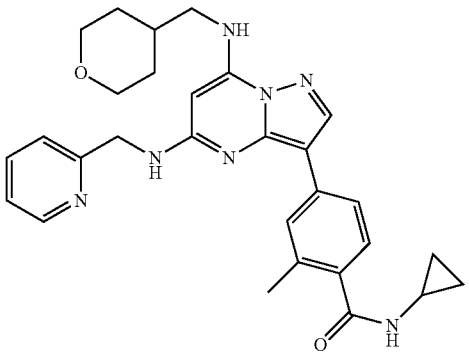 [SMILES: Cc1cc(-c2cnn3c(NCC4CCOCC4)cc(NCc4ccccn4)nc23)ccc1C(=O)NC1CC1] | C73<br>[$C_{29}H_{33}N_7O_2$ + H]+<br>512.3; 512.4<br>free base;<br>97.3% at 254 nm | (400 MHz, CD₃OD) δ ppm 8.51 (d, J = 5.0 Hz, 1H), 8.18 (s, 1H), 7.83 (s, 1H), 7.71-7.79 (m, 1H), 7.50 (d, J = 8.0 Hz, 1H), 7.30-7.24 (m, 1H), 7.22 (d, J = 8.0 Hz, 1H), 5.44 (s, 1H), 4.77 (s, 2H), 3.94 (dd, J = 11.0, 3.8 Hz, 2H), 3.37 (d, J = 12.0 Hz, 2H), 3.23-3.14 (m, 2H), 2.84 (tt, J = 7.3, 3.8 Hz, 1H), 2.34 (s, 3H), 2.00-1.87 (m, 1H), 1.75-1.64 (m, 2H), 1.41-1.26 (m, 2H), 0.84-0.76 (m, 2H), 0.66-0.57 (m, 2H). |

| Structure | Example number<br>MS calcd;<br>MS ESI [M + H]+<br>Salt Form;<br>HPLC purity | ¹H NMR |
|---|---|---|
| | C74<br>[C₂₉H₃₃N₇O₂ + H]+<br>512.3; 512.4<br>free base;<br>98.4% at 254 nm | (400 MHz, CD₃OD) δ ppm 8.64 (d, J = 2.0 Hz, 1H), 8.39 (dd, J = 4.8, 1.5 Hz, 1H), 8.18 (s, 1H), 7.91 (dt, J = 7.9, 1.8 Hz, 1H), 7.88 (s, 1H), 7.80 (dd, J = 8.2, 1.6 Hz, 1H), 7.39 (dd, J = 8.4, 4.9 Hz, 1H), 7.27 (d, J = 8.0 Hz, 1H), 5.40 (s, 1H), 4.71 (s, 2H), 3.96 (dd, J = 11.0, 3.5 Hz, 2H), 3.41 (td, J = 11.9, 1.9 Hz, 2H), 3.21 (d, J = 7.0 Hz, 2H), 2.84 (tt, J = 7.4, 3.8 Hz, 1H), 2.38 (s, 3H), 2.05-1.91 (m, 1H), 1.77-1.69 (m, 2H), 1.44-1.30 (m, 2H), 0.85-0.77 (m, 2H), 0.65-0.60 (m, 2H). |
| | C75<br>[C₂₉H₃₄N₈O₂ + H]+<br>527.3; 527.4<br>free base;<br>99.3% at 254 nm | (400 MHz, CD₃OD) δ ppm 8.64 (d, J = 1.5 Hz, 1H), 8.39 (dd, J = 5.0, 1.5 Hz, 1H), 8.19 (s, 1H), 7.91 (d, J = 7.8 Hz, 1H), 7.88 (s, 1H), 7.80 (dd, J = 8.0, 1.5 Hz, 1H), 7.38 (dd, J = 7.9, 4.9 Hz, 1H), 7.28 (d, J = 8.0 Hz, 1H), 5.41 (s, 1H), 4.71 (s, 2H), 3.74 (t, J = 4.6 Hz, 4H), 3.45 (t, J = 6.4 Hz, 2H), 2.85 (tt, J = 7.4, 3.8 Hz, 1H), 2.77 (t, J = 6.1 Hz, 2H), 2.61 (br, s, 4H), 2.38 (s, 3H), 0.85-0.78 (m, 2H), 0.66-0.59 (m, 2H). |
| | C76<br>[C₂₇H₃₅N₇O₂ + H]+<br>490.3; 490.4<br>free base;<br>97.9% at 254 nm | (400 MHz, CD₃OD) δ ppm 8.19 (s, 1H), 8.03 (s, 1H), 7.92 (dd, J = 8.2, 1.4 Hz, 1H), 7.32 (d, J = 8.0 Hz, 1H), 5.38-5.34 (m, 1H), 3.71-3.78 (m, 4H), 3.48-3.40 (m, 2H), 3.36-3.33 (m, 2H), 2.86 (tt, J = 7.4, 3.8 Hz, 1H), 2.70-2.75 (m, 2H), 2.60-2.52 (m, 4H), 2.45 (s, 3H), 1.26-1.15 (m, 1H), 0.86-0.78 (m, 2H), 0.66-0.60 (m, 2H), 0.58-0.52 (m, 2H), 0.35-0.29 (m, 2H). |

-continued

| Structure | Example number<br>MS calcd;<br>MS ESI [M + H]+<br>Salt Form;<br>HPLC purity | 1H NMR |
|---|---|---|
| (structure) | C77<br>[C28H37N7O2 + H]+<br>504.3; 504.4<br>free base;<br>95.9% at 254 nm | (400 MHz, CD3OD) δ ppm 8.19 (s, 1H), 8.10 (s, 1H), 7.90 (dd, J = 7.9, 1.4 Hz, 1H), 7.31 (d, J = 8.0 Hz, 1H), 5.33 (s, 1H), 4.35 (quint, J = 6.5 Hz, 1H), 3.76-3.71 (m, 4H), 3.42 (t, J = 6.4 Hz, 2H), 2.85 (tt, J = 7.3, 3.8 Hz, 1H), 2.71 (t, J = 6.4 Hz, 2H), 2.52-2.58 (m, 4H), 2.45 (br, s, 3H), 2.20-2.08 (m, 2H), 1.86-1.51 (m, 6H), 0.86-0.78 (m, 2H), 0.66-0.60 (m, 2H). |
| (structure) | C78<br>[C29H40N6O3 + H]+<br>521.3; 521.4<br>free base;<br>99.1% at 254 nm | (400 MHz, CD3OD) δ ppm 8.17 (s, 1H), 8.10 (s, 1H), 7.86 (dd, J = 8.2, 1.6 Hz, 1H), 7.31 (d, J = 8.3 Hz, 1H), 5.50 (s, 1H), 4.31 (br, s, 1H), 4.01-3.92 (m, 3H), 3.59 (dd, J = 11.2, 8.4 Hz, 1H), 3.44 (td, J = 11.8, 1.8 Hz, 2H), 3.26-3.20 (m, 2H), 2.86 (tt, J = 7.4, 3.8 Hz, 1H), 2.47 (s, 3H), 2.08-1.96 (m, 1H), 1.80-1.73 (m, 2H), 1.46-1.32 (m, 2H), 1.07 (s, 9H), 0.85-0.79 (m, 2H), 0.66-0.60 (m, 2H). |
| (structure) | C79<br>[C28H36N6O4 + H]+<br>521.3; 521.3<br>free base;<br>98.8% at 254 nm | (400 MHz, CD3OD) δ ppm 8.20 (s, 1H), 8.04-8.02 (m, 1H), 7.89 (dd, J = 8.2, 1.4 Hz, 1H), 7.33 (d, J = 8.0 Hz, 1H), 5.42 (d, J = 1.5 Hz, 1H), 4.26 (dd, J = 11.0, 4.8 Hz, 1H), 4.09-4.01 (m, 1H), 4.01-3.95 (m, 3H), 3.76 (td, J = 9.2, 4.8 Hz, 1H), 3.52 (td, J = 11.2, 2.5 Hz, 1H), 3.43 (t, J = 11.4 Hz, 2H), 3.26-3.20 (m, 3H), 2.89-2.81 (m, 1H), 2.46 (s, 3H), 2.12-1.97 (m, 2H), 1.79-1.66 (m, 3H), 1.46-1.33 (m, 2H), 0.85-0.79 (m, 2H), 0.66-0.60 (m, 2H). |

| Structure | Example number MS calcd; MS ESI [M + H]+ Salt Form; HPLC purity | 1H NMR |
|---|---|---|
| 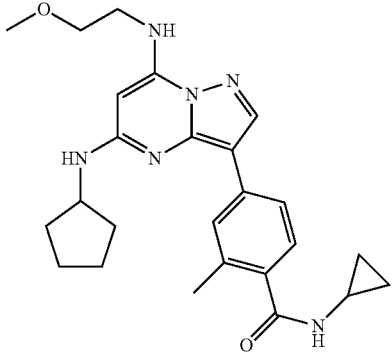 [SMILES: COCCNc1cc(NC2CCCC2)nc2c(-c3ccc(C(=O)NC4CC4)c(C)c3)cnn12] | C80<br>[C25H32N6O2 + H]+<br>449.3; 449.3<br>free base;<br>99.3% at 254 nm | (400 MHz, CD3OD) δ ppm 8.17 (s, 1H), 8.09 (s, 1H), 7.90 (d, J = 8.0 Hz, 1H), 7.30 (d, J = 8.0 Hz, 1H), 5.38-5.32 (m, 1H), 4.39-4.28 (m, 1H), 3.70-3.62 (m, 2H), 3.52-3.44 (m, 2H), 3.42 (s, 3H), 2.85 (tt, J = 7.3, 3.9 Hz, 1H), 2.44 (s, 3H), 2.15-2.09 (m, 2H), 1.85-1.53 (m, 6H), 0.86-0.77 (m, 2H), 0.66-0.59 (m, 2H). |
| 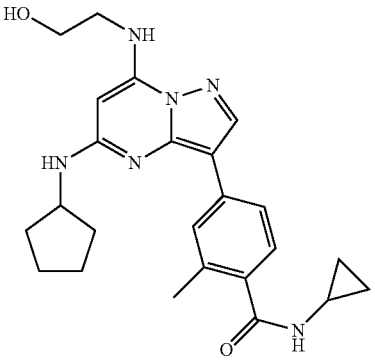 [SMILES: Cc1cc(-c2cnn3c(NCCO)cc(NC4CCCC4)nc23)ccc1C(=O)NC1CC1] | C81<br>[C24H30N6O2 + H]+<br>435.2; 435.3<br>free base;<br>99.6% at 254 nm | (400 MHz, CD3OD) δ ppm 8.17 (s, 1H), 8.09 (s, 1H), 7.89 (dd, J = 8.0, 1.5 Hz, 1H), 7.30 (d, J = 8.0 Hz, 1H), 5.35 (s, 1H), 4.34 (quint, J = 6.6 Hz, 1H), 3.82 (t, J = 5.6 Hz, 2H), 3.43 (t, J = 5.6 Hz, 2H), 2.85 (tt, J = 7.3, 3.8 Hz, 1H), 2.44 (s, 3H), 2.18-2.07 (m, 2H), 1.86-1.51 (m, 6H), 0.85-0.77 (m, 2H), 0.66-0.59 (m, 2H). |
| 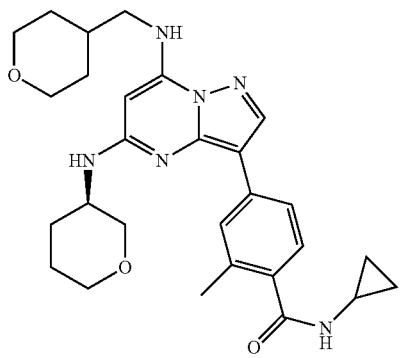 [SMILES: Cc1cc(-c2cnn3c(NCC4CCOCC4)cc(N[C@@H]4CCCOC4)nc23)ccc1C(=O)NC1CC1] | C82<br>[C28H36N6O3 + H]+<br>505.3; 505.4<br>free base;<br>99.8% at 254 nm | (400 MHz, CD3OD) δ ppm 8.20 (s, 1H), 8.05 (s, 1H), 7.91 (dd, J = 8.3, 1.5 Hz, 1H), 7.32 (d, J = 8.0 Hz, 1H), 5.37 (s, 1H), 4.12-4.20 (m, 2H), 3.94-4.01 (m, 2H), 3.80-3.88 (m, 1H), 3.49-3.58 (m, 1H), 3.43 (td, J = 11.7, 1.6 Hz, 2H), 3.33-3.37 (m, 1H), 3.21 (d, J = 7.0 Hz, 2H), 2.80-2.90 (m, 1H), 2.45 (s, 3H), 2.09-2.17 (m, 1H), 1.93-2.07 (m, 1H), 1.81-1.90 (m, 1H), 1.61-1.79 (m, 4H), 1.38 (qd, J = 12.3, 4.4 Hz, 2H), 0.78-0.85 (m, 2H), 0.60-0.66 (m, 2H). |
| 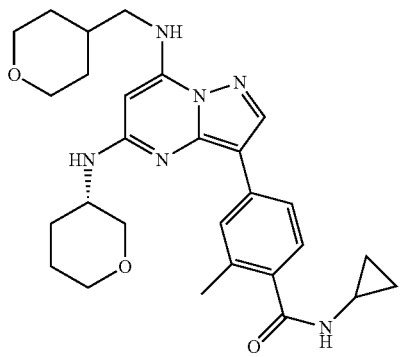 [SMILES: Cc1cc(-c2cnn3c(NCC4CCOCC4)cc(N[C@H]4CCCOC4)nc23)ccc1C(=O)NC1CC1] | C83<br>[C28H36N6O3 + H]+<br>505.3; 505.4<br>free base;<br>99.0% at 254 nm | (400 MHz, CD3OD) δ ppm 8.20 (s, 1H), 8.05 (s, 1H), 7.91 (dd, J = 8.3, 1.5 Hz, 1H), 7.32 (d, J = 8.0 Hz, 1H), 5.37 (s, 1H), 4.12-4.20 (m, 2H), 3.94-4.01 (m, 2H), 3.80-3.88 (m, 1H), 3.49-3.58 (m, 1H), 3.43 (td, J = 11.7, 1.6 Hz, 2H), 3.33-3.37 (m, 1H), 3.21 (d, J = 7.0 Hz, 2H), 2.80-2.90 (m, 1H), 2.45 (s, 3H), 2.09-2.17 (m, 1H), 1.93-2.07 (m, 1H), 1.81-1.90 (m, 1H), 1.61-1.79 (m, 4H), 1.38 (qd, J = 12.3, 4.4 Hz, 2H), 0.78-0.85 (m, 2H), 0.60-0.66 (m, 2H). |

-continued

| Structure | Example number<br>MS calcd;<br>MS ESI [M + H]+<br>Salt Form;<br>HPLC purity | 1H NMR |
|---|---|---|
| 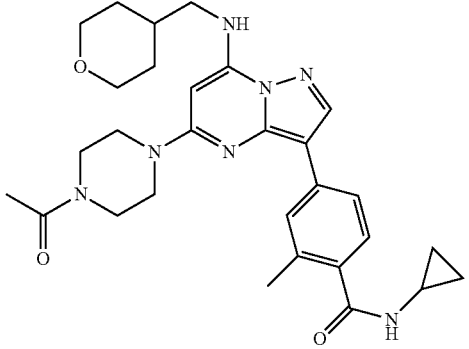 [SMILES: CC(=O)N1CCN(c2cc(NCC3CCOCC3)n3ncc(-c4ccc(C(=O)NC5CC5)c(C)c4)c3n2)CC1] | C84<br>[C29H37N7O3 + H]+<br>532.3; 532.4<br>free base;<br>97.3% at 254 nm | (400 MHz, CD3OD) δ ppm 8.26 (s, 1H), 7.96-7.91 (m, 2H), 7.32 (d, J = 7.8 Hz, 1H), 5.60 (s, 1H), 3.97 (dd, J = 11.2, 3.4 Hz, 2H), 3.83-3.76 (m, 2H), 3.71 (s, 4H), 3.70-3.66 (m, 2H), 3.43 (td, J = 11.8, 2.0 Hz, 2H), 3.29 (d, J = 7.0 Hz, 2H), 2.86 (tt, J = 7.3, 3.7 Hz, 1H), 2.45 (s, 3H), 2.17 (s, 3H), 2.06-1.93 (m, 1H), 1.76 (dd, J = 12.7, 1.6 Hz, 2H), 1.40 (qd, J = 12.4, 4.4 Hz, 2H), 0.86-0.79 (m, 2H), 0.66-0.60 (m, 2H). |
| 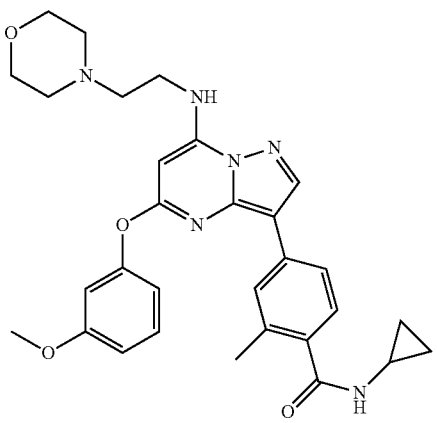 [SMILES: COc1cccc(Oc2cc(NCCN3CCOCC3)n3ncc(-c4ccc(C(=O)NC5CC5)c(C)c4)c3n2)c1] | C85<br>[C30H34N6O4 + H]+<br>543.3; 543.4<br>free base;<br>98.8% at 254 nm | (400 MHz, CD3OD) δ ppm 8.34 (s, 1H), 7.87 (s, 1H), 7.64 (dd, J = 8.0, 1.3 Hz, 1H), 7.36 (t, J = 7.9 Hz, 1H), 7.20 (d, J = 8.0 Hz, 1H), 6.92-6.78 (m, 3H), 5.78 (s, 1H), 3.81 (s, 3H), 3.76-3.69 (m, 4H), 3.51 (s, 2H), 2.83 (tt, J = 7.4, 3.8 Hz, 1H), 2.71 (t, J = 6.4 Hz, 2H), 2.55 (br, s, 4H), 2.28 (s, 3H), 0.84-0.77 (m, 2H), 0.63-0.57 (m, 2H). |
| 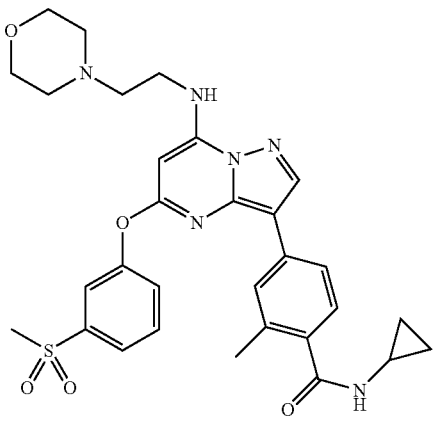 [SMILES: Cc1cc(-c2cnn3c(NCCN4CCOCC4)cc(Oc4cccc(S(C)(=O)=O)c4)nc23)ccc1C(=O)NC1CC1] | C86<br>[C30H34N6O5S + H]+<br>591.2; 591.4<br>free base;<br>97.6% at 254 nm | (400 MHz, CD3OD) δ ppm 8.40-8.36 (m, 1H), 7.93-7.88 (m, 2H), 7.80-7.70 (m, 2H), 7.69-7.62 (m, 2H), 7.20 (d, J = 7.8 Hz, 1H), 5.96 (s, 1H), 3.76 (m, J = 4.5 Hz, 4H), 3.60 (t, J = 6.4 Hz, 2H), 3.16 (s, 3H), 2.86-2.80 (m, 1H), 2.78 (t, J = 6.3 Hz, 2H), 2.64-2.56 (m, 4H), 2.26 (s, 3H), 0.84-0.77 (m, 2H), 0.63-0.57 (m, 2H). |

| Structure | Example number MS calcd; MS ESI [M + H]+ Salt Form; HPLC purity | 1H NMR |
|---|---|---|
| 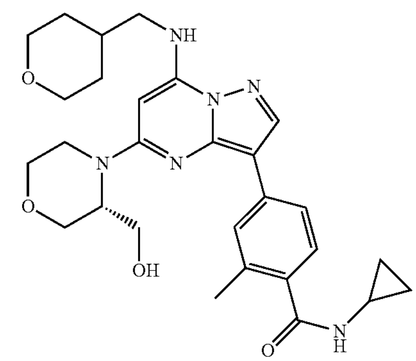 [SMILES: Cc1cc(-c2cnn3c(NCC4CCOCC4)cc(N4CCOC[C@H]4CO)nc23)ccc1C(=O)NC1CC1] | C87 [C28H36N6O4 + H]+ 521.3; 521.4 free base; 98.0% at 254 nm | (400 MHz, CD3OD) δ ppm 8.25 (s, 1H), 7.98-7.90 (m, 2H), 7.32 (d, J = 8.0 Hz, 1H), 5.60 (s, 1H), 4.38-4.29 (m, 1H), 4.26-4.17 (m, 2H), 4.05-3.92 (m, 4H), 3.76-3.59 (m, 3H), 3.44 (td, J = 11.8, 2.0 Hz, 2H), 3.31-3.28 (m, 2H), 3.28-3.22 (m, 1H), 2.85 (tt, J = 7.4, 3.8 Hz, 1H), 2.45 (s, 3H), 2.08-1.94 (m, 1H), 1.81-1.73 (m, 2H), 1.47-1.34 (m, 2H), 0.86-0.78 (m, 2H), 0.65-0.59 (m, 2H). |
| 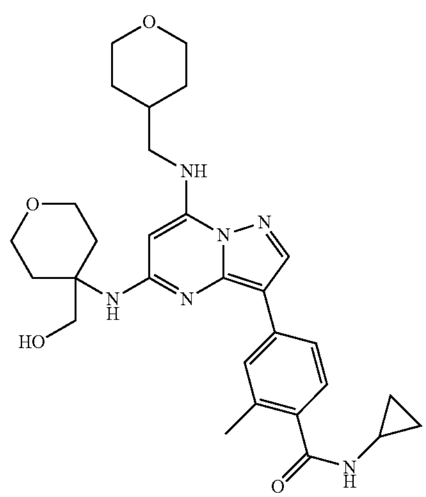 [SMILES: Cc1cc(-c2cnn3c(NCC4CCOCC4)cc(NC4(CO)CCOCC4)nc23)ccc1C(=O)NC1CC1] | C88 [C29H38N6O4 + H]+ 535.3; 535.5 free base; 99.3% at 254 nm | (400 MHz, CD3OD) δ ppm 8.16 (s, 1H), 7.90 (s, 1H), 7.73 (dd, J = 8.2, 1.4 Hz, 1H), 7.32 (d, J = 8.0 Hz, 1H), 5.56 = 5.54 (m, 1H), 4.02-3.96 (m, 4H), 3.81-3.76 (m, 3H), 3.50-3.41 (m, 2H), 3.35-3.30 (m, 2H), 3.25 (d, J = 6.8 Hz, 2H), 2.90-2.82 (m, 1H), 2.44 (s, 3H), 2.42-2.38 (m, 1H), 2.10-1.98 (m, 1H), 1.89-1.72 (m, 4H), 1.47-1.34 (m, 2H), 0.85-0.79 (m, 2H), 0.65-0.60 (m, 2H). |
| 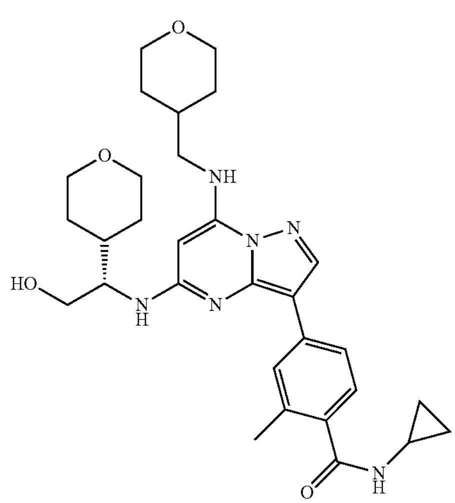 [SMILES: Cc1cc(-c2cnn3c(NCC4CCOCC4)cc(N[C@H](CO)C4CCOCC4)nc23)ccc1C(=O)NC1CC1] | C89 [C30H40N6O4 + H]+ 549.3; 549.5 free base; 98.4% at 254 nm | (400 MHz, CD3OD) δ ppm 8.19 (s, 1H), 8.01 (s, 1H), 7.92-7.83 (m, 1H), 7.30 (d, J = 8.0 Hz, 1H), 5.34 (s, 1H), 4.23-4.08 (m, 1H), 4.00-43.68 (m, 6H), 3.46-3.22 (m, 4H), 3.05 (d, J = 7.0 Hz, 2H), 2.84 (tt, J = 7.3, 3.7 Hz, 1H), 2.44 (s, 3H), 2.08-1.96 (m, 1H), 1.90-1.69 (m, 3H), 1.67-1.42 (m, 4H), 1.35-1.13 (m, 2H), 0.84-0.76 (m, 2H), 0.65-0.57 (m, 2H). |

-continued

| Structure | Example number<br>MS calcd;<br>MS ESI [M + H]+<br>Salt Form;<br>HPLC purity | ¹H NMR |
|---|---|---|
| | C90<br>[$C_{29}H_{38}N_6O_4$ + H]+<br>535.3; 535.5<br>free base;<br>98.4% at 254 nm | (400 MHz, CD₃OD) δ ppm 8.20 (s, 1H), 7.92-7.99 (m, 2H), 7.29 (d, J = 8.5 Hz, 1H), 5.36 (s, 1H), 4.62 (br. s., 1H), 4.17 (dd, J = 9.3, 5.3 Hz, 1H), 4.06-3.98 (m, 2H), 3.95 (dd, J = 11.2, 3.4 Hz, 2H), 3.85-3.73 (m, 3H), 3.57 (dq, J = 9.3, 7.0 Hz, 1H), 3.40 (td, J = 11.8, 2.0 Hz, 2H), 3.18 (d, J = 7.0 Hz, 2H), 2.90-2.81 (m, 1H), 2.45 (s, 3H), 2.01-1.88 (m, 1H), 1.76-1.65 (m, 2H), 1.35 (qd, J = 12.5, 4.5 Hz, 2H), 1.19 (t, J = 7.0 Hz, 3H), 0.87-0.77 (m, 2H), 0.66-0.60 (m, 2H). |
| | C91<br>[$C_{33}H_{39}N_7O_4$ + H]+<br>598.3; 598.4<br>free base;<br>98.5% at 254 nm | (400 MHz, CDCl₃) δ ppm 8.27 (s, 1H), 7.81 (s, 1H), 7.67 (d, J = 8.0 Hz, 1H), 7.37-7.30 (m, 1H), 7.27-7.24 (m, 1H), 6.87-6.78 (m, 4H), 5.62 (s, 1H), 3.88-3.82 (m, 4H), 3.82-3.75 (m, 4H), 3.48-3.41 (m, 2H), 3.22-3.15 (m, 4H), 2.93-2.85 (m, 1H), 2.78 (t, J = 5.9 Hz, 2H), 2.56 (br. s., 4H), 2.38 (s, 3H), 1.59-1.55 (m, 1H), 0.91-0.83 (m, 2H), 0.64-0.56 (m, 2H). |
| | C92<br>[$C_{29}H_{38}N_6O_3$ + H]+<br>519.3; 519.4<br>free base;<br>99.1% at 254 nm | (400 MHz, CD₃OD) δ ppm 8.17 (s, 1H), 8.09 (s, 1H), 7.90 (dd, J = 8.0, 1.3 Hz, 1H), 7.30 (d, J = 8.0 Hz, 1H), 5.45 (s, 1H), 4.39-4.29 (m, 1H), 3.79-3.67 (m, 4H), 3.65 (s, 2H), 3.37 (s, 2H), 2.85 (tt, J = 7.3, 3.8 Hz, 1H), 2.44 (s, 3H), 2.19-2.09 (m, 2H),<br>1.86-1.74 (m, 2H), 1.74-1.53 (m, 8H), 0.86-0.78 (m, 2H), 0.67-0.59 (m, 2H). |

-continued

| Structure | Example number<br>MS calcd;<br>MS ESI [M + H]+<br>Salt Form;<br>HPLC purity | 1H NMR |
|---|---|---|
| | C93<br>[C29H38N6O4 + H]+<br>535.3; 535.4<br>free base;<br>98.7% at 254 nm | NMR (400 MHz, CD3OD) δ ppm 8.19 (s, 1H), 8.10 (s, 1H), 7.86 (dd, J = 7.9, 1.6 Hz, 1H), 7.31 (d, J = 8.3 Hz, 1H), 5.47 (s, 1H), 4.25-4.14 (m, 1H), 4.08-4.00 (m, 2H), 3.79-3.69 (m, 4H), 3.68-3.65 (m, 2H), 3.62 (td, J = 11.7, 2.3 Hz, 2H), 3.39 (s, 2H), 2.89-2.82 (m, 1H), 2.45 (s, 3H), 2.19-2.10 (m, 2H), 1.69-1.56 (m, 6H), 0.85-0.78 (m, 2H), 0.66-0.61 (m, 2H). |
| | C94<br>[C28H36N6O4 + H]+<br>521.3; 521.4<br>free base;<br>99.3% at 254 nm | (400 MHz, CD3OD) δ ppm 8.20 (s, 1H), 8.10 (s, 1H), 7.88-7.83 (m, 1H), 7.31 (d, J = 8.0 Hz, 1H), 5.42 (s, 1H), 4.25-4.13 (m, 1H), 4.08-3.99 (m, 2H), 3.86- 3.72 (m, 4H), 3.61 (td, J = 11.6, 1.9 Hz, 2H), 3.35-3.28 (m, 2H), 2.91-2.80 (m, 1H), 2.45 (s, 3H), 2.19-2.09 (m, 2H), 1.84-1.73 (m, 2H), 1.69-1.55 (m, 4H), 0.86-0.78 (m, 2H), 0.67-0.60 (m, 2H). |
| | C95<br>[C28H36N6O3 + H]+<br>505.3; 505.4<br>free base;<br>99.6% at 254 nm | (400 MHz, CD3OD) δ ppm 8.19 (s, H), 8.09 (s, 1H), 7.90 (dd, J = 8.0, 1.5 Hz, 1H), 7.30 (d, J = 8.0 Hz, 1H), 5.41 (s, 1H), 4.34 (quin, J = 6.7 Hz, 1H), 3.87- 3.72 (m, 4H), 3.35-3.27 (m, 2H), 2.91-2.81 (m, 1H), 2.44 (s, 3H), 2.20-2.08 (m, 2H), 1.87-1.51 (m, 10H), 0.86-0.77 (m, 2H), 0.67-0.60 (m, 2H). |

| Structure | Example number<br>MS calcd;<br>MS ESI [M + H]+<br>Salt Form;<br>HPLC purity | ¹H NMR |
|---|---|---|
| | C96<br>[$C_{31}H_{37}N_7O_3$ + H]+<br>556.3; 556.5<br>free base;<br>95.2% at 254 nm | (400 MHz, CD₃OD) δ ppm 8.35 (s, 1H), 7.90 (s, 1H), 7.71-7.65 (m, 1H), 7.28 (t, J = 8.2 Hz, 1H), 7.22 (d, J = 8.0 Hz, 1H), 6.72-6.63 (m, 2H), 6.58 (dd, J = 7.8, 1.8 Hz, 1H), 5.75 (s, 1H), 3.77-3.70 (m, 4H), 3.51 (t, J = 6.3 Hz, 2H), 2.96 (s, 6H), 2.84 (tt, J = 7.4, 3.7 Hz, 1H), 2.71 (t, J = 6.4 Hz, 2H), 2.55 (br. s., 4H), 2.29 (s, 3H), 0.85-0.76 (m, 2H), 0.64-0.58 (m, 2H). |
| | C97<br>[$C_{29}H_{31}ClN_6O_3$ + H]+<br>547.2; 547.3<br>free base;<br>95.3% at 254 nm | (400 MHz, CD₃OD) δ ppm 8.35 (s, 1H), 7.81 (s, 1H), 7.64 (d, J = 7.0 Hz, 1H), 7.40-7.49 (m, 1H), 7.37 (t, J = 2.1 Hz, 1H), 7.34-7.27 (m, 1H), 7.22 (d, J = 8.0 Hz, 2H), 5.86 (s, 1H), 3.75 (t, J = 4.5 Hz, 4H), 3.57 (t, J = 6.4 Hz, 2H), 2.88-2.80 (m, 1H), 2.77 (t, J = 6.4 Hz, 2H), 2.59 (br. s., 4H), 2.29 (s, 3H), 0.77-0.83 (s, 2H), 0.57-0.64 (m, 2H). |
| | C98<br>[$C_{28}H_{30}N_6O_4$ + H]+<br>515.2; 515.3<br>free base;<br>97.7% at 254 nm | NMR (400 MHz, CD₃OD) δ ppm 8.55 (d, J = 2.8 Hz, 1H), 8.48 (dd, J = 4.8, 1.3 Hz, 1H), 8.36 (s, 1H), 7.86-7.80 (m, 1H), 7.73 (s, 1H), 7.62-7.54 (m, 2H), 7.19 (d, J = 8.0 Hz, 1H), 6.06 (s, 1H), 3.87-3.74 (m, 4H), 3.47 (s, 2H), 2.89-2.77 (m, 1H), 2.26 (s, 3H), 1.87-1.75 (m, 2H), 1.72-1.61 (m, 2H), 0.84-0.76 (m, 2H), 0.65-0.56 (m, 2H). |

| Structure | Example number<br>MS calcd;<br>MS ESI [M + H]+<br>Salt Form;<br>HPLC purity | ¹H NMR |
|---|---|---|
| | C99<br>[C$_{29}$H$_{32}$N$_6$O$_4$ + H]+<br>529.3; 529.4<br>free base;<br>97.8% at 254 nm | (400 MHz, CD$_3$OD) δ ppm 8.57 (d, J = 2.3 Hz, 1H), 8.49 (dd, J = 4.8, 1.3 Hz, 1H), 8.36 (s, 1H), 7.87-7.83 (m, 1H), 7.75 (s, 1H), 7.62-7.57 (m, 2H), 7.19 (d, J = 8.0 Hz, 1H), 6.10 (s, 1H), 3.82-3.68 (m, 6H), 3.54 (s, 2H), 2.87-2.79 (m, 1H), 2.26 (s, 3H), 1.63-1.66 (m, 4H), 0.82-0.78 (m, 2H), 0.63-0.58 (m, 2H). |
| | C100<br>[C$_{26}$H$_{26}$N$_6$O$_3$ + H]+<br>471.2 471.1;<br>free base;<br>91.9% at 254 nm | (400 MHz, CDCl$_3$ + drops of CD$_3$OD) δ ppm 8.58 (br. s., 1H), 8.49 (br. s., 1H), 8.22 (s, 1H), 7.73-7.61 (m, 2H), 7.52 (d, J = 8.0 Hz, 1H), 7.46-7.39 (m, 1H), 7.21 (d, J = 8.8 Hz, 1H), 5.76 (s, 1H), 4.93 (t, J = 6.4 Hz, 2H), 4.50 (t, J = 5.8 Hz, 2H), 3.76 (d, J = 6.5 Hz, 2H), 3.41 (d, J = 11.5 Hz, 1H), 2.85 (br. s., 1H), 2.31 (br. s., 3H), 0.94-0.82 (m, 2H), 0.62-0.53 (m, 2H); |
| | C101<br>[C$_{28}$H$_{32}$N$_6$O$_4$ + H]+<br>493.2; 493.3<br>free base;<br>94% at 254 nm | (400 MHz, CDCl$_3$) δ ppm 8.24 (s, 1H), 7.83 (s, 1H), 7.77 (d, J = 8.0 Hz, 1H), 7.38 (d, J = 8.0 Hz, 1H), 6.79 (t, J = 4.8 Hz, 1H), 5.95 (br. s., 1H), 5.74 (quint, J = 5.9 Hz, 1H), 5.50 (s, 1H), 5.07 (t, J = 7.2 Hz, 2H), 4.83 (dd, J = 7.8, 5.5 Hz, 2H), 3.82-3.73 (m, 4H), 3.45-3.38 (m, 2H), 2.97-2.87 (m, 1H), 2.76 (t, J = 6.0 Hz, 2H), 2.59-2.50 (s, 7H), 0.94-0.85 (m, 2H), 0.63 (m, 2H); |

| Structure | Example number<br>MS calcd;<br>MS ESI [M + H]+<br>Salt Form;<br>HPLC purity | 1H NMR |
|---|---|---|
| | C102<br>[C$_{26}$H$_{32}$N$_6$O$_3$ + H]+<br>477.3; 477.3<br>free base;<br>93% at 254 nm | (400 MHz, CD$_3$OD) δ ppm 8.20 (s, 1H), 7.98 (s, 1H), 7.88 (d, J = 8.3 Hz, 1H), 7.32 (d, J = 8.0 Hz, 1H), 5.38 (s, 1H), 5.14 (m, 1H), 5.07-5.00 (m, 2H), 4.68 (t, J = 6.4 Hz, 2H), 3.98 (dd, J = 11.3, 3.3 Hz, 2H), 3.43 (td, J = 11.7, 1.9 Hz, 2H), 3.23 (d, J = 7.0 Hz, 2H), 2.86 (tt, J = 7.3, 3.8 Hz, 1H), 2.47 (s, 3H), 2.06-1.95 (m, 1H), 1.75 (d, J = 12.8 Hz, 2H), 1.46-1.32 (m, 2H), 0.85-0.76 (m, 2H), 0.66-0.60 (m, 2H). |
| | C103<br>[C$_{27}$H$_{34}$N$_6$O$_2$ + H]+<br>475.3; 475.6;<br>HCl salt;<br>98.5% at 254 nm | (400 MHz, CD$_3$OD) δ ppm 8.18 (s, 1H), 7.47 (s, 1H), 7.45-7.39 (m, 2H), 5.54 (s, 1H), 3.98 (dd, J = 11.0, 3.0 Hz, 2H), 3.50-3.43 (m, 4H), 2.92-2.87 (m, 1H), 2.48 (s, 3H), 2.08 (s, br, 1H), 1.80-1.73 (m, 2H), 1.50-1.37 (m, 2H), 0.87-0.81 (m, 2H), 0.71-0.63 (m, 4H), 0.43-0.37 (m, 2H). |
| | C104<br>[C$_{29}$H$_{40}$N$_6$O$_3$ + H]+<br>521.3; 521.3<br>TFA salt;<br>99.3% at 254 nm | (400 MHz, CD$_3$OD) δ ppm 8.19 (s, 1H), 7.55-7.37 (m, 3H), 5.67 (s, 1H), 3.98 (dd, J = 11.6, 3.6 Hz, 2H), 3.87 (s, br, 1H), 3.69-3.57 (m, 2H), 3.47-3.33 (m, 7H), 2.91-2.85 (m, 1H), 2.46 (s, 3H), 2.12-1.98 (m, 2H), 1.77-1.70 (m, 2H), 1.48-1.35 (m, 2H), 1.10-1.04 (m, 6H), 0.85-0.80 (m, 2H), 0.66-0.61 (m, 2H). |

| Structure | Example number<br>MS calcd;<br>MS ESI [M + H]+<br>Salt Form;<br>HPLC purity | ¹H NMR |
|---|---|---|
| 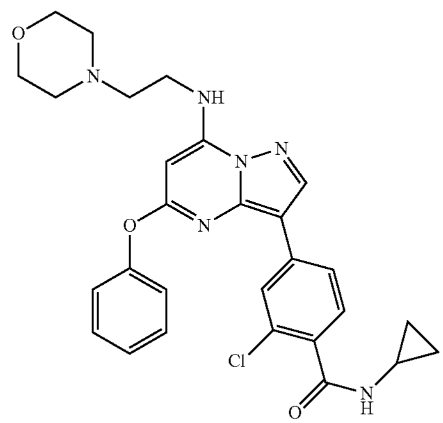 [SMILES: O=C(NC1CC1)c1ccc(-c2cnn3c(NCCN4CCOCC4)cc(Oc4ccccc4)nc23)cc1Cl] | C105<br>[$C_{28}H_{29}ClN_6O_3$ + H]+<br>533.2; 533.2<br>TFA salt;<br>99.1% at 254 nm | (400 MHz, CD$_3$OD) δ ppm 8.27 (s, 1H), 7.96 (s, 1H), 7.64 (d, J = 7.6 Hz, 1H), 7.45 (t, J = 7.6 Hz, 2H), 7.29-7.22 (m, 4H), 5.89 (s, 1H), 4.15-3.80 (m, 6H), 3.80-3.50 (m, 4H), 3.35-3.15 (m, 2H), 2.89-2.82 (m, 1H), 0.84-0.78 (m, 2H), 0.67-0.60 (m, 2H). |
| 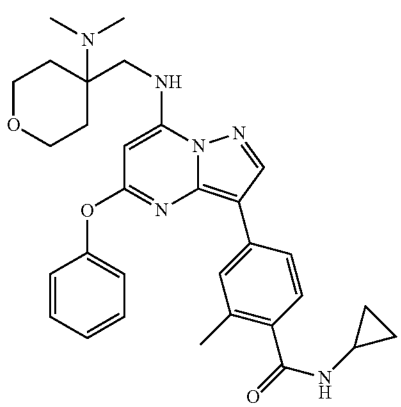 [SMILES: Cc1cc(-c2cnn3c(NCC4(N(C)C)CCOCC4)cc(Oc4ccccc4)nc23)ccc1C(=O)NC1CC1] | C106<br>[$C_{31}H_{36}N_6O_3$ + H]+<br>541.3; 541.3<br>TFA salt;<br>96.1% at 254 nm | (400 MHz, CD$_3$OD) δ ppm 8.40 (s, 1H), 7.81 (s, 1H), 7.62 (d, J = 8.0 Hz, 1H), 7.48 (t, J = 7.6 Hz, 2H), 7.33-7.27 (m, 3H), 7.19 (d, J = 8.0 Hz, 1H), 6.18 (s, 1H), 4.07 (s, 2H), 4.06-3.98 (m, 2H), 3.72 (t, J = 5.3 Hz, 2H), 3.32 (quint, J = 1.6 Hz, 1H), 2.94 (s, 6H), 2.87-2.79 (m, 1H), 2.25 (s, 3H), 2.27-2.01 (m, 2H), 0.83-0.77 (m, 2H), 0.63-0.58 (m, 2H). |
| 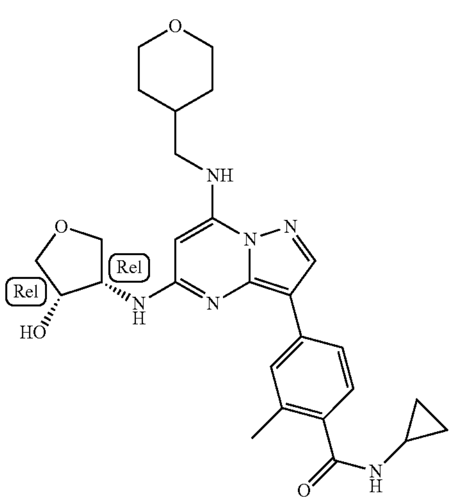 [SMILES: Cc1cc(-c2cnn3c(NCC4CCOCC4)cc(N[C@H]4COC[C@H]4O)nc23)ccc1C(=O)NC1CC1] | C107<br>[$C_{27}H_{34}N_6O_4$ + H]+<br>507.3; 507.2<br>TFA salt;<br>98.5% at 254 nm | (400 MHz, CD$_3$OD) δ ppm 8.20 (s, 1H), 7.48 (s, 1H), 7.46-7.37 (m, 2H), 5.62 (s, 1H), 4.55-4.50 (m, 1H), 4.41 (q, J = 6.0 Hz, 1H), 4.21 (dd, J = 8.4, 7.2 Hz, 1H), 4.07 (dd, J = 10.0, 4.8 Hz, 1H), 3.99 (dd, J = 11.4, 7.4 Hz, 2H), 3.83 (dd, J = 9.8, 2.6 Hz, 1H), 3.73-3.67 (m, 1H), 3.50-3.40 (m, 4H), 2.92-2.86 (m, 1H), 2.46 (s, 3H), 2.13-2.01 (m, 1H), 1.78-1.72 (m, 2H), 1.50-1.38 (m, 2H), 0.86-0.81 (m, 2H), 0.67-0.61 (m, 2H). |

-continued

| Structure | Example number<br>MS calcd;<br>MS ESI [M + H]+<br>Salt Form;<br>HPLC purity | 1H NMR |
|---|---|---|
| 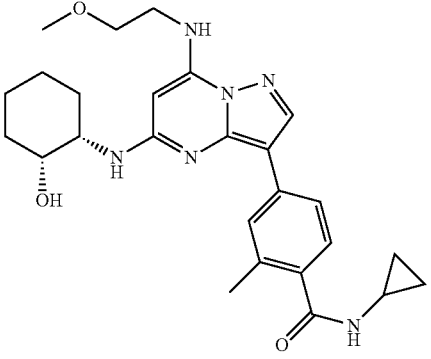 [SMILES: COCCNc1cc(N[C@H]2CCCC[C@H]2O)nc2c(-c3ccc(C(=O)NC4CC4)c(C)c3)cnn12] | C108<br>[C26H34N6O3 + H]+<br>479.3; 479.2<br>TFA salt;<br>98.9% at 254 nm | (400 MHz, CD3OD) δ ppm 8.20 (s, 1H), 7.47 (s, 1H), 7.46-7.40 (m, 2H), 5.73 (s, 1H), 4.05-3.98 (m, 1H), 3.95-3.83 (m, 1H), 3.77-3.68 (m, 4H), 3.42 (s, 3H), 2.92-2.87 (m, 1H), 2.47 (s, 3H), 1.90-1.67 (m, 6H), 1.60-1.43 (m, 2H), 0.87-0.81 (m, 2H), 0.66-0.62 (m, 2H). |
| 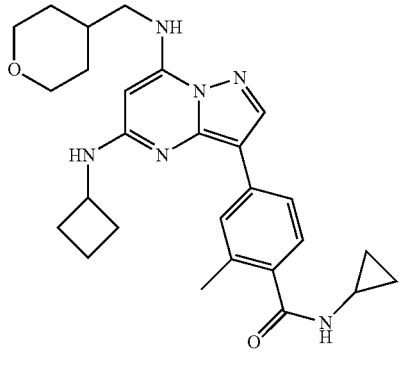 [SMILES: Cc1cc(-c2cnn3c(NCC4CCOCC4)cc(NC4CCC4)nc23)ccc1C(=O)NC1CC1] | C109<br>[C27H34N6O2 + H]+<br>475.3; 475.2<br>TFA salt;<br>99.4% at 254 nm | (400 MHz, CD3OD) δ ppm 8.17 (s, 1H), 7.45 (s, 1H), 7.43-7.38 (m, 2H), 5.41 (s, 1H), 4.30 (quint, J = 7.90, 1H), 3.98 (dd, J = 11.6, 3.2 Hz, 2H), 3.49-3.40 (m, 4H), 2.92-2.87 (m, 1H), 2.46 (s, 3H), 2.17-2.00 (m, 3H), 1.96-1.87 (m, 2H), 1.78-1.72 (m, 2H), 1.49-1.38 (m, 2H), 0.86-0.81 (m, 2H), 0.67-0.62 (m, 2H). |
| 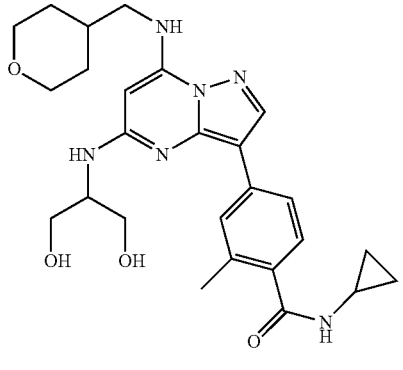 [SMILES: Cc1cc(-c2cnn3c(NCC4CCOCC4)cc(NC(CO)CO)nc23)ccc1C(=O)NC1CC1] | C110<br>[C26H34N6O4 + H]+<br>495.3; 495.3<br>HCl salt;<br>97.4% at 254 nm | (400 MHz, CD3OD) δ ppm 8.20 (s, 1H), 7.55-7.30 (m, 3H), 5.74 (s, 1H), 4.10-3.65 (m, 7H), 3.55-3.25 (m, 4H), 2.93-2.83 (m, 1H), 2.46 (s, 3H), 2.20-2.04 (m, 1H), 1.85-1.65 (m, 2H), 1.55-1.30 (m, 2H), 0.85-0.75 (m, 2H), 0.70-0.58 (m, 2H). |
| 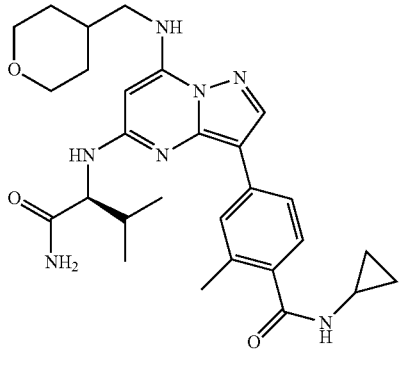 [SMILES: Cc1cc(-c2cnn3c(NCC4CCOCC4)cc(N[C@H](C(N)=O)C(C)C)nc23)ccc1C(=O)NC1CC1] | C111<br>[C28H37N7O3 + H]+<br>520.3; 520.3<br>HCl salt;<br>98.7% at 254 nm | (400 MHz, CD3OD) δ ppm 8.22 (s, 1H), 7.60-7.30 (m, 3H), 5.46 (s, 1H), 4.40-3.85 (m, 3H), 3.75-3.25 (m, 4H), 2.92-2.84 (m, 1H), 2.46 (s, 3H), 2.40-2.25 (m, 1H), 2.20-1.98 (m, 1H), 1.85-1.65 (m, 2H), 1.60-1.35 (m, 2H), 1.25-1.00 (m, 6H), 0.85-0.75 (m, 2H), 0.70-0.58 (m, 2H). |

| Structure | Example number MS calcd; MS ESI [M + H]+ Salt Form; HPLC purity | ¹H NMR |
|---|---|---|
| | C112<br>[C$_{29}$H$_{36}$N$_6$O$_3$ + H]+<br>517.3; 517.3<br>HCl salt;<br>97.5% at 254 nm | (400 MHz, CD$_3$OD) δ ppm 8.15 (s, 1H), 7.52-7.33 (m, 3H), 4.70-4.55 (m, 2H), 4.05-3.65 (m, 6H), 3.55-3.47 (m, 4H), 2.92-2.82 (m, 1H), 2.55 (s, 3H), 2.30-2.00 (m, 5H), 1.85-1.73 (m, 2H), 1.55-1.37 (m, 2H), 0.86-0.80 (m, 2H), 0.65-0.60 (m, 2H). |
| | C113<br>[C$_{28}$H$_{36}$N$_6$O$_3$+ H]+<br>505.3; 505.3<br>HCl salt;<br>98.0% at 254 nm | (400 MHz, CD$_3$OD) δ ppm 8.19 (s, 1H), 7.53-7.35 (m, 3H), 3.98 (s, 2H), 3.65-3.30 (m, 8H), 2.92-2.84 (m, 1H), 2.47 (s, 3H), 2.20-2.05 (m, 1H), 1.85-1.67 (m, 2H), 1.52-1.38 (m, 2H), 0.85-0.78 (m, 2H), 0.72-0.52 (m, 6H). |
| | C114<br>[C$_{29}$H$_{39}$N$_7$O$_3$ + H]+<br>534.3; 534.6<br>free base;<br>99.6% at 254 nm | (400 MHz, CD$_3$OD) δ ppm 8.19 (s, 1H), 7.98-7.94 (m, 2H), 7.30 (d, J = 7.6 Hz, 1H), 5.37 (s, 1H), 4.00-3.96 (m, 2H), 3.73-3.71 (m, 4H), 3.66 (t, J = 6.8 Hz, 2H), 3.43 (t, J = 9.6 Hz, 2H), 3.24 (d, J = 6.8 Hz, 2H), 2.87-2.84 (m, 1H), 2.71-2.68 (m, 2H), 2.59 (s, 4H), 2.45 (s, 3H), 2.03-2.00 (m, 1H), 1.77-1.75 (m, 2H), 1.45-1.35 (m, 2H), 0.84-0.79 (m, 2H), 0.64-0.60 (m, 2H). |
| | C115<br>[C$_{31}$H$_{40}$N$_6$O$_4$ + H]+<br>562.3; 562.3;<br>free base;<br>96.8% at 254 nM | (400 MHz, CD$_3$OD) δ ppm 8.31 (s, 1H), 8.00 (s, 1H), 7.86-7.84 (m, 1H), 7.32 (d, J = 8.0 Hz, 1H), 5.56 (s, 1H), 5.22-5.21 (m, 1H), 4.72-4.67 (m, 2H), 4.63-4.59 (m, 2H), 3.97-3.94 (m, 2H), 3.55-3.50 (m, 1H), 3.44-3.41 (m, 2H), 3.27-3.23 (m, 2H), 2.88-2.84 (m, 1H), 2.73-2.63 (m, 2H), 2.44 (s, 3H), 2.26-2.17 (m, 9H), 1.74-1.71 (m, 2H), 1.42-1.32 (m, 2H), 0.84-0.79 (m, 2H), 0.65-0.61 (m, 2H). |

-continued

| Structure | Example number<br>MS calcd;<br>MS ESI [M + H]+<br>Salt Form;<br>HPLC purity | 1H NMR |
|---|---|---|
| 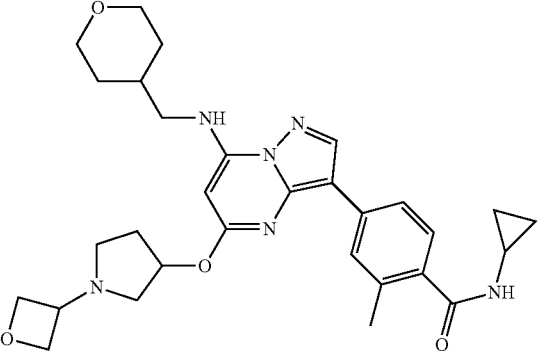 [SMILES: Cc1cc(-c2cnn3c(NCC4CCOCC4)cc(OC4CCN(C5COC5)C4)nc23)ccc1C(=O)NC1CC1] | C116<br>[C30H38N6O4 + H]+<br>547.3; 547.6;<br>TFA salt;<br>96.7% at 254 nM | (400 MHz, CD3OD) δ ppm 8.36 (s, 1H), 7.93-7.88 (m, 2 H), 7.34 (d, J = 8.0 Hz, 1H), 5.87 (s, 1H), 5.67 (s, 1H), 4.97-4.92 (m, 3H), 4.77-4.74 (m, 2H), 4.63-4.59 (m, 1H), 3.96-3.65 (m, 7H), 3.56-3.45 (m, 3H), 2.89-2.84 (m, 1H), 2.68-2.66 (m, 1H), 2.46 (s, 3H), 2.06-1.98 (m, 1H), 1.76-1.73 (m, 2H), 1.45-1.35 (m, 2H), 0.85-0.80 (m, 2H), 0.65-0.61 (m, 2H). |
| 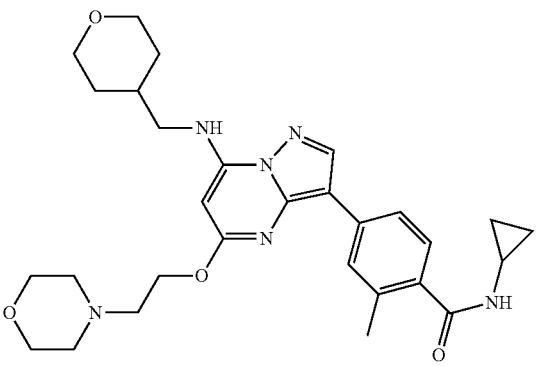 [SMILES: Cc1cc(-c2cnn3c(NCC4CCOCC4)cc(OCCN4CCOCC4)nc23)ccc1C(=O)NC1CC1] | C117<br>[C29H38N6O4 + H]+<br>535.3 535.3<br>TFA salt;<br>97.6% at 254 nM | (400 MHz, CD3OD) δ ppm 8.35 (s, 1H), 7.93-7.89 (m, 2H), 7.34 (d, J = 8.0 Hz, 1H), 5.69 (s, 1H), 4.91-4.88 (m, 2H), 4.86 (t, J = 4.8 Hz, 2H), 4.03-3.96 (m, 4H), 3.79-3.76 (m, 2H), 3.72-3.65 (m, 4H), 3.45-3.40 (m, 2H), 3.30-3.38 (m, 2H), 2.89-2.84 (m, 1H), 2.46 (s, 3H), 2.06-1.99 (m, 1H), 1.76-1.73 (m, 2H), 1.45-1.35 (m, 2H), 0.85-0.80 (m, 2H), 0.65-0.61 (m, 2H). |
| 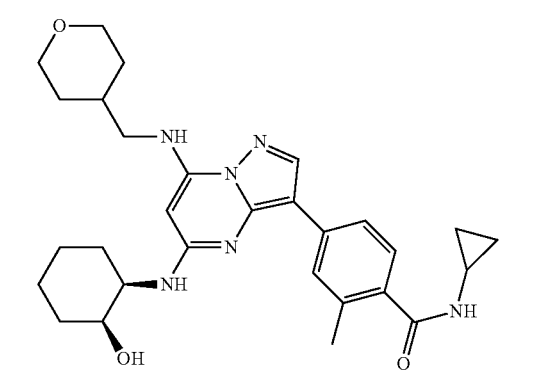 [SMILES: Cc1cc(-c2cnn3c(NCC4CCOCC4)cc(N[C@@H]4CCCC[C@@H]4O)nc23)ccc1C(=O)NC1CC1] | C118<br>[C29H38N6O3 + H]+<br>519.3; 519.3;<br>TFA salt;<br>98.9% at 254 nM | (400 MHz, CD3OD) δ ppm 8.21 (s, 1H), 7.47 (s, 1H), 7.43 (m, 2H), 5.69 (s, 1H), 4.01-3.95 (m, 4H), 3.47-3.41 (m, 4H), 2.91-2.85 (m, 1H), 2.47 (s, 3H), 2.10-2.04 (m, 1H), 1.82-1.69 (m, 8H), 1.56-1.37 (m, 4H), 0.86-0.81 (m, 2H), 0.65-0.61 (m, 2H). |
| 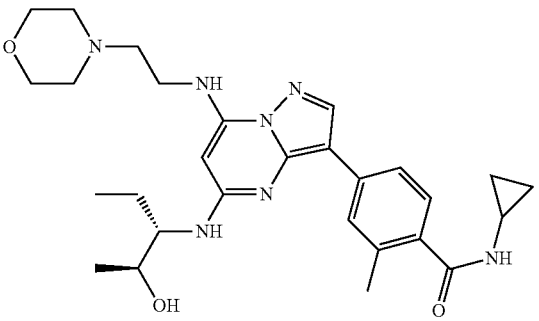 [SMILES: CC[C@H](Nc1cc(NCCN2CCOCC2)n2ncc(-c3ccc(C(=O)NC4CC4)c(C)c3)c2n1)[C@H](C)O] | C119<br>[C28H39N7O3 + H]+<br>522.3; 522.3;<br>free base;<br>95% at 254 nM | (400 MHz, CD3OD) δ ppm 8.18 (s, 1H), 7.98 (s, 1H), 7.89 (d, J = 8.4 Hz, 1H), 7.31 (d, J = 8.4 Hz, 1H), 5.43 (s, 1H), 4.04-3.97 (m, 2H), 3.74 (t, J = 4.8 Hz, 4H), 3.46-3.42 (m, 2H), 2.88-2.82 (m, 1H), 2.74-2.70 (m, 2H), 2.56 (br.s, 4H), 2.45 (s, 3H), 1.81-1.73 (m,1H), 1.7-1.61 (m, 1H), 1.22 (d, J = 6.4 Hz, 3H), 1.03 (t, J = 8.0 Hz, 3H), 0.84-0.79 (m, 2H), 0.64-0.60 (m, 2H). |

-continued

| Structure | Example number<br>MS calcd;<br>MS ESI [M + H]+<br>Salt Form;<br>HPLC purity | ¹H NMR |
|---|---|---|
| | C120<br>[$C_{30}H_{39}N_7O_3$ + H]+<br>547.3; 547.3;<br>di-TFA salt;<br>98.7% at 254 nM | (400 MHz, CD$_3$OD) δ ppm 8.22 (s, 1H), 7.81-7.65 (m, 2H), 7.35 (d, J = 7.6 Hz, 1H), 4.93-4.85 (m, 2H), 4.81-4.75 (m, 1H), 4.74-4.70 (m, 2H), 4.60-4.54 (m, 1H), 4.00-3.96 (m, 3H), 3.79-3.70 (m, 3H), 3.53-3.40 (m, 3H), 3.36-3.31 (m, 2H), 2.87-2.84 (m, 1H), 2.69-2.60 (m, 1H), 2.46 (s, 3H), 2.32-2.24 (m, 1H), 2.08-1.99 (m, 1H), 1.77-1.74 (m, 2H), 1.46-1.35 (m, 2H), 0.85-0.80 (m, 2H), 0.64-0.61 (m, 2H). |
| | C121<br>[$C_{28}H_{38}N_6O_3$ + H]+<br>507.3; 507.3;<br>TFA salt;<br>99.5% at 254 nM | (400 MHz, CD$_3$OD) δ ppm 8.21 (s, 1H), 7.49 (s, 1H), 7.46-7.41 (m, 2H), 5.70 (s, 1H), 4.00-3.97 (m, 2H), 3.85-3.67 (m, 3H), 3.46-3.41 (m, 4H), 2.91-2.85 (m, 1H), 2.47 (s, 3H), 2.11-2.02 (m, 2H), 1.76-1.73 (m, 2H), 1.47-1.77 (m, 2H), 1.08 (t, J = 6.8 Hz, 6H), 0.86-0.81 (m, 2H), 0.65-0.61 (m, 2H). |
| | C122<br>[$C_{31}H_{41}N_7O_3$ + H]+<br>560.3; 560.3;<br>di-TFA salt;<br>99.9% at 254 nM | (400 MHz, CD$_3$OD) δ ppm 8.21 (s, 1H), 7.61-7.58 (m, 2H), 7.38 (d, J = 8.0 Hz, 1H), 4.90-4.83 (m, 5H), 4.48-4.45 (m, 1H), 4.19-4.15 (m, 1H), 4.00-3.96 (m, 2H), 3.65-3.43 (m, 6H), 3.14-3.06 (m, 2H), 2.90-2.86 (m, 1H), 2.45-2.36 (m, 5H), 2.10-1.92 (m, 3H), 1.77-1.74 (m, 2H), 1.47-1.37 (m, 2H), 0.85-0.81 (m, 2H), 0.65-0.61 (m, 2H). |
| | C123<br>[$C_{28}H_{36}N_6O_3$ + H]+<br>505.3; 505.3;<br>TFA salt;<br>97.1% at 254 nM | (400 MHz, CD$_3$OD) δ ppm 8.22 (s, 1H), 7.50 (s, 1H), 7.46-7.40 (m, 2H), 5.58 (s, 1H), 4.10-4.05 (m, 1H), 4.00-3.97 (m, 2H), 3.91-3.86 (m, 1H), 3.46-3.38 (m, 4 H), 2.87-2.85 (m, 1H), 2.46 (s, 3H), 2.31-2.24 (m, 1H), 2.12-2.06 (m, 2H), 1.94-1.69 (m, 6H), 1.46-1.36 (m, 2H), 0.86-0.81 (m, 2H), 0.65-0.61 (m, 2H). |

| Structure | Example number MS calcd; MS ESI [M + H]+ Salt Form; HPLC purity | 1H NMR |
|---|---|---|
| 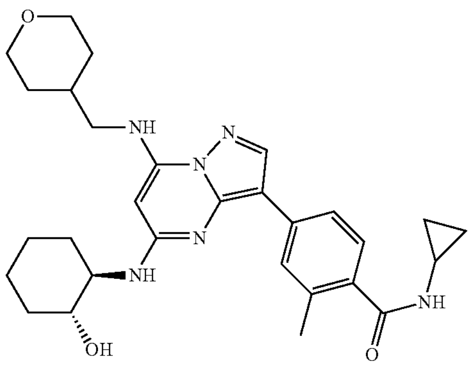 [SMILES: Cc1cc(-c2cnn3c(NCC4CCOCC4)cc(N[C@@H]4CCCC[C@H]4O)nc23)ccc1C(=O)NC1CC1] | C124 [C29H38N6O3 + H]+ 519.3; 519.3; TFA salt; 99.5% at 254 nM | (400 MHz, CD3OD) δ ppm 8.24 (s, 1H), 7.51 (s, 1H), 7.46-7.41 (m, 2H), 5.64 (s, 1 H), 3.98 (dd, J = 11.2, 3.2 Hz, 2H), 3.53 (m, 2H), 3.46-3.38 (m, 4H), 2.90-2.85 (m, 1H), 2.47 (s, 3H), 2.12-2.03 (m, 3H), 1.81-1.73 (m, 4H), 1.47-1.34 (m, 6H), 0.86-0.81 (m, 2H), 0.65-0.61 (m, 2H). |
| 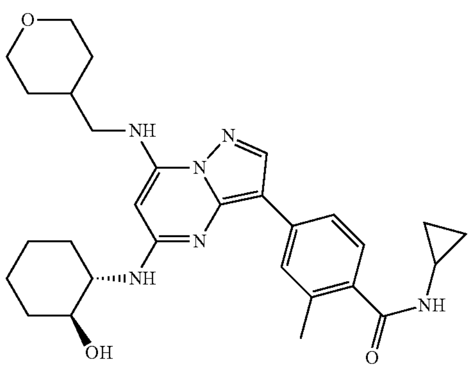 [SMILES: Cc1cc(-c2cnn3c(NCC4CCOCC4)cc(N[C@H]4CCCC[C@@H]4O)nc23)ccc1C(=O)NC1CC1] | C125 [C29H38N6O3 + H]+ 519.3; 519.3; TFA salt; 99.1% at 254 nM | (400 MHz, CD3OD) δ ppm 8.24 (s, 1H), 7.52 (s, 1H), 7.46-7.42 (m, 2H), 5.64 (s, 1H), 4.00-3.97 (m, 2H), 3.53 (m, 2H), 3.46-3.35 (m, 4H), 2.90-2.85 (m, 1H), 2.47 (s, 3H), 2.12-2.03 (m, 3H), 1.80-1.73 (m, 4H), 1.54-1.34 (m, 6H), 0.86-0.81 (m, 2H), 0.65-0.61 (m, 2H). |
| 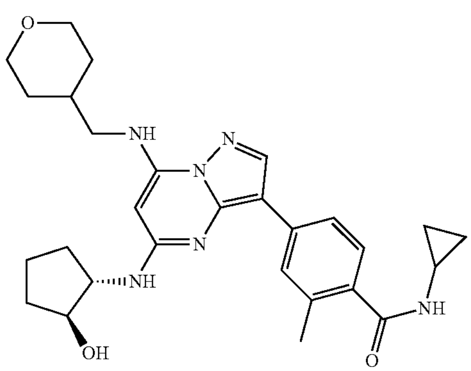 [SMILES: Cc1cc(-c2cnn3c(NCC4CCOCC4)cc(N[C@H]4CCC[C@@H]4O)nc23)ccc1C(=O)NC1CC1] | C126 [C28H36N6O3 + H]+ 505.3; 505.3; free base; 97.6% at 254 nM | (400 MHz, CD3OD) δ ppm 8.20 (s, 1H), 7.47 (s, 1H), 7.42 (br. s, 2H), 5.60 (s, 1H), 4.30-4.27 (m, 1H), 4.07-4.02 (m, 1H), 4.00-3.97 (m, 2H), 3.47-3.41 (m, 4H), 2.89-2.85 (m, 1H), 2.47 (s, 3H), 2.22-2.18 (m, 1H), 2.11-1.91 (m, 3H), 1.82-1.69 (m, 5H), 1.48-1.38 (m, 2H), 0.86-0.81 (m, 2H), 0.65-0.61 (m, 2H). |
| 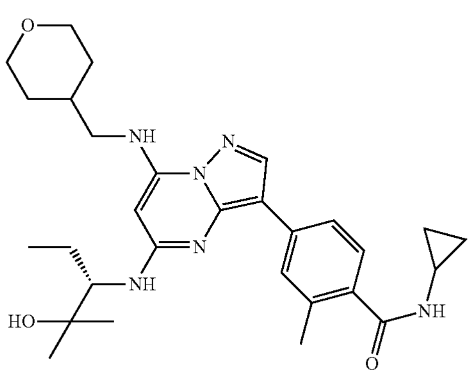 [SMILES: CC[C@H](Nc1cc(NCC2CCOCC2)n2ncc(-c3ccc(C(=O)NC4CC4)c(C)c3)c2n1)C(C)(C)O] | C127 [C29H40N6O3 + H]+ 521.3; 521.3; free base; 98.9% at 254 nM | (400 MHz, CD3OD) δ ppm 8.17 (s, 1H), 7.97 (s, 1H), 7.86 (dd, J = 8.0 Hz, 1.6 Hz, 1H), 7.32 (d, J = 8.0 Hz, 1H), 5.46 (s, 1H), 4.08 (br. s, 1H), 3.98 (dd, J = 11.6, 3.6 Hz, 2H), 3.47-3.43 (m, 2H), 3.25 (d, J = 7.2 Hz, 2H), 2.85-2.82 (m, 1H), 2.46 (s, 3H), 2.05-2.00 (m, 1H), 1.99-1.86 (m, 1H), 1.78-1.75 (m, 2H), 1.52-1.34 (m, 3H), 1.28 (s, 3H), 1.24 (s, 3H), 1.01 (t, J = 7.2 Hz, 3H), 0.84-0.79 (m, 2H), 0.64-0.60 (m, 2H). |

-continued

| Structure | Example number<br>MS calcd;<br>MS ESI [M + H]+<br>Salt Form;<br>HPLC purity | ¹H NMR |
|---|---|---|
| | C128<br>[$C_{29}H_{42}N_6O_3$ + H]+<br>523.3; 523.3;<br>free base;<br>98.7% at 254 nM | (400 MHz, CD₃OD) δ ppm 8.18 (s, 1H), 8.02 (s, 1H), 7.89 (dd, J = 8.0, 1.2 Hz, 1H), 7.31 (d, J = 8.0 Hz, 1H), 5.56 (s, 1H), 3.40-3.34 (m, 3H), 3.30 (s, 3H), 2.88-2.83 (m, 1H), 2.47 (s, 3H), 2.31-2.25 (m, 1H), 1.32 (s, 9H), 1.26 (s, 3H), 1.05 (t, J = 6.4 Hz, 6H), 0.84-0.79 (m, 2H), 0.65-0.61 (m, 2H). |
| | C129<br>[$C_{27}H_{36}N_6O_3$ + H]+<br>493.3; 493.3;<br>TFA salt;<br>97.1% at 254 nM | (400 MHz, CD₃OD) δ ppm 8.21 (s, 1H), 7.49 (s, 1H), 7.46-7.41 (m, 2H), 5.72 (s, 1H), 4.31-4.28 (m, 1H), 4.05-3.00 (m, 1H), 3.61-3.53 (m, 2H), 3.29 (s, 3H), 2.91-2.85 (m, 1H), 2.47 (s, 3H), 2.23-2.05 (m, 1H), 2.03-1.93 (m, 2H), 1.82-1.68 (m, 3H), 1.31 (s, 6H), 0.86-0.81 (m, 2H), 0.65-0.61 (m, 2H). |
| | C130<br>[$C_{29}H_{40}N_6O_3$ + H]+<br>521.3; 521.3;<br>HCl salt;<br>98.2% at 254 nM | (400 MHz, CD₃OD) δ ppm 8.21 (s, 1H), 7.48 (s, 1H), 7.43 (s, 2H), 5.67 (s, 1H), 3.99-3.92 (m, 3H), 3.85-3.74 (m, 1H), 3.69-3.58 (m, 1H), 3.50-3.40 (m, 4H), 2.90-2.85 (m, 1H), 2.47 (s, 3H), 2.13-2.03 (m, 1H), 1.77-1.73 (m, 3H), 1.58-1.38 (m, 4H), 1.03-0.98 (m, 6H), 0.85-0.81 (m, 2H), 0.65-0.61 (m, 2H). |
| | C131<br>[$C_{30}H_{40}N_6O_3$ + H]+<br>533.3; 533.3;<br>free base;<br>96.7% at 254 nM | (400 MHz, CD₃OD) δ ppm 8.13 (s, 1H), 7.78-7.74 (m, 2H), 7.31 (d, J = 8.0 Hz, 1H), 5.58 (s, 1H), 4.49 (br, s, 1H), 3.97 (dd, J = 10.8, 2.8 Hz, 2H), 3.46-3.43 (m, 2H), 3.43-3.40 (m, 2H), 3.28-3.21 (m, 2H), 2.87-2.82 (m, 1H), 2.44 (s, 3H), 2.04-2.00 (m, 1H), 1.98-1.80 (m, 2H), 1.77-1.64 (m, 6H), 1.46-1.33 (m, 4H), 1.28-1.22 (m, 1H), 0.84-0.79 (m, 2H), 0.64-0.60 (m, 2H). |

| Structure | Example number MS calcd; MS ESI [M + H]+ Salt Form; HPLC purity | 1H NMR |
|---|---|---|
| 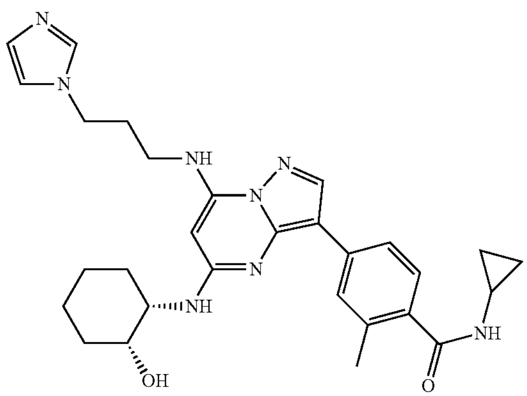 [SMILES: Cc1cc(-c2cnn3c(NCCCn4ccnc4)cc(N[C@H]4CCCC[C@H]4O)nc23)ccc1C(=O)NC1CC1] | C132 [C29H36N8O2 + H]+ 529.3; 529.2; free base; 96.4% at 254 nM | (400 MHz, CD3OD) δ ppm 8.19 (s, 1H), 8.05 (s, 1H), 7.83 (dd, J = 8.0, 1.2 Hz, 1H), 7.71 (s, 1H), 7.31 (d, J = 8.0 Hz, 1H), 7.19 (s, 1H), 7.00 (s, 1H), 5.34 (s, 1H), 4.21-4.14 (m, 4H), ), 3.40-3.29 (m, 2H), 2.88-2.83 (m, 1H), 2.45 (s, 3H), 2.24-2.17 (m, 2H), 1.87-1.64 (m, 6H), 1.49-1.47 (m, 2H), 0.84-0.79 (m, 2H), 0.65-0.61 (m, 2H). |
| 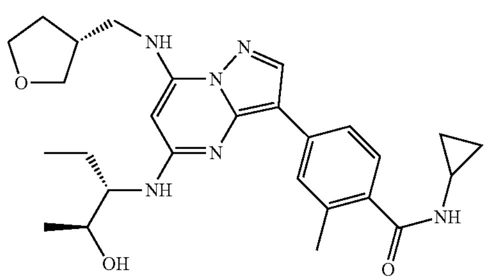 [SMILES: CC[C@H](Nc1cc(NC[C@H]2CCOC2)n2ncc(-c3ccc(C(=O)NC4CC4)c(C)c3)c2n1)[C@H](C)O] | C133 [C27H36N6O3 + H]+ 493.3; 493.4; free base; 99.2% at 254 nM | (400 MHz, CD3OD) δ ppm 8.38 (br, s, 1H), 8.17 (s, 1H), 7.98 (s, 1H), 7.89-7.87 (m, 1H), 7.31 (d, J = 8.0 Hz, 1H), 5.45 (s, 1H), 4.01-3.91 (m, 3H), 3.88-3.84 (m, 1H), 3.80-3.68 (m, 1H), 3.68-3.64 (m, 1H), 2.87-2.83 (m, 1H), 2.73-2.70 (m, 1H), 2.45 (s, 3H), 2.16-2.12 (m, 1H), 1.79-1.73 (m, 2H), 1.69-1.63 (m, 1H), 1.22 (d, J = 6.4 Hz, 3H), 1.03 (t, J = 7.6 Hz, 3H), 0.84-0.79 (m, 2H), 0.64-0.60 (m, 2H). |
| 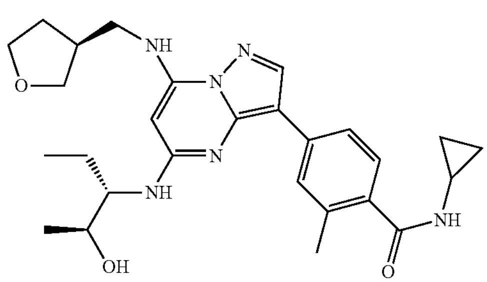 [SMILES: CC[C@H](Nc1cc(NC[C@@H]2CCOC2)n2ncc(-c3ccc(C(=O)NC4CC4)c(C)c3)c2n1)[C@H](C)O] | C134 [C27H36N6O3 + H]+ 493.3; 493.4; free base; 95.5% at 254 nM | (400 MHz, CD3OD) δ ppm 8.17 (s, 1H), 7.98 (s, 1H), 7.89 (dd, J = 8.0, 1.2 Hz, 1H), 7.31 (d, J = 8.4 Hz, 1H), 5.45 (s, 1H), 4.85-4.95 (m, 2H), 4.00-3.89 (m, 3H), 3.87-3.85 (m, 1H), 3.80-3.75 (m, 1H), 3.68-3.65 (m, 1H), 2.87-2.83 (m, 1H), 2.73-2.71 (m, 1H), 2.45 (s, 3H), 2.17-2.13 (m, 1H), 1.80-1.74 (m, 2H), 1.69-1.65 (m, 1H), 1.22 (d, J = 6.4 Hz, 3H), 1.03 (t, J = 7.6 Hz, 3H), 0.84-0.79 (m, 2H), 0.64-0.60 (m, 2H). |
| 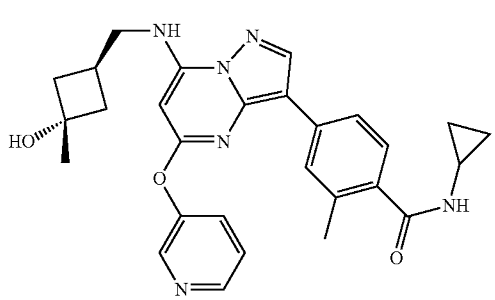 [SMILES: Cc1cc(-c2cnn3c(NC[C@H]4C[C@](C)(O)C4)cc(Oc4cccnc4)nc23)ccc1C(=O)NC1CC1] | C135 [C28H30N6O3 + H]+ 499.2; 499.3; free base; 98.9% at 254 nM | (400 MHz, CD3OD) δ ppm 8.55 (dd, J = 2.8, 0.4 Hz, 1H), 8.47 (dd, J = 4.8, 1.6 Hz, 1H), 8.33 (s, 1H), 7.83-7.80 (m, 1H), 7.72 (s, 1H), 7.58-7.55 (m, 2H), 7.18 (d, J = 8.0 Hz, 1H), 5.89 (s, 1H), 3.49 (d, J = 7.6 Hz, 2H), 2.87-2.78 (m, 1H), 2.28- 2.23 (m, 5H), 1.97-1.92 (m, 2H), 1.36 (s, 3H), 0.82-0.77 (m, 2H), 0.62-0.58 (m, 2H). |

| Structure | Example number<br>MS calcd;<br>MS ESI [M + H]+<br>Salt Form;<br>HPLC purity | 1H NMR |
|---|---|---|
| | C136<br>[C27H34N6O3 + H]+<br>491.3; 491.3;<br>TFA salt;<br>98.2% at 254 nm | (400 MHz, CDCl3) δ ppm 9.35 (br, s, 2H), 7.91 (s, 1H), 7.36-7.28 (m, 1H), 7.25-7.17 (m, 2H), 7.13 (t, J = 5.6 Hz, 1H), 6.47 (d, J = 3.0 Hz, 1H), 5.13 (s, 1H), 4.21 (br, s, 1H), 4.11-3.97 (m, 4H), 3.94-3.86 (m, 1H), 3.80 (dd, J = 9.5, 3.5 Hz, 1H), 3.44 (t, J = 11.2 Hz, 2H), 3.37 (t, J = 6.4 Hz, 2H), 2.97-2.85 (m, 1H), 2.44-2.29 (m, 4H), 2.18-1.97 (m, 2H), 1.76 (d, J = 12.5 Hz, 2H), 1.56-1.37 (m, 2H), 0.95-0.78 (m, 2H), 0.71-0.57 (m, 2H). |
| | C137<br>[C27H34N6O4 + H]+<br>507.3; 507.3;<br>TFA salt;<br>98.8% at 254 nm | (400 MHz, CDCl3) δ ppm 9.33-8.18 (m, 1H), 7.98 (s, 1H), 7.70 (s, 1H), 7.64 (d, J = 8.0 Hz, 1H), 7.29 (s, 1H), 6.94 (br, s, 1H), 6.61 (d, J = 2.8 Hz, 1H), 5.46 (br, s, 1H), 5.33 (s, 1H), 4.06-3.84 (m, 7H), 3.83-3.52 (m, 5H), 3.37 (br, s, 2H), 3.15-2.73 (m, 3H), 2.43 (s, 3H), 2.33-2.21 (m, 1H), 2.21-2.09 (m, 1H), 0.97-0.80 (m, 2H), 0.72-0.53 (m, 2H). |
| | C138<br>[C27H34N6O3 + H]+<br>491.3; 419.3;<br>TFA salt;<br>99.4% at 254 nm | (400 MHz, CD3OD) δ ppm 8.21 (s, 1H), 7.58-7.44 (m, 2H), 7.43-7.35 (m, 1H), 4.56-4.44 (m, 1H), 4.08-3.94 (m, 4H), 3.93-3.81 (m, 2H), 3.51-3.38 (m, 4H), 2.94-2.82 (m, 1H), 2.46 (s, 3H), 2.44-2.37 (m, 1H), 2.15-1.97 (m, 2H), 1.76 (d, J = 12.8 Hz, 2H), 1.43 (qd, J = 12.4, 4.4 Hz, 2H), 0.88-0.78 (m, 2H), 0.69-0.58 (m, 2H). |
| | C139<br>[C27H34N6O3 + H]+<br>491.3; 491.2;<br>TFA salt;<br>99.2% at 254 nm | (400 MHz, CDCl3) δ ppm 8.95-9.65 (m, 2H), 7.94 (br, s, 1H), 7.44-7.18 (m, 2H), 6.89 (br, s, 2H), 6.59-6.22 (m, 1H), 5.76 (br, s, 1H), 4.03 (br, s, 2H), 3.67 (br, s, 2H), 3.51-3.18 (m, 4H), 2.99-2.81 (m, 1H), 2.42 (br, s, 3H), 2.16-1.88 (m, 1H), 1.82-1.62 (m, 2H), 1.59-1.27 (m, 2H), 1.01 (d, J = 5.0 Hz, 4H), 0.91-0.78 (m, 2H), 0.64 (br, s, 2H). |

-continued

| Structure | Example number<br>MS calcd;<br>MS ESI [M + H]+<br>Salt Form;<br>HPLC purity | 1H NMR |
|---|---|---|
| | C140<br>[C26H34N6O4S + H]+<br>527.2; 527.2;<br>HCl salt;<br>99.9% at 254 nm | (400 MHz, DMSO-d6) δ ppm 8.42 (br, s, 1 H), 8.22 (br, s, 1 H), 8.08-7.56 (m, 3H), 7.39-7.24 (m, 2H), 7.18 (s, 1H), 7.04 (s, 1H), 5.44 (br, s, 2H), 4.03 (br, s, 1H), 3.96-3.84 (m, 2H), 3.25-3.17 (m, 2H), 2.99 (s, 3H), 2.87-2.74 (m, 1H), 2.37 (s, 3H), 2.13-1.89 (m, 4H), 1.60-1.40 (m, 2H), 0.73-0.61 (m, 2H), 0.59-0.45 (m, 2H). |
| | C141<br>[C29H36N6O3 + H]+<br>517.3; 517.3;<br>free base;<br>97.8% at 254 nm | (400 MHz, CDCl3) δ ppm 8.13 (s, 1H), 7.95 (s, 1H), 7.83 (d, J = 8.0 Hz, 1H), 7.35 (d, J = 8.0 Hz, 1H), 6.14 (t, J = 6.0 Hz, 1H), 5.93 (d, J = 2.5 Hz, 1H), 5.06 (s, 1H), 4.84 (d, J = 5.5 Hz, 1H), 4.82 (s, 2H), 4.67 (s, 2H), 4.29-4.16 (m, 1H), 4.03 (dd, J = 11.8, 3.3 Hz, 2H), 3.41 (td, J = 11.9, 1.9 Hz, 2H), 3.20 (t, J = 6.4 Hz, 2H), 2.96-2.79 (m, 3H), 2.53 (s, 3H), 2.20-2.09 (m, 2H), 2.01-1.88 (m, 1H), 1.75 (d, J = 11.0 Hz, 2H), 1.50-1.35 (m, 2H), 0.93-0.84 (m, 2H), 0.66-0.58 (m, 2H). |
| | C142<br>[C27H34N6O3 + H]+<br>491.3; 491.2;<br>HCl salt;<br>98.4% at 254 nm | (400 MHz, CD3OD) δ ppm 8.14 (s, 1H), 7.52-7.38 (m, 3H), 4.64 (br, s, 1H), 3.99 (dd, J = 11.3, 3.8 Hz, 2H), 3.84 (d, J = 7.5 Hz, 3H), 3.65 (d, J = 10.8 Hz, 1H), 3.53-3.39 (m, 4H), 2.94-2.83 (m, 1H), 2.47 (s, 3H), 2.33-2.01 (m, 3H), 1.77 (d, J = 12.3 Hz, 2H), 1.53-1.36 (m, 2H), 0.89-0.79 (m, 2H), 0.72-0.59 (m, 2H). |
| | C143<br>[C27H34N6O3 + H]+<br>491.3; 491.2;<br>HCl salt;<br>98.4% at 254 nm | (400 MHz, CD3OD) δ ppm 8.14 (s, 1H), 7.52-7.38 (m, 3H), 4.64 (br, s, 1H), 3.99 (dd, J = 11.3, 3.8 Hz, 2H), 3.84 (d, J = 7.5 Hz, 3H), 3.65 (d, J = 10.8 Hz, 1H), 3.53-3.39 (m, 4H), 2.94-2.83 (m, 1H), 2.47 (s, 3H), 2.33-2.01 (m, 3H), 1.77 (d, J = 12.3 Hz, 2H), 1.53-1.36 (m, 2H), 0.89-0.79 (m, 2H), 0.72-0.59 (m, 2H). |

| Structure | Example number<br>MS calcd;<br>MS ESI [M + H]+<br>Salt Form;<br>HPLC purity | ¹H NMR |
|---|---|---|
| | C144<br>[C$_{27}$H$_{28}$N$_6$O$_3$ + H]+<br>485.2; 485.3;<br>HCl salt;<br>98.8% at 254 nm | (400 MHz, CD$_3$OD) δ ppm 9.13 (d, J = 2.3 Hz, 1H), 8.86 (d, J = 5.8 Hz, 1H), 8.77-8.69 (m, 1H), 8.40 (s, 1H), 8.26 (dd, J = 8.8, 5.8 Hz, 1H), 7.67 (s, 1H), 7.59 (d, J = 8.0 Hz, 1H), 7.24 (d, J = 8.0 Hz, 1H), 6.07 (s, 1H), 4.53-4.39 (m, 1H), 3.57 (d, J = 8.0 Hz, 2H), 2.89-2.79 (m, 1H), 2.76-2.61 (m, 1H), 2.30 (s, 3H), 2.29-2.21 (m, 2H), 2.21-2.08 (m, 2H), 0.85-0.78 (m, 2H), 0.65-0.58 (m, 2H). |
| | C145<br>[C$_{27}$H$_{34}$N$_6$O$_3$ + H]+<br>491.3; 491.2;<br>HCl salt;<br>97.8% at 254 nm | (400 MHz, CD$_3$OD) δ ppm 8.19 (s, 1H), 7.52-7.34 (m, 3H), 4.51-4.37 (m, 1H), 4.11-3.91 (m, 3H), 3.73-3.53 (m, 4H), 2.94-2.82 (m, 1H), 2.76-2.59 (m, 1H), 2.48 (s, 3H), 2.30-2.20 (m, 2H), 2.19-2.00 (m, 4H), 1.75-1.58 (m, 2H), 0.90-0.76 (m, 2H), 0.71-0.56 (m, 2H). |
| | C146<br>[C$_{29}$H$_{30}$F$_2$N$_6$O$_2$ + H]+<br>533.2; 533.7;<br>HCl salt;<br>99.4% at 254 nm | (400 MHz, CD$_3$OD) δ ppm 8.39 (s, 1H), 7.83 (s, 1H), 7.63 (dd, J = 8.0, 1.5 Hz, 1H), 7.55-7.42 (m, 1H), 7.22 (d, J = 8.0 Hz, 1H), 7.15-7.03 (m, 3H), 3.79 (d, J = 19.8 Hz, 2H), 3.42 (br, s, 2H), 3.30-3.18 (m, 2H), 2.91-2.80 (m, 1H), 2.35-2.21 (m, 5H), 2.19-1.96 (m, 2H), 0.87-0.76 (m, 2H), 0.68-0.58 (m, 2H). |
| | C147<br>[C$_{29}$H$_{32}$FN$_7$O$_2$ + H]+<br>530.3; 530.4;<br>di-HCl salt;<br>99.4% at 254 nm | (400 MHz, CD$_3$OD) δ ppm 9.15 (d, J = 2.5 Hz, 1H), 8.87 (d, J = 5.5 Hz, 1H), 8.79-8.70 (m, 1H), 8.45 (s, 1H), 8.32-8.21 (m, 1H), 7.69 (s, 1H), 7.61 (d, J = 8.0 Hz, 1H), 7.25 (d, J = 8.0 Hz, 1H), 6.28 (s, 1H), 3.87 (d, J = 21.8 Hz, 2H), 3.62-3.49 (m, 2H), 3.30-3.23 (m, 1H), 2.94 (s, 3H), 2.89-2.79 (m, 1H), 2.31 (s, 8H), 0.82 (dd, J = 7.0, 1.8 Hz, 2H), 0.61 (dd, J = 3.8, 2.0 Hz, 2H). |

| Structure | Example number<br>MS calcd;<br>MS ESI [M + H]+<br>Salt Form;<br>HPLC purity | 1H NMR |
|---|---|---|
| | C148<br>[C27H34N6O2 + H]+<br>475.3; 475.4;<br>HCl salt;<br>99.3% at 254 nm | (400 MHz, CD3OD) δ ppm 8.22 (s, 1H), 7.51-7.36 (m, 3H), 5.68 (s, 1H), 3.77 (s, 2H), 3.37-3.33 (m, 2H), 2.93-2.84 (m, 1H), 2.47 (s, 3H), 2.07-1.95 (m, 4H), 1.93-1.72 (m, 4H), 1.34-1.19 (m, 1H), 0.88-0.78 (m, 2H), 0.69-0.59 (m, 4H), 0.45-0.37 (m, 2H). |
| | C149<br>[C26H28N6O2 + H]+<br>457.2 457.4;<br>TFA salt;<br>100% at 254 nm | (400 MHz, CD3OD) δ ppm 8.93 (d, J = 7.8 Hz, 2H), 8.57-8.50 (m, 1H), 7.97 (d, J = 7.5 Hz, 1H), 7.93 (s, 1H), 7.37 (d, J = 7.8 Hz, 1H), 6.89 (d, J = 7.8 Hz, 2H), 6.53 (s, 1H), 3.41 (d, J = 7.0 Hz, 2H), 2.90-2.83 (m, 1H), 2.46 (s, 3H), 2.18-2.08 (m, 1H), 1.07 (d, J = 6.8 Hz, 6H), 0.85-0.77 (m, 2H), 0.66-0.59 (m, 2H). |
| | C150<br>[C28H30N6O2 + H]+<br>483.2 483.2;<br>TFA salt;<br>100% at 254 nm | (400 MHz, CD3OD) δ ppm 8.88 (d, J = 6.0 Hz, 2H), 8.71 (d, J = 6.0 Hz, 2H), 8.56 (s, 1H), 8.12-8.04 (m, 2H), 7.39 (d, J = 7.8 Hz, 1H), 6.94 (s, 1H), 4.02-3.94 (m, 2H), 3.53 (d, J = 7.3 Hz, 2H), 3.44 (t, J = 11.5 Hz, 2H), 2.92-2.82 (m, 1H), 2.49 (s, 3H), 2.16-2.04 (m, 1H), 1.80 (d, J = 13.1 Hz, 2H), 1.53-1.38 (m, 2H), 0.87-0.79 (m, 2H), 0.67-0.60 (m, 2H). |
| | C151<br>[C27H31N7O2 + H]+<br>486.3 486.2;<br>free base;<br>100% at 254 nm | (400 MHz, CD3OD) δ ppm 8.47 (s, 1H), 8.05 (s, 1H), 7.96-7.91 (m, 1H), 7.54 (d, J = 2.0 Hz, 1H), 7.36 (d, J = 8.0 Hz, 1H), 6.94 (d, J = 2.3 Hz, 1H), 6.52 (s, 1H), 4.38 (s, 3H), 4.02-3.92 (m, 2H), 3.50-3.39 (m, 4H), 2.90-2.82 (m, 1H), 2.46 (s, 3H), 2.11-1.99 (m, 1H), 1.82-1.73 (m, 2H), 1.50-1.36 (m, 2H), 0.86-0.77 (m, 2H), 0.67-0.59 (m, 2H). |

| Structure | Example number MS calcd; MS ESI [M + H]+ Salt Form; HPLC purity | 1H NMR |
|---|---|---|
| 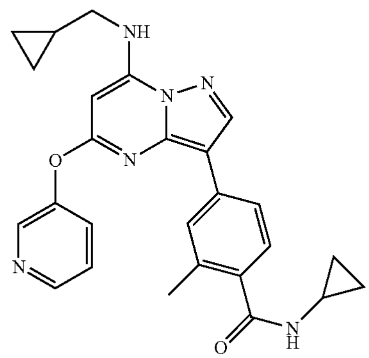 [SMILES: Cc1cc(-c2cnn3c(NCC4CC4)cc(Oc4cccnc4)nc23)ccc1C(=O)NC1CC1] | C152<br>[C26H26N6O2 + H]+<br>455.2 455.2;<br>HCl salt;<br>95.9% at 254 nm | (400 MHz, CD3OD) δ ppm 9.10 (s, 1H), 8.82 (d, J = 6.0 Hz, 1H), 8.73-8.66 (m, 1H), 8.41 (s, 1H), 8.24-8.15 (m, 1H), 7.69 (s, 1H), 7.60 (d, J = 8.3 Hz, 1H), 7.23 (d, J = 8.0 Hz, 1H), 6.07 (s, 1H), 3.39 (d, J = 7.0 Hz, 2H), 2.89-2.78 (m, 1H), 2.29 (s, 3H), 1.37-1.23 (m, 1H), 0.86-0.75 (m, 2H), 0.70-0.56 (m, 4H), 0.45-0.38 (m, 2H). |
| 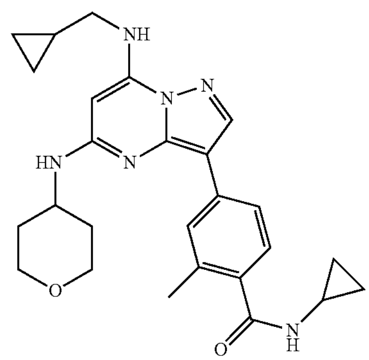 [SMILES: Cc1cc(-c2cnn3c(NCC4CC4)cc(NC4CCOCC4)nc23)ccc1C(=O)NC1CC1] | C153<br>[C26H32N6O2 + H]+<br>461.3 461.3;<br>TFA salt;<br>96.4% at 254 nm | (400 MHz, CD3OD) δ ppm 8.20 (s, 1H), 7.70-7.60 (m, 1H), 7.59-7.49 (m, 1H), 7.42-7.36 (m, 1H), 5.59-5.51 (m, 1H), 4.11-3.94 (m, 3H), 3.61 (t, J = 10.8 Hz, 2H), 3.42-3.34 (m, 2H), 2.91-2.83 (m, 1H), 2.46 (s, 3H), 2.12-2.03 (m, 2H), 1.70-1.56 (m, 2H), 1.31-1.21 (m, 1H), 0.87-0.79 (m, 2H), 0.69-0.59 (m, 4H), 0.43-0.36 (m, 2H). |
| 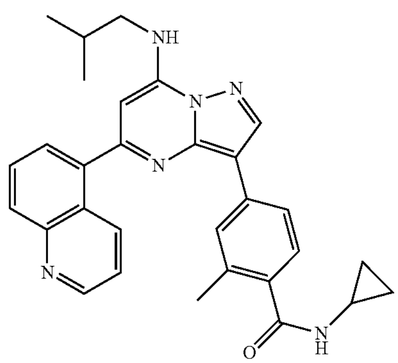 [SMILES: Cc1cc(-c2cnn3c(NCC(C)C)cc(-c4cccc5ncccc45)nc23)ccc1C(=O)NC1CC1] | C154<br>[C30H30N6O + H]+<br>491.2 491.2;<br>TFA salt;<br>99.3% at 254 nm | (400 MHz, CD3OD) δ ppm 9.38 (d, J = 9.5 Hz, 1H), 9.09-9.02 (m, 1H), 8.55 (s, 1H), 8.23 (d, J = 8.5 Hz, 1H), 8.12-7.99 (m, 3H), 7.96-7.89 (m, 1H), 7.84-7.76 (m, 1H), 7.29 (d, J = 8.0 Hz, 1H), 6.56 (s, 1H), 3.39 (d, J = 7.3 Hz, 3H), 2.88-2.79 (m, 1H), 2.38 (s, 3H), 2.19-2.06 (m, 1H), 1.07 (d, J = 6.8 Hz, 6H), 0.84-0.74 (m, 2H), 0.64-0.54 (m, 2H). |
| 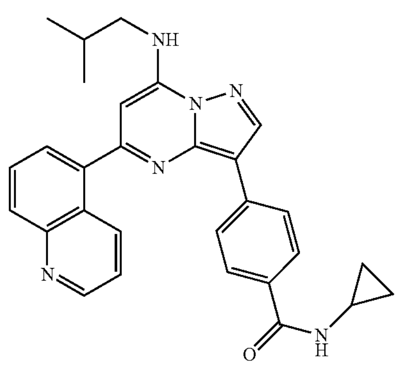 [SMILES: CC(C)CNc1cc(-c2cccc3ncccc23)nc2c(-c3ccc(C(=O)NC4CC4)cc3)cnn12] | C155<br>[C29H28N6O + H]+<br>477.2 477.2;<br>TFA salt;<br>96.2% at 254 nm | (400 MHz, CD3OD) δ ppm 9.67 (d, J = 8.8 Hz, 1H), 9.22-9.18 (m, 1H), 8.61 (s, 1H), 8.34-8.29 (m, 1H), 8.26-8.19 (m, 2H), 8.18-8.13 (m, 2H), 8.04-7.97 (m, 1H), 7.78 (d, J = 8.5 Hz, 2H), 6.63 (s, 1H), 3.41 (d, J = 7.0 Hz, 2H), 2.87-2.79 (m, 1H), 2.19-2.07 (m, 1H), 1.07 (d, J = 6.5 Hz, 6H), 0.84-0.76 (m, 2H), 0.66-0.59 (m, 2H). |

| Structure | Example number MS calcd; MS ESI [M + H]+ Salt Form; HPLC purity | 1H NMR |
|---|---|---|
| | C156 [C27H34N6O3 + H]+ 491.3 491.2; HCl salt 96.2% at 254 nm | (400 MHz, CD3OD) δ ppm 8.20 (s, 1H), 7.49-7.38 (m, 3H), 5.63 (s, 1H), 4.16-4.07 (m, 1H), 4.04-3.92 (m, 3H), 3.67-3.56 (m, 4H), 2.92-2.83 (m, 1H), 2.47 (s, 5H), 2.31-2.16 (m, 1H), 2.11-2.00 (m, 2H), 1.80-1.57 (m, 4H), 0.86-0.78 (m, 2H), 0.66-0.59 (m, 2H). |
| | C157 [C27H36N6O2 + H]+ 477.3 477.3; HCl salt 100% at 254 nm | (400 MHz, CD3OD) δ ppm 8.20 (s, 1H), 7.53-7.33 (m, 3H), 5.78-5.50 (m, 1H), 3.98 (s, 2H), 3.48-3.33 (m, 2H), 2.93-2.82 (m, 1H), 2.47 (s, 3H), 2.20-2.03 (m, 1H), 1.74 (br, s, 6H), 1.62-1.39 (m, 2H), 1.05 (d, J = 5.5 Hz, 6H), 0.82 (d, J = 6.3 Hz, 2H), 0.63 (d, J = 2.3 Hz, 2H). |
| | C158 [C26H36N6O2 + H]+ 465.3 465.4; HCl salt 100% at 254 nm | (400 MHz, CD3OD) δ ppm 8.20 (s, 1H), 7.51-7.38 (m, 3H), 5.67 (br, s, 1H), 3.93-3.57 (m, 3H), 2.91-2.83 (m, 1H), 2.47 (s, 3H), 2.16-1.99 (m, 2H), 1.12-1.00 (m, 12H), 0.86-0.78 (m, 2H), 0.66-0.56 (m, 2H). |
| | C159 [C27H28N6O3 + H]+ 485.2 485.2; HCl salt 98.6% at 254 nm | (400 MHz, CD3OD) δ ppm 9.14 (s, 1H), 8.85 (d, J = 5.5 Hz, 1H), 8.79-8.72 (m, 1H), 8.40 (s, 1H), 8.30-8.21 (m, 1H), 7.68 (s, 1H), 7.59 (d, J = 7.8 Hz, 1H), 7.23 (d, J = 8.0 Hz, 1H), 6.06 (s, 1H), 4.17-4.06 (m, 1H), 3.54 (d, J = 6.5 Hz, 2H), 2.88-2.78 (m, 1H), 2.53-2.43 (m, 1H), 2.29 (s, 4H), 1.81-1.68 (m, 2H), 0.84-0.77 (m, 2H), 0.62-0.56 (m, 2H). |

| Structure | Example number MS calcd; MS ESI [M + H]+ Salt Form; HPLC purity | 1H NMR |
|---|---|---|
| 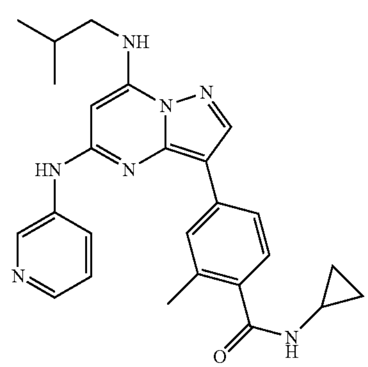 [SMILES: Cc1cc(-c2cnn3c(NCC(C)C)cc(Nc4cccnc4)nc23)ccc1C(=O)NC1CC1] | C160 [C26H29N7O + H]+ 456.2 457.2; HCl salt; 98.8% at 254 nm | (400 MHz, CD3OD) δ ppm 9.70 (s, 1H), 8.65 (d, J = 8.3 Hz, 1H), 8.42-8.34 (m, 1H), 8.31 (s, 1H), 8.02-7.93 (m, 1H), 7.88-7.77 (m, 2H), 7.43 (d, J = 8.3 Hz, 1H), 3.24 (d, J = 6.8 Hz, 2H), 2.94-2.84 (m, 1H), 2.47 (s, 3H), 2.17-2.02 (m, 1H), 1.06 (d, J = 6.8 Hz, 6H), 0.90-0.80 (m, 2H), 0.70-0.60 (m, 2H). |
| 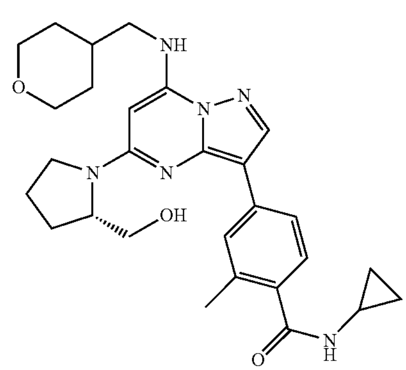 [SMILES: Cc1cc(-c2cnn3c(NCC4CCOCC4)cc(N4CCC[C@H]4CO)nc23)ccc1C(=O)NC1CC1] | C161 [C28H36N6O3 + H]+ 505.3 505.3; HCl salt; 95.5% at 254 nm | (400 MHz, CD3OD) δ ppm 8.24 (s, 1H), 7.52-7.36 (m, 3H), 5.52 (br, s, 1H), 4.31 (br, s, 1H), 4.02-3.93 (m, 2H), 3.89-3.81 (m, 1H), 3.80-3.65 (m, 3H), 3.53-3.38 (m, 4H), 2.91-2.82 (m, 1H), 2.45 (s, 3H), 2.33-2.20 (m, 1H), 2.18-2.02 (m, 3H), 1.97-1.88 (m, 1H), 1.79-1.69 (m, 2H), 1.50-1.37 (m, 2H), 0.87-0.78 (m, 2H), 0.66-0.57 (m, 2H). |
| 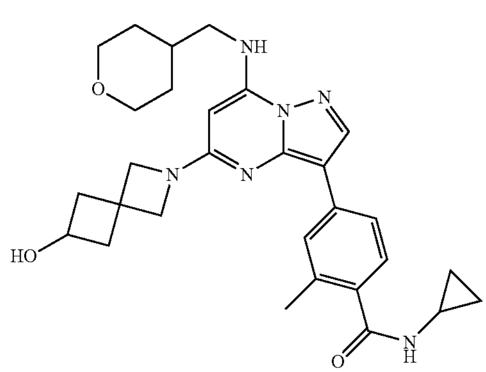 [SMILES: Cc1cc(-c2cnn3c(NCC4CCOCC4)cc(N4CC5(CC(O)C5)C4)nc23)ccc1C(=O)NC1CC1] | C162 [C29H36N6O3 + H]+ 517.3 517.3; free base; 96.2% at 254 nm | (400 MHz, CD3OD) δ ppm 8.20 (s, 1H), 7.94 (s, 1H), 7.89 (d, J = 8.0 Hz, 1H), 7.30 (d, J = 8.0 Hz, 1H), 5.15 (s, 1H), 4.14-4.03 (m, 4H), 4.01-3.92 (m, 2H), 3.50-3.39 (m, 3H), 3.27 (s, 2H), 2.89-2.80 (m, 1H), 2.65-2.54 (m, 2H), 2.44 (s, 3H), 2.22-2.11 (m, 2H), 2.05-1.93 (m, 1H), 1.80-1.70 (m, 2H), 1.47-1.32 (m, 2H), 0.85-0.76 (m, 2H), 0.66-0.57 (m, 2H). |
| 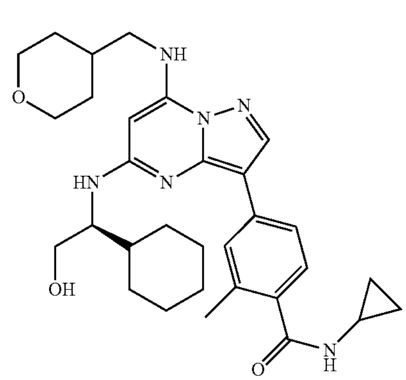 [SMILES: Cc1cc(-c2cnn3c(NCC4CCOCC4)cc(N[C@H](CO)C4CCCCC4)nc23)ccc1C(=O)NC1CC1] | C163 [C31H42N6O3 + H]+ 547.3; 547.3 HCl salt; 97.9% at 254 nm | (400 MHz, CD3OD) δ ppm 8.20 (s, 1H), 7.55-7.32 (m, 3H), 5.68 (br, s, 1H), 3.97 (d, J = 11.5 Hz, 2H), 3.90-3.51 (m, 3H), 3.42 (t, J = 11.2 Hz, 4H), 2.93-2.78 (m, 1H), 2.46 (s, 3H), 2.15-1.97 (m, 1 H), 1.93-1.63 (m, 8H), 1.50-1.07 (m, 7H), 0.86-0.77 (m, 2H), 0.69-0.55 (m, 2 H). |

| Structure | Example number<br>MS calcd;<br>MS ESI [M + H]+<br>Salt Form;<br>HPLC purity | 1H NMR |
|---|---|---|
| | C164<br>[C28H36N6O3 + H]+<br>505.3; 505.3;<br>HCl salt;<br>99.4% at 254 nm | (400 MHz, CD3OD) δ ppm 8.20 (s, 1H), 7.97 (s, 1H), 7.85 (s, 1H), 7.31 (d, J = 8.0 Hz, 1H), 5.35 (s, 1H), 4.44-4.29 (m, 1H), 3.97 (dd, J = 11.3, 3.8 Hz, 2H), 3.86-3.77 (m, 1H), 3.76-3.58 (m, 2H), 3.53-3.38 (m, 3H), 3.28 (d, J = 7.0 Hz, 2H), 2.90-2.79 (m, 1H), 2.44 (s, 3H), 2.21-1.91 (m, 5H), 1.76 (d, J = 12.5 Hz, 2H), 1.49-1.32 (m, 2H), 0.81 (dd, J = 7.0, 1.8 Hz, 2H), 0.62 (dd, J = 4.0, 2.0 Hz, 2H). |
| | C165<br>[C30H40N6O3 + H]+<br>533.3; 534.3;<br>HCl salt;<br>96.0% at 254 nm | (400 MHz, CD3OD) δ ppm 8.20 (s, 1H), 7.58-7.24 (m, 3H), 5.68 (br, s, 1H), 4.10-3.60 (m, 5H), 3.45-3.38 (m, 4H), 2.87 (br, s, 1 H), 2.46 (s, 3H), 2.31-1.99 (m, 2H), 1.98-1.83 (m, 2H), 1.80-1.54 (m, 6H), 1.50-1.25 (m, 4H), 0.82 (d, J = 6.0 Hz, 2H), 0.62 (br, s, 2H). |
| | C166<br>[C28H36N6O3 + H]+<br>505.3; 505.3;<br>HCl salt;<br>99.4 % at 254 nm | (400 MHz, CD3OD) δ ppm 8.21 (s, 1H), 8.06-7.82 (m, 2 H), 7.30 (d, J = 7.8 Hz, 1H), 5.25 (s, 1H), 3.97 (d, J = 7.5 Hz, 2H), 3.84-3.51 (m, 5H), 3.43 (t, J = 11.4 Hz, 2H), 3.26 (d, J = 6.5 Hz, 2H), 2.94-2.77 (m, 1H), 2.62-2.50 (m, 1H), 2.44 (s, 3H), 2.23-2.09 (m, 1H), 2.08-1.94 (m, 1H), 1.89-1.81 (m, 1H), 1.76 (d, J = 12.5 Hz, 2H), 1.48-1.31 (m, 2H), 0.88-0.73 (m, 2H), 0.68-0.52 (m, 2H). |
| | C167<br>[C28H36N6O3 + H]+<br>505.3; 505.3;<br>HCl salt;<br>97.7% at 254 nm | (400 MHz, CD3OD) δ ppm 8.21 (s, 1H), 8.06-7.82 (m, 2 H), 7.30 (d, J = 7.8 Hz, 1H), 5.25 (s, 1H), 3.97 (d, J = 7.5 Hz, 2H), 3.84-3.51 (m, 5H), 3.43 (t, J = 11.4 Hz, 2H), 3.26 (d, J = 6.5 Hz, 2H), 2.94-2.77 (m, 1H), 2.62-2.50 (m, 1H), 2.44 (s, 3H), 2.23-2.09 (m, 1H), 2.08-1.94 (m, 1H), 1.89-1.81 (m, 1H), 1.76 (d, J = 12.5 Hz, 2H), 1.48-1.31 (m, 2H), 0.88-0.73 (m, 2H), 0.68-0.52 (m, 2H). |

| Structure | Example number<br>MS calcd;<br>MS ESI [M + H]+<br>Salt Form;<br>HPLC purity | 1H NMR |
|---|---|---|
| | C168<br>[C29H39N7O2 + H]+<br>518.3; 518.4;<br>di-HCl salt;<br>99.0% at 254 nm | (400 MHz, CD3OD) δ ppm 8.22 (s, 1H), 7.65-7.20 (m, 3H), 6.24-5.48 (m, 2H), 4.46-4.28 (m, 1H), 4.19-3.96 (m, 2H), 3.94-3.62 (m, 1H), 3.59-3.38 (m, 4H), 3.25-3.08 (m, 1H), 2.87 (br, s, 1H), 2.47 (s, 3H), 2.19 (br, s, 4H), 2.00-1.45 (m, 7H), 0.97-0.74 (m, 2H), 0.71-0.50 (m, 2H). |
| | C169<br>[C28H36FN7O + H]+<br>506.3; 506.4;<br>di-HCl salt;<br>98.0% at 254 nm | (400 MHz, CD3OD) δ ppm 8.22 (br, s, 1H), 7.57-7.33 (m, 3H), 5.76 (br, s., 1H), 4.34-4.12 (m, 1H), 4.05-3.79 (m, 2H), 3.53-3.37 (m, 2H), 3.28-3.15 (m, 2H), 2.94-2.81 (m, 1H), 2.47 (s, 3H), 2.35-1.98 (m, 6H), 1.91-1.57 (m, 6H), 0.82 (m, J = 6.3 Hz, 2H), 0.68-0.54 (m, 2H). |
| | C170<br>[C29H38FN7O + H]+<br>520.3; 520.4;<br>di-HCl salt;<br>98.0% at 254 nm | (400 MHz, CD3OD) δ ppm 8.23 (s, 1H), 7.53-7.33 (m, 3H), 5.75 (br, s, 1H), 4.34-4.11 (m, 1H), 4.03-3.80 (m, 2H), 3.64-3.44 (m, 3H), 3.00-2.79 (m, 4H), 2.47 (s, 3H), 2.39-2.06 (m, 6H), 1.92-1.55 (m, 7H), 0.88-0.76 (m, 2H), 0.62 (m, J = 1.8 Hz, 2H). |

-continued

| Structure | Example number<br>MS calcd;<br>MS ESI [M + H]+<br>Salt Form;<br>HPLC purity | ¹H NMR |
|---|---|---|
| | C171<br>[C$_{27}$H$_{34}$N$_6$O$_2$ + H]+<br>475.3; 475.4;<br>HCl salt;<br>98.0% at 254 nm | (400 MHz, CD$_3$OD) δ ppm 8.16 (s, 1H), 8.08 (s, 1H), 7.89 (dd, J = 8.2, 1.6 Hz, 1H), 7.29 (d, J = 8.0 Hz, 1H), 5.30 (s, 1H), 4.42-4.25 (m, 1H), 4.15-4.02 (m, 1H), 2.86-2.83 (m, J = 7.4 Hz, 1H), 2.51-2.45 (m, 2H), 2.44 (s, 3H), 2.22-2.04 (m, 3H), 1.83-1.51 (m, 8H), 0.87-0.76 (m, 2H), 0.68-0.55 (m, 2H). |
| | C172<br>[C$_{27}$H$_{34}$N$_6$O$_2$ + H]+<br>475.3; 475.4;<br>HCl salt;<br>97.5% at 254 nm | (400 MHz, CD$_3$OD) δ ppm 8.18 (s, 1H ), 7.55-7.29 (m, 3H), 5.54 (br, s, 1H), 4.50-4.37 (m, 1H), 4.26-4.07 (m, 1H), 3.62 (d, J = 6.8 Hz, 2H), 2.92-2.83 (m, 1H), 2.75-2.61 (m, 1H), 2.46 (s, 3H), 2.31-2.02 (m, 6H), 1.92-1.56 (m, 6H), 0.91-0.75 (m, 2H), 0.71-0.52 (m, 2H). |
| | C173<br>[C$_{28}$H$_{35}$FN$_6$O$_2$ + H]+<br>507.3; 507.4;<br>HCl salt;<br>98.0% at 254 nm | (400 MHz, CD$_3$OD) δ ppm 8.33 (s, 1H), 7.80-7.52 (m, 2H), 7.39 (br, s, 1H), 5.49 (br, s, 1H), 4.10-3.80 (m, 2H), 3.53-3.38 (m, 3H), 3.28-3.05 (m, 2H), 2.88 (br, s, 1H), 2.45 (s, 3H), 2.33-1.57 (m, 12H), 0.92-0.75 (m, 2H), 0.70-0.50 (m, 2H). |
| | C174<br>[C$_{29}$H$_{37}$FN$_6$O$_2$ + H]+<br>521.3; 521.5;<br>HCl salt;<br>98.0% at 254 nm | (400 MHz, CD$_3$OD) δ ppm 8.33 (s, 1H), 7.86 (br, s, 1H), 7.76 (d, J = 5.8 Hz, 1H), 7.34 (d, J = 7.5 Hz, 1H), 5.86 (br, s, 1H), 5.50 (br, s, 1H), 3.81 (d, J = 19.8 Hz, 2H), 3.64-3.38 (m, 2H), 3.25-3.13 (m, 2H), 2.99-2.72 (m, 5H), 2.44 (s, 3H), 2.34-2.00 (m, 6H), 1.98-1.56 (m, 6H), 0.92-0.72 (m, 2H), 0.67-0.44 (m, 2H). |

| Structure | Example number<br>MS calcd;<br>MS ESI [M + H]+<br>Salt Form;<br>HPLC purity | 1H NMR |
|---|---|---|
| | C175<br>[C29H38N6O3 + H]+<br>519.3; 519.3<br>TFA salt;<br>96.6% at 254 nm | (400 MHz, CD3OD) δ ppm 8.21 (s, 1H), 7.54-7.38 (m, 3H), 5.57 (s, 1H), 4.00-3.86 (m, 3H), 3.81-3.55 (m, 4H), 3.44 (d, J = 7.0 Hz, 2H), 2.93-2.82 (m, 1H), 2.48 (s, 3H), 2.15-1.49 (m, 13H), 0.91-0.78 (m, 2H), 0.69-0.52 (m, 2H). |
| | C176<br>[C29H32N6O3 + H]+<br>513.3; 513.2<br>TFA salt;<br>98.6% at 254 nm | (400 MHz, CD3OD) δ ppm 8.91 (d, J = 2.0 Hz, 1H), 8.71 (d, J = 5.3 Hz, 1H), 8.44-8.32 (m, 2H), 8.06-7.91 (m, 1H), 7.70 (s, 1H), 7.58 (d, J = 8.3 Hz, 1H), 7.21 (d, J = 8.0 Hz, 1H), 5.98 (s, 1H), 4.01-3.84 (m, 1H), 3.38 (d, J = 7.0 Hz, 2H), 2.88-2.79 (m, 1H), 2.28 (s, 3H), 1.96-1.51 (m, 9H), 0.84-0.76 (m, 2H), 0.64-0.58 (m, 2H). |
| | C177<br>[C29H32N6O3 + H]+<br>513.3; 513.2<br>HCl salt;<br>99.8% at 254 nm | (400 MHz, CD3OD) δ ppm 9.05-8.87 (m, 1H), 8.74 (d, J = 5.5 Hz, 1H), 8.42-8.51 (m, 1H), 8.39 (s, 1H), 8.09-8.00 (m, 1H), 7.70 (s, 1H), 7.59 (d, J = 8.0 Hz, 1H), 7.22 (d, J = 8.0 Hz, 1H), 6.00 (s, 1H), 3.62-3.48 (m, 1H), 3.44-3.33 (m, 2H), 2.87-2.79 (m, 1H), 2.29 (s, 3H), 2.22-2.10 (m, 1H), 2.09-1.49 (m, 4H), 1.40-1.05 (m, 4H), 0.93-0.75 (m. 2H), 0.67-0.53 (m, 2H). |
| | C178<br>[C30H34FN7O2 + H]+<br>544.3; 544.3<br>di-TFA salt;<br>96.5% at 254 nm | (400 MHz, CD3OD) δ ppm 8.38 (s, 1H), 7.85 (s, 1H), 7.64 (dd, J = 7.80, 1.5 Hz, 1H), 7.55-7.45 (m, 1H), 7.21 (d, J = 8.0 Hz, 1H), 7.18-6.97 (m, 3H), 5.92 (s, 1H), 3.62 (t, J = 6.3 Hz, 2H), 2.92 (s, 3H), 2.89 (t, J = 6.0 Hz, 2H), 2.86-2.79 (m, 1H), 2.28 (s, 3H), 0.84-0.78 (m, 2H), 0.64-0.57 (m, 2H); 8H peaks due to the piperazine are either very broad or obscured by the peaks due the solvent and H2O at 3.33 ppm and/or 4.88 pm. |

-continued

| Structure | Example number<br>MS calcd;<br>MS ESI [M + H]+<br>Salt Form;<br>HPLC purity | 1H NMR |
|---|---|---|
| 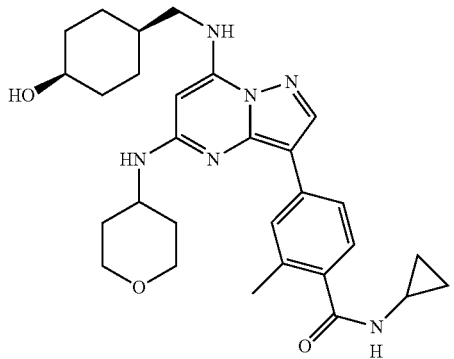 | C179<br>[C29H38N6O3 + H]+<br>519.3; 519.3<br>TFA salt;<br>99.4% at 254 nm | (400 MHz, CD3OD) δ ppm 8.20 (s, 1H), 7.64-7.47 (m, 2H), 7.41 (d, J = 8.3 Hz, 1H), 5.58 (s, 1H), 4.10-3.92 (m, 4H), 3.70-3.56 (m, 2H), 3.43 (d, J = 6.0 Hz, 2H), 2.95-2.83 (m, 1H), 2.47 (s, 3H), 2.13-2.04 (m, 2H), 1.93-1.74 (m., 3H), 1.72-1.48 (m, 8H), 0.91-0.79 (m, 2H), 0.69-0.57 (m, 2H). |
| 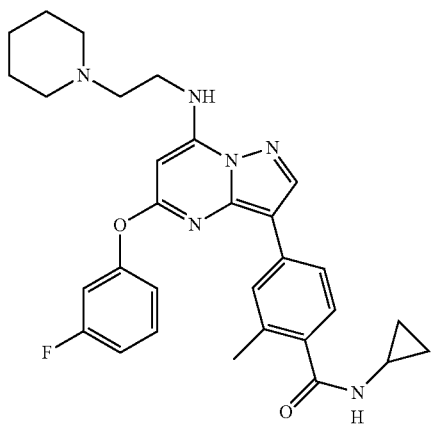 | C180<br>[C30H33FN6O2 + H]+<br>529.3; 529.3<br>TFA salt;<br>97.1% at 254 nm | (400 MHz, CD3OD) δ ppm 8.39 (s, 1H), 7.83 (s, 1H), 7.67-7.58 (m, 1H), 7.56-7.41 (m, 1H), 7.21 (d, J = 8.0 Hz, 1H), 7.16-7.01 (m, 3H), 6.01 (s, 1H), 3.90 (t, J = 6.3 Hz, 2H), 3.74-3.57 (m, 2H), 3.48 (t, J = 6.3 Hz, 2H), 3.11-2.99 (m, 2H), 2.90-2.75 (m, 1H), 2.27 (s, 3H), 2.03-1.92 (m, 2H), 1.92-1.73 (m, 3H), 1.66-1.48 (m, 1H), 0.81 (s, 2H), 0.68-0.52 (m, 2H). |
| 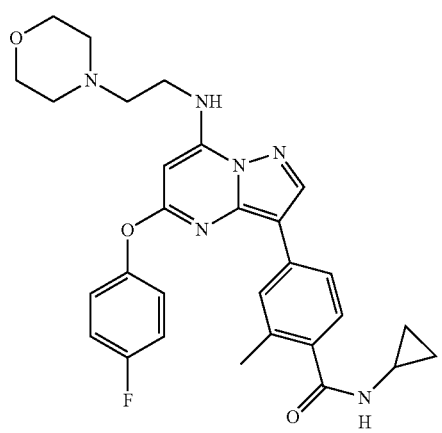 | C181<br>[C29H31FN6O3 + H]+<br>530.2; 530.3<br>TFA salt;<br>97.9% at 254 nm | (400 MHz, CD3OD) δ ppm 8.35 (s, 1H), 7.79 (s, 1H), 7.59 (dd, J = 8.0, 1.8 Hz, 1H), 7.30-7.14 (m, 5H), 5.98 (s, 1H), 4.17-3.98 (br. s., 2H), 3.91 (t, J = 6.3 Hz, 2H), 3.98-3.74 (br.s., 2H), 3.55 (t, J = 6.2 Hz, 3H), 3.74-3.45 (br.s, 2H) 3.40-3.15 (br.s. 2H), 2.87-2.80 (m, 1H), 2.26 (s, 3H), 0.85-0.77 (m, 2H), 0.66-0.54 (m, 2H). |

| Structure | Example number<br>MS calcd;<br>MS ESI [M + H]+<br>Salt Form;<br>HPLC purity | ¹H NMR |
|---|---|---|
| (structure) | C182<br>[C$_{30}$H$_{33}$FN$_6$O$_3$ + H]+<br>545.3 545.3;<br>TFA salt;<br>98.5% at 254 nm | (400 MHz, CD$_3$OD) δ ppm 8.36 (s, 1H), 7.82 (s, 1H), 7.60 (d, J = 9.3 Hz, 1H), 7.53-7.41 (m, 1H), 7.20 (d, J = 8.0 Hz, 1H), 7.16-7.02 (m, 3H), 5.98 (s, 1H), 4.18-4.05 (m, 0.5H), 3.89 (br. s., 2.5H), 3.79-3.65 (m, 1H), 3.49 (br. s., 3H), 3.45-3.34 (m, 1H), 3.21-3.07 (m, 1H), 2.88-2.77 (m, 1H), 2.27 (s, 3H), 2.23-1.67 (m, 4H), 0.85-0.77 (m, 2H), 0.66-0.55 (m, 2H). |
| (structure) | C183<br>[C$_{30}$H$_{41}$N$_7$O$_3$ + H]+<br>548.3; 548.4<br>TFA salt;<br>98.3% at 254 nm | (400 MHz, CD$_3$OD) δ ppm 8.22 (s, 1H), 7.60-7.35 (m, 3H), 5.79 (s, 1H), 4.14-3.93 (m, 4H), 3.92-3.63 (m, 2H), 3.60-3.49 (m, 3H), 3.48-3.37 (m, 1H), 3.23-3.07 (m, 1H), 2.87 (s, 1H), 2.48 (s, 3H), 2.25-1.39 (m, 12H), 0.88-0.79 (m, 2H), 0.68-0.61 (m, 2H). |
| (structure) | C184<br>[C$_{29}$H$_{37}$F$_2$N$_7$O + H]+<br>538.3; 538.4<br>TFA salt;<br>97.8% at 254 nm | (400 MHz, CD$_3$OD) δ ppm 8.19 (s, 1H), 7.52-7.37 (m, 3H), 5.69 (s, 1H), 4.29-4.20 (m, 1H), 4.10-3.99 (m, 2H), 3.72-3.46 (m, 6H), 2.94-2.80 (m, 1H), 2.46 (s, 3H), 2.44-2.33 (m, 4H), 2.24-2.06 (m, 2H), 1.91-1.58 (m, 6H), 0.89-0.77 (m, 2H), 0.69-0.51 (m, 2H). |

| Structure | Example number<br>MS calcd;<br>MS ESI [M + H]+<br>Salt Form;<br>HPLC purity | 1H NMR |
|---|---|---|
| (structure shown) | C185<br>[C28H32F2N8O2 + H]+<br>551.3; 551.4<br>HCl salt;<br>98.1% at 254 nm | (400 MHz, CD3OD) δ ppm 8.42 (s, 1H), 7.96 (s, 1H), 7.88 (s, 1H), 7.75 (d, J = 7.8 Hz, 1H), 7.66 (s, 1H), 7.32 (d, J = 8.3 Hz, 1H), 6.02 (s, 1H), 4.00-3.91 (m, 5H), 3.85 (br. s., 2H), 3.61 (t, J = 5.9 Hz, 2H), 3.42 (br. s., 2H), 2.93-2.76 (m, 1H), 2.52-2.32 (m, 7H), 0.86-0.75 (m, 2H), 0.69-0.55 (m, 2H). |
| (structure shown) | C186<br>[C28H36N6O2 + H]+<br>489.3; 489.4<br>TFA salt;<br>98.2% at 254 nm | (400 MHz, CD3OD) δ ppm 8.18 (s, 1H), 7.48-7.36 (m, 3H), 5.52 (s, 1H), 4.23-4.10 (m, 1H), 3.65-3.57 (m, 2H), 2.93-2.75 (m, 2H), 2.46 (s, 3H), 2.31-2.21 (m, 2H), 2.20-2.11 (m, 3H), 2.06-1.89 (m, 2H), 1.89-1.50 (m, 6H), 1.37 (s, .3H), 0.87-0.79 (m, 2H), 0.68-0.56 (m, 2H). |
| (structure shown) | C187<br>[C27H29FN6O2 + H]+<br>489.2; 489.2<br>TFA salt;<br>94.0% at 254 nm | (400 MHz, CD3OD) δ ppm 8.39 (s, 1H), 7.83 (d, J = 0.5 Hz, 1H), 7.70-7.59 (m, 1H), 7.55-7.45 (m, 1H), 7.20 (d, J = 8.0 Hz, 1H), 7.15-6.98 (m, 3H), 6.05 (s, 1H), 3.90 (t, J = 6.3 Hz, 2H), 3.54 (t, J = 6.0 Hz, 2H), 3.02 (s, 6H), 2.84 (s, 1H), 2.27 (s, 3H), 0.85-0.75 (m, 2H), 0.66-0.57 (m, 2H). |

Example B

TTK Inhibition Assay

Active TTK was purchased from Invitrogen as an amino terminal GST fusion of full length TTK. Amino terminal 6 histidine, sumo tagged human TTK (residues 1-275) was expressed in *E. coli*, and purified to >95% homogeneity by Ni²⁺ agarose, gel filtration, and ion exchange chromatography.

TTK activity was measured using an indirect ELISA detection system. GST-TTK (0.68 nM) was incubated in the presence of either 16 M ATP (Sigma cat#A7699) or 100 μM ATP, 50 mM Hepes pH 7.2, 1 mM EGTA, 10 mM MgCl₂, and 0.1% Pluronic in a 96 well microtitre plate pre-coated with amino terminal 6 histidine, sumo tagged TTK (amino acid residues 1-275).

The reaction was allowed to proceed for 30 minutes, followed by 5 washes of the plate with Wash Buffer (phosphate buffered saline supplemented with 0.2% Tween 20), and incubation for 30 minutes with a 1:3000 dilution of primary antibody (Cell Signaling cat#9381). The plate was washed 5 times with Wash Buffer, incubated for 30 minutes in the presence of secondary antibody coupled to horse radish peroxidase (BioRad cat#1721019, 1:3000 concentration), washed an additional 5 times with Wash Buffer, and incubated in the presence of TMB substrate (Sigma cat#T0440). The colourimetric reaction was allowed to continue for 5 minutes, followed by addition of stop solution (0.5 N sulphuric acid), and quantified by detection at 450 nm with either a monochromatic or filter based plate reader (Molecular Devices M5 or Beckman DTX880, respectively).

Compound inhibition was determined at either a fixed concentration (10 µM) or at a variable inhibitor concentration (typically 0.5 µM to 0.001 µM in a 10 point dose response titration). Compounds were pre-incubated in the presence of enzyme for 5 minutes prior to addition of ATP and the activity remaining quantified using the above described activity assay. The % Inhibition of a compound was determined using the following formula; % Inhibition=100×(1−(experimental value−background value)/(high activity control−background value)). The $IC_{50}$ value was determined using a non-linear 4 point logistic curve fit (XLfit4, IDBS) with the formula; $(A+(B/(1+((x/C)\hat{}D))))$, where A=background value, B=range, C=inflection point, D=curve fit parameter.

In Table 1 and 2 below, $IC_{50}$ value ranges for compound examples are given using 16 µM ATP (Sigma cat#A7699). The $IC_{50}$ ranges are indicated as "A," "B," and "C," for values less than or equal to 0.1 µM; those greater than 0.1 µM and less than or equal to 0.5 µM; and those greater than 0.5 µM, respectively. $IC_{50}$ ranges denoted with an asterisk indicated that 16 µM ATP (Sigma cat#A7699) was used in the assay.

In Table 3 below, $IC_{50}$ value ranges for exemplary compounds are given using 100 µM ATP. The $IC_{50}$ ranges are indicated as "A," "B," and "C," for values less than or equal to 0.1 µM; those greater than 0.1 µM and less than or equal to 0.5 µM; and those greater than 0.5 µM, respectively. $IC_{50}$ ranges denoted with an asterisk indicated that 16 µM ATP (Sigma cat#A7699) was used in the assay.

Example C

Cancer Cell Line Data on Exemplary Compounds of the Invention

Breast cancer cells (MDA-MB-231 and MDA-MB-468), colon cancer cells (HCT116) and ovarian cancer cells (PA-1 and OVCAR-3) were seeded (1000 to 4000 in 80 µl per well depending on the cell growth rate) into 96 well plates 24 hours before compound overlay. Compounds were prepared as 10 mM stock solutions in 100% DMSO which were diluted with DMEM (Dulbecco's Modified Eagle's Medium) cell growth Medium (Invitrogen, Burlington, ON, Canada) containing 10% FBS (Fetal Bovine Serum) to concentrations ranging from 50 nM to 250 µM. Aliquots (20 µl) from each concentration were overlaid to 80 µl of the pre-seeded cells in the 96 well plates to make final concentrations of 10 nM to 50 µM. The cells were cultured for 5 days before the Sulforhodamine B assay (SRB) was performed to determine the compound's cell growth inhibition activity.

Sulforhodamine B (purchased from Sigma, Oakville, ON, Canada) is a water-soluble dye that binds to the basic amino acids of the cellular proteins. Thus, colorimetric measurement of the bound dye provides an estimate of the total protein mass that is related to the cell number. the cells are fixed in situ by gently aspirating off the culture media and adding 50 µl ice cold 10% Trichloroacetic Acid (TCA) per well and incubate at 4° C. for 30-60 min, The plates are washed with $H_2O$ five times and allowed to air dry for 5 min. Addition of 50 µl 0.4% (w/v) SRB solution in 1% (v/v) acetic acid to each well and incubation for 30 min at RT completes the staining reaction. Following staining, plates are washed four times with 1% acetic acid to remove unbound dye and then allowed to air dry for 5 min. The stain is solubilized with 100 µl of 10 mM Tris pH 10.5 per well. Absorbance is read at 570 nm.

The percentage (%) of relative growth inhibition was calculated by comparing to DMSO treated only cells (100%). $GI_{50}$'s were determined for compounds with cytotoxic activity. The $GI_{50}$ was calculated using GraphPad PRISM software (GraphPad Software, Inc., San Diego, Calif., USA). $GI_{50}$ (growth inhibition) is the compound concentration that causes 50% inhibition of cell growth.

In Table 1 below, $GI_{50}$ value ranges for compound examples against breast cancer cell lines (MDA-MB-468), colon cancer cell lines (HCT116) and ovarian cancer cell lines (PA-1) are given. The example compounds demonstrated varying growth inhibition/cell killing activity against cells of breast cancer, colon cancer, and ovarian cancer. The $GI_{50}$ ranges are indicated as "A," "B," and "C," for values less than or equal to 0.1 µM; those greater than 0.1 µM and less than or equal to 0.5 µM; and those greater than 0.5 µM, respectively.

In Table 2 below, $GI_{50}$ value ranges for compound examples against breast cancer cell lines (MDA-MB-231), colon cancer cell lines (HCT116) and ovarian cancer cell lines (PA-1) are given. The example compounds demonstrated varying growth inhibition/cell killing activity against cells of breast cancer, colon cancer, and ovarian cancer. The $GI_{50}$ ranges are indicated as "A," "B," and "C," for values less than or equal to 0.1 M; those greater than 0.1 M and less than or equal to 0.5 M; and those greater than 0.5 M, respectively.

In Table 3 below, $GI_{50}$ value ranges for compound examples against breast cancer cell lines (MDA-MB-468), colon cancer cell lines (HCT116) and ovarian cancer cell lines (OVCAR-3) are given. The example compounds demonstrated varying growth inhibition/cell killing activity against cells of breast cancer, colon cancer, and ovarian cancer. The $GI_{50}$ ranges are indicated as "A," "B," and "C," for values less than or equal to 0.1 µM; those greater than 0.1 µM and less than or equal to 0.5 µM; and those greater than 0.5 µM, respectively.

Example D

Colon and Ovarian Cancer Tumor-Initiating Cell Data of Exemplary Compounds

Materials and Methods:

Non-tissue or tissue cultured treated T-75 flask and 96-well plates were purchased from VWR. Vitamin B-27 supplement, MEM NEAA (minimum essential medium non essential amino acids), sodium pyruvate, L-glutamine, N2 supplement, penicillin-streptomycin and fungizone/amphotericin B were obtained from Invitrogen. Lipid mixture, heparin and EGF were purchased from Sigma; bFGF from BD Biosciences. Tumor Initiating Cells (TICs) from colon were routinely maintained using non-tissue cultured treated T-75 flasks in DMEM:F12 medium containing 0.2XB-27 supplement, 4 ug/ml heparin, 1×MEM NEAA, 1×sodium pyruvate, 1 mM glutamine, 10 pg/ul bFGF, 20 pg/ul EGF, 1× N2 supplement, lipid mixture, penicillin-streptomycin and fungizone/amphotericin B. Ovarian TICs were routinely maintained using tissue cultured treated T-75 flasks in DMEM:F12 medium containing IXB-27 supplement, 4 ug/ml heparin, 20 pg/ul bFGF, 20 pg/ul EGF and penicillin-streptomycin.

Assay Protocol:

Compounds described herein were dissolved in DMSO and further diluted in cell culture medium for $GI_{50}$ determination. Colon TICs were trypsinized and seeded into non-tissue cultured treated 96-well plates with 4,000 cells/well. After 24 h, compound was added into the cell culture at different concentrations, and the final concentration of DMSO was adjusted to 0.1%. Cells were then cultured at 37° C. for 9 days. Ovarian TICs were trypsinized and seeded into tissue cultured treated 96-well plates with 1,000 cells/well. After 24 h, compound was added into the cell culture at different concentrations, and the final concentration of DMSO was adjusted to 0.1%. Cells were then cultured at 37° C. for 6 days. Cell viability was assessed by Alamar Blue assay: 10 ul of Alamar Blue was added into each well. After 4 hours incubation at 37° C., fluorescence was recorded at excitation 544 and emission 590. $GI_{50}$ (Growth inhibition) was calculated using GraphPad Prism 4.0 software. Cell growth inhibition data for compounds described herein is tabulated below.

In Table 1 below, $GI_{50}$ value ranges for compound examples against TICs (Colon 12 and Ovarian 2393A) are given. The $GI_{50}$ ranges are indicated as "A," "B," and "C," for values less than or equal to 0.1 μM; those greater than 0.1 μM and less than or equal to 0.5 μM; and those greater than 0.5 μM, respectively.

TABLE 1

In vitro activity of Compound Examples

| Example # | TTK $IC_{50}$ Range | Cancer Cell Line $GI_{50}$ Range | | Tumor Initiating Cell $GI_{50}$ Range | |
|---|---|---|---|---|---|
| | | HCT116 | MDA-MB-468 | PA-1 | Ovarian 2393A | Colon 12 |
| A1 | B* | ND | ND | ND | ND | ND |
| A2 | A* | B | B | A | B | A |
| A3 | A* | A | A | A | B | A |
| A4 | A* | B | B | B | B | A |
| A5 | A* | B | C | B | C | B |
| A6 | A* | B | C | A | B | B |
| A7 | A* | C | C | B | C | C |
| A8 | C* | C | C | C | ND | ND |
| A9 | C* | ND | ND | ND | ND | ND |
| A10 | A* | B | C | B | ND | ND |
| A11 | A* | B | C | B | ND | ND |
| A12 | C* | C | C | C | ND | ND |
| A13 | A* | C | C | B | ND | ND |
| A14 | A* | B | C | B | C | C |
| A15 | A* | B | C | B | B | B |

ND—not determined
$IC_{50}$ ranges denoted with an asterisk indicated that 16 μM ATP (Sigma cat# A7699) was used in the assay.

TABLE 2

In vitro activity of Compound Examples

| Example # | TTK $IC_{50}$ Range | Cancer Cell Line $GI_{50}$ Range | | | Tumor Initiating Cell $GI_{50}$ Range | |
|---|---|---|---|---|---|---|
| | | HCT116 | MDA-MB-231 | PA-1 | Ovarian 2393A | Colon 12 |
| B2 | A* | C | C | B | C | B |
| B3 | A* | A | B | A | B | B |
| B1 | A* | A | A | A | A | A |
| B4 | A* | ND | ND | ND | ND | ND |
| B5 | A* | A | A | A | A | A |
| B14 | A* | A | A | A | A | A |
| B15 | C* | ND | ND | ND | ND | ND |
| B6 | A* | B | B | A | B | B |
| B16 | A* | A | A | A | A | A |
| B18 | A* | A | B | A | A | A |
| B7 | A* | A | A | A | A | A |
| B8 | A* | B | B | A | B | B |
| B19 | A* | B | B | A | B | B |
| B20 | A* | A | A | A | A | A |
| B17 | A* | A | A | A | A | A |
| B9 | A* | A | A | A | A | A |
| B10 | A* | B | C | B | ND | ND |
| B11 | A* | B | B | B | ND | ND |
| B12 | A* | A | A | A | A | A |
| B13 | A* | A | A | A | B | A |
| B29 | A* | B | C | B | C | B |
| B21 | A* | A | B | A | ND | ND |
| B22 | A* | A | A | A | ND | ND |
| B25 | A* | A | A | A | ND | ND |
| B23 | A* | B | B | B | ND | ND |
| B26 | A* | A | B | A | ND | ND |
| B24 | A* | A | A | A | ND | ND |
| B31 | A* | A | A | A | ND | ND |
| B30 | A* | ND | ND | ND | ND | ND |
| B27 | A* | ND | ND | ND | ND | ND |
| B28 | A* | ND | ND | ND | ND | ND |
| B32 | A* | ND | ND | ND | ND | ND |
| B33 | A* | ND | ND | ND | ND | ND |

ND—not determined
$IC_{50}$ ranges denoted with an asterisk indicated that 16 μM ATP (Sigma cat# A7699) was used in the assay.

TABLE 3

In vitro activity of Compound Examples

| Example # | TTK $IC_{50}$ Range | Cancer Cell Line $GI_{50}$ Range | | | Tumor Initiating Cell $GI_{50}$ Range | |
|---|---|---|---|---|---|---|
| | | MDA-MB-468 | HCT116 | OVCAR-3 | Ovarian 2393A | Colon 12 |
| C1 | A* | ND | ND | ND | ND | ND |
| C2 | B* | ND | ND | ND | ND | ND |
| C3 | C* | ND | ND | ND | ND | ND |
| C4 | B* | ND | ND | ND | ND | ND |
| C5 | C* | ND | ND | ND | ND | ND |
| C6 | A* | ND | ND | ND | ND | ND |
| C7 | A* | C | C | C | B | B |
| C8 | A* | B | B | B | ND | ND |
| C9 | A* | C | C | B | ND | ND |
| C10 | A* | C | C | C | C | C |
| C11 | A* | C | C | C | B | B |
| C12 | A* | ND | ND | ND | ND | ND |
| C13 | A* | B | B | C | ND | ND |
| C14 | A* | A | A | A | A | A |
| C15 | A* | ND | ND | ND | ND | ND |
| C16 | A* | ND | ND | ND | ND | ND |
| C17 | C* | ND | ND | ND | ND | ND |
| C18 | C* | ND | ND | ND | ND | ND |
| C19 | A* | B | C | C | ND | ND |
| C20 | A* | B | A | B | B | A |
| C21 | A* | A | A | A | A | A |
| C22 | A* | B | B | B | ND | ND |
| C23 | A* | C | B | C | ND | ND |

TABLE 3-continued

In vitro activity of Compound Examples

| Example # | TTK IC$_{50}$ Range | Cancer Cell Line GI$_{50}$ Range | | | Tumor Initiating Cell GI$_{50}$ Range | |
|---|---|---|---|---|---|---|
| | | MDA-MB-468 | HCT116 | OVCAR-3 | Ovarian 2393A | Colon 12 |
| C24 | A* | A | A | A | A | A |
| C25 | A* | B | A | B | B | A |
| C26 | A* | B | A | B | A | A |
| C27 | A* | B | A | B | ND | ND |
| C28 | A | A | A | A | A | A |
| C29 | A | ND | ND | ND | ND | ND |
| C30 | A | C | C | C | ND | ND |
| C31 | A | A | A | A | A | A |
| C32 | A | A | A | A | A | A |
| C33 | A | A | A | A | ND | ND |
| C34 | A | A | A | A | ND | ND |
| C35 | A | A | A | A | ND | ND |
| C36 | A | A | A | A | ND | ND |
| C37 | A | A | A | A | A | A |
| C38 | A | A | A | A | A | A |
| C39 | A | A | A | A | A | A |
| C40 | A | A | A | B | B | A |
| C41 | A | A | A | A | B | A |
| C42 | A | A | A | A | A | A |
| C43 | A | A | A | A | ND | ND |
| C44 | A | A | A | A | ND | ND |
| C45 | A | A | A | A | B | A |
| C46 | A | A | A | B | A | A |
| C47 | A | A | A | A | ND | ND |
| C48 | A | B | B | B | B | B |
| C49 | A | B | B | B | ND | ND |
| C50 | C | ND | ND | ND | ND | ND |
| C51 | A | B | B | B | ND | ND |
| C52 | A | B | B | C | ND | ND |
| C53 | A | ND | ND | ND | ND | ND |
| C54 | A | B | B | B | ND | ND |
| C55 | A | B | A | B | ND | ND |
| C56 | A | A | A | A | ND | ND |
| C57 | A | B | B | B | ND | ND |
| C58 | A | B | A | B | ND | ND |
| C59 | A | B | B | B | ND | ND |
| C60 | A | ND | ND | ND | ND | ND |
| C61 | A | A | A | A | ND | ND |
| C62 | A | B | B | B | ND | ND |
| C63 | A | ND | ND | ND | ND | ND |
| C64 | A | ND | ND | ND | ND | ND |
| C65 | A | ND | ND | ND | ND | ND |
| C66 | A | B | B | B | ND | ND |
| C67 | A | ND | ND | ND | ND | ND |
| C68 | A | B | C | B | ND | ND |
| C69 | B | ND | ND | ND | ND | ND |
| C70 | A | ND | ND | ND | ND | ND |
| C71 | A | B | B | C | ND | ND |
| C72 | A | A | A | B | ND | ND |
| C73 | A | ND | ND | ND | ND | ND |
| C74 | A | B | B | C | ND | ND |
| C75 | A | ND | ND | ND | ND | ND |
| C76 | A | ND | ND | ND | ND | ND |
| C77 | A | B | B | B | ND | ND |
| C78 | A | B | B | B | ND | ND |
| C79 | A | C | C | C | ND | ND |
| C80 | A | ND | ND | ND | ND | ND |
| C81 | A | ND | ND | ND | ND | ND |
| C82 | A | B | B | B | ND | ND |
| C83 | A | B | A | B | ND | ND |
| C84 | A | ND | ND | ND | ND | ND |
| C85 | A | B | B | B | ND | ND |
| C86 | B | ND | ND | ND | ND | ND |
| C87 | A | B | B | C | ND | ND |
| C88 | A | B | C | C | ND | ND |
| C89 | A | C | B | C | ND | ND |
| C90 | A | B | B | C | ND | ND |
| C91 | A | ND | ND | ND | ND | ND |
| C92 | A | C | B | C | ND | ND |
| C93 | A | ND | ND | ND | ND | ND |
| C94 | A | C | C | C | ND | ND |
| C95 | A | C | B | C | ND | ND |
| C96 | A | C | C | C | ND | ND |
| C97 | A | B | A | B | ND | ND |
| C98 | A | C | B | C | ND | ND |
| C99 | A | C | B | C | ND | ND |
| C100 | A | B | B | B | A | A |
| C101 | B | ND | ND | ND | ND | ND |
| C102 | A | ND | ND | ND | ND | ND |
| C103 | A | B | A | B | ND | ND |
| C104 | A | B | A | B | ND | ND |
| C105 | A | A | A | A | ND | ND |
| C106 | B | ND | ND | ND | ND | ND |
| C107 | A | B | B | C | ND | ND |
| C108 | A | B | A | B | ND | ND |
| C109 | A | B | A | B | ND | ND |
| C110 | A | ND | ND | ND | ND | ND |
| C111 | A | B | B | B | ND | ND |
| C112 | A | ND | ND | ND | ND | ND |
| C113 | A | B | B | B | ND | ND |
| C114 | A | C | C | C | ND | ND |
| C115 | A | ND | ND | ND | ND | ND |
| C116 | A | B | A | B | B | B |
| C117 | A | ND | ND | ND | ND | ND |
| C118 | A | B | A | B | B | B |
| C119 | A | ND | ND | ND | ND | ND |
| C120 | A | B | B | C | C | C |
| C121 | A | B | B | C | ND | ND |
| C122 | A | ND | ND | ND | ND | ND |
| C123 | A | A | A | B | ND | ND |
| C124 | A | B | B | B | ND | ND |
| C125 | A | A | A | B | ND | ND |
| C126 | A | A | A | A | ND | ND |
| C127 | A | B | A | B | ND | ND |
| C128 | A | ND | ND | ND | ND | ND |
| C129 | A | ND | ND | ND | ND | ND |
| C130 | A | B | A | B | A | A |
| C131 | A | B | B | C | ND | ND |
| C132 | A | B | C | C | ND | ND |
| C133 | A | B | B | B | ND | ND |
| C134 | A | B | B | B | ND | ND |
| C135 | A | A | A | B | ND | ND |
| C136 | A | A | A | B | ND | ND |
| C137 | A | ND | ND | ND | ND | ND |
| C138 | A | B | A | B | ND | ND |
| C139 | A | B | B | B | ND | ND |
| C140 | A | ND | ND | ND | ND | ND |
| C141 | A | B | A | B | ND | ND |
| C142 | B | ND | ND | ND | ND | ND |
| C143 | B | C | C | C | ND | ND |
| C144 | A | A | A | A | A | A |
| C145 | A | B | B | B | B | B |
| C146 | A | A | A | B | A | A |
| C147 | A | B | B | C | ND | ND |
| C148 | A | B | B | C | ND | ND |
| C149 | B | ND | ND | ND | ND | ND |
| C150 | A | B | B | B | B | B |
| C151 | A | B | A | B | ND | ND |
| C152 | A | A | A | A | ND | ND |
| C153 | A | B | A | B | ND | ND |
| C154 | B | ND | ND | ND | ND | ND |
| C155 | C | ND | ND | ND | ND | ND |
| C156 | A | B | B | B | ND | ND |
| C157 | A | A | A | A | ND | ND |
| C158 | A | A | A | B | ND | ND |
| C159 | A | A | A | A | ND | ND |
| C160 | A | ND | ND | ND | ND | ND |
| C161 | A | B | A | B | ND | ND |
| C162 | A | ND | ND | ND | ND | ND |
| C163 | A | B | A | B | ND | ND |
| C164 | A | B | B | C | ND | ND |
| C165 | A | B | A | B | B | A |
| C166 | A | ND | ND | ND | ND | ND |
| C167 | A | ND | ND | ND | ND | ND |

TABLE 3-continued

In vitro activity of Compound Examples

| Example # | TTK IC$_{50}$ Range | Cancer Cell Line GI$_{50}$ Range | | | Tumor Initiating Cell GI$_{50}$ Range | |
|---|---|---|---|---|---|---|
| | | MDA-MB-468 | HCT116 | OVCAR-3 | Ovarian 2393A | Colon 12 |
| C168 | A | ND | ND | ND | ND | ND |
| C169 | A | C | B | C | ND | ND |
| C170 | A | B | B | C | ND | ND |
| C171 | A | A | A | B | ND | ND |
| C172 | A | A | A | A | ND | ND |
| C173 | A | C | B | C | ND | ND |
| C174 | A | C | B | C | ND | ND |
| C175 | A | A | A | B | B | B |
| C176 | A | A | A | A | A | A |
| C177 | A | B | B | B | A | A |
| C178 | A | A | A | B | ND | ND |
| C179 | A | A | A | A | ND | ND |
| C180 | A | B | A | B | ND | ND |
| C181 | A | B | A | B | ND | ND |
| C182 | A | A | A | A | A | A |
| C183 | A | B | C | C | ND | ND |
| C184 | A | ND | ND | ND | ND | ND |
| C185 | A | ND | ND | ND | ND | ND |
| C186 | A | B | A | B | ND | ND |
| C187 | A | A | A | B | A | A |

ND—not determined

IC$_{50}$ ranges denoted with an asterisk indicated that 16 μM ATP (Sigma cat# A7699) was used in the assay.

What is claimed is:

1. A compound represented by the following structural formula:

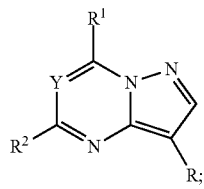

(I-0)

or a pharmaceutically acceptable salt thereof, wherein:
Y is N or CH;
R is phenyl or monocyclic 5-6 membered heteroaryl, both of which are substituted with —C(=O)NR$^d$R$^e$, —NHC(=O)R$^5$, —C(=S)NR$^d$R$^e$, or —NHC(=S)R$^5$ and optionally substituted with one or more groups selected from halogen, hydroxy, (C$_1$-C$_3$)alkyl, (C$_1$-C$_3$)haloalkyl, (C$_1$-C$_3$)alkoxy, and (C$_1$-C$_3$)haloalkoxy;
R$^1$ is —NR$^{a1}$R$^{b1}$, —OR$^{c1}$, —SR$^{c1}$, —SOR$^{c1}$, or —SO$_2$R$^{c1}$;
R$^2$ is —NR$^{a2}$R$^{b2}$, —OR$^{c2}$, —SR$^{c2}$, optionally substituted phenyl or optionally substituted 5-10 membered heteroaryl;
R$^5$ is optionally substituted (C$_1$-C$_3$)alkyl, optionally substituted (C$_3$-C$_7$)cycloalkyl, optionally substituted 3-7 membered monocyclic heterocycloalkyl, optionally substituted phenyl, or optionally substituted 5-6 membered monocyclic heteroaryl;
R$^{a1}$ and R$^{b1}$ are each independently selected from —H, optionally substituted (C$_1$-C$_6$)alkyl, optionally substituted (C$_3$-C$_7$)cycloalkyl, optionally substituted 3-7 membered monocyclic heterocycloalkyl, optionally substituted phenyl, and optionally substituted 5-6 membered monocyclic heteroaryl; or
R$^{a1}$ and R$^{b1}$, together with the nitrogen to which they are attached, form an optionally substituted 3-7 membered ring;
R$^{a2}$ and R$^{b2}$ are each independently selected from —H, optionally substituted (C$_1$-C$_6$)alkyl, optionally substituted (C$_3$-C$_7$)cycloalkyl, optionally substituted 3-7 membered monocyclic heterocycloalkyl, optionally substituted phenyl, and optionally substituted 5-6 membered monocyclic heteroaryl; or
R$^{a2}$ and R$^{b2}$, together with the nitrogen to which they are attached, form an optionally substituted 3-8 membered ring;
R$^{c1}$ is optionally substituted (C$_1$-C$_6$)alkyl, optionally substituted (C$_3$-C$_7$)cycloalkyl, optionally substituted 3-7 membered monocyclic heterocycloalkyl, optionally substituted phenyl, or optionally substituted 5-6 membered monocyclic heteroaryl;
R$^{c2}$ is optionally substituted (C$_1$-C$_6$)alkyl, optionally substituted (C$_3$-C$_7$)cycloalkyl, optionally substituted 3-7 membered monocyclic heterocycloalkyl, optionally substituted phenyl, or optionally substituted 5-6 membered monocyclic heteroaryl;
R$^d$ and R$^e$ are each independently selected from —H, optionally substituted (C$_1$-C$_7$)alkyl, optionally substituted (C$_3$-C$_7$)cycloalkyl, optionally substituted 3-7 membered monocyclic heterocycloalkyl, optionally substituted phenyl, and optionally substituted 5-6 membered monocyclic heteroaryl; or
R$^d$ and R$^e$, together with the nitrogen to which they are attached, form an optionally substituted 3-7 membered ring.

2. A compound represented by the following structural formula:

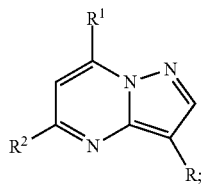

(I)

or a pharmaceutically acceptable salt thereof, wherein:
R is phenyl or monocyclic 5-6 membered heteroaryl, both of which are substituted with —C(=O)NR$^d$R$^e$, —NHC(=O)R$^5$, —C(=S)NR$^d$R$^e$, or —NHC(=S)R$^5$ and optionally substituted with one or more groups selected from halogen, hydroxy, (C$_1$-C$_3$)alkyl, (C$_1$-C$_3$)haloalkyl, (C$_1$-C$_3$)alkoxy, and (C$_1$-C$_3$)haloalkoxy;
R$^1$ is NR$^{a1}$R$^{b1}$, —OR$^{c1}$, —SR$^{c1}$, —SOR$^{c1}$, or —SO$_2$R$^{c1}$;
R$^2$ is —NR$^{a2}$R$^{b2}$, —OR$^{c2}$, —SR$^{c2}$, optionally substituted phenyl or optionally substituted 5-6 membered monocyclic heteroaryl;
R$^5$ is optionally substituted (C$_1$-C$_3$)alkyl, optionally substituted (C$_3$-C$_7$)cycloalkyl, optionally substituted 3-7 membered monocyclic heterocycloalkyl, optionally substituted phenyl, or optionally substituted 5-6 membered monocyclic heteroaryl;
R$^{a1}$ and R$^{b1}$ are each independently selected from —H, optionally substituted (C$_1$-C$_6$)alkyl, optionally substituted ($C_3$-$C_7$)cycloalkyl, optionally substituted 3-7 membered monocyclic heterocycloalkyl, optionally substituted phenyl, and optionally substituted 5-6 membered monocyclic heteroaryl;

$R^{a2}$ and $R^{b2}$ are each independently selected from —H, optionally substituted ($C_1$-$C_6$)alkyl, optionally substituted ($C_3$-$C_7$)cycloalkyl, optionally substituted 3-7 membered monocyclic heterocycloalkyl, optionally substituted phenyl, and optionally substituted 5-6 membered monocyclic heteroaryl; or $R^{a2}$ and $R^{b2}$, together with the nitrogen to which they are attached, form an optionally substituted 3-7 membered ring;

$R^{c1}$ is optionally substituted ($C_1$-$C_6$)alkyl, optionally substituted ($C_3$-$C_7$) cycloalkyl, optionally substituted 3-7 membered monocyclic heterocycloalkyl, optionally substituted phenyl, or optionally substituted 5-6 membered monocyclic heteroaryl;

$R^{c2}$ is optionally substituted ($C_1$-$C_6$)alkyl, optionally substituted ($C_3$-$C_7$)cycloalkyl, optionally substituted 3-7 membered monocyclic heterocycloalkyl, optionally substituted phenyl, or optionally substituted 5-6 membered monocyclic heteroaryl; and $R^d$ and $R^e$ are each independently selected from —H, optionally substituted ($C_1$-$C_7$)alkyl, optionally substituted ($C_3$-$C_7$)cycloalkyl, optionally substituted 3-7 membered monocyclic heterocycloalkyl, optionally substituted phenyl, and optionally substituted 5-6 membered monocyclic heteroaryl; or $R^d$ and $R^e$, together with the nitrogen to which they are attached, form an optionally substituted 3-7 membered ring.

3. The compound of claim 2, wherein the compound is represented by the following structural formula:

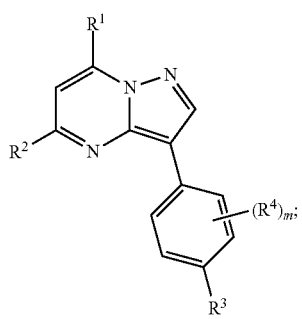

(I-A)

or a pharmaceutically acceptable salt thereof, wherein:

$R^3$ is —C(=O)NR$^d$R$^e$ or —NHC(=O)R$^5$;

each $R^4$ is independently selected from hydrogen, halogen, hydroxy, ($C_1$-$C_3$)alkyl, ($C_1$-$C_3$)haloalkyl, and ($C_1$-$C_3$)alkoxy; and m is 1, 2, or 3.

4. The compound of claim 3, wherein the compound is represented by the following structural formula:

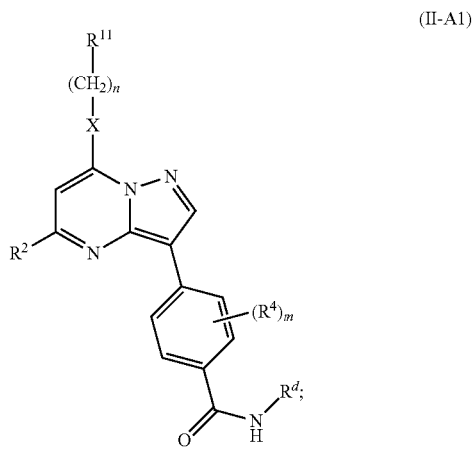

(II-A1)

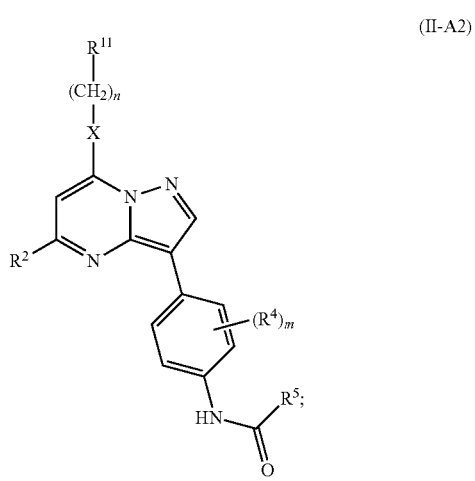

(II-A2)

or a pharmaceutically acceptable salt thereof, wherein:

X is NH or O;

$R^5$ is selected from ($C_1$-$C_3$)alkyl and ($C_3$-$C_7$)cycloalkyl, each of which is optionally substituted with one or more groups selected from halogen, hydroxy, ($C_1$-$C_3$)alkyl, ($C_1$-$C_3$)haloalkyl, and ($C_1$-$C_3$)alkoxy;

$R^{11}$ is ($C_1$-$C_3$)alkyl, ($C_3$-$C_7$)cycloalkyl, 3-7 membered monocyclic heterocycloalkyl, phenyl, or 5-6 membered monocyclic heteroaryl, each of which is optionally substituted with one or more groups selected from halogen, hydroxy, CN, amino, ($C_1$-$C_3$)alkyl, ($C_1$-$C_3$)haloalkyl, ($C_1$-$C_3$)alkoxy, —C(=O)NH$_2$, —C(=O)NH($C_1$-$C_3$)alkyl, —C(=O)N(($C_1$-$C_3$)alkyl)$_2$, and —SO$_2$($C_1$-$C_3$)alkyl;

$R^d$ is independently selected from —H, ($C_1$-$C_3$)alkyl, ($C_3$-$C_7$)cycloalkyl, 4-5 membered heterocycloalkyl wherein each of the ($C_1$-$C_3$)alkyl, ($C_3$-$C_7$)cycloalkyl, and 4-5 membered heterocycloalkyl is optionally substituted with one or more groups selected from halogen, hydroxy, ($C_1$-$C_3$)alkyl, ($C_1$-$C_3$)haloalkyl, and ($C_1$-$C_3$)alkoxy; and n is 0, 1, 2, or 3.

5. The compound of claim 4, wherein the compound is represented by the following structural formula:

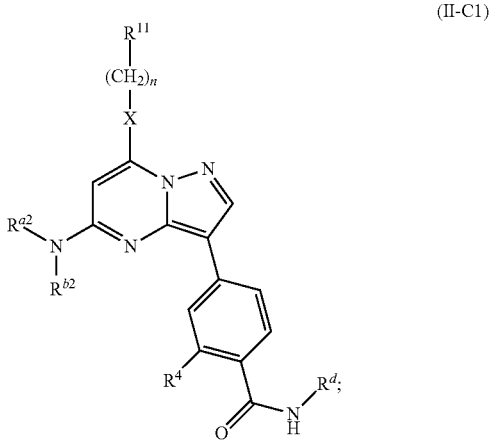

(II-C1)

or a pharmaceutically acceptable salt thereof.

6. The compound of claim 5, wherein $R^{b2}$ is —H or $CH_3$.

7. The compound of claim 6, wherein $R^{a2}$ is $(C_1-C_6)$alkyl, $(C_3-C_7)$cycloalkyl, 3-7 membered monocyclic heterocycloalkyl, phenyl, and 5-6 membered monocyclic heteroaryl; wherein each of which is optionally substituted with one or more groups selected from halogen, hydroxy, CN, $(C_1-C_3)$alkyl, $(C_1-C_3)$haloalkyl, $(C_1-C_3)$alkoxy, $(C_1-C_3)$hydroxyalkyl, 3-7 membered monocyclic heterocycloalkyl.

8. The compound of claim 7, wherein $R^{a2}$ is methyl, ethyl, propyl, isopropyl, butyl, isobutyl, tert-butyl, pentyl, cyclopropyl, cyclobutyl, cyclopentyl, cyclohexyl, oxetanyl, tetrahydro-2H-pyranyl, tetrahydrofuranyl, piperidinyl, pyridyl, or phenyl, wherein each of the methyl, ethyl, propyl, isopropyl, isobutyl, tert-butyl, cyclopropyl, cyclobutyl, cyclopentyl, cyclohexyl, oxetanyl, tetrahydro-2H-pyranyl, tetrahydrofuranyl, piperidinyl, pyridyl, and phenyl is optionally substituted with one or more groups selected from halogen, hydroxy, CN, $(C_1-C_3)$alkyl, $(C_1-C_3)$haloalkyl, $(C_1-C_3)$alkoxy, and oxetanyl.

9. The compound of claim 5, wherein $R^{a2}$ and $R^{b2}$, together with the nitrogen to which they are attached, form a 3-7 membered monocyclic heterocycloalkyl, optionally substituted with one or more groups selected from halogen, CN, hydroxy, $(C_1-C_3)$alkyl, $(C_1-C_3)$haloalkyl, $(C_1-C_3)$hydroxylalkyl, $(C_1-C_3)$alkoxy, —C(=O)H, —C(=O)($C_3-C_7$)cycloalkyl, —C(=O)($C_1-C_3$)alkyl, and 3-7 membered monocyclic heterocycloalkyl.

10. The compound of claim 4, wherein the compound is represented by the following structural formula:

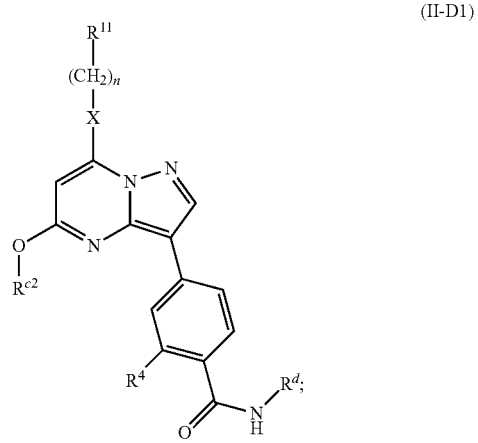

(II-D1)

or a pharmaceutically acceptable salt thereof.

11. The compound of claim 10, wherein $R^{c2}$ is $(C_1-C_6)$alkyl, $(C_3-C_7)$cycloalkyl, 3-7 membered monocyclic heterocycloalkyl, phenyl, or 5-6 membered monocyclic heteroaryl, each of which is optionally substituted with one or more groups selected from halogen, hydroxy, $(C_1-C_3)$alkyl, $(C_1-C_3)$haloalkyl, $(C_1-C_3)$hydroxylalkyl, $(C_1-C_3)$alkoxy, —C(=O) $(C_1-C_3)$alkyl, —C(=O)($C_3-C_7$)cycloalkyl, —C(=O)H, and 3-7 membered monocyclic heterocycloalkyl.

12. The compound of claim 11, wherein $R^{c2}$ is cyclobutyl, cyclopentyl, cyclohexyl, tetrahydro-2H-pyranyl, phenyl, pyridyl, oxetanyl, tetrahydrofuranyl, pyrrolidinyl, piperidinyl, or azetidinyl, wherein each substitutable carbon atom in the cyclobutyl, cyclopentyl, cyclohexyl, tetrahydro-2H-pyranyl, phenyl, pyridyl, oxetanyl, tetrahydrofuranyl, pyrrolidinyl, piperidinyl and azetidinyl is optionally substituted with one or more groups selected from halogen, $(C_1-C_3)$alkyl, $(C_1-C_3)$haloalkyl, $(C_1-C_3)$hydroxylalkyl, $(C_1-C_3)$alkoxy, oxetanyl; and each substitutable nitrogen atom in the azetidinyl, pyrrolidinyl, or piperidinyl, is optionally substituted with $(C_1-C_3)$alkyl, $(C_3-C_5)$heterocycloalkyl, $(C_1-C_3)$hydroxylalkyl, —C(=O) $(C_1-C_3)$alkyl, —C(=O) $(C_3-C_5)$cycloalkyl, or —C(=O)H.

13. The compound of claim 12, wherein $R^4$ is chlorine or methyl, and $R^d$ is cyclopropyl.

14. The compound of claim 13, wherein $R^{11}$ is $(C_1-C_6)$alkoxy, ethyl, propyl, isopropyl, isobutyl, tert-butyl, cyclopropyl, cyclobutyl, cyclopentyl, cyclohexyl, morpholinyl, tetrahydro-2H-pyranyl, piperidinyl, piperazinyl, pyridinyl, imidazolyl, or oxetanyl, wherein each substitutable carbon atom in the ethyl, propyl, isopropyl, isobutyl, tert-butyl, cyclopropyl, cycylobutyl, cyclopentyl, cyclohexyl, morpholinyl, tetrahydro-2H-pyranyl, piperidinyl, piperazinyl, pyridinyl, imidazolyl, and oxetanyl is optionally substituted with halogen, hydroxy, $(C_1-C_3)$alkyl, $(C_1-C_3)$haloalkyl, or $(C_1-C_3)$alkoxy; and each substitutable nitrogen atom in the piperazinyl is optionally substituted with $(C_1-C_3)$alkyl, $(C_1-C_3)$haloalkyl, $(C_1-C_3)$hydroxylalkyl, oxetanyl, tetrahydro-2H-pyranyl, —C(=O)($C_3-C_5$)cycloalkyl, —C(=O)($C_1-C_3$)alkyl, or —C(=O)H.

15. The compound of claim 3, wherein $R^1$ is —NHR$^{b1}$, $R^{b1}$ is $(C_1-C_4)$alkyl optionally substituted with one or more groups selected from hydroxy, $(C_1-C_3)$alkoxy, hydroxy($C_1-C_3$)alkyl, —SO$_2$($C_1-C_3$)alkyl, $(C_3-C_7)$cycloalkyl, or 3-7 membered heterocycloalkyl containing one ring heteroatom, the heteroatom being oxygen, wherein the $(C_3-C_7)$cycloalkyl or the 3-7 membered heterocycloalkyl substituent is optionally substituted with halogen, hydroxyl, or $(C_1-C_3)$alkyl.

16. The compound of claim 15, wherein $R^{b1}$ is $(C_1-C_4)$alkyl optionally substituted with one or more groups selected from hydroxy, $(C_1-C_3)$alkoxy, hydroxymethyl, —SO$_2$($C_1-C_3$)alkyl, cyclopropyl, cyclobutyl, cyclohexyl, oxetanyl, tetrahydrofuranyl, tetrahydropyranyl, wherein the cyclobutyl, cyclohexyl, oxetanyl, tetrahydrofuranyl, or tetrahydropyranyl substituent is optionally substituted with 1-2 groups selected from hydroxy or $(C_1-C_3)$alkyl.

17. The compound of claim 16, wherein $R^2$ is $R^{c2}$ or —OR$^{c2}$, and $R^{c2}$ is $(C_3-C_7)$cycloalkyl; 4-7 membered heterocycloalkyl containing one ring heteroatom which is oxygen; phenyl; or 5-6 membered nitrogen-containing heteroaryl; each of which is optionally substituted with halogen, hydroxy, $(C_1-C_3)$alkyl, $(C_1-C_3)$alkoxy, or —SO$_2$($C_1-C_3$)alkyl.

18. The compound of claim 16, wherein $R^2$ is 4-10 membered heterocycloalkyl containing one ring heteroatom which is nitrogen optionally substituted with hydroxy, hydroxy($C_1$-$C_3$)alkyl, —C(=O)($C_1$-$C_3$)alkyl, or ($C_3$-$C_7$)cycloalkyl;

5-10 membered nitrogen-containing heteroaryl;

$OR^{c2}$, wherein $R^{c2}$ is phenyl optionally substituted with halogen, ($C_1$-$C_3$)alkyl, —N($R^{a1}$)$_2$ or 4-6 membered heterocycloalkyl containing one ring heteroatom which is nitrogen; pyridinyl optionally substituted with halogen or ($C_1$-$C_3$)alkyl; piperidinyl optionally substituted with 4-6 membered heterocycloalkyl containing one ring heteroatom which is oxygen, or ($C_1$-$C_3$)alkoxy; pyrrolidinyl optionally substituted with 4-6 membered heterocycloalkyl containing one ring heteroatom which is oxygen or ($C_1$-$C_3$)alkoxy; or azetidinyl optionally substituted with 4-6 membered heterocycloalkyl containing one ring heteroatom which is oxygen or ($C_1$-$C_3$)alkoxy; wherein $R^{a1}$ is H or ($C_1$-$C_3$)alkyl, or $NHR^{b2}$ or $N(($C_1$-$C_3$)alkyl)$R^{b2}$ wherein $R^{b2}$ is ($C_1$-$C_4$)alkyl, ($C_3$-$C_7$)cycloalkyl, 3-7 membered heterocycloalkyl containing one ring heteroatom which is oxygen, phenyl, or 5-6 membered nitrogen-containing heteroaryl;

wherein the ($C_1$-$C_4$)alkyl represented by $R^{b2}$ is optionally substituted with one or more groups selected from hydroxy, —C(=O)NH$_2$, ($C_1$-$C_4$)alkyl, hydroxy($C_1$-$C_3$)alkyl, ($C_3$-$C_7$)cycloalkyl, 3-7 membered heterocycloalkyl containing one ring heteroatom which is oxygen, and wherein the ($C_3$-$C_7$)cycloalkyl, 3-7 membered heterocycloalkyl, phenyl, and 5-6 membered nitrogen-containing heteroaryl substituents in the group represented by $R^{b2}$ are optionally substituted with hydroxy, halogen, ($C_1$-$C_3$)alkyl, ($C_1$-$C_3$)alkoxy, hydroxy($C_1$-$C_3$)alkyl.

19. The compound of claim 18, wherein $R^2$ is azetidinyl optionally substituted with hydroxyl, hydroxymethyl, ($C_3$-$C_6$)cycloalkyl, or —C(=O)($C_1$-$C_3$)alkyl; pyrrolidinyl optionally substituted with hydroxyl, hydroxymethyl, ($C_3$-$C_6$)cycloalkyl, or —C(=O)($C_1$-$C_3$)alkyl; piperidinyl optionally substituted with hydroxyl, hydroxymethyl, ($C_3$-$C_6$)cycloalkyl, or —C(=O)($C_1$-$C_3$)alkyl; piperazinyl optionally substituted with hydroxyl, hydroxymethyl, ($C_3$-$C_6$)cycloalkyl, or —C(=O)($C_1$-$C_3$)alkyl; morpholinyl optionally substituted with hydroxyl, hydroxymethyl, ($C_3$-$C_6$)cycloalkyl, or —C(=O)($C_1$-$C_3$)alkyl;

pyridinyl, quinolinyl, $OR^{c2}$, wherein $R^{c2}$ is phenyl optionally substituted with —N($R^{a1}$)$_2$ or with 4-6 membered heterocycloalkyl with one ring heteroatom which is nitrogen; pyridinyl optionally substituted with halogen; piperidinyl optionally substituted with oxetanyl; or pyrrolidinyl optionally substituted with oxetanyl; wherein $R^{a1}$ is H or ($C_1$-$C_3$)alkyl;

—NH-cyclopentyl, —N—(($C_1$-$C_3$)alkyl)-cyclopentyl or $NHR^{b2}$, wherein $R^{b2}$ is phenyl or pyridinyl, each of which is optionally substituted with halo or ($C_1$-$C_3$)alkyl;

cyclopropyl optionally substituted with hydroxyl, hydroxymethyl, or oxetanyl; cyclobutyl optionally substituted with hydroxyl, hydroxymethyl, or oxetanyl; cyclopentyl optionally substituted with hydroxyl, hydroxymethyl, or oxetanyl; cyclohexanyl optionally substituted with hydroxyl, hydroxymethyl, or oxetanyl;

tetrahydropyranyl optionally substituted with hydroxyl or hydroxymethyl, tetrahydrofuranyl optionally substituted with hydroxyl or ($C_1$-$C_3$)alkoxy; oxetanyl; or ($C_1$-$C_4$)alkyl, wherein the ($C_1$-$C_4$)alkyl is optionally substituted with one or more groups selected from hydroxy, —C(=O)NH$_2$, ($C_1$-$C_4$)alkoxy, hydroxy($C_1$-$C_3$)alkyl, ($C_3$-$C_6$)cycloalkyl, 3-6 membered heterocycloalkyl containing one ring heteroatom which is oxygen.

20. A pharmaceutical composition comprising a compound of claim 2 and a pharmaceutically acceptable carrier or diluent.

21. A method for treating cancer, wherein the cancer is pancreatic cancer, prostate cancer, lung cancer, melanoma, breast cancer, colon cancer, or ovarian cancer the method comprising: administering to a subject in need thereof an effective amount of the compound of claim 2.

22. The compound of claim 10, wherein n is 0, 1, or 2.

* * * * *